United States Patent
Siegel et al.

(10) Patent No.: US 11,597,778 B2
(45) Date of Patent: Mar. 7, 2023

(54) HUMAN MONOCLONAL AUTOANTIBODIES TO ADAMTS13 AND USES THEREOF

(71) Applicant: THE TRUSTEES OF THE UNIVERSITY OF PENNSYLVANIA, Philadelphia, PA (US)

(72) Inventors: Donald L. Siegel, Lansdale, PA (US); Stephen Kacir, Norristown, PA (US); Eric Ostertag, Lexington, KY (US); X. Long Zheng, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 657 days.

(21) Appl. No.: 15/564,679

(22) PCT Filed: Apr. 6, 2016

(86) PCT No.: PCT/US2016/026224
§ 371 (c)(1),
(2) Date: Oct. 5, 2017

(87) PCT Pub. No.: WO2016/164468
PCT Pub. Date: Oct. 13, 2016

(65) Prior Publication Data
US 2019/0031771 A1 Jan. 31, 2019

Related U.S. Application Data

(60) Provisional application No. 62/144,186, filed on Apr. 7, 2015.

(51) Int. Cl.
| | |
|---|---|
| C07K 16/40 | (2006.01) |
| A61K 49/00 | (2006.01) |
| A61K 38/48 | (2006.01) |
| C12Q 1/37 | (2006.01) |
| G01N 33/564 | (2006.01) |
| A61K 39/00 | (2006.01) |

(52) U.S. Cl.
CPC .......... C07K 16/40 (2013.01); A61K 38/4886 (2013.01); A61K 49/0004 (2013.01); A61K 49/0008 (2013.01); C12Q 1/37 (2013.01); C12Y 304/24087 (2013.01); G01N 33/564 (2013.01); A61K 2039/505 (2013.01); C07K 2317/21 (2013.01); C07K 2317/33 (2013.01); C07K 2317/622 (2013.01); C07K 2317/76 (2013.01); G01N 2333/96486 (2013.01); G01N 2500/04 (2013.01); G01N 2500/20 (2013.01)

(58) Field of Classification Search
None
See application file for complete search history.

(56) References Cited

U.S. PATENT DOCUMENTS

| | | |
|---|---|---|
| 2006/0251655 A1 | 11/2006 | Soejima et al. |
| 2010/0115637 A1 | 5/2010 | Schwarz et al. |
| 2012/0315650 A1 | 12/2012 | Ferrari et al. |

FOREIGN PATENT DOCUMENTS

WO 2013096793 A1 6/2013

OTHER PUBLICATIONS

Rieger et al. (Blood 2005 106:1262-1267).*
Rudikoff et al. (Proc Natl Acad Sci USA 1982 vol. 79 p. 1979.*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Owens et al. (JIM, 1994, 168:149-165).*
International Search Report and Written Opinion for PCT International Application No. PCT/US2016/026224 dated Sep. 21, 2016.
Ai, et al., "The Proximal Carboxyl-Terminal Domains of ADAMTS13 Determine Substrate Specificity and Are All Required for Cleavage of Von Willebrand Factor", J Biol Chem. 280(33), Aug. 2005, 29428-29434.
Akiyama, et al., "Crystal structures of the noncatalytic domains of ADAMTS13 reveal multiple discontinuous exosites for von Willebrand factor", Proc Natl Acad Sci U S A. 106(46), Nov. 2009, 19274-19279.
Casina, et al., "High-resolution epitope mapping by HX MS reveals the pathogenic mechanism and a possible therapy for autoimmune TTP syndrome", Proc Natl Acad Sci U S A. 112(31), Aug. 2015, 9620-9625.
Chang, et al., "Genetic and Immunological Properties of Phage-Displayed Human anti-Rh(D) Antibodies: Implications for Rh(D) Epitope Topology", Blood. 91(8), Apr. 1998, 3066-3078.
Chauhan, et al., "Formation of platelet strings and microthrombi in the presence of ADAMTS-13 inhibitor does not require P-selectin or b3 integrin", Journal of Thrombosis and Haemostasis 5, 2006, 583-589.
Chauhan, et al., "Systemic antithrombotic effects of ADAMTS13", J Exp Med. 203(3), Mar. 2006, 767-776.

(Continued)

*Primary Examiner* — Sharon X Wen
(74) *Attorney, Agent, or Firm* — Saul Ewing LLP

(57) ABSTRACT

The present invention relates to compositions and methods of use of anti-ADAMTS13 autoantibodies and fragments thereof. In one aspect, the invention includes a composition comprising an isolated anti-ADAMTS13 autoantibody or fragment thereof. In other aspects, methods are described for generating an in vivo model of thrombotic thrombocytopenic purpura (TTP) comprising introducing at least one anti-ADAMTS13 autoantibody or fragment thereof into a model organism and identifying an anti-autoimmune reagent for treating TTP.

17 Claims, 26 Drawing Sheets

Specification includes a Sequence Listing.

(56) References Cited

OTHER PUBLICATIONS

Dörner, et al., "Delineation of Selective Influences Shaping the Mutated Expressed Human Ig Heavy Chain Repertoire", J Immunol. 160(6), Mar. 1998, 2831-2841.

Feys, et al., "Thrombotic thrombocytopenic purpura directly linked with ADAMTS13 inhibition in the baboon (*Papio ursinus*)", Blood. 116(12), Sep. 2010, 2005-2010.

Froehlich-Zahnd, et al., "Evidence for a Role of anti-ADAMTS13 Autoantibodies Despite Normal ADAMTS13 Activity in Recurrent Thrombotic Thrombocytopenic Purpura", Haematologica 97(2), Feb. 2012, 297-303.

Jian, et al., "Gain-of-function ADAMTS13 variants that are resistant to autoantibodies against ADAMTS13 in patients with acquired thrombotic thrombocytopenic purpura", Blood. 119(16), Apr. 2012, 3836-3843.

Kappers-Klunne, et al., "Splenectomy for the Treatment of Thrombotic Thrombocytopenic Purpura", Br J Haematol. 130(5), Sep. 2005, 768-776.

Laje, et al., "Correction of murine ADAMTS13 deficiency by hematopoietic progenitor cell-mediated gene therapy", Blood. 113(10), Mar. 2009, 2172-2180.

Luken, et al., "Multiple B-cell clones producing antibodies directed to the spacer and disintegrin/thrombospondin type-1 repeat 1 (TSP1) of ADAMTS13 in a patient with acquired thrombotic thrombocytopenic purpura", J Thromb Haemost. 4(11), Nov. 2006, 2355-2364.

Miao, et al., "Long-Term and Therapeutic-Level Hepatic Gene Expression of Human Factor IX after Naked Plasmid Transfer in Vivo", Mol Ther. 3(6), Jun. 2001, 947-957.

Muia, et al., "Allosteric Activation of ADAMTS13 by Von Willebrand Factor", Proc Natl Acad Sci U S A. 111(52), Dec. 2014, 18584-18589.

Niiya, et al., "Correction of ADAMTS13 Deficiency by In Utero Gene Transfer of Lentiviral Vector encoding ADAMTS13 Genes", Mol Ther. 17(1), Jan. 2009, 34-41.

Ostertag, et al., "ADAMTS13 Autoantibodies Cloned From Patients With Acquired Thrombotic Thrombocytopenic Purpura: 1. Structural and Functional Characterization in Vitro", Transfusion 2016;56(7):, Jul. 2016, 1763-1774.

Ostertag, et al., "ADAMTS13 Autoantibodies Cloned From Patients With Acquired Thrombotic Thrombocytopenic Purpura: 2. Pathogenicity in an Animal Model", Transfusion 56(7), Jul. 2016, 1775-1785.

Payne, et al., "Genetic and functional characterization of human pemphigus vulgaris monoclonal autoantibodies isolated by phage display", J Clin Invest. 115(4), Apr. 2005, 888-899.

Pos, et al., "Residues Arg568 and Phe592 Contribute to an Antigenic Surface for anti-ADAMTS13 Antibodies in the Spacer Domain", Haematologica 96(11), Nov. 2011, 1670-1677.

Pos, et al., "VH1-69 Germline Encoded Antibodies Directed Towards ADAMTS13 in Patients With Acquired Thrombotic Thrombocytopenic Purpura", J Thromb Haemost. 7(3), Mar. 2009, 421-428.

Roark, et al., "Genetic Analysis of Autoantibodies in Idiopathic Thrombotic Thrombocytopenic Purpura Reveals Evidence of Clonal Expansion and Somatic Mutation", Blood. 100(4), Aug. 2002, 1388-1398.

Schaller, et al., "Acquired thrombotic thrombocytopenic purpura. Development of an autoimmune response", Hamostaseologie. 33(2), May 2013, 121-130.

Schaller, et al., "The splenic autoimmune response to ADAMTS13 in thrombotic thrombocytopenic purpura contains recurrent antigen-binding CDR3 motifs", Blood 124(23), Nov. 2014, 3469-3479.

Soejima, et al., "ADAMTS-13 cysteine-rich/spacer domains are functionally essential for vonWillebrand factor cleavage", Blood. 102(9), Nov. 2003, 3232-3237.

South, et al., "Conformational activation of ADAMTS13", Proc Natl Acad Sci U S A. 111(52), Dec. 2014, 18578-18583.

Yeh, et al., "Disulfide Bond Reduction of Von Willebrand Factor by ADAMTS-13", J Thromb Haemost. 8(12), Dec. 2010, 2778-2788.

Zaitzev, et al., "Targeting of a Mutant Plasminogen Activator to Circulating Red Blood Cells for Prophylactic Fibrinolysis", J Pharmacol Exp Ther. 332(3), Mar. 2010, 1022-1031.

Zhang, et al., "Long-term expression of human alpha1-antitrypsin gene in mouse liver achieved by intravenous administration of plasmid DNA using a hydrodynamicsbased procedure", Gene Ther. 7(15), Aug. 2000, 1344-1349.

Zhang, et al., "The cooperative activity between the carboxyl-terminal TSP1 repeats and the CUB domains of ADAMTS13 is crucial for recognition of vonWillebrand factor under flow", Blood. 110(6), Sep. 2007, 1887-1894.

Zheng, "ADAMTS13 and von Willebrand Factor in Thrombotic Thrombocytopenic Purpura", Annu Rev Med. 66, 2015, 211-225.

Zheng, et al., "Multiple domains of ADAMTS13 are targeted by autoantibodies against ADAMTS 13 in patients with acquired idiopathic thrombotic thrombocytopenic purpura", Haematologica 95(9), Sep. 2010, 1555-1562.

\* cited by examiner

A

B

A control scFv scFv 1-420

Comparison of CDR2 amino acid residues for V$_H$1-69 encoded antibody heavy chains

| Antibody | Heavy chain amino acid | | | | | | | Reference |
|---|---|---|---|---|---|---|---|---|
| | 56 | 57 | 58 | 59 | 60 | 61 | 62 | |
| 1-69*01 germline gene | I | I | P | I | – | – | F | IMGT[1] |
| 1-69*09 & *10 germline genes | I | I | P | I | – | – | L | IMGT[1] |
| 1-9, I-10, I-27 | . | . | . | . | – | – | . | Luken[2], Pos[3] |
| B-2, B-6, B-5, 3j | . | . | . | . | – | – | Y | Schaller[4] |
| II-1 | . | . | . | . | – | – | . | Pos[3] |
| 3b | . | . | . | . | – | – | Y | Schaller[4] |
| 1-416 | V | . | . | V | – | – | L | Present Invention |
| 1-420, 1-401, 1-458, 1-450, 1-418, 1-413, 2-103, 2-106, 2-302, 4-303, 3-302, 3-305, 3-405, 3-301 | . | . | . | . | – | – | L | |
| 1-428, 1-304, 1-408, 1-405, 1-423 | . | V | . | V | – | – | L | |
| 1-431 | F | . | . | . | – | – | L | |
| 1-417, 1-303, 1-406 | F | . | . | . | – | – | L | |
| 1-438 | V | . | . | . | – | – | L | |
| 1-434, 1-432, 2-204, 2-305, 2-406, 2-203, 2-206, 2-408 | V | V | . | . | – | – | L | |
| 2-102 | . | T | . | . | – | – | L | |
| 2-207, 2-301, 2-304 | . | . | . | M | – | – | L | |
| 4-307 | . | . | . | . | – | – | . | |
| PX4-3 | . | . | . | F | – | – | L | Payne[5] |

Antibodies are grouped by identical CDR2 amino acid residues in positions 56-62. Replacement mutations are indicated with letters, identities with ".", and gaps with "–". CDR2 numbering designations per Brochet et al.[1]

(1) Brochet et al., Nucleic Acids Research 2008;36:W503-W8
(2) Luken et al., J Thromb Haemost 2006;4:2355-64
(3) Pos et al., J Thromb Haemost 2009;7:421-8
(4) Schaller et al., Blood 2014;124:3469-79
(5) Payne et al., J Clin Invest 2005;115:888-99

| Antibody | Total Framework Replacement Mutations | Total Framework Silent Mutations | Total CDR1 & CDR2 Replacement Mutations |
|---|---|---|---|
| 1-416 | 11 | 4 | 8 |
| 1-428 | 11 | 3 | 7 |
| 1-304 | 11 | 2 | 7 |
| 1-431 | 6 | 4 | 5 |
| 1-417 | 8 | 3 | 5 |
| 1-303 | 5 | 5 | 4 |
| 1-408 | 5 | 4 | 6 |
| 1-406 | 8 | 2 | 5 |
| 1-401, 1-458 | 8 | 2 | 5 |
| 1-420 | 7 | 2 | 5 |
| 1-438 | 7 | 3 | 6 |
| 1-434 | 9 | 2 | 6 |
| 1-432 | 6 | 3 | 6 |
| 1-405 | 10 | 4 | 7 |
| 1-450 | 12 | 5 | 4 |
| 1-423 | 11 | 5 | 5 |
| 1-418 | 8 | 5 | 5 |
| 1-413 | 10 | 7 | 5 |
| 2-204 | 2 | 2 | 3 |
| 2-102 | 2 | 3 | 5 |
| 2-207, 2-301 | 6 | 1 | 3 |
| 2-304 | 7 | 1 | 3 |
| 2-305, 2-406 | 3 | 4 | 3 |
| 2-103 | 2 | 0 | 2 |
| 2-106 | 2 | 1 | 2 |
| 2-302 | 5 | 1 | 2 |
| 2-203 | 2 | 3 | 1 |
| 2-206 | 3 | 1 | 3 |
| 2-408 | 5 | 0 | 3 |
| 4-303 | 1 | 3 | 3 |
| 3-302, 3-305, 3-405 | 7 | 6 | 6 |
| 4-307 | 7 | 3 | 4 |
| 3-301 | 5 | 3 | 1 |
| 1-437 | 4 | 2 | 4 |
| 1-404 | 6 | 2 | 4 |
| 1-441 | 6 | 2 | 3 |
| 1-403, 1-415 | 1 | 2 | 5 |
| 21-402 | 6 | 5 | 5 |
| 1-410 | 3 | 2 | 0 |
| 1-407 | 0 | 1 | 0 |
| 2-108 | 4 | 0 | 0 |
| 1-440 | 1 | 2 | 1 |
| 1-451 | 2 | 1 | 1 |
| 21-201 | 3 | 1 | 1 |
| 21-303 | 6 | 7 | 4 |

FIG. 9A (continued)

| Total CDR1 & CDR2 Silent Mutations | Total Replacement Mutations | Total Silent Mutations | R:S ratio FR | R:S ratio CDR1 & CDR2 |
|---|---|---|---|---|
| 0 | 19 | 4 | 2.8 | >5.0 |
| 0 | 18 | 3 | 3.7 | >7.0 |
| 0 | 18 | 2 | 5.5 | >7.0 |
| 1 | 11 | 5 | 1.5 | 5.0 |
| 2 | 13 | 6 | 2.7 | 2.5 |
| 2 | 9 | 7 | 1.0 | 2.0 |
| 0 | 11 | 4 | 1.3 | >5.0 |
| 1 | 13 | 3 | 4.0 | 5.0 |
| 3 | 13 | 5 | 4.0 | 1.7 |
| 3 | 12 | 5 | 3.5 | 1.7 |
| 0 | 13 | 3 | 2.3 | >5.0 |
| 2 | 15 | 4 | 4.5 | 3.0 |
| 1 | 12 | 4 | 2.0 | 6.0 |
| 0 | 17 | 4 | 2.5 | >7.0 |
| 1 | 17 | 6 | 2.6 | 4.0 |
| 1 | 16 | 6 | 2.2 | 5.0 |
| 1 | 13 | 6 | 1.6 | 5.0 |
| 1 | 15 | 8 | 1.4 | 5.0 |
| 1 | 5 | 3 | 1.0 | 3.0 |
| 0 | 7 | 1 | 2.0 | >5.0 |
| 0 | 9 | 1 | 6.0 | >3.0 |
| 0 | 10 | 1 | 7.0 | >3.0 |
| 1 | 6 | 5 | 0.8 | 3.0 |
| 0 | 4 | 0 | >2.0 | >2.0 |
| 0 | 4 | 1 | 2.0 | >2.0 |
| 0 | 7 | 1 | 5.0 | >2.0 |
| 0 | 3 | 3 | 0.7 | >1.0 |
| 1 | 6 | 3 | 3.0 | 3.0 |
| 0 | 8 | 0 | >5.0 | >3.0 |
| 0 | 4 | 3 | 0.3 | >3.0 |
| 2 | 13 | 8 | 1.2 | 3.0 |
| 1 | 13 | 4 | 2.3 | 4.0 |
| 0 | 6 | 3 | 1.7 | >1.0 |
| 0 | 8 | 2 | 2.0 | >4.0 |
| 0 | 10 | 2 | 3.0 | >4.0 |
| 0 | 9 | 2 | 3.0 | >3.0 |
| 0 | 6 | 2 | 0.5 | >5.0 |
| 1 | 13 | 6 | 1.2 | 5.0 |
| 0 | 3 | 2 | 1.5 | - |
| 0 | 0 | 1 | 0.0 | - |
| 1 | 4 | 1 | >4.0 | 0.0 |
| 0 | 2 | 2 | 0.5 | >1.0 |
| 0 | 3 | 1 | 2.0 | >1.0 |
| 0 | 4 | 1 | 3.0 | >1.0 |
| 1 | 10 | 8 | 0.9 | 4.0 |

| Total CDR1 & CDR2 Replacement Mutations | Total CDR1 & CDR2 Silent Mutations | Total Replacement Mutations | Total Silent Mutations | R:S ratio FR | R:S ratio CDR1 & CDR2 |
|---|---|---|---|---|---|
| 0 | 0 | 8 | 10 | 1.5 | - |
| 0 | 0 | 5 | 7 | 2.5 | - |
| 3 | 1 | 18 | 27 | 1.7 | 3.0 |
| 0 | 0 | 4 | 4 | >4.0 | - |
| 0 | 0 | 5 | 7 | 2.5 | - |
| 0 | 0 | 6 | 8 | 3.0 | - |
| 0 | 0 | 2 | 4 | 1.0 | - |
| 0 | 0 | 5 | 3 | 1.7 | - |
| 1 | 1 | 8 | 10 | 3.5 | 1.0 |
| 1 | 1 | 6 | 9 | 2.5 | 1.0 |
| 0 | 0 | 4 | 7 | 1.3 | - |
| 0 | 0 | 3 | 4 | 3.0 | - |
| 4 | 1 | 16 | 24 | 1.2 | 4.0 |
| 1 | 0 | 9 | 12 | 2.7 | >1.0 |
| 1 | 0 | 6 | 10 | 1.3 | >1.0 |
| 3 | 1 | 14 | 24 | 1.1 | 3.0 |
| 0 | 0 | 4 | 6 | 2.0 | - |
| 0 | 0 | 4 | 8 | 2.0 | - |
| 0 | 0 | 3 | 8 | 0.6 | - |
| 0 | 0 | 5 | 7 | 2.6 | - |
| 1 | 0 | 6 | 8 | >5.0 | >1.0 |
| 1 | 0 | 12 | 16 | 1.8 | >1.0 |
| 2 | 0 | 7 | 13 | 1.0 | >2.0 |
| 0 | 0 | 4 | 7 | 1.3 | - |
| 0 | 0 | 5 | 7 | 2.5 | - |
| 0 | 0 | 5 | 5 | >5.0 | - |
| 0 | 0 | 4 | 9 | 2.0 | - |
| 1 | 0 | 6 | 9 | 1.7 | >1.0 |
| 0 | 0 | 6 | 9 | 3.0 | - |
| 2 | 0 | 5 | 7 | 1.5 | >2.0 |
| 1 | 0 | 5 | 9 | 1.0 | >1.0 |
| 1 | 0 | 4 | 9 | 0.6 | >1.0 |
| 2 | 0 | 10 | 13 | 2.7 | >2.0 |
| 1 | 0 | 7 | 10 | 2.0 | >1.0 |
| 3 | 0 | 11 | 13 | 4.0 | >3.0 |
| 0 | 0 | 3 | 5 | 1.5 | - |
| 3 | 0 | 9 | 14 | 1.2 | - |
| 2 | 0 | 8 | 12 | 2.3 | - |
| 1 | 1 | 8 | 12 | 1.8 | 1.0 |
| 0 | 0 | 3 | 4 | 3.0 | - |
| 1 | 1 | 12 | 16 | 2.8 | 1.0 |
| 2 | 3 | 18 | 18 | 2.7 | 0.7 |
| 0 | 0 | 3 | 5 | 0.7 | - |
| 2 | 0 | 10 | 14 | 2.0 | >2.0 |
| 2 | 0 | 13 | 19 | 1.8 | >2.0 |
| 2 | 0 | 14 | 18 | 3.0 | >2.0 |
| 0 | 0 | 3 | 5 | 1.5 | - |
| 0 | 0 | 4 | 9 | 1.0 | - |
| 0 | 0 | 2 | 4 | 1.0 | - |
| 0 | 0 | 5 | 7 | 2.5 | - |
| 2 | 0 | 9 | 15 | 1.3 | >2.0 |

FIG. 9B (continued)

| scFv | FL-A13 | delCUB | MDTCS | MDT | T2-8 | T5-8 + CUB | CUB |
|---|---|---|---|---|---|---|---|
| E1M2 | - | - | - | - | - | - | - |
| 1-437 | + | + | + | + | - | - | - |
| 1-303 | + | + | + | - | - | - | - |
| 1-304 | + | + | + | - | - | - | - |
| 1-416 | + | + | + | - | - | - | - |
| 1-428 | + | + | + | - | - | - | - |
| 1-431 | + | + | + | - | - | - | - |
| 1-420 | + | + | + | - | - | - | - |
| 1-434 | + | + | + | - | - | - | - |
| 3-301 | + | + | + | - | - | - | - |
| 2-102 | + | + | + | - | - | - | - |
| 2-103 | + | + | + | - | - | - | - |
| 1-438 | + | + | + | - | - | - | - |
| 3-302 | + | + | + | - | - | - | - |
| 3-405 | + | + | + | - | - | - | - |
| 1-441 | + | - | - | - | - | + | + |
| 1-403 | + | - | - | - | - | + | + |
| z1-402 | + | - | - | - | - | + | + |
| 1-440 | + | - | - | - | - | + | + |
| z1-201 | + | - | - | - | - | + | + |
| 1-407 | + | - | - | - | - | + | + |
| z1-303 | + | - | - | - | - | + | - |
| 1-404 | + | + | + | - | - | + | w |
| 1-410 | + | w | w | - | - | + | - |

FIG. 10C

HUMAN MONOCLONAL AUTOANTIBODIES TO ADAMTS13 AND USES THEREOF

CROSS-REFERENCE TO RELATED APPLICATION

The present application is a 35 U.S.C. § 371 national phase application from, and claims priority to, International Application No. PCT/US2016/026224, filed Apr. 6, 2016 and published under PCT Article 21(2) in English, which is entitled to priority under 35 U.S.C. § 119(e) to U.S. Provisional Patent Application No. 62/144,186, filed Apr. 7, 2015, all of which applications are incorporated herein by reference in their entireties.

STATEMENT REGARDING FEDERALLY SPONSORED RESEARCH OR DEVELOPMENT

This invention was made with government support under grant numbers HL081012, HL007775, HL110860 and HL115187 awarded by the National Institutes of Health. The government has certain rights in the invention.

BACKGROUND OF THE INVENTION

Current therapeutic approaches to the treatment of antibody-mediated autoimmune disease are generally limited to the use of systemic immunosuppression with its attendant side effects rather than therapy that solely targets just the pathogenic autoantibodies.

The acquired form of thrombotic thrombocytopenic purpura (TTP) is an example of an autoimmune disorder that the majority of patients have reduced activity levels of the VWF-cleaving protease ADAMTS13 due to the development of autoantibodies that inhibit its function. Decreased ADAMTS13 activity results in the accumulation of ultralarge VWF (UL-VWF) multimers that foster systemic platelet aggregation in the microcirculation when coincident with additional factors, such as endothelial injury, and can lead to severe thrombocytopenia, microangiopathic hemolytic anemia, varying degrees of organ dysfunction, and death.

First-line therapy for TTP is non-specific comprising daily therapeutic plasma exchange (TPE), which reduces mortality from ~90% to ~20%, presumably by repeated depletion of a fraction of circulating autoantibodies as well as replenishment of ADAMTS13 levels until the disease resolves on its own. Depending on a patient's response to TPE, systemic immunosuppressive agents including corticosteroids and the B-cell depletion agent rituximab, and, less commonly, cyclophosphamide, vincristine, or cyclosporine, may be used in conjunction with TPE. Notwithstanding improvements in the recognition, early initiation of therapy, and the use of combination therapies, the mortality for patients diagnosed with TTP has remained relatively constant since the initial introduction of TPE over 25 years ago.

Recently, a number of alternative therapeutic approaches for TTP have been proposed including the infusion of excess quantities of recombinant ADAMTS13 to override autoantibody inhibition, and the development of agents that would target UL-VWF multimers either by reducing their size or by blocking their interactions with platelets. However, it is not clear that these approaches would necessarily obviate the need for TPE and/or agents that induce generalized immunosuppression since these modalities affect pathogenesis downstream of the effects of the autoantibody-mediated ADAMTS13 inhibition, rather than by affecting the pathogenic ADAMTS13 inhibitors themselves. Moreover, there is the potential downside of inhibiting normal hemostatic processes that are mediated through some of the same pathways.

There is a need in the art for the development of more effective and targeted therapies to treat thrombotic thrombocytopenic purpura (TTP). The present invention addresses this need.

SUMMARY OF THE INVENTION

As disclosed herein, the present invention includes compositions and methods of use of anti-ADAMTS13 autoantibodies and fragments thereof.

In one aspect, the invention includes an isolated anti-ADAMTS13 autoantibody or fragment thereof.

In one aspect, the invention includes isolated nucleic acid sequence encoding an anti-ADAMTS13 autoantibody or fragment thereof.

In another aspect, the invention includes a method for generating an in vivo model of thrombotic thrombocytopenic purpura (TTP) comprising introducing at least one anti-ADAMTS13 autoantibody or fragment thereof into a model organism.

In another aspect, the invention includes an anti-autoimmune reagent, wherein the anti-autoimmune reagent specifically binds to an anti-ADAMTS13 autoantibody or fragment thereof.

In yet another aspect, the invention includes a method for identifying an anti-autoimmune reagent for treating thrombotic thrombocytopenic purpura (TTP). The method of the invention comprises contacting a panel of agents with at least one anti-ADAMTS13 autoantibody or fragment thereof and identifying the agents that bind to the anti-ADAMTS13 autoantibody or fragment thereof.

In still another aspect, the invention includes a method of inhibiting the binding of an anti-ADAMTS13 autoantibody or fragment thereof to ADAMTS13. The method comprises contacting the anti-ADAMTS13 autoantibody or fragment thereof with a composition comprising an anti-autoimmune reagent that specifically binds to the anti-ADAMTS13 autoantibody or fragment thereof.

In another aspect, the invention includes a method of identifying an ADAMTS13 variant that does not bind an anti-ADAMTS13 autoantibody or fragment thereof. The method comprises contacting an ADAMTS13 protein with an anti-ADAMTS13 autoantibody or fragment thereof, wherein when the ADAMTS13 protein does not bind the anti-ADAMTS13 autoantibody or fragment thereof, then the ADAMTS13 protein is a variant that does not bind an anti-ADAMTS13 autoantibody or fragment thereof.

In yet another aspect, the invention includes a method for treating thrombotic thrombocytopenic purpura (TTP) in a subject in need thereof, the method comprising administering to the subject a composition comprising an effective amount of an ADAMTS13 variant, wherein the ADAMTS13 variant is resistant to inhibition by an anti-ADAMTS13 autoantibody or fragment thereof.

In various embodiments of the above aspects or any other aspect of the invention delineated herein, the anti-ADAMTS13 autoantibody or fragment thereof comprises a heavy chain selected from the group consisting of SEQ ID NOs: 46-90. In another embodiment, the anti-ADAMTS13 autoantibody or fragment thereof comprises a light chain selected from the group consisting of SEQ ID NOs: 142-192.

In another embodiment, the anti-ADAMTS13 autoantibody or fragment thereof comprises a single chain variable fragment (scFv). In another embodiment, the anti-AD-AMTS13 autoantibody or fragment thereof is capable of decreasing ADAMTS13 activity. In yet another embodiment, the ADAMTS13 activity is selected from the group consisting of proteolytic activity, disulfide reducing activity, interacting or attaching to an endothelial cell surface, and any combination thereof.

In a further embodiment, the anti-ADAMTS13 autoantibody or fragment thereof binds at least one of the ADAMTS13 region selected from the group consisting of amino-terminal (MDT1) domain, carboxy-terminal (T5-8/CUB) domain and cysteine-rich/spacer region.

In one embodiment, the isolated nucleic acid sequence encoding an anti-ADAMTS13 autoantibody or fragment thereof comprises a heavy chain nucleic acid sequence selected from the group consisting of SEQ ID NOs: 1-45. In another embodiment, the isolated nucleic acid sequence encoding the anti-ADAMTS13 autoantibody or fragment thereof comprises a light chain nucleic acid sequence selected from the group consisting of SEQ ID NOs: 91-141.

In another embodiment, the isolated nucleic acid sequence encodes a single chain variable fragment (scFv).

In yet another embodiment, the isolated nucleic acid sequence encoding an anti-ADAMTS13 autoantibody or fragment thereof has an identity of at least 80% to at least one heavy chain nucleic acid sequence selected from the group consisting of SEQ ID NOs: 1-45. In yet another embodiment, the isolated nucleic acid sequence encoding an anti-ADAMTS13 autoantibody or fragment thereof has an identity of at least 80% to at least one light chain nucleic acid sequence selected from the group consisting of SEQ ID NOs: 91-141.

In one embodiment, the in vivo model organism of thrombotic thrombocytopenic purpura (TTP) of the invention is selected from the group consisting of a non-mammalian organism and a non-human mammalian organism. In another embodiment, the mammalian organism is selected from the group consisting of a non-human primate, an ovine, a bovine, a porcine, a canine, a feline and a murine organism.

In another embodiment, the method of the invention for generating an in vivo model of TTP comprises introducing the anti-ADAMTS13 autoantibody or fragment thereof by formulating the anti-ADAMTS13 autoantibodies or fragments thereof in a composition for administration to the model organism. In yet another embodiment, the introduction of the anti-ADAMTS13 autoantibody or fragment thereof further comprises injecting the anti-ADAMTS13 autoantibodies or fragments thereof into the model organism. In yet another embodiment, the introduction of the anti-ADAMTS13 autoantibody or fragment thereof comprises inducing in vivo expression in the model organism. In a further embodiment, the in vivo expression comprises delivering nucleic acids to the model organism. In yet a further embodiment, the delivery of the nucleic acids is through a method selected from the group consisting of injection through hydrodynamic delivery, electroporation, transfection, transduction and other methods of viral delivery, and any combination thereof.

In one embodiment, the anti-autoimmune reagent of the invention blocks binding of the anti-ADAMTS13 autoantibody or fragment thereof to ADAMTS13. In another embodiment, the anti-autoimmune reagent specifically binds to at least one amino acid sequence selected from the group consisting of SEQ ID NOs: 46-90; 142-192.

In one embodiment, the identification of agents that bind to the anti-ADAMTS13 autoantibody or fragment thereof of the invention comprises identifying agents that block binding of the anti-ADAMTS13 autoantibody or fragment thereof to ADAMTS13. In another embodiment, the binding of the anti-ADAMTS13 autoantibody or fragment thereof to ADAMTS13 is blocked to at least one of the ADAMTS13 regions selected from the group consisting of amino-terminal (MDT1) domain, carboxy-terminal (T5-8/CUB) domain and cysteine-rich/spacer region.

In one embodiment, the ADAMTS13 variant that does not bind an anti-ADAMTS13 autoantibody or fragment thereof comprises a preserved or enhanced proteolytic activity as compared to a native ADAMTS13. In another embodiment, the ADAMTS13 variant is useful for treating thrombotic thrombocytopenic purpura (TTP). In yet another embodiment, the ADAMTS13 variant is resistant to inhibition by an anti-ADAMTS13 autoantibody or fragment thereof comprising at least one amino acid sequence selected from the group consisting of SEQ ID NOs: 46-90; 142-192.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 3A: scFv 1-416 inhibited ADAMTS13 in the absence of rabbit IgG and in the presence of pre-immune rabbit IgG, but not in the presence of post-immune anti-scFv 1-416 rabbit IgG (right-hand set of bars; *, P=0.006; **, P=0.008; N.S., not significant). No scFv or irrelevant human anti-Rh(D) scFv E1M2 had any effect on ADAMTS13 activity under any rabbit IgG conditions (left-hand and middle sets of bars). Residual ADAMTS13 activity with scFv 1-416 and no rabbit IgG or pre-immune IgG (white and gray bars in right-hand set of bars) is higher than in FIG. 1A because the amount of scFv was 2.5-fold lower here to increase the sensitivity of rabbit post-immune IgG blocking. FIG. 3B: In the presence of scFv 1-428, ADAMTS13 activity was inhibited when mixed with no rabbit or pre-immune rabbit IgG, but was "rescued" in presence of post-immune rabbit IgG (4th set of bars) as for scFv 1-416 in FIG. 3A (*, P=0.002; **, P=0.0006). Results were unchanged if performed in the presence of an 8-fold excess of human $V_H$3-33-encoded anti-Rh(D) scFv E1M2 (5th set of bars) or human anti-keratinocyte $V_H$1-69-encoded PX4-3 (6th set of bars). First 3 sets of bars are controls showing show that scFv's E1M2 and PX4-3 had no effect on ADAMTS13 activity themselves. In this experiment, the amount of rabbit IgG was titered down to the point of just being able to block 1-428 in order to increase its sensitivity to any effects of E1M2 or PX4-3. FIG. 3C: Gray bars show reduction of ADAMTS13 activity in normal plasma when mixed with heat-treated (56° C. for 30 min to destroy any residual patient plasma ADAMTS13) TTP4-TTP7 plasmas and pre-immune rabbit IgG. Black bars show various degrees of "rescue" of ADAMTS13 activity if TTP4-TTP7 plasmas were pre-incubated with post-immune rabbit anti-idiotypic IgG raised against one of 4 inhibitory scFv's as indicated. All differences significant (P range, 0.005-0.041) except for those marked "N.S." (P range, 0.059-0.098). ADAMTS13 activities are averages of 2 measurements except for TTP7/1-431 which were measured once (*).

FIG. 4A: Dose response curve showing residual murine ADAMTS13 activity when normal mouse plasma was mixed in vitro with increasing amounts of human ADAMTS13 inhibitory scFv's 1-416, 1-420, 1-428, 1-431 or irrelevant anti-Rh(D) scFv negative control E1M2. FIG. 4B: Time course of murine ADAMTS13 inhibition in vivo following intraperitoneal injection of scFv 1-420 (inset: over 24 hour period).

FIG. 5A: Time course of murine ADAMTS13 inhibition in vivo following hydrodynamic tail vein delivery into 2 pairs of mice with pLIVE plasmid containing scFv 1-420 cDNA (triangles and circles) or negative control human platelet factor 4 scFv X24-3 cDNA (diamonds and squares). FIG. 5B: Western blot of plasma immunoprecipitated in vivo-expressed scFv drawn 7 days post scFv cDNA injection. Lanes 1-3 show negative control scFv X24-3 for 3 mice; lanes 4-6 show scFv 1-420 for 3 mice; lane 7 represents the amount of scFv 1-420 immunoprecipitated from an equivalent volume of mouse plasma spiked with 20 ng purified scFv 1-420 protein. FIG. 5C: ADAMTS13 "inhibitor assay" performed on a 1:1 mix of normal human plasma and heat-inactivated murine plasma (56° C. for 30 min to destroy endogenous mouse ADAMTS13) derived from 2 untransfected mice (left-hand set of bars), 2 mice transfected with control scFv plasmid (middle set of bars), and 5 mice transfected with plasmid containing scFv 1-420 cDNA (right-hand set of bars).

FIG. 6A: Intravital microscopy and time-lapse video illustrating formation of platelet thrombus over a 180-second period post laser injury. Platelets were labeled with Alexa[488]-conjugated F(ab')2 fragments of anti-mouse CD41 in control scFv-transfected animal (normal ADAMTS13 activity, left panel) and scFv 1-420-transfected animal (<10% normal ADAMTS13 activity, right panel). Blood flow in direction of arrows. Bar represents 30 μm in all video frames. FIG. 6B: Length/width aspect ratios for platelet thrombi were averaged for 28 injuries in 5 control mice and 33 injuries in 7 scFv 1-420-transfected mice and plotted +SEM as a function of time. Arterioles of 20-40 μm diameter were selected. To the right of each tracing, VWF multimer analyses of plasma from representative pair of control and ADAMTS13-inhibited mice shows accumulation of UL-VWF in scFv 1-420-transfected mouse.

FIG. 7A: Platelet counts in mice expressing control scFv (upper panel) and 1-420 scFv (lower panel) antibodies following Shigatoxin-2 (Stx-2) injection on Day 0. ADAMTS13 activities prior to Stx-2 injections are listed on the right-hand side of each panel. FIG. 7B: Kaplan-Meier survival curves for mice expressing control scFv and scFv 1-420. P value determined using GraphPad Prism software (La Jolla, Calif.) and the log-rank Mantel-Cox test. FIG. 7C: Peripheral blood smears (panels 1, 2) and organ histology (panels 3 through 8) in representative control scFv (left-hand panel set) and scFv 1-420 (right-hand panel set) expressing mice. Arrows in panel 2 point to schistocytes. Original magnifications, ×100; insets, ×500.

FIG. 8 is a table comparing CDR2 amino acid residues for $V_H$1-69 encoded antibody heavy chains. Antibodies are grouped by identical CDR2 amino acid residues in positions 56-62. Replacement mutations are indicated with letters, identities with ".", and gaps with "--". CDR2 numbering designations per Brochet et al., (Nucl. Acids Res., 2008, 36:W503-W508).

FIGS. 9A-9B are series of tables showing the alignment of anti-ADAMTS13 (FIG. 9A, five panels from the left toward the right) heavy and (FIG. 9B, five panels from the left toward the right) light chains to their most likely germline immunoglobulin genes. Antibodies are grouped by B cell clonotype based on CDR3 region as described in text. Clonotypes are grouped by $V_H$ or $V_L$ genes then by $J_H$ or $J_L$ genes (italicized letters and shaded lines). Replacement mutations are indicated with letters, silent mutations with "*", identities with and gaps with "--". Numbering and framework/CDR regions designations per Brochet et al., Nucl. Acids Res., 2008, 36:W503-W508. Framework and CDR1/CDR2 replacement and silent mutations and their respective replacement-to-silent mutation ratios ("R:S") are indicated to the right of each sequence. In general, mutations in CDR3 regions are difficult to assess due to junctional additions and deletions of nucleotides so mutations were not scored in these regions.

FIGS. 10A-10C are series of graphs demonstrating the identification of anti-ADAMTS13 scFv binding domains. FIG. 10A: Cartoon depicting the ADAMTS13 constructs used for epitope determination (based on Zheng et al., Haemat., 2010, 95:1555-1562). Domain abbreviations as defined in the legend to FIG. 2. FIG. 10B: Representative examples of Western blots of full-length and truncated ADAMTS13 constructs immunoprecipitated by the scFv indicated at the bottom left or bottom right of each panel. Included are examples of scFv specific for the six types of binding specificities shown in FIG. 2: CS domain (1-416, 1-304, 1-420, 1-428), MDT domain (1-437), CUB domain (1-441), T5-8+CUB domain (zl-303), CS/CUB domains (1-404), CS/T5-8+CUB domains (1-410). ScFv E1M2 is anti-red blood cell Rh(D) antigen negative control. FIG. 10C: ADAMTS13 domains bound by human recombinant scFv (Plus signs denote positive reactivity toward the respective ADAMTS13 construct; negative signs, no signal detected; w, weak signal detected. Abbreviations for ADAMTS13 constructs illustrated and defined herein (FIGS. 10A-10B). E1M2 is negative control scFv specific for human red cell Rh(D) antigen).

DETAILED DESCRIPTION

Definitions

Figures 1A, 1B:
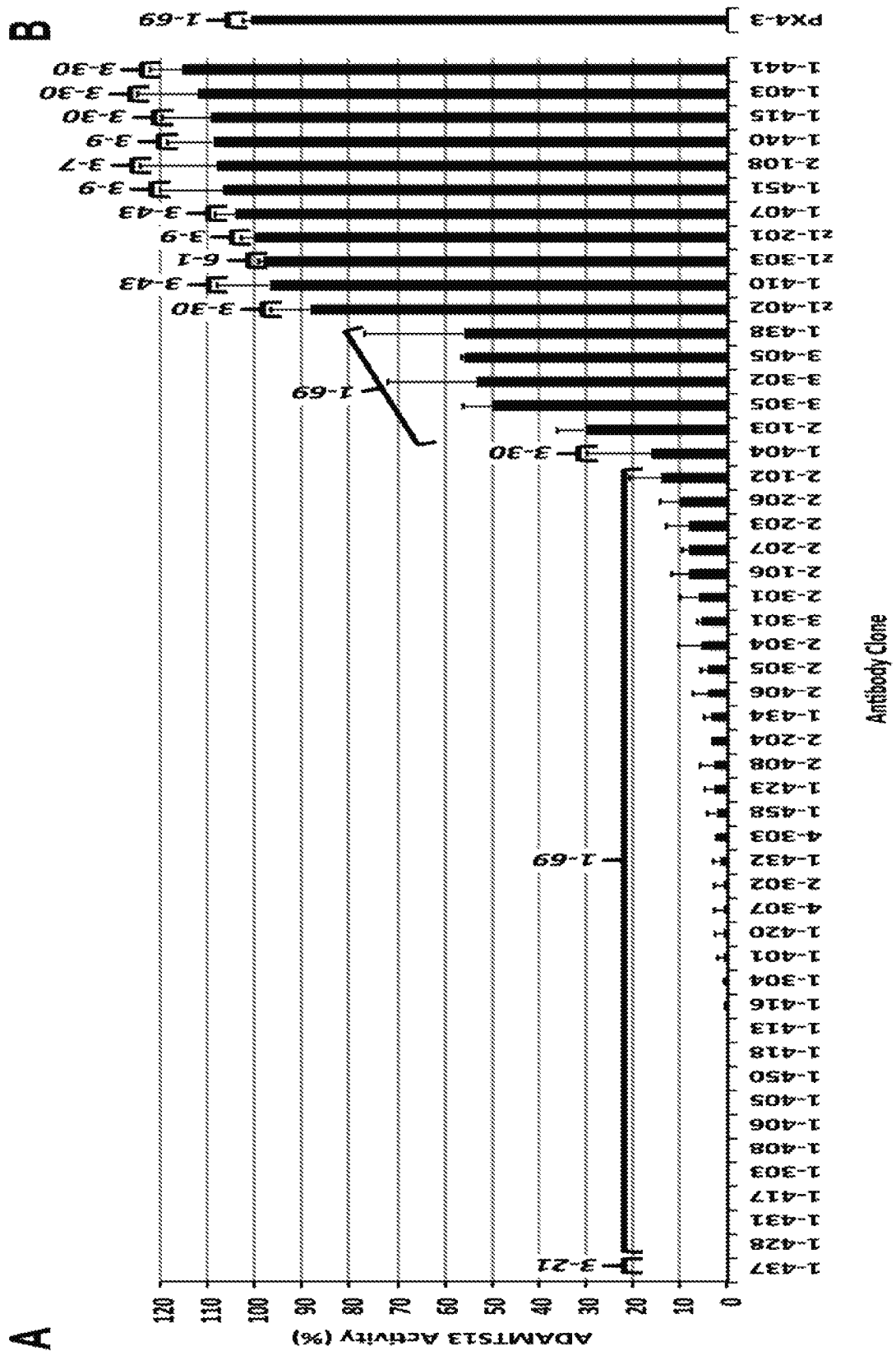
FIGS. 1A-1B are series of histograms demonstrating the inhibitory activity of human anti-ADAMTS13 monoclonal antibodies. ADAMTS13 activities of normal human plasma were measured using FRETS-VWF73 in the presence of (FIG. 1A) recombinant anti-ADAMTS13 scFv clones or PBS control (defined as 100% activity) or (FIG. 1B)>5-fold more of an irrelevant keratinocyte-binding human $V_H$1-69-encoded scFv PX4-3. Values for each scFv are the averages of 3 independent measurements (+/−SD). For reference, germline $V_H$ genes from Table 2 are indicated above each bar.

Unless defined otherwise, all technical and scientific terms used herein have the same meaning as commonly understood by one of ordinary skill in the art to whom the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "ADAMTS13" refers to a disintegrin and/or metalloproteinase with a thrombospondin type 1 motif, member 13, also known as von Willebrand Factor-cleaving protease (VWFCP). ADAMTS13 is a zinc-containing metalloprotease enzyme that cleaves von Willebrand factor (vWF). It is generally secreted into the blood and degrades vWF into smaller subunits to decrease its activity. ADAMTS13 shares many properties with the other family members in the ADAMTS family, all of which are characterized by a protease domain, an adjacent disintegrin domain, and one or more thrombospondin domains. ADAMTS13 has 8 thrombospondin domains and lacks a hydrophobic transmembrane domain, thus it is not anchored in the cell membrane.

As used herein, to "alleviate" a disease, disorder or condition means reducing the severity of one or more symptoms of the disease, disorder or condition.

The term "antibody," as used herein, refers to an immunoglobulin molecule that specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, single-domain antibodies, such as camelid antibodies (Riechmann, 1999, Journal of Immunological Methods 231:25-38), composed of either a VL or a VH domain that exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody that is generated using recombinant DNA technology, such as, for example, an antibody expressed by a bacteriophage as described herein. The term should also be construed to mean an antibody that has been generated by the synthesis of a DNA molecule encoding the antibody and the DNA molecule expresses an antibody protein, or an amino acid sequence specifying the antibody, wherein the DNA or amino acid sequence has been obtained using synthetic DNA or amino acid sequence technology that is available and well known in the art.

As used herein, an "autoantibody" or an "autoimmune antibody" is an antibody produced by the immune system that is directed against one or more of the host's own proteins. Autoantibodies may be produced by a host's immune system when it fails to distinguish between "self" and "non-self" proteins. Usually the immune system is able to discriminate by recognizing foreign substances ("non-self") and ignoring the host's own cells ("self"). When the immune system ceases to recognize one or more of the host's normal constituents as "self," it may produce to autoantibodies that attack its own cells, tissues, and/or organs.

As used herein, an "anti-autoimmune reagent" refers to an agent that is capable of binding to an autoimmune antibody and/or inhibiting function of an autoimmune antibody, such as disrupting the interaction of the autoantibody with its antigen. Examples of anti-autoimmune reagents include but are not limited to an antibody against an anti-ADAMTS13 antibody, idiotypic antibody, peptide, polypeptide, small molecule or other agent that binds to the anti-ADAMTS13 antibody and/or prevents binding between the anti-ADAMTS13 antibody and ADAMTS13. The anti-autoimmune reagent can be any agent that binds to an anti-ADAMTS13 antibody or inhibits its function. In some instances, the anti-autoimmune reagent is an agent that disrupts binding between the anti-ADAMTS13 antibody and ADAMTS13. In another aspect, the anti-autoimmune reagent is an idiotypic antibody, peptide, polypeptide, small molecule or other agent that can bind to an anti-ADAMTS13 antibody.

By the term "Fab/phage" as used herein, is meant a phage particle that expresses the Fab portion of an antibody.

By the term "scFv/phage" as used herein, is meant a phage particle that expresses the Fv portion of an antibody as a single chain.

"Phage," or "phage particle," as these terms are used herein, include bacteriophage that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3X, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make "phage-like" particles. That is, these particles resemble phage on the outside, but on the inside they contain plasmid (also referred to as a "phagemid") DNA. In other words, the phagemid DNA need not encode any M13 phage proteins, except a piece of M13 gene III fused to the DNA for antibody or peptide. Thus, it should be understood that the terms "phage," "phage particle," "phage-like particle" and "phagemid" are used interchangeably herein.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Non-self" antigens are those antigens on substances entering or present in the body that are detectably different or foreign from the animal's own constituents, whereas "self" antigens are those that, in the healthy animal, are not detectably different or foreign from its own constituents. However, under certain conditions, including in certain disease states, an individual's immune system will identify its own constituents as "non-self" and initiate an immune response against "self" material, at times causing more damage or discomfort as from an invading microbe or foreign material, and often producing serious illness in an individual.

As used herein, the term "autologous" is meant to refer to any material derived from the same individual to whom it is later to be re-introduced into the individual.

"Derivative" in the context of proteins and peptides includes any purposefully generated amino acid sequence that in its entirety, or in part, comprises a substantially similar amino acid sequence to a desired protein. The term derivative can also be applied to the antibodies described herein such that "derivative" includes any purposefully generated peptide, which in its entirety, or in part, comprises a substantially similar amino acid sequence to an anti-ADAMTS13 antibody or an anti-idiotypic antibody that is capable of specifically binding to an anti-ADAMTS13 antibody. Derivatives of the antibodies may be characterized by single or multiple amino acid substitutions, deletions, additions, or replacements. Derivatives may include: (a) derivatives that one or more amino acid residues are substituted with conservative or non-conservative amino acids; (b) derivatives that one or more amino acids are added; (c) derivatives that one or more of the amino acids of the amino acid sequence includes a substituent group; (d) derivatives that amino acid sequences or a portion thereof is fused to another peptide (e.g., serum albumin or protein transduction domain); (e) derivatives that one or more nonstandard amino acid residues (e.g., those other than the 20 standard L-amino acids found in naturally occurring proteins) are incorporated or substituted into the amino acid sequences; (1) derivatives that one or more non-amino acid linking groups are incorporated into or replace a portion of the amino acids; and (g) derivatives that one or more amino acid is modified by glycosylation, acetylation, myristoylation, and the like.

The terms "disease," "disorder," and "condition" refer to thrombotic thrombocytopenic purpura (TTP) is an example of an autoimmune disorder that the majority of patients have reduced activity levels of the VWF-cleaving protease ADAMTS13 due to the development of autoantibodies that inhibit its function. Decreased ADAMTS13 activity results in the accumulation of ultralarge VWF (UL-VWF) multimers that foster systemic platelet aggregation in the microcirculation when coincident with additional factors, such as endothelial injury, and can lead to severe thrombocytopenia, microangiopathic hemolytic anemia, varying degrees of organ dysfunction, and death.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence that is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence that differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

As applied to a protein sequence, "homology" as used herein refers to a protein sequence that has about 50% sequence similarity. More preferably, the sequence has about 75% sequence similarity, even more preferably, has at least about 80%, 85%, 90%, 91%, 92%, 93%, 94%, 95%, 96%, 97%, 98%, 99% sequence similarity.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in that residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues that are found neither in the recipient antibody nor in the imported CDR or framework sequences. These modifications are made to further refine and optimize antibody performance. In general, the humanized antibody will comprise substantially all of at least one, and typically two, variable domains, that all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

The term "hydrodynamic delivery" refers to the delivery of nucleic acids while controlling the hydrodynamic pressure in capillaries to enhance endothelial and parenchymal cell permeability to the nucleic acids. Hydrodynamic delivery uses a hydrodynamic force generated by a pressurized injection of a large volume of a nucleic acid solution into the blood vessel so as to permeabilize the capillary endothelium and generate pores in the plasma membrane of the surrounding parenchyma cells so that the nucleic acids or other macromolecules of interest may reach the cell interior. See also Zhang, et al., Gene Ther., 2000, 7:1344-1349 and Miao, et al., Mol. Ther., 2001, 3:947-957.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent that two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical. As applied to nucleic acid sequences, "identity" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Immunization" is the process of administering an immunogenic composition and stimulating an immune response to an antigen in a host (i.e., rodents and rabbits). Preferred hosts are mammals, such as primates (e.g., humans) as well as veterinary animals and agricultural animals.

An "immunogen" is an immunogenic composition used to immunized the host. "Immunogen" also refers to a substance that is able to stimulate or induce a humoral antibody and/or cell-mediated immune response in a mammal. In some instances, the immunogen comprises an anti-ADAMTS13 pathogenic antibody or any fragment thereof.

An "immune response" refers to the activities of the immune system, including activation and proliferation of specific cytotoxic T-cells and B-cells resulting in antigen-specific antibody production, after contact with an antigen.

As used herein, an "instructional material" includes a publication, a recording, a diagram, or any other medium of expression that can be used to communicate the usefulness of the compositions and methods of the invention. The instructional material of the kit of the invention may, for example, be affixed to a container that contains the nucleic acid, peptide, and/or composition of the invention or be shipped together with a container that contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment that has been separated from sequences that flank it in a naturally occurring state, e.g., a DNA fragment that has been removed from the sequences that are normally adjacent to the fragment, e.g., the sequences adjacent to the fragment in a is genome that it naturally occurs. The term also applies to nucleic acids that have been substantially purified from other components that naturally accompany the nucleic acid, e.g., RNA or DNA or proteins, that naturally accompany it in the cell. The term therefore includes, for example, a recombinant DNA that is incorporated into a vector, into an autonomously replicating plasmid or virus, or into the genomic DNA of a prokaryote or eukaryote, or that exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

The term "model organism" refers to a non-human species that is easy to maintain and breed in a laboratory setting and has particular experimental advantages. Model organisms as used herein provide an in vivo model to research the effects of a human disease and/or biological activities associated with a disease, such as thrombotic thrombocytopenic purpura (TTP).

As used herein, the term "modulate" is meant to refer to any change in biological state, i.e. increasing, decreasing, and the like. For example, the term "modulate" refers to the ability to regulate positively or negatively the expression or activity of, for example, an anti-ADAMTS13 pathogenic antibody, including but not limited to transcription of the desired anti-ADAMTS13 pathogenic antibody mRNA, stability of the desired anti-ADAMTS13 pathogenic antibody mRNA, translation of the desired anti-ADAMTS13 pathogenic antibody mRNA, stability of the desired anti-ADAMTS13 pathogenic antibody polypeptide, post-translational modifications of the desired anti-ADAMTS13 pathogenic antibody, or any combinations thereof. Further, the term modulate can be used to refer to an increase, decrease, masking, altering, overriding or restoring of activity of an anti-ADAMTS13 pathogenic antibody.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) that "U" replaces "T."

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, that there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "recombinant polypeptide" is one that is produced upon expression of a recombinant nucleic acid.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence that is required for expression of a gene product operably linked to the promoter/regulatory sequence. In some instances, this sequence may be the core promoter sequence and in other instances, this sequence may also include an enhancer sequence and other regulatory elements that are required for expression of the gene product. The promoter/regulatory sequence may, for example, be one that expresses the gene product in a tissue specific manner.

A "constitutive" promoter is a nucleotide sequence that, when operably linked with a polynucleotide that encodes or specifies a gene product, causes the gene product to be produced in a cell under most or all physiological conditions of the cell.

An "inducible" promoter is a nucleotide sequence that, when operably linked with a polynucleotide that encodes or specifies a gene product, causes the gene product to be produced in a cell substantially only when an inducer that corresponds to the promoter is present in the cell.

A "tissue-specific" promoter is a nucleotide sequence that, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GFRα4.

"Single chain antibodies" refer to antibodies formed by recombinant DNA techniques that immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883: Ward et al. (1989) Nature 334: 54454; Skerra et al. (1988) Science 242:1038-1041.

By the term "specifically binds," as used herein, is meant a compound, e.g., a protein, a nucleic acid, an antibody, and the like, which recognizes and binds a specific molecule, but does not substantially recognize or bind other molecules in a sample.

The term "subject" is intended to include living organisms that an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

By "transgenic" is meant any animal that includes a nucleic acid sequence that is inserted by artifice into a cell and becomes a part of the genome of the animal that develops from that cell. Such a transgene may be partly or entirely heterologous to the transgenic animal. Although transgenic mice represent another embodiment of the invention, other transgenic mammals including, without limitation, transgenic rodents (for example, hamsters, guinea pigs, rabbits, and rats), and transgenic pigs, cattle, sheep, and goats are included in the definition.

As used herein, a "substantially purified" cell is a cell that is essentially free of other cell types. A substantially purified cell also refers to a cell that has been separated from other cell types that it is normally associated in its naturally occurring state. In some instances, a population of substantially purified cells refers to a homogenous population of cells. In other instances, this term refers simply to cell that have been separated from the cells that they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

As used herein, a "therapeutic agent" is a molecule or atom, which is conjugated to an anti-autoimmune reagent to produce a conjugate that is useful for therapy. Examples of therapeutic agents include drugs, toxins, enzymes, hormones, cytokines, immunomodulators, anti-tumor agents, chemotherapeutic agents, anti-cell proliferation agents, boron compounds, and therapeutic radioisotopes.

The term "transfected" or "transformed" or "transduced" as used herein refers to a process that exogenous nucleic acid is transferred or introduced into the host cell. A "transfected" or "transformed" or "transduced" cell is one that has been transfected, transformed or transduced with exogenous nucleic acid. The cell includes the primary subject cell and its progeny.

As used herein, to "treat" means reducing the frequency that symptoms of a disease, disorder, or adverse condition, and the like, are experienced by a patient. Such non-limiting conditions include bona fide illness as well as cosmetic or other conditions.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter that comprises an isolated nucleic acid and that can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds that facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Detailed Description
Anti-ADAMTS13 Autoantibodies

The present invention relates to compositions and methods of use of anti-ADAMTS13 autoantibodies and fragments thereof. The invention described herein includes autoantibodies or fragments thereof and methods that utilize such autoantibodies and fragments thereof. A better understanding of the repertoire of autoantibody expression within an individual patient and across multiple patients on a molecular level may be achieved by examining autoantibody clonality, epitope specificity, idiotypic relatedness, and functional significance in vivo. This knowledge is important for designing innovative therapies that specifically target pathogenic autoantibodies or the B cells that produce them, and providing animal models to test such approaches.

In one aspect, the invention includes a composition comprising at least one isolated anti-ADAMTS13 autoantibody or fragment. The anti-ADAMTS13 autoantibody or fragment is further identified as comprising a heavy chain selected from the group consisting of SEQ ID NOs: 46-90 or comprising a light chain selected from the group consisting of SEQ ID NOs: 142-192. In one embodiment, the anti-ADAMTS13 autoantibody or fragment comprises a single chain variable fragment (scFv). In another embodiment, the anti-ADAMTS13 autoantibody or fragment thereof binds at least one of the ADAMTS13 region selected from the group consisting of amino-terminal (MDT1) domain, carboxy-terminal (T5-8/CUB) domain and cysteine-rich/spacer region. In yet another embodiment, the anti-ADAMTS13 autoantibody or fragment thereof is capable of decreasing ADAMTS13 activity, such as proteolytic activity, disulfide reducing activity (Yeh, et al., J. Thromb. Haemost., 2010, 8:2778-2788), interaction or attachment to an endothelial cell surface, other functions of ADAMTS13, and any combination thereof.

In another embodiment, the anti-ADAMTS13 autoantibody or fragment thereof has a homology of at least 80% to at least one heavy chain selected from the group consisting of SEQ ID NOs: 46-90. In yet another embodiment, the anti-ADAMTS13 autoantibody or fragment thereof has a homology of at least 80% to at least one light chain selected from the group consisting of SEQ ID NOs: 142-192. The isolated anti-ADAMTS13 autoantibody or fragment thereof may share at least 80%, 85%, 86%, 87%, 88%, 89%, 90%, 91%, 92%, 93%, 94%, 95%, 96%, 97%, 98%, 99%, or more homology with at least one antibody selected from the group consisting of SEQ ID NOs: 52-102.

In another aspect, the invention includes a composition comprising at least one isolated nucleic acid sequence encoding an anti-ADAMTS13 autoantibody or fragment thereof. The isolated nucleic acid sequence comprises a heavy chain nucleic acid sequence selected from the group consisting of SEQ ID NOs: 1-45 and a light chain nucleic acid sequence selected from the group consisting of SEQ ID NOs: 91-141. In one embodiment, the isolated nucleic acid sequence encodes a single chain variable fragment (scFv).

In another embodiment, the isolated nucleic acid sequence has an identity of at least 80% to at least one heavy chain nucleic acid sequence selected from the group consisting of SEQ ID NOs: 1-45. In yet another embodiment, the isolated nucleic acid sequence has an identity of at least 80% to at least one light chain nucleic acid sequence selected from the group consisting of SEQ ID NOs: 91-141. The isolated nucleic acid sequence may share at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more identity with either a heavy chain or a light chain nucleic acid sequence selected from the group consisting of SEQ ID NOs: 1-45 or 91-141, respectively.

Much of what is known about ADAMTS13-specific autoantibodies has been obtained from the analysis of polyclonal mixtures of immunoglobulin derived from TTP patients. Such studies have shown that anti-ADAMTS13 autoantibodies are predominantly of the IgG isotype subclass IgG1 and IgG4 many that recognize epitopes in the spacer domain of the protease. Binding of autoantibodies to the spacer domain of ADAMTS13 is thought to inhibit cleavage of VWF by blocking amino acid motifs involved in complex formation of ADAMTS13 with the unfolded VWF A2 domain. However, nearly all patient plasmas have circulating autoantibodies that recognize at least one additional domain of ADAMTS13 other than the spacer domain. The potential functional significance of autoantibodies directed to non-spacer domains has been largely unexplored due to the inherent difficulty in studying complex autoantibody repertoires using heterogeneous mixtures of IgG contained in patient plasma.

A limited number of inhibitory anti-ADAMTS13 monoclonal autoantibodies directed to the spacer domain of ADAMTS13 have been cloned from the peripheral blood lymphocytes or spleen of four TTP patients. It is not clear whether human anti-ADAMTS13 autoantibodies specific for other domains also inhibit ADAMTS13 proteolytic activity or interfere with other functions of the protease. A few of these human spacer domain-specific inhibitory antibodies cloned from different patients were found to be encoded by the human germline heavy chain variable region gene $V_H1$-69 suggesting a potential property of ADAMTS13 inhibitory antibodies one might exploit as a therapeutic target. However, the structural features conferred by this single immunoglobulin gene that confer ADAMTS13 inhibition are not clear nor is the extent that $V_H1$-69-encoded antibodies are representative of circulating autoantibodies expressed in TTP patient plasma. Furthermore, the clinical relevance of the in vivo properties of these cloned human autoantibodies in an animal model has not been tested. Indeed, to date, there are no published reports describing animal models of human autoantibody-mediated TTP. Models have been developed that ADAMTS13 deficiency in mice is mediated by xenoantibodies to ADAMTS13, e.g. by rabbit polyclonal anti-human ADAMTS13 antibodies, or by mouse monoclonal antibodies to the ADAMTS13 metalloprotease domain in baboons. These antibodies and models may not be suitable to test agents that block the idiotopes of human anti-ADAMTS13 autoantibodies or to test novel engineered preparations of ADAMTS13 that have been designed to be uninhibitable by human antibodies directed to human autoepitopes.

In one embodiment, the invention includes anti-autoimmune antibodies or reagents directed against anti-ADAMTS13 antibodies. The anti-autoimmune antibodies of the invention can be monoclonal antibodies (mAb) in some aspects, or polyclonal antibodies in other aspects. The anti-autoimmune antibodies of the invention that are useful for the compositions, methods and kits of the invention can be from any source, and in addition may be chimeric. In one embodiment, sources of anti-autoimmune antibodies can be from a mouse, or a rat, a plant, or a human in other embodiments. Anti-autoimmune antibodies of the invention that are useful for the compositions, and methods of the invention have reduced antigenicity in humans (to reduce or eliminate the risk of formation of anti-human antibodies), and in another embodiment, are not antigenic in humans. Chimeric anti-autoimmune antibodies for use the invention contain in one embodiment, human amino acid sequences and include humanized antibodies that are non-human antibodies substituted with sequences of human origin to reduce or eliminate immunogenicity, but retains the antigen binding characteristics of the non-human antibody. In one embodiment, the anti-autoimmune antibodies of the invention directed against anti-ADAMTS13 antibodies are used therapeutically to treat TTP. In some embodiments, TTP is prevented or reduced.

In another aspect, the invention includes a method of identifying an ADAMTS13 variant that does not bind an anti-ADAMTS13 autoantibody or fragment thereof. The method comprises contacting an ADAMTS13 protein with an anti-ADAMTS13 autoantibody or fragment thereof, wherein when the ADAMTS13 protein does not bind the anti-ADAMTS13 autoantibody or fragment thereof, then the ADAMTS13 protein is a variant that does not bind an anti-ADAMTS13 autoantibody or fragment thereof.

In yet another aspect, the invention includes a method for treating thrombotic thrombocytopenic purpura (TTP) in a subject in need thereof, the method comprising administering to the subject a composition comprising an effective amount of an ADAMTS13 variant, wherein the ADAMTS13 variant is resistant to inhibition by an anti-ADAMTS13 autoantibody or fragment thereof.

In one embodiment, the ADAMTS13 variant is resistant to inhibition by an anti-ADAMTS13 autoantibody or fragment thereof comprising at least one amino acid sequence selected from the group consisting of SEQ ID NOs: 46-90; 142-192. In another embodiment, the ADAMTS13 variant that does not bind an anti-ADAMTS13 autoantibody or fragment thereof comprises a preserved or enhanced proteolytic activity as compared to a native ADAMTS13. In yet another embodiment, the ADAMTS13 variant is useful for treating thrombotic thrombocytopenic purpura (TTP).

Peptidomimetic compounds can also be made where individual amino acids are replaced by analogous structures, for example gem-diaminoalkyl groups or alkylmalonyl groups, with or without modified termini or alkyl, acyl or amine substitutions to modify their charge. The use of such alternative structures can provide significantly longer half-life in the body, since they are more resistant to breakdown under physiological conditions.

Methods for combinatorial synthesis of peptide analogs and for screening of peptides and peptide analogs are well known in the art (see, for example, Gallop et al., 1994 J. Med. Chem. 37: 1233). It is particularly contemplated that the compounds of the invention are useful as templates for design and synthesis of compounds of improved activity, stability and bioavailability. Preferably where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted parent amino acid.

The antibodies of the present invention include those cloned from a phage antibody library, as described in detail elsewhere herein. For example, a cDNA library is generated from mRNA obtained from a population of antibody-producing cells. The mRNA encodes rearranged immunoglobulin genes and thus, the cDNA encodes the same. Amplified cDNA is cloned into expression vectors creating a library of phage that express human Fab or scFv fragments on their surface. Phage that display the antibody of interest are selected by antigen binding and are propagated in bacteria to produce soluble human Fab or scFv immunoglobulin. Thus, in contrast to conventional monoclonal antibody synthesis, this procedure immortalizes DNA encoding human immunoglobulin rather than cells that express human immunoglobulin.

Using the information provided herein, the antibodies of the present invention can be produced recombinantly using standard techniques well known to those of skill in the art. For example, the sequences provided herein can be used to express one or more antibodies. The nucleic acid sequence may be optimized to reflect particular codon "preferences" for various expression systems according to standard methods well known to those of skill in the art.

Using the sequence information provided herein, the nucleic acids may be synthesized according to a number of standard methods known to those of skill in the art. Oligonucleotide synthesis, is preferably carried out on commercially available solid phase oligonucleotide synthesis machines or manually synthesized using the solid phase phosphoramidite triester method described by Beaucage et. al., 1981, Tetrahedron Letts. 22:1859-1862.

Once a nucleic acid encoding an antibody is synthesized, it may be amplified and/or cloned according to standard methods in order to produce recombinant antibodies of the invention. Molecular cloning techniques to achieve these ends are known in the art. A wide variety of cloning and in vitro amplification methods suitable for the construction of recombinant nucleic acids are known to those skilled in the art. Examples of these techniques and instructions sufficient to direct the skilled artisan are found in Berger and Kimmel, Guide to Molecular Cloning Techniques, Methods in Enzymology volume 152 Academic Press, Inc., San Diego, Calif. (Berger); Sambrook et al., 2002 Molecular Cloning. A Laboratory Manual Vol. 1-3, Cold Spring Harbor Laboratory, Cold Spring Harbor Press, NY, (Sambrook). Methods of producing recombinant immunoglobulins are also known in the art. See, Cabilly, U.S. Pat. No. 4,816,567; and Queen et al., 1989 Proc. Nat'l Acad. Sci. USA.

Examples of techniques sufficient to direct persons of skill through in vitro amplification methods, including the polymerase chain reaction (PCR), the ligase chain reaction (LCR), and other DNA or RNA polymerase-mediated techniques are found in Berger, Sambrook, and Ausubel, as well as U.S. Pat. Nos. 4,683,202 and 5,426,039.

Once the nucleic acid encoding a desired antibody is isolated and cloned, a skilled artisan may express the recombinant gene(s) in a variety of engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of the desired antibodies.

For some uses of the anti-autoimmune antibodies or reagents directed against anti-ADAMTS13 antibodies, including in vivo in humans and in vitro detection assays, it may be preferable to use chimeric, hybrid, primatized, humanized, or human antibodies. Methods for producing chimeric and hybrid antibodies are known in the art. See e.g., Morrison, 1985 Science 229: 1202-1207; U.S. Pat. Nos. 6,965,024, 5,807,715; 4,816,567; and 4,816,397. Humanized antibodies are antibody molecules from non-human species that bind the desired antigen having one or more complementarity determining regions (CDRs) from the non-human species and framework regions and constant domains from a human immunoglobulin molecule. Often, framework residues in the human framework regions are substituted with the corresponding residue from the CDR donor antibody to alter and in some instances improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089. Antibodies can be humanized using a variety of techniques known in the art including, for example, CDR-grafting and chain shuffling. Humanized antibodies may be generated using any of the methods disclosed in U.S. Pat. Nos. 5,693,762, 5,693,761, 5,585,089, 6,180,370.

Models of Thrombotic Thrombocytopenic Purpura (TTP)

The present invention also includes the generation of an in vivo model of thrombotic thrombocytopenic purpura (TTP). In one aspect, the invention includes a method for generating an in vivo model of thrombotic thrombocytopenic purpura (TTP) comprising introducing at least one anti-ADAMTS13 autoantibody or fragment thereof into a model organism. The model organism may include a non-mammalian organism or a non-human mammalian organism, such as a non-human primate, an ovine, a bovine, a porcine, a canine, a feline and a murine organism.

For in vivo models of TTP of the present invention, the generation of anti-ADAMTS13 autoantibodies or fragments thereof may be expressed or introduced into a model organism, preferably a model organism that does not spontaneously develop autoimmune diseases. In one embodiment, introducing the anti-ADAMTS13 autoantibody or fragment thereof comprises formulating the anti-ADAMTS13 autoantibodies or fragments thereof in a composition for administration to the model organism. Such an embodiment may further comprise injecting the anti-ADAMTS13 autoantibodies or fragments thereof into the model organism. In another embodiment, introducing the anti-ADAMTS13 autoantibody or fragment thereof comprises inducing in vivo expression. One example of inducing in vivo expression is through injection of nucleic acids, such as hydrodynamic delivery, to the model organism. Other examples of methods of inducing in vivo expression may include electroporation, transfection, transduction and other methods of viral delivery, and any combination thereof. Introducing the anti-ADAMTS13 autoantibodies or fragments thereof may be exemplified by methods known in the art and is not limited to the methods described herein.

In vivo models generated by the methods described herein may be useful for further characterizing TTP, identifying anti-autoimmune reagents or therapeutic agents, characterizing an anti-autoimmune reagent or therapeutic agent, or any other purpose described herein or known in the art.

Screening for Anti-Autoimmune Reagents

The present invention is partly based on the identification of an anti-autoimmune reagent or therapeutic agent, such as peptides or small molecules, that bind a desired autoantibody or fragment thereof. In some instances, the autoantibody or fragment thereof is a disease associated-pathogenic antibody, for example a pathogenic anti-ADAMTS13 autoantibody. Accordingly, a peptide that binds to a disease associated-pathogenic antibody is an example of an anti-autoimmune reagent. However, the invention also includes anti-autoimmune reagents that bind to non-pathogenic antibodies. In one aspect, the invention includes a method for identifying an anti-autoimmune reagent for treating thrombotic thrombocytopenic purpura (TTP) comprising contacting a panel of agents with at least one anti-ADAMTS13 autoantibody or fragment thereof and identifying the agents that bind to the anti-ADAMTS13 autoantibody or fragment thereof. In one embodiment, identifying the agents comprises identifying agents that blocks binding of the anti-ADAMTS13 autoantibody or fragment thereof to ADAMTS13.

There are several examples of methods that use peptides or nucleotides to develop libraries of potential receptor, enzyme, or antibody interacting peptides. These libraries have been incorporated into systems that allow the expression of random peptides on the surface of different phage or bacteria. The use of phage display technology to produce and screen libraries of polypeptides for binding to a selected target has been widely used. A basic concept of phage display methods is the establishment of a physical association between DNA encoding a polypeptide to be screened and the target polypeptide. This physical association is provided by the phage particle, which displays a polypeptide as part of a capsid enclosing the phage genome that encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

A phage display library may be screened to identify peptides that bind to an anti-ADAMTS13 antibody (e.g., a pathogenic anti-ADAMTS13 antibody). Accordingly, the invention includes peptides that specifically bind pathogenic anti-ADAMTS13 antibodies. However, the invention should not be limited to only these peptides. Rather, the invention encompasses using any disease-associated pathogenic antibody to screen libraries of peptides or small molecules to identify therapeutic reagents. However, the invention also contemplates peptides and small molecules that bind to non-pathogenic antibodies. This is because a non-pathogenic can be used in the phage display library screening procedure to identify the corresponding binding molecule, and in some cases non-pathogenic antibodies when used in combination or under certain conditions may prove to cause pathology.

Anti-Autoimmune Reagent

The invention provides a composition comprising an anti-autoimmune reagent. The anti-autoimmune reagent includes any agent that is capable of binding to an autoimmune antibody. In one aspect, an anti-autoimmune reagent specifically binds to an anti-ADAMTS13 antibody. In such an aspect, the anti-autoimmune reagent blocks binding of the anti-ADAMTS13 autoantibody or fragment thereof to ADAMTS13. In one embodiment, the anti-autoimmune reagent is an antibody that binds to an autoantibody or fragment thereof. In another embodiment, the anti-autoimmune reagent is a peptide or small molecule that binds to an autoantibody or fragment thereof. For example, the anti-autoimmune reagent binds to a pathogenic autoantibody or the anti-ADAMTS13 autoantibody or fragment thereof. In one embodiment, the anti-autoimmune reagent blocks the binding of the anti-ADAMTS13 autoantibody or fragment thereof to at least one of the ADAMTS13 regions selected from the group consisting of amino-terminal (MDT1) domain, carboxy-terminal (T5-8/CUB) domain and cysteine-rich/spacer region. In another embodiment, the anti-autoimmune reagent for treating TTP specifically binds to at least one amino acid sequence selected from the group consisting of SEQ ID NOs: 46-90; 142-192.

Also described herein are compositions and methods for treatment of diseases or conditions, such as thrombotic thrombocytopenic purpura (TTP). In one aspect, the invention includes a method of inhibiting the binding of an anti-ADAMTS13 autoantibody or fragment thereof to ADAMTS13 comprising contacting the anti-ADAMTS13 autoantibody or fragment thereof with a composition comprising an anti-autoimmune reagent that specifically binds to the anti-ADAMTS13 autoantibody or fragment thereof. The composition may include a pharmaceutical composition and further include a pharmaceutically acceptable carrier. A therapeutically effective amount of the pharmaceutical composition comprising the anti-autoimmune reagent directed against the anti-ADAMTS13 autoantibody or fragment thereof may be administered.

In one aspect, the invention includes identifying an anti-autoimmune reagent for treating thrombotic thrombocytopenic purpura (TTP) comprising contacting a panel of agents with at least one anti-ADAMTS13 autoantibody or fragment thereof and identifying the agents that bind to the anti-ADAMTS13 autoantibody or fragment thereof. In this embodiment, identifying the agents comprises identifying agents that blocks binding of the anti-ADAMTS13 autoantibody or fragment thereof to ADAMTS13. In another aspect, the invention includes a method of inhibiting the binding of an anti-ADAMTS13 autoantibody or fragment thereof to ADAMTS13 comprising contacting the anti-ADAMTS13 autoantibody or fragment thereof with a composition comprising an anti-autoimmune reagent that specifically binds to the anti-ADAMTS13 autoantibody or fragment thereof.

The compositions comprising a therapeutic agent described herein can be administered to an animal, preferably a mammal, even more preferably a human, to suppress an immune reaction, such as those common to autoimmune diseases such as TTP.

Compositions of the invention can be administered in dosages and routes and at times to be determined in appropriate pre-clinical and clinical experimentation and trials. The compositions of the invention may be administered multiple times at dosages within these ranges. Administration of these compositions may be combined with other methods useful to treat the desired disease or condition as determined by those of skill in the art.

The administration of the compositions of the invention may be carried out in any convenient manner known to those of skill in the art. The compositions of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally. In other instances, the cells of the invention are injected directly into a site of inflammation in the subject, a local disease site in the subject, a lymph node, an organ, a tumor, and the like.

Pharmaceutical Compositions

Pharmaceutical compositions of the present invention may comprise a therapeutic agent as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount". "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the therapeutic agents described herein may be administered at a dosage of $10^4$ to $10^9$ cells/kg body weight, preferably $10^5$ to $10^6$ cells/kg body weight, including all integer values within those ranges. Therapeutic compositions may also be administered multiple times at these dosages. The therapeutic agents can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments of the present invention, the methods described herein, or other methods known in the art where therapeutic agents are directed to autoantibodies and administered to a patient alone or in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the therapeutic agents of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the therapeutic agents of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations that become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Isolation of Human Anti-ADAMTS13 Monoclonal Autoantibodies

Antibody phage display libraries expressing $IgG_{1-4}$ κ/λ-derived single chain variable region fragments (scFv) were created from the splenic B-cells or peripheral blood B cells of 4 unrelated patients with autoantibody-mediated TTP ("TTP1⇆-"TTP4") (Table 1) using methods previously described (Siegel, Cold Spring Harbor, N.Y.: Cold Spring Harbor Press, 2001:23.1-0.32; Roark et al., Blood 2002; 100:1388-98; Payne et al., J Clin Invest 2005; 115:888-99). Briefly, cDNAs encoding the rearranged immunoglobulin heavy chain and light chain variable regions were amplified by PCR and cloned into the pComb3X phagemid vector (Scripps Research Institute, La Jolla, Calif.). After electroporation into XL1-Blue *E. coli* (Stratagene, La Jolla) and co-infection with VCSM13 helper phage (Stratagene), DNA encoding each scFv sequence was packaged into a filamentous phage particle expressing the encoded protein on its surface.

Relevant demographic and clinical data are shown in Table 1. Peripheral blood (in 0.38% citrate) for serological and ADAMTS13 activity assays and for isolation of mononuclear cells for library construction (in 16 U/ml sodium heparin) were collected from TTP2, TTP3, and TTP4 prior to their first plasma exchange. Citrated blood was centrifuged at 1500 g for 15 min at 25° C. and plasma was collected and stored at −80° C. Mononuclear cells were isolated by density sedimentation with Ficoll-Paque (GE Healthcare Life Sciences, Pittsburgh. Pa.) following manufacturer's instructions and stored at −80° C. The TTP1 antibody library was generated from 15 g of splenic tissue following splenectomy after a 42-week relapsing/remitting course.

Antibody libraries were selected against full-length human recombinant ADAMTS13 coated in wells of enzyme immunoassay plates (Technoclone GmbH, Vienna, Austria) using previously-described methods for solid phase selection (Payne, et al., J. Clin. Invest., 2005, 115:888-899). For TTP1, the library was also selected against the TSP1 5-8/CUB fragment of ADAMTS13 prepared as described (Ai, et al., J. Biol. Chem., 2005, 280:29428-29434). After 4 rounds of selection for each library, randomly picked antibody clones were assessed for binding to ADAMTS13 by phage ELISA using ADAMTS13-coated plates, HRP-conjugated anti-M13 antibody (GE Healthcare Life Sciences) as described (Payne, et al., J. Clin. Invest., 2005, 115:888-899). Positive binding clones (>10-fold absorbance above background with irrelevant phage-displayed scFv) were identified from each patient's library. Nucleotide sequences of the heavy and light chains of each scFv were determined using pComb3X-specific sequencing primers to identify unique antibodies. Nucleotide sequences were analyzed for homology to known human $V_H$, D, $J_H$, Vκ, Jκ, Vλ, and Jλ immunoglobulin heavy or light chain germline gene segments using IMGT/V-QUEST (www.imgt.org/).

Production of Soluble scFv Antibody Fragments in Bacteria

Soluble scFv preparations (i.e. antibodies unlinked to phage) of each positive clone identified through phage ELISA were used to confirm ADAMTS13 binding and to perform ADAMTS13 inhibition assays, epitope mapping, and generation of rabbit anti-idiotypic antibodies as detailed below. The TOP 10F' non-suppressor strain of E. coli (Invitrogen, Life Technologies, Grand Island, N.Y.) was infected with individual phage clones and scFv molecules with carboxy terminus 6xHis sequence (for purification) and a hemagglutinin (HA) peptide tag (for detection) were then purified from the bacterial periplasmic space using sucrose shock and nickel-chelation affinity chromatography. ScFV's were dialyzed against PBS, concentrated by Amicon ultrafiltration (Millipore, Billerica, Mass.), and quantified by SDS-PAGE using molecular weight standards of known mass (Novex NuPAGE, Life Technologies). Binding of ADAMTS13 by soluble scFv (150 ng scFv per well) was assessed by ELISA with recombinant ADAMTS13-coated enzyme immunoassay plate wells and HRP-conjugated anti-HA secondary antibody (Roche Diagnostics, Indianapolis, Ind.). Negative controls included identically-prepared scFv specific for irrelevant antigens including E1M2, a red cell Rh(D)-specific scFv, PX4-3, a keratinocyte desmoglein-specific scFv, and X24-3, a human platelet factor 4-specific scFv.

Production of Soluble scFv Antibody Fragments in Insect Cell Culture

Soluble scFv of selected ADAMTS13-positive clones were expressed in Drosophila S2 cells to prepare antibodies for injection into mice and for experiments requiring antibodies expressing a V5 vs. HA tag. The multiple cloning site of the plasmid pMT/BiPN5-His A (Invitrogen) was modified to introduce a pair of Sfi I sites so that scFv constructs could be shuttled easily from their Sfi I cloning sites in the pComb3X phagemid vector. To express a phage display-derived scFv in S2 cells, the desired scFv construct was removed from the pComb3X phagemid by Sfi 1 digestion, gel purified, and ligated into Sfi 1-digested and gel-purified PMT vector from above. PMT plasmids and pCoBlast (Invitrogen) were co-transfected into S2 cells at a ratio of 19:1 using FuGene6 (Promega, Madison, Wis.), stable transfectants were established using Blasticidin (Invitrogen), and induction of scFv expression with CuSO4 was performed as per manufacturer's instructions as modified as previously described (Zaitsev, et al, J. Pharmacol. Exp. Ther., 2010, 332:1022-1031). V5-tagged scFv's were separated from cell media components by dialysis into 300 mM NaCl/50 mM NaPO4, pH 8.00 buffer and a first-round purification using Ni-NTA agarose (Qiagen, Germantown, Md.) following manufacturer's instructions. After Centricon ultrafiltration (10 kDa MW, Millipore) and further purification by size exclusion gel chromatography on Sephadex G-75 (GE Healthcare Life Sciences), scFv preparations were once again concentrated by ultrafiltration and stored at −80° C. until use.

Epitope Mapping

Epitope mapping of selected scFv was performed by immunoprecipitation (IP) of mammalian cell culture-produced full-length and truncated forms of ADAMTS13 modified for IP with HA-tagged scFv instead of polyclonal TTP patient serum IgG. Incubation mixtures comprising 500 µL of PBS containing 25-100 ng of an ADAMTS13 construct, 600 ng of E. coli-produced scFv, 0.1% protease inhibitor cocktail (#P8849, Sigma, St. Louis, Mo.), 0.05% Tween 20 (Pierce Biotechnologies, Rockford, Ill.), and 1% bovine serum albumin were rotated overnight at 4° C. followed by addition of 304 anti-HA agarose beads (Roche). Beads were incubated for 2 hours at room temperature, washed 5 times with 1 mL of 0.05% Tween 20/PBS, and the final bead pellet was resuspended in 50 µL NuPAGE LDS gel electrophoresis sample buffer containing DTT (Novex) and heated at 85° C. for 5 min. Electrophoresis and Western blotting were performed per manufacturer's instructions using NuPAGE 4-12% Bis-Tris gels loaded with 15 µL sample per well. Immunoprecipitated ADAMTS13 constructs were visualized on X-ray film with a chemiluminescent substrate (ECL, Amersham, GE Healthcare Life Sciences) on PVDF membranes developed with HRP-conjugated mouse anti-V5 antibody (Invitrogen) at 1:5000 dilution in blocking buffer (2.5% non-fat dry milk, 0.5% Tween, TBS).

Generation of Rabbit Anti-ADAMTS13 Anti-Idiotypic Antibodies

A pair of New Zealand White rabbits were each immunized with 1 of 4 purified HA-tagged E. coli-produced scFv preparations (scFv 1-416, 1-420, 1-428, or 1-431) over a period of 90 days by Pocono Rabbit Farm & Laboratory (Canadensis, PA), a laboratory animal care facility accredited, registered, and assured by AAALAC International, the USDA, and OLAW, respectively, following their standard IACUC-approved protocol for rabbit protein immunization. Rabbit IgG was purified using recombinant Protein G agarose (Invitrogen) following manufacturer's instructions from sera. Rabbit IgG was quantified by $OD_{280}$ using an extinction coefficient of 1.4. Immunity to recombinant scFv was verified by comparing respective rabbit pre-immune sera with post-immune sera by ELISA using plates pre-coated with 10 µg/mL mouse anti-V5 tag antibody (Invitrogen) to capture S2 cell-produced VS-tagged scFv's and developed with a 1:5000 dilution of HRP-conjugated donkey anti-rabbit IgG (Amersham). VS-tagged scFv were used here and in all subsequent assays of scFv with rabbit IgG to avoid any anti-HA tag antibodies that may have been produced from HA-tagged scFv immunogens. Reactivity of rabbit IgG to VS-tagged scFv's pre-/post-immunization increased nearly 100-fold.

Intraperitoneal Injection of Anti-ADAMTS13 Antibodies in Mice

Two- to three-month-old mice (C57BL/6 or CAST/Ei, Jackson Laboratory, Bar Harbor, Me.) were anesthetized with ketamine/xylazine and blood samples (50 µL) were obtained from their jugular veins before and after intraperitoneal injection of 100 µL PBS containing 30 µg Drosophila S2 cell-produced scFv. Blood samples were taken at various time points and anticoagulated with 5 µL PBS containing 5 U/mL heparin. Plasma was separated from cells at 1500 g for 15 min and frozen at −80° C. for ADAMTS13 activity assays and/or VWF multimer analyses.

In Vivo Production of Human scFv Antibodies in Mice by Hydrodynamic Delivery

Figure 11:
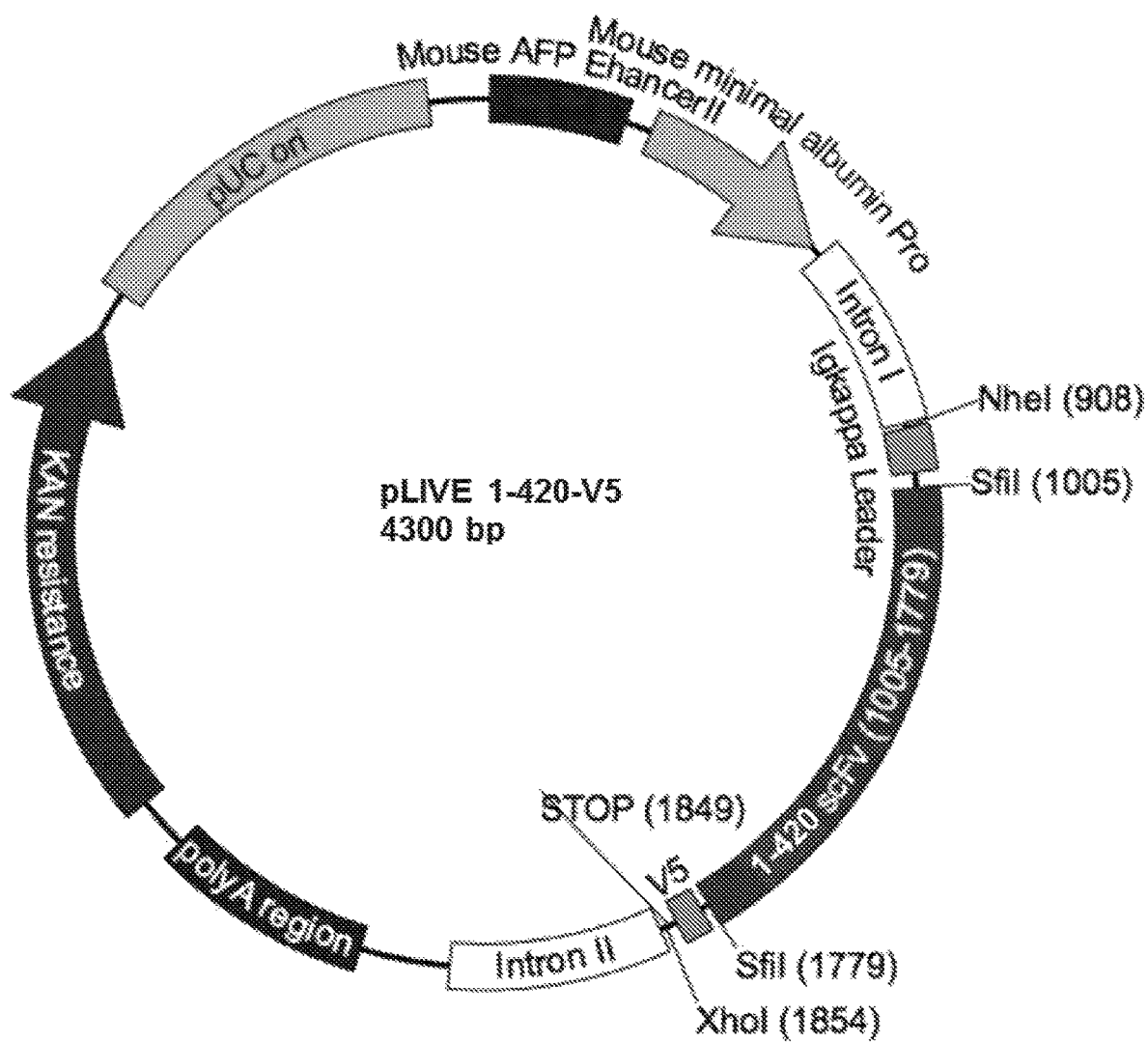
FIG. 11 is a schematic diagram of pLIVE plasmid vector modified for in vivo scFv expression. Shown are positions of Ig-kappa leader sequence, Sfi I restriction sites for inserting pComb3X-derived scFv construct, and V5-tag sequence.

ScFv cDNA was cloned into the pLIVE in vivo expression vector (Mirus, Madison, Wis.) and injected via tail vein into 2- to 3-month-old mice (C57BL/6 or CAST/Ei) per manufacturer's instructions. Briefly, mice were warmed by heat lamp for several minutes and 30 µg of pLIVE/scFv DNA diluted in 2 mL TransIT-QR hydrodynamic delivery solution were injected in the tail over 4 to 7 seconds using a syringe equipped with a 30-gauge needle. To facilitate the cloning of scFv constructs from the pComb3X phagemid vector into pLIVE with the subsequent secretion of antibody from murine liver, the multiple cloning site of the pLIVE vector was first modified with an immunoglobulin kappa-chain leader sequence followed by Sfi I restriction sites and a V5-tag sequence for subsequent detection in mouse plasma (FIG. 11 for details). Plasmid DNA for injection was produced in XL1-Blue and purified using an endotoxin-free plasmid purification kit (Qiagen). Just prior to and after DNA delivery, blood samples (~100 µL) were collected from the retro-orbital sinus under light anesthesia with isoflurane into heparinized capillary tubes at various time points and transferred to 10 µl of 1.9% sodium citrate. Plasma was separated by centrifugation and stored at −80° C.

Cremaster Arteriole Laser Injury Model in scFv-Expressing Mice

Platelet thrombus formation in C57BL/6 mice pre-injected 7 days earlier with pLIVE expression vector containing scFv 1-420 anti-ADAMTS13 antibody or control scFv cDNA was examined by intravital video-microscopy following cremaster arteriole laser injury. Thrombi were imaged using an Olympus BX61WI microscope (Olympus, Center Valley, Pa.) with a 60x/0.9 numeric aperture water immersion objective and captured using a Cooke SensiCam CCD camera (Cooke, Auburn Hills, Mich.) coupled to a Lambda DG4 widefield excitation system (Sutter, Novato, Calif.). The microscope, camera, and DG4 were all controlled using Slidebook 5.0 software (Intelligent Imaging Innovations). F(ab')2 fragments of rat anti-mouse CD41 IgG (BD Pharmingen, San Diego, Calif.) were F(ab')2 conjugated to Alexa$^{488}$ according to the manufacturer's instructions (Life Technologies). F(ab')$_2$ fragments were infused via jugular vein (0.1 mg/kg) immediately prior to first injury. Arterioles of 20-40 µm were selected. Vascular injury was induced with a pulsed nitrogen dye laser (SRS NL100, Photonic Instruments, St. Charles, Ill.) focused on the vessel wall through the microscope objective. Analysis of time-lapse videos (750 frames per injury) was performed using Slidebook 5.0 (Intelligent Imaging Innovations, Denver, Colo.). After background fluorescence was subtracted from all images in one injury video, the resulting thrombus fluorescence was analyzed in the software to calculate an X/Y aspect ratio. A median filter was applied to each injury before taking the average of all injuries.

Shigatoxin Challenge in scFv-Expressing Mice

CAST/Ei mice were injected with pLIVE expression vector containing scFv 1-420 anti-ADAMTS13 or control scFv cDNA and monitored for 10 days for ADAMTS13 activity, VWF multimer size, and scFv expression prior to Shigatoxin-2 challenge (Stx-2, Toxin Technology, Sarasota, Fla.). At day 10, Stx-2 (50 pg1g body weight) was injected via tail vein. Complete blood counts were performed just prior to and for up to 10 days following Stx-2 using a Hemavet M2950HV analyzer (Drew Scientific, Waterbury, Conn.). Blood smears were stained with Wright stain and tissues were processed and stained with hematoxylin-eosin.

ADAMTS13 Activity Assays and VWF Multimer Analysis

Human and murine ADAMTS13 activities were measured in the presence or absence of various factors (recombinant scFv, TTP patient plasma IgG, rabbit anti-idiotypic IgG) using a commercial FRETS-VWF73 peptide (Peptide International, Louisville, Ky.). Components to be measured were mixed in a volume of 8 µL as described in FIG. legends, added to 42 µL of substrate buffer and 50 µl of diluted FRETS-VWF73 reagent. Fluorescence emission from cleavage of FRETS-VWF73 was measured using a Synergy 2 Multi-Mode Reader (BioTek, Winooski, Vt.) equipped with 340 nm excitation and 440 nm emission filters. vWF multimers were visualized as previously described (Laje, et al., Blood, 2009, 113:2172-2180; Niiya, et al., Mol. Ther., 2009, 17:34-41).

Adapting pMT/RiP/V5-his A Plasmid Vector for Expression of pComb3X Phagemid-Derived scFv Antibody Clones The multiple cloning site of the plasmid vector pMT/BiPN5-His A was modified to incorporate Sfi I restriction sites to facilitate easy shuttling of scFv sequences from the pComb3X phage display vector. Modification of the pMT vector also required removal of an endogenous Sfi I site in the BiP secretion signal sequence. This was accomplished by digesting pMT/BiPN5-His A with Sfi I and BstB I and ligating a double-stranded oligonucleotide formed by annealing single-stranded oligonucleotides "PMT FOR" (5'-<u>TTGCC</u> TTT GTT GGC CTC TCG CTC GGG AGA TCT GCG GCC CAG GCG GCC CCA TGG CCC GGG GTA CCT ACT AGT GGC CAG GCC GGC <u>CAGTT</u>-3' SEQ ID NO: 193) and "PMT REV" (5'-<u>CGAACTG</u> GCC GGC CTG GCC ACT AGT AGG TAC CCC GGG CCA TGG GGC CGC CTG GGC CGC AGA TCT CCC GAG CGA GAG GCC AAC AAA <u>GGCAACGA</u>-3' SEQ ID NO: 194), where the single-underlined bases on the 5' forward strand alter the BiP Sfi I site, the double-underlined bases at the 3' forward end complete a BstB I site, and the 2 sets of bases in bold provide the new Sfi I sites, 5'-GGCCNNNNNGGCC-3' SEQ ID NO: 195, where N's match those on either side of scFv sequences in the pComb3X vector. To shuttle a scFv, pComb3xDNA is digested with Sfi I restriction enzyme and ligated into Sfi I-cut modified pMT/BiP/V5-His A.

Adapting pLIVE In Vivo Expression Vector for Secretion of pComb3X Phagemid-Derived scFv Antibody Clones The multiple cloning site of pLIVE plasmid vector was modified to contain an Ig-kappa leader sequence upstream from Sfi I restriction sites and a V5-tag sequence to facilitate secretion of V5-tagged scFv antibody fragments from murine liver following hydrodynamic delivery. pLIVE vector was first digested with Nhe I and Xho I restriction enzymes and a double-stranded oligonucleotide formed from the annealing of "V5 FOR" (5'-CTAGCACTAGTGGCCAGGCCGGCCAGTTCGAA GGTAAGCCTATCCCTAACCCTCTCCTCGGTCTCGAT TCTACGCGTACCGGTTAGC-3' SEQ ID NO: 196) and "V5 REV" (5'-TCGAGCTAACCGGTACG CGTAGAATCGAGACCGAGGAGAGGGTTAGGGATAG GCTTACCTTCGAACTGGCCGGCCTGGCCACTAGTG-3' SEQ ID NO: 197) was ligated in to the cut and gel-purified vector to introduce the 3' Sfi I restriction site (bold), the V5 tag sequence (underlined), and a stop codon (italics). The resultant plasmid was digested with Nhe I and Sfi I and a second double-stranded oligonucleotide formed from the annealing of "LEAD FOR" (5'-CTAGC ATGGAGACAGACACACTCCTGCTATGGGTACTGCT GCTCTGGGTTCCAGGTTCCACTGGTGACG- GAGCTGCGGCCCAGGCGGCCC- CATGGCCCGGGGTACCTA CTAGTGGCCAGGC-3' SEQ ID NO: 198) and "LEAD REV" (5'-TGGC-CACTAGTAGGTACCCCGGGC-CATGGGGCCGCCTGGGCCGCAGCTCC GTCACCAGTGGAACCTGGAACCCAGAGCAGCAGT ACCCATAGCAGGAGTGTGTCTGTCTCCATG-3' SEQ ID NO: 199) was ligated in to the cut and gel-purified vector to introduce the Ig kappa-chain leader sequence (underline) and 5' Sfi I restriction site (bold). ScFv constructs were cloned into the modified pLIVE vector using Sfi I sites as above for the modified pMT vector.

Tables

Table 1 lists patient demographics, clinical data, and number of anti-ADAMTS13 antibodies isolated.

Table 2 lists the genetic features and clonality of anti-ADAMTS13 heavy chains.

Table 3 lists the genetic features and clonality of anti-ADAMTS13 light chains.

Table 4 lists the percentage of ADAMTS13 activity in presence of scFv inhibitors: rabbit anti-idiotypic IgG.

The results of the experiments are now described.

Cloning Human Anti-ADAMTS13 Autoantibodies from TTP Patients body-mediated TTP. Patients were diagnosed with acquired TTP on the basis of thrombocytopenia, microangiopathic hemolytic anemia, and <10% plasma ADAMTS13 activity in the setting of inhibitory immunoglobulin. Table 1 shows relevant demographic and clinical data. Peripheral blood for library construction was collected from TTP2-TTP4 just prior to their first plasma exchange and comprised $\sim 1 \times 10^6$ IgG-positive B-cells. Splenic tissue from TTP1 was obtained following splenectomy after a 42-week relapsing/remitting course and comprised $\sim 6 \times 10^9$ IgG-positive B-cells. Antibody libraries contained $4.6 \times 10^8$, $3.6 \times 10^8$, $7.4 \times 10^8$, and $6.6 \times 10^7$ independent transformants, respectively, which represent complexities within (or higher) than the range considered ideal for libraries constructed from immune vs. non-immune sources (Rader et al., Phage Display: A Laboratory Manual. Cold Spring Harbor, N.Y.: Cold Spring Harbor Press, 2001:10.1-0.20). Antibody libraries for each patient were each selected ("panned") against full-length human recombinant ADAMTS13. Library TTP1 was also panned against recombinant TSP1 5-8/CUB fragment of ADAMTS13 (Zhang et al., Blood 2007; 110:1887-94). After four rounds of panning for each library, antigen-positive clones were identified by ADAMTS13 ELISA. Nucleotide sequences for the heavy and light chains of each were determined to identify the number of unique antibodies obtained from each patient. The last column of Table 1 tabulates the number of antibody clones sampled from each patient library, the number of positives, and, of these, the number of unique antibodies. In sum, a cohort of 51 unique human monoclonal anti-ADAMTS13 antibodies was assembled for further study. Nomenclature for antibody clones are in the form "X-Y" where "X" is TTP patient number and "Y" is an arbitrary number.

TABLE 1

Patient demographics, clinical data, and number of anti-ADAMTS13 antibodies isolated

| Patient | Age/Sex/Race | Hgb (g/dL) | Plt (× 10^9/L) | LDH (U/L) | Cr (mg/dL) | No. TPE | Source of B cells | No. scFv sampled/ positive/unique |
|---|---|---|---|---|---|---|---|---|
| TTP1* | 10 y/M/W | 8.7 | 9 | 8845 | 0.9 | 109 | spleen† | 75/67/31‡ |
| TTP2§ | 28 y/F/W | 9.6 | 7 | 2763 | 0.5 | 64 | PB‖ | 32/22/14 |
| TTP3¶ | 47 y/F/B | 11.5 | 35 | 761 | 1.1 | 48 | PB‖ | 16/12/4 |
| TTP4# | 59 y/M/W | 9 | 14 | 3427 | 1.5 | 13 | PB‖ | 17/10/2 |

Patients were diagnosed with acquired TTP on the basis of thrombocytopenia, microangiopathic hemolytic anemia, and <1-% plasma ADAMRS13 activity in the setting of inhibitory IgG.

M indicates male; F, female; W, White; B, Black; Hgb, hemoglobin concentration; Plt, platelet count; LDH, lactate dehydeogenase; Cr, creatine; TPE, therapeutic plasma exchange procedure; PB, peripheral blood

*Patient's course of TTP relapsed/remitted over period of 42 weeks until splenectomy. No recurrence in 12 years of follow-up.

†Antibody library constructed from 15 g spleen comprising $\sim 6 \times 10^9$ IgG-positive B cells.

‡Of 31 unique positive clones, 28 were onbtained from selection against full-length ADAMTS13 and 3 were obtained from selection against the TSP1 5-8/CUB fragment of ADAMTS13.

§Patient had history of well-controlled lupus since 18 years of age. Experienced miscarriage a few months beforediagnosis of TTP. Clinical course complicated by multiple subarachnoid hemorrhages and grand mal seizures. Diagnosed with lumphoma 12 years post-TTP.

‖Antibody library constructed from $\sim 1 \times 10^8$ IgG-positive B cells isolated from 50 ml peripheral blood collected prior to first plasma exchange.

¶This episode of TTP was a relapse from initial diagnosis of TTP made 2 years earlier. Had splenectomy after this episode and no recurremnce in over 10 years.

Patient responded rapidly to TPE and has not had relapse in the past 8 years.

Antibody phage display libraries expressing $IgG_{1-4}$ κ/λ isotypes of single chain variable region fragments (scFv) (i.e. heavy and light chain variable regions tethered together by a short peptide linker) were created from the splenic B-cells ("TTP1") or peripheral blood B cells ("TTP2", "TTP3" and "TTP4") of 4 unrelated patients with autoanti- Structural Analysis of Anti-ADAMTS13 Autoantibodies Shows Evidence of Clonal Expansion and Somatic Mutation The nucleotide sequences of the 51 antibodies showed use of the human heavy chain variable region gene $V_H 1$-69 for 75% of the anti-ADAMTS13 antibodies (Table 2), a bias reported previously (Pos et al., J Thromb Haemost 2009;

7:421-8). However, 13 of the 51 antibodies were derived from diverse $V_H3$- and $V_H6$-family genes as well. That splenic tissue derived from TTP1 vs. peripheral blood lymphocytes from TTP2-TTP4 yielded the largest number of unique antibodies with the greatest genetic diversity was not surprising given that the TTP1 library was constructed from >1000-fold more B-cells. Furthermore, the spleen may be a reservoir for long-lived memory B-cells producing ADAMTS13 autoantibodies given that splenectomy is associated with long-term remission in TTP patients (Kappers-Klunne et al., Br J Haematol 2005; 130:768-76).

To rule out the possibility that the relatively high gene usage of $V_H1$-69 for anti-ADAMTS13 antibodies across all 4 patients was due to preselection factors (i.e. cloning artifacts during library construction), the diversity of each unpanned scFv patient library was assessed. By sequencing dozens of randomly-picked clones, it was determined that there was significant heterogeneity in $V_H$ gene representation before selection similar to that typically found for IgG-secreting lymphocytes in the repertoire of adults.

Figure 9A:
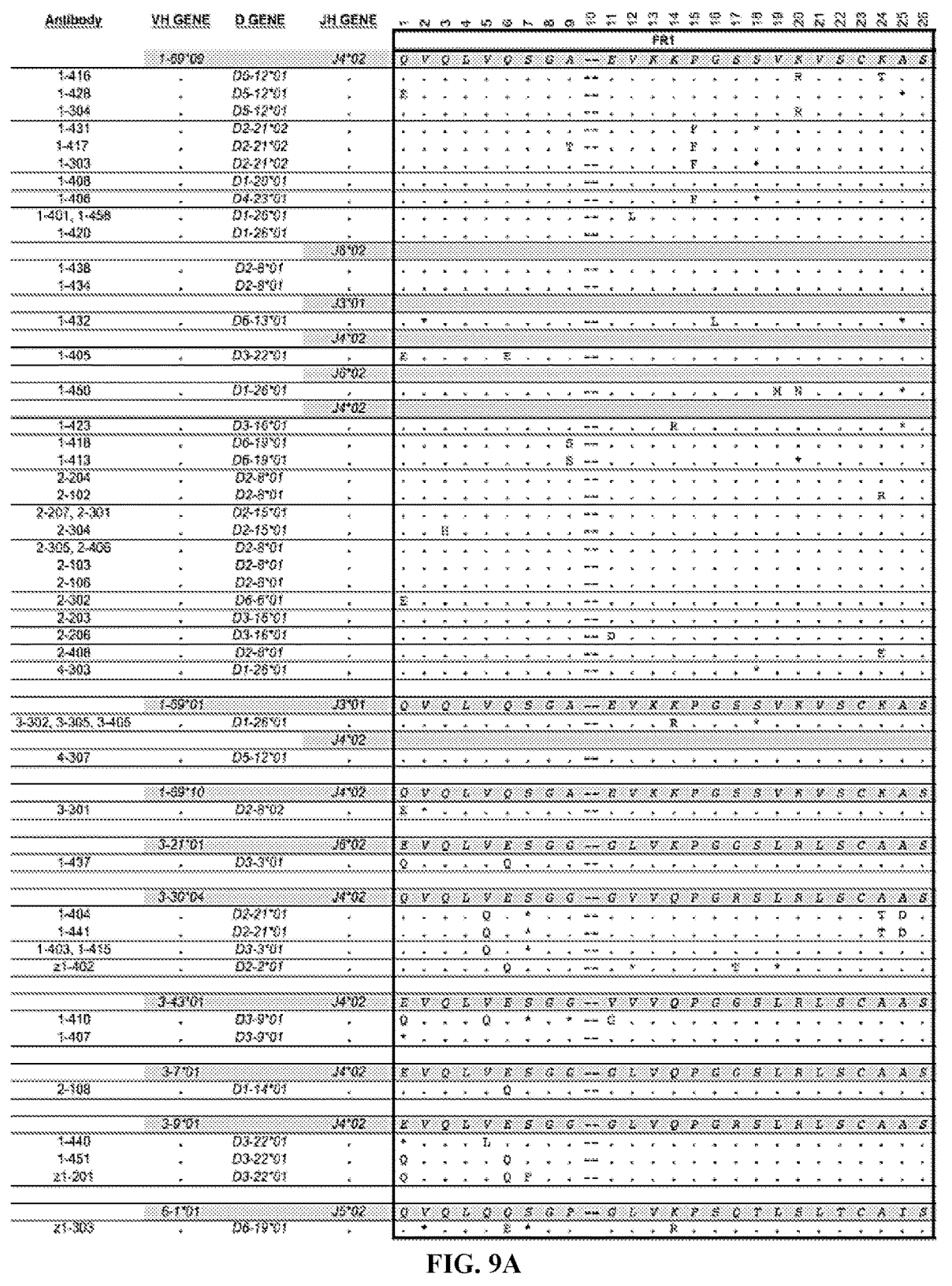
Figure 9A:
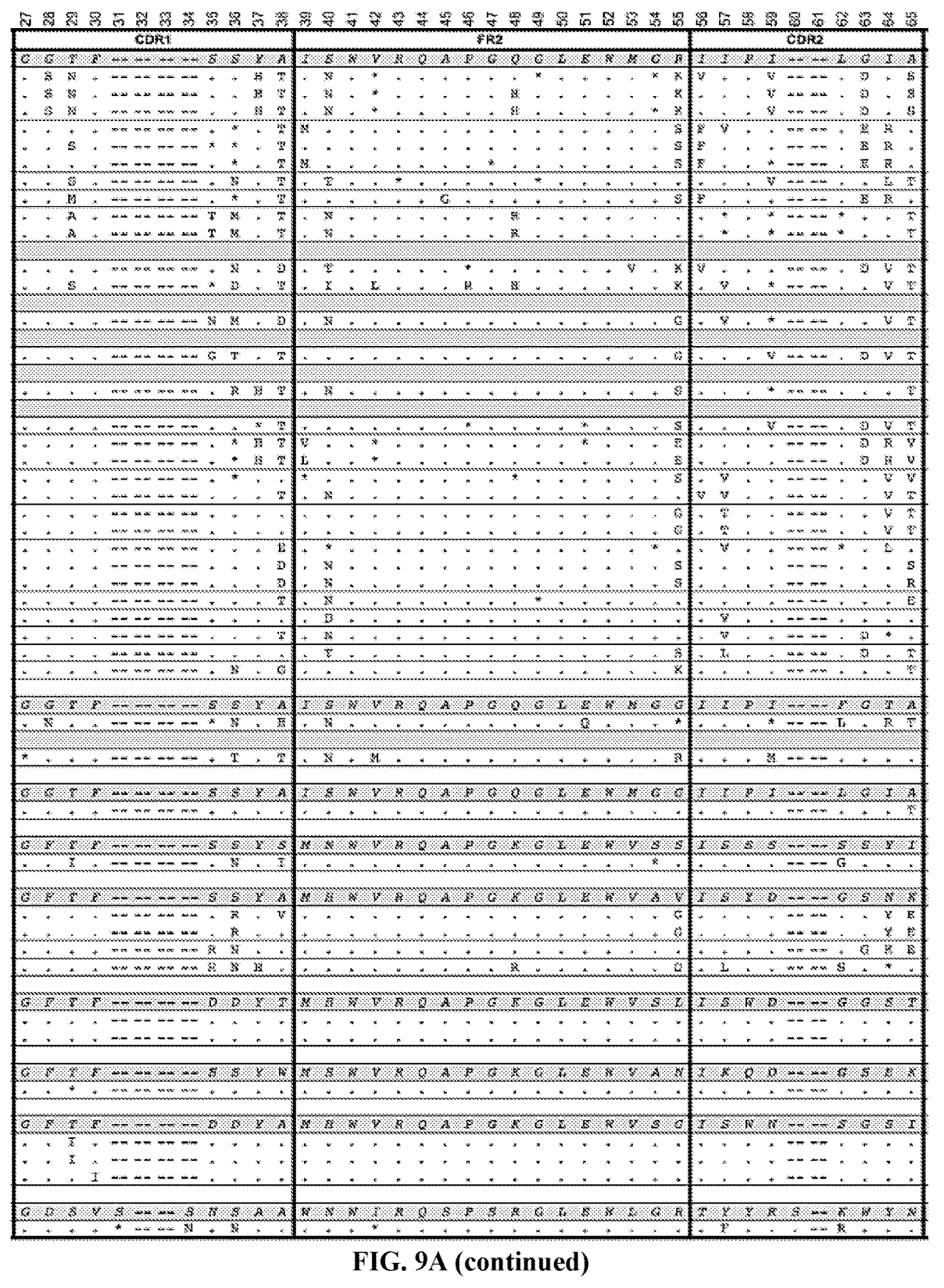
Figure 9A:
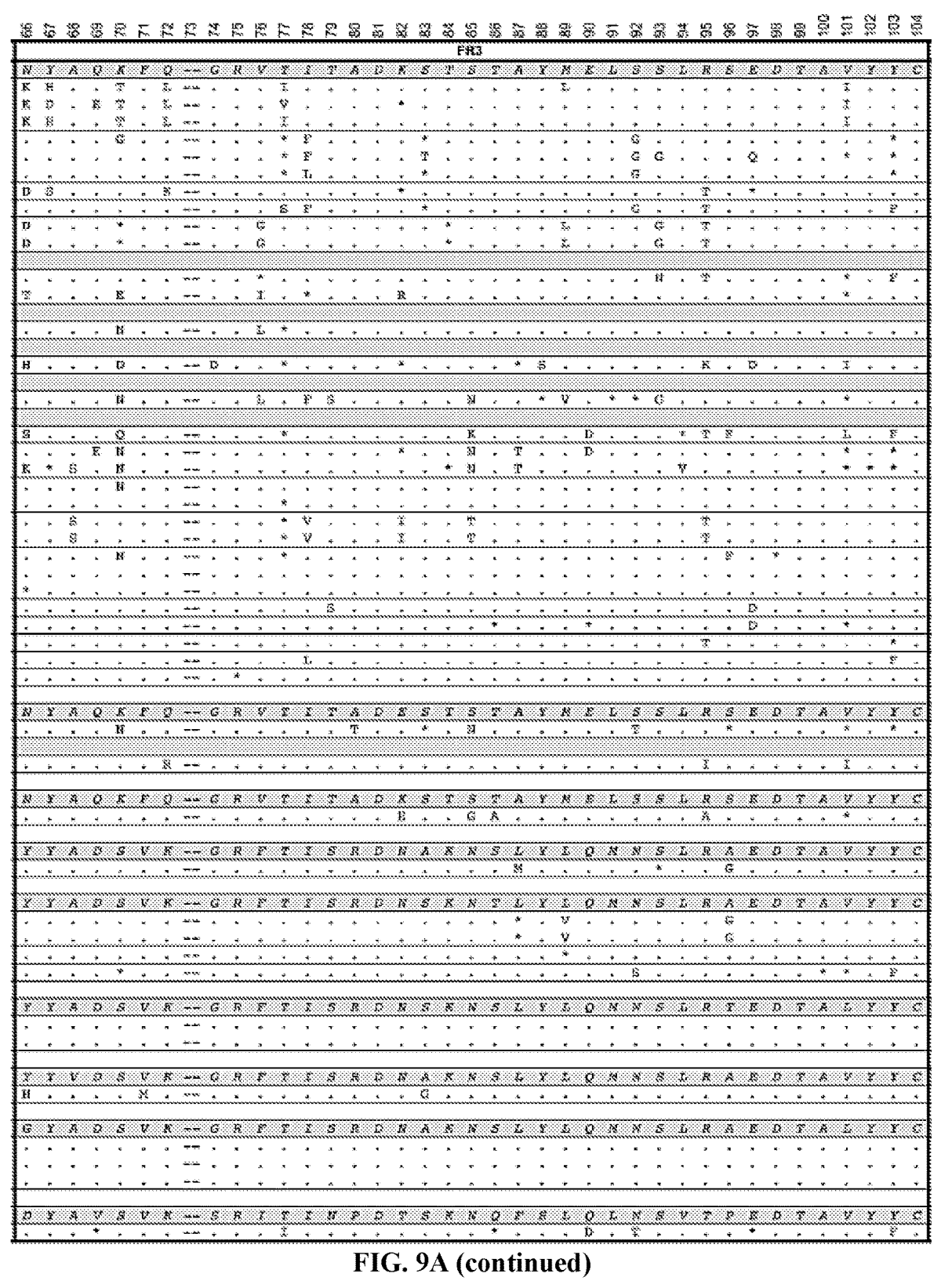
Figure 9B:
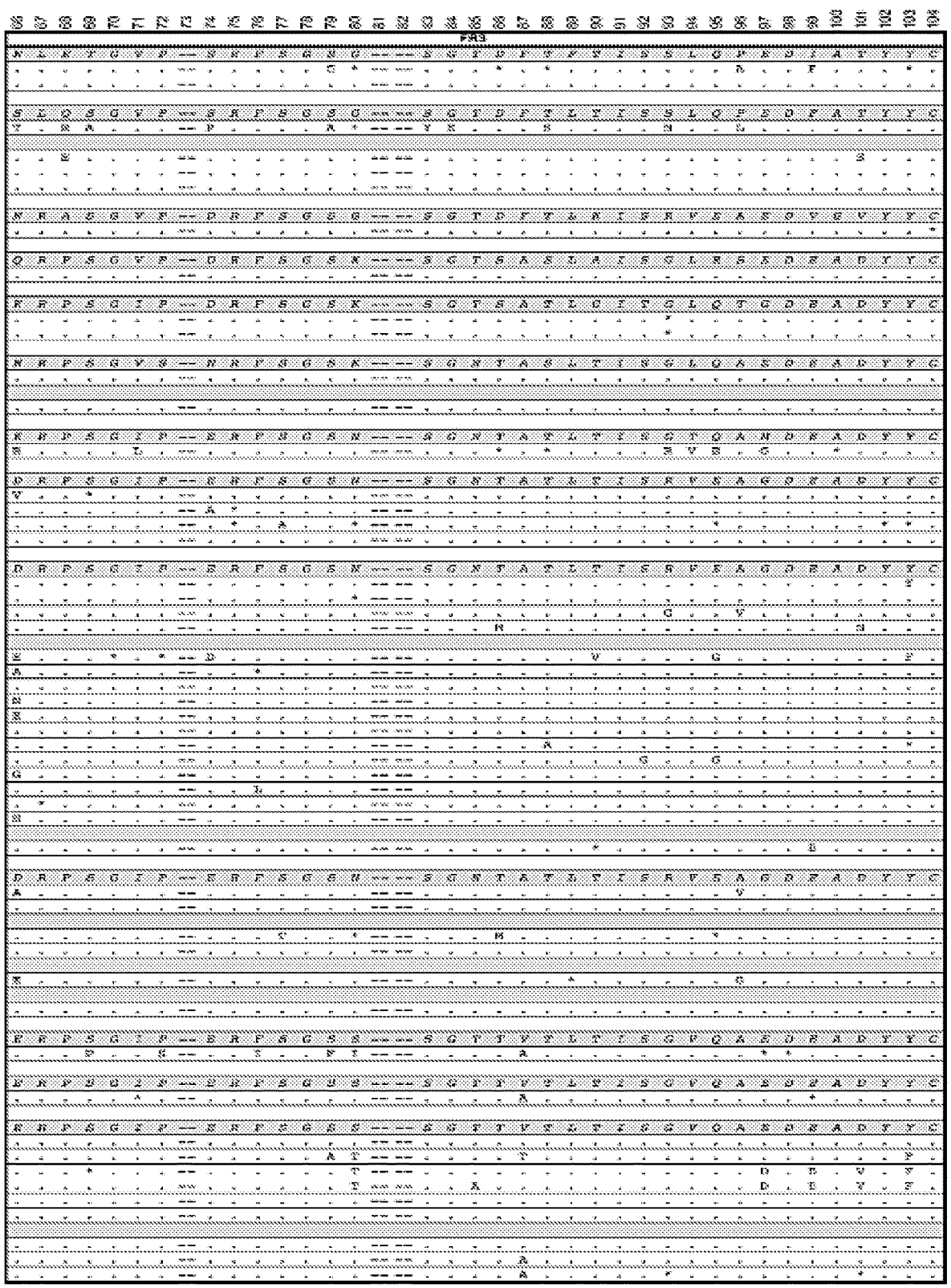

Table 2 also shows the D and $J_H$ gene segments that had rearranged with $V_H$ genes to form the entire heavy chain variable regions (i.e., $V_HDJ_H$) and their complementarity determining region-3 (HC-CDR3), the region of greatest diversity in an antibody's heavy chain. By exploiting the fact that there is only a remote probability that two B-cells will not only randomly select an identical combination of $V_H$, D, and $J_H$, but will also splice the genes together to create identical HC-CDR3 regions (theoretical probably <1 in $10^{11}$), one can use an HC-CDR3 to identify a B-cell clonotype. This is indicated in Table 2 by each separate line. For example, the heavy chains of antibodies 1-416, 1-428 and 1-304 would be predicted to have each been derived from the same original parental B-cell within patient TTP1 because they each share the identical HC-CDR3 ("AMDSVYGNFDF"; SEQ ID NO: 200) though those 3 heavy chains are otherwise unique due to somatic mutation elsewhere in the heavy chain (FIG. 9A). Counting the number of different HC-CDR3 regions suggests that the 51 scFv heavy chains were derived from clonal expansion of 30 individual B-cells. Antibody light chain analysis showed use of both kappa and lambda, but light chains lack D segments which make it difficult to confidently assign discrete B-cell origins to every light chain that share similar CDR3's (Table 3). FIGS. 9A-9B provide sequence alignments of all 51 antibody heavy and light chains and indicates positions of replacement and silent mutations with respect to their most likely immunoglobulin germline genes.

Together, these data (Tables 2 and 3 and FIGS. 9A-9B) demonstrate that within each of the four TTP patients, the autoimmune response to ADAMTS13 was oligoclonal with multiple B-cells expanding to produce groups of related antibodies that underwent further somatic mutation. The relatively high ratios of replacement-to-silent mutations in HC-CDR1 and HC-CDR2 (>4.7, FIG. 9A) are characteristic of antigen-driven clonal expansion (Dorner et al., J Immunol 1998; 160:2831-41) as it was previously found in the autoimmune repertoires in idiopathic thrombocytopenic purpura (Roark et al., Blood 2002; 100:1388-98) and pemphigus (Payne et al., J Clin Invest 2005; 115:888-99), and alloimmune Rh(D) repertoire (Chang et al., Blood 1998; 91:3066-78).

TABLE 2

Genetic features and clonality of anti-ADAMTS13 heavy chains

| Patient | Antibodies grouped by heavy chain clonotype | $V_H$ family | $V_H$ gene | D gene | $J_H$ gene | HC-CDR3 |
|---|---|---|---|---|---|---|
| TTP1 | 1-416, 1-428, 1-304 | 1 | 1-69*09 | D5-12*01 | J4*02 | AMDSVYGNFDF (SEQ ID NO: 200) |
| | 1-431, 1-417, 1-303 | 1 | 1-69*09 | D221*02 | J4*02 | ARDLGDFGDS (SEQ ID NO: 201) |
| | 1-408 | 1 | 1-69*09 | D1-20*01 | J4*02 | ARDSVIGTSD (SEQ ID NO: 202) |
| | 1-406 | 1 | 1-69*09 | D4-23*01 | J4*02 | ARDVGDFGDS (SEQ ID NO: 203) |
| | 1-458†, 1-401†, 1-420 | 1 | 1-69*09 | D1-26*01 | J4*02 | AREFSGGNYFDF (SEQ ID NO: 204) |
| | 1-438, 1-434 | 1 | 1-69*09 | D2-8*01 | J6*02 | ARFLWGLDV (SEQ ID NO: 205) |
| | 1-432 | 1 | 1-69*09 | D6-13*01 | J3*01 | ARGVAAGWNAFDV (SEQ ID NO: 206) |
| | 1-405 | 1 | 1-69*09 | D3-22*01 | J4*02 | ARSSYYSTFDY (SEQ ID NO: 207) |
| | 1-450 | 1 | 1-69*09 | D1-26*01 | J6*02 | ASGDYYYDMAV (SEQ ID NO: 208) |
| | 1-423 | 1 | 1-69*09 | D3-16*01 | J4*02 | SIGRYTYGHFDT (SEQ ID NO: 209) |
| | 1-418, 1-413 | 1 | 1-69*09 | D6-19*01 | J4*02 | (T/V)SNGWSNFDF (SEQ ID NO: 210) |

TABLE 2-continued

Genetic features and clonality of anti-ADAMTS13 heavy chains

| Patient | Antibodies grouped by heavy chain clonotype | $V_H$ family | $V_H$ gene | D gene | $J_H$ gene | HC-CDR3 |
|---|---|---|---|---|---|---|
| | 1-437 | 3 | 3-21*01 | D3-3*01 | J6*02 | AAAYDFWSGYYF (SEQ ID NO: 211) |
| | 1-404, 1-441 | 3 | 3-30*04 | D2-21*01 | J4*02 | ARDLRGGEDY (SEQ ID NO: 212) |
| | 1-403†, 1-415† | 3 | 3-30*04 | D3-3*01 | J4*02 | ARDTFSYYDFWRAFDY (SEQ ID NO: 213) |
| | z1-402 | 3 | 3-30*04 | D2-2*01 | J4*02 | AASSYFPFDF (SEQ ID NO: 214) |
| | 1-410, 1-407 | 3 | 3-43*01 | D3-9*01 | J4*02 | AKDNGYDILTDYLD(S/Y) (SEQ ID NO: 215) |
| | 1-440, 1-451, z1-201 | 3 | 3-9*01 | D3-22*01 | J4*02 | AKDPNSLYRSGSFDY (SEQ ID NO: 216) |
| | z1-303 | 6 | 6-1*01 | D6-19*01 | J5*02 | AREGQWLPNYFDP (SEQ ID NO: 217) |
| TTP2 | 2-204, 2-102 | 1 | 1-69*09 | D2-8*01 | J4*02 | ARDKGYANNYGAY (SEQ ID NO: 218) |
| | 2-207†, 2-301†, 2-304 | 1 | 1-69*09 | D2-15*01 | J4*02 | ARDQGYANDYGAY (SEQ ID NO: 219) |
| | 2-103, 2-106, 2-305†, 2-406† | 1 | 1-69*09 | D2-8*01 | J4*02 | ARDQGYANNYGAY (SEQ ID NO: 220) |
| | 2-302 | 1 | 1-69*09 | D6-6*01 | J4*02 | ARDQVFGAY (SEQ ID NO: 221) |
| | 2-203 | 1 | 1-69*09 | D3-16*01 | J4*02 | ARDRGYANTYGAY (SEQ ID NO: 222) |
| | 2-206 | 1 | 1-69*09 | D3-16*01 | J4*02 | ARDRGYDNKYGAY (SEQ ID NO: 223) |
| | 2-408 | 1 | 1-69*09 | D2-8*01 | J4*02 | ARDRGYSNNYGAY (SEQ ID NO: 224) |
| | 2-108 | 3 | 3-7*01 | D1-14*01 | J4*02 | ARSPGYYFDY (SEQ ID NO: 225) |
| TTP3 | 3-305†, 3-405†, 3-302† | 1 | 1-69*01 | D1-26*01 | J3*01 | AREARDSFDF (SEQ ID NO: 226) |
| | 3-301 | 1 | 1-69*10 | D2-8*02 | J4*02 | ARDDTGRDDYFEY (SEQ ID NO: 227) |
| TTP4 | 4-307 | 1 | 1-69*01 | D5-12*01 | J4*02 | ARSGYSDAFDI (SEQ ID NO: 228) |
| | 4-303 | 1 | 1-69*09 | D1-26*01 | J4*02 | ARGGGSYDFFDY (SEQ ID NO: 229) |

All antibodies were obtained by selecting phage display antibody libraries against full-length ADAMTS13 except those with names beginning with "z" which were isolated by selecting the TTP1 library against the TSP1 5-8/CUB fragment of ADAMTS13.
HC-CDR3 indicates heavy chain complementarity determining region 3.
†Members of a clonotype identical at the heavy chain amino acid level but comprise unique antibodies due to mutations in the associated light chains (see Table 5 and FIG. 9B).

Relationship of ADAMTS13 Inhibitory Autoantibodies to Genetic Background and Epitope Specificity Inhibitory activities of anti-ADAMTS13 antibodies varied from 0% to ~100% residual ADAMTS13 activity (FIG. 1A). For reference, the germline $V_H$ gene from which the particular recombinant scFv was derived is shown above each bar. With only two exceptions (1-437 and 1-404), antibodies that significantly inhibited ADAMTS13 were encoded by $V_H$1-69 (P=1.4×10$^{-6}$). In contrast, anti-keratinocyte PX4-3 scFv is also encoded by $V_H$1-69 (FIG. 1B) and had no effect on ADAMTS13 activity even when incubated with ADAMTS13 at a 5-fold greater concentration, indicating inhibitory activity is not conferred simply by the use of this heavy chain gene.

Figure 2:
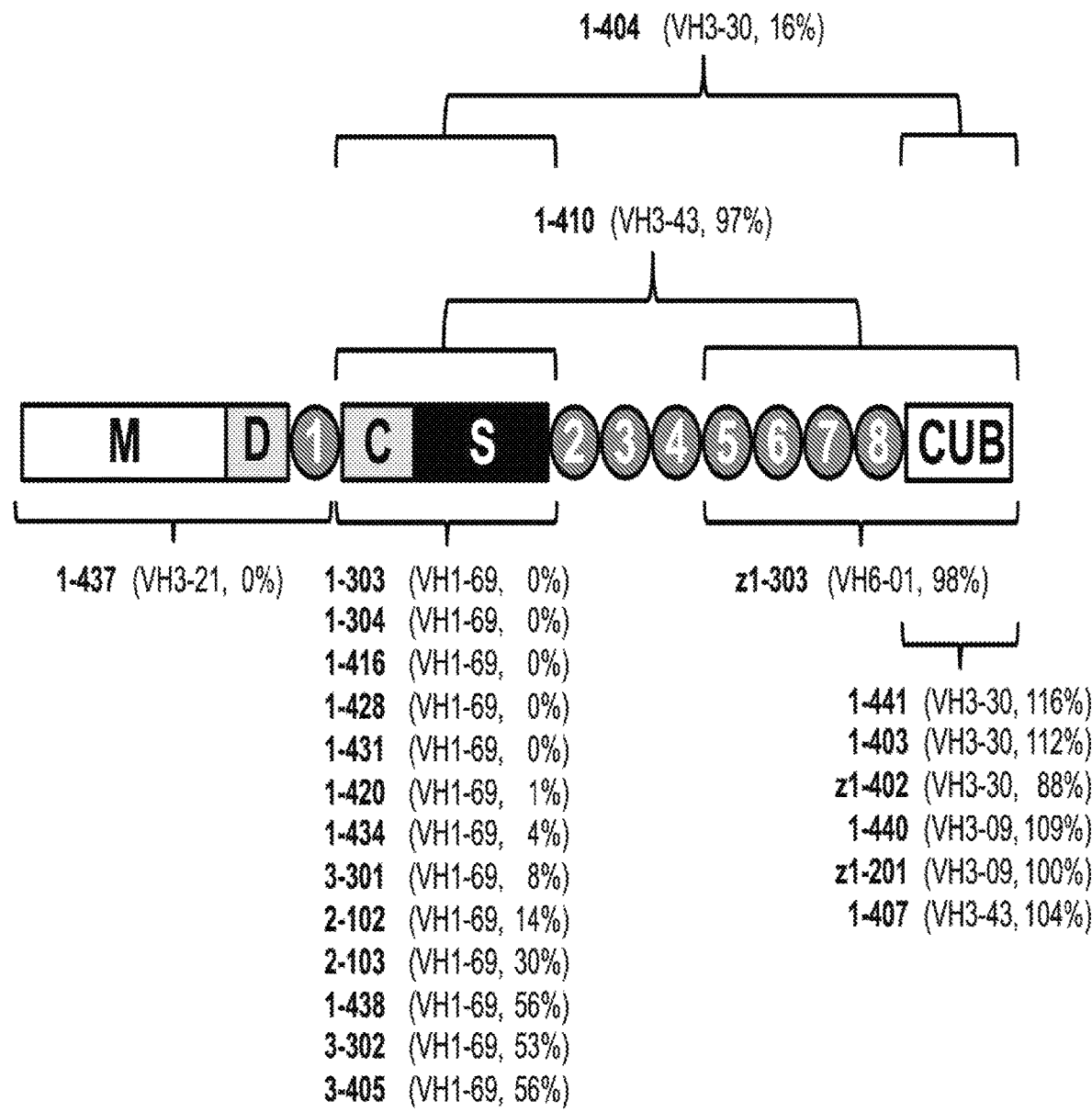
FIG. 2 is a graph illustrating epitope specificities of anti-ADAMTS13 scFv. Using overlapping fragments of ADAMTS13 and immunoprecipitation with selected scFv, binding regions for antibodies were derived and indicated in a cartoon map of ADAMTS13. For reference, heavy chain germline $V_H$ genes from Table 2 and ADAMTS13 inhibitory activities (percent residual activity from FIG. 1) are indicated in parentheses next to the name of each clone. Raw data for this experiment are in FIGS. 10A-10C. Domain abbreviations: M, metalloprotease; D, disintegrin; 1 through 8, thrombospondin type 1 motifs 1 through 8; C, cysteine-rich domain; S, spacer domain; CUB, pair of CUB domains (complement Clr/Cls, Uegf, bone morphogenic protein 1).
Figure 10A:
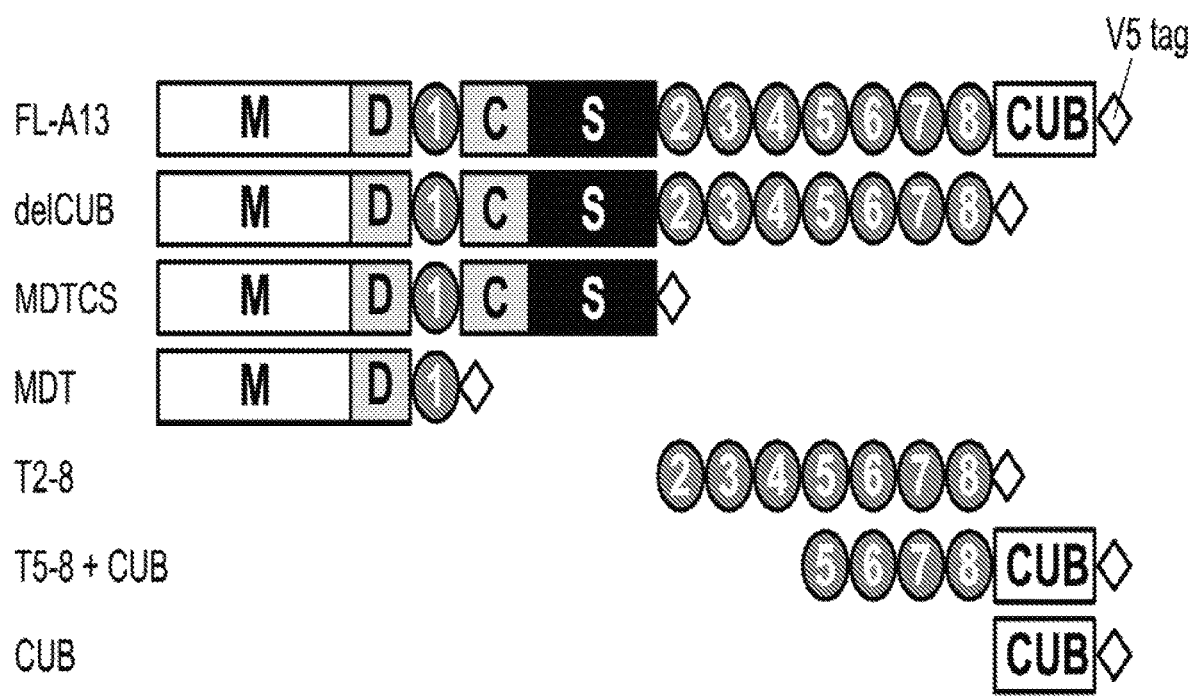
Figure 10B:
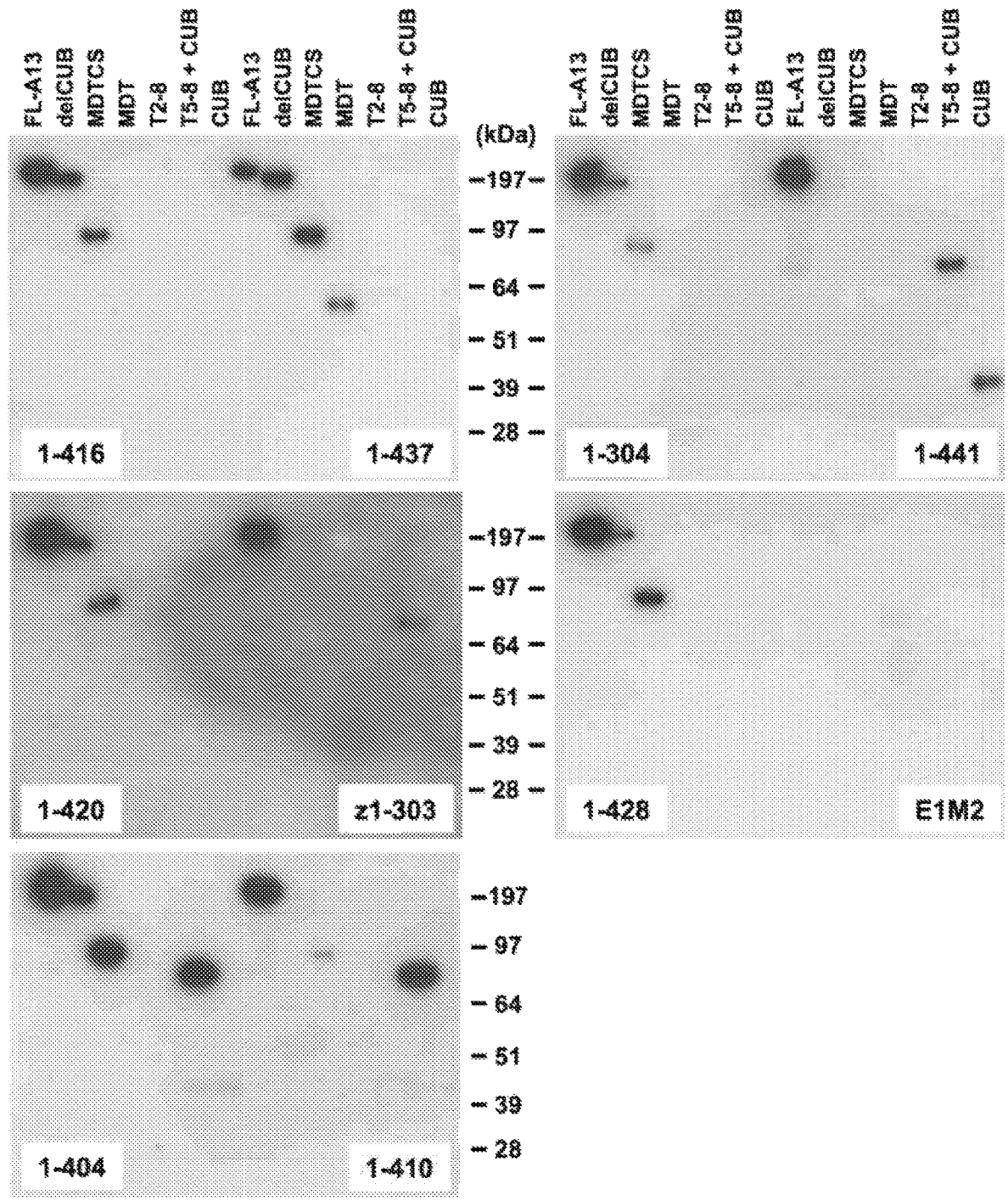

Epitope mapping was performed with a subset of 23 scFv's with different genetic backgrounds and inhibitory activities in order to investigate whether the ability of an anti-ADAMTS13 antibody to inhibit ADAMTS13 proteolytic activity in vitro is related to where it binds the enzyme. FIG. 2 summarizes the results (raw data in FIGS. 10A-10C) and illustrates a diversity in epitope specificities similar to that found in patient plasma (Soejima et al., Blood 2003; 102:3232-7; Pos et al., Haematologica 2011; 96:1670-7).

With only one clear exception (1-437), antibodies that inhibit ADAMTS13 proteolytic activity in vitro require the cysteine-rich/spacer region for binding. This finding is consistent with previous studies suggesting that antibodies that bind to the cysteine-rich/spacer region interfere with engagement of ADAMTS13 with VWF substrate (Soejima et al., Blood 2003; 102:3232-7; Akiyama et al., Proc Natl Acad Sci USA 2009; 106:19274-9). The fact that all 13 $V_H$1-69-encoded scFv's in this group require this region for binding is consistent with other reports (Luken et al., J Thromb Haemost 2006; 4:2355-64; Pos et al., J Thromb Haemost 2009; 7:421-8; Schaller et al., Blood 2014; 124: 3469-79) and suggests that there is a feature expressed by $V_H$1-69 (independent of HC-CDR3 that is encoded primarily by the D gene, not $V_H$) that is either permissive or required (but not sufficient vis-a-vis anti-keratinocyte PX4-3 above) for an antibody to recognize features presented by immunodominant residues in cysteine-rich/spacer region-containing domains of ADAMTS13. For scFv's 1-420, 1-416, and 3-301, these results are also consistent with those of a separate study using hydrogen-deuterium exchange mass spectrometry in which their specificity for the ADAMTS13 spacer region was shown at near amino acid resolution (Casina et al., Proc Natl Acad Sci USA 2015; 112:9620-5).

Of the non-$V_H$1-69 inhibitory antibodies, 1-437 maps to a fragment containing the metalloprotease domain (potentially explaining its inhibitory activity), and the idiotope of 1-404 appears to make contact independently with both cysteine-rich/spacer-containing and CUB domains, perhaps stabilizing ADAMTS13 in a "closed" inactive conformation (South et al., Proc Natl Acad Sci USA 2014; 111:18578-83). ScFv 1-410 also binds to both cysteine-rich/spacer-containing domains and TSP 5-8/CUB domains but is not inhibitory. The 7 remaining scFv's target the C-terminal domains and do not inhibit enzymatic activity in vitro. It should be recognized, however, that ADAMTS13 activity assayed by measuring the cleavage of VWF peptides vs. VWF multimers may miss pathogenic effects of certain antibodies including those that target the C-terminal domains of ADAMTS13.

ADAMTS13 Autoantibodies Share Cross-Reactive Idiotypes

The observation that 13 of the 15 inhibitory scFv's in the present subset of antibodies were bound to identical ADAMTS13 regions and were encoded by the same $V_H$ gene suggested that their idiotypes (the areas of their variable regions that make contact with ADAMTS13) shared common structural features. If inhibitory anti-ADAMTS13 antibodies did share idiotypes within and across patients, there would be rationale for developing therapies that recognize these common features to block antibody binding or attenuate their production. However, in general, the most important contributing factors to the structure of an antibody's idiotype are its heavy and light chain CDR3 loops which, for these antibodies, appeared to be quite varied in length and amino acid sequence (Table 2 above and Table 3 below, FIGS. 9A-9B). This would suggest that their idiotypes were quite different.

To explore idiotypic diversity within a set of ADAMTS13 autoantibodies, rabbit antisera were raised to $V_H$1-69-encoded 1-416, 1-420, 1-428, and 1-431. Antibodies 1-416 and 1-428 shared the same heavy chain CDR3 while the heavy chain CDR3's of antibodies 1-420 and 1-431 were each distinct (Table 2) as were the light chain CDR3's in each of the 4 antibodies (Table 3).

TABLE 3

Genetic features and clonality of anti-ADAMTS13 light chains

| Patient | Antibodies grouped by similar LC-LCDR3 | Isotype | $V_L$ family | $V_L$ gene | $J_L$ gene | LC-CDR3 |
|---|---|---|---|---|---|---|
| TTP1 | 1-407, 1-410 | kappa | κ1 | KV1-33*01 | KJ4*01 | QQY(A/D)NLPLT (SEQ ID NO: 230) |
| | 1-403 | kappa | κ1 | KV1-39*01 | KJ4*01 | QQSHNVPLT (SEQ ID NO: 231) |
| | 1-440, 1-451, z1-201 | kappa | κ1 | KV1-39*01 | KJ3*01 | QQSYSTP(F/Y)T (SEQ ID NO: 232) |
| | z1-402 | kappa | κ2 | KV2-28*01 | KJ2*01 | MQALQTPQT (SEQ ID NO: 233) |
| | 1-404, 1-441 | lambda | λ1 | LV1-51*01 | LJ2*01 | GTWDSSLSAVV (SEQ ID NO: 234) |
| | 1-415 | lambda | λ2 | LV2-14*01 | LJ2*01 | SSYTSSSTVV (SEQ ID NO: 235) |
| | 1-437 | lambda | λ2 | LV2-14*01 | LJ1*01 | SSYTSSTPYV (SEQ ID NO: 236) |

TABLE 3-continued

Genetic features and clonality of anti-ADAMTS13 light chains

| Patient | Antibodies grouped by similar LC-LCDR3 | Isotype | $V_L$ family | $V_L$ gene | $J_L$ gene | LC-CDR3 |
|---|---|---|---|---|---|---|
| | 1-458 | lambda | λ3 | LV3-21*01 | LJ2*01 | QVWDRSSDHVV (SEQ ID NO: 237) |
| | 1-432 | lambda | λ3 | LV3-21*02 | LJ3*02 | QVWDSRSDHQV (SEQ ID NO: 238) |
| | 1-438, 1-434 | lambda | λ3 | LV3-21*02 | LJ2*01 | QVWDSSSDH(K/V)V (SEQ ID NO: 239) |
| | z1-303 | lambda | λ3 | LV3-21*02 | LJ2*01 | QVWDSSRDHVV (SEQ ID NO: 240) |
| | 1-423 | lambda | λ3 | LV3-21*03 | LJ3*02 | QVWDSNSDHQV (SEQ ID NO: 241) |
| | 1-401 | lambda | λ3 | LV3-21*03 | LJ2*01 | QVWDSSNDHSV (SEQ ID NO: 242) |
| | 1-417 | lambda | λ3 | LV3-21*03 | LJ7*01 | QVWDSSNDQVV (SEQ ID NO: 243) |
| | 1-303 | lambda | λ3 | LV3-21*03 | LJ1*01 | QVWDSSSDHYV (SEQ ID NO: 244) |
| | 1-420 | lambda | λ3 | LV3-21*03 | LJ2*01 | QVWDSSSDYVV (SEQ ID NO: 245) |
| TTP2 | 2-108 | lambda | λ1 | LV1-47*01 | LJ*01 | AAWDDSLRVYV (SEQ ID NO: 255) |
| | 2-102 | lambda | λ3 | LV3-21*02 | LJ3*02 | QVWDSRSDYWV (SEQ ID NO: 256) |
| | 2-103 | lambda | λ3 | LV3-21*02 | LJ3*02 | QVWDSSSDHWV (SEQ ID NO: 257) |
| | 2-106 | lambda | λ3 | LV3-21*02 | LJ3*02 | QVWDSSSDHWV (SEQ ID NO: 257) |
| | 2-406 | lambda | λ3 | LV3-21*02 | LJ3*02 | QVWESSSDHWV (SEQ ID NO: 258) |
| | 2-204 | lambda | λ3 | LV3-21*02 | LJ1*01 | QVWESTTDHYV (SEQ ID NO: 259) |
| | 2-305 | lambda | λ3 | LV3-21*02 | LJ3*02 | QVWDSNSDHWV (SEQ ID NO: 260) |
| | 2-301 | lambda | λ3 | LV3-21*02 | LJ3*02 | QVWHSSSDHWV (SEQ ID NO: 261) |
| | 2-207 | lambda | λ3 | LV3-21*02 | LJ3*02 | QVWDSSSDHWV (SEQ ID NO: 257) |
| | 2-304 | lambda | λ3 | LV3-21*02 | LJ3*02 | QVWDSSSDHWV (SEQ ID NO: 257) |
| | 2-203 | lambda | λ3 | LV3-21*02 | LJ3*02 | QVWDSSSDHWV (SEQ ID NO: 257) |
| | 2-206 | lambda | λ3 | LV3-21*02 | LJ3*02 | QVWDSSSDHWV (SEQ ID NO: 257) |
| | 2-302 | lambda | λ3 | LV3-21*02 | LJ3*02 | QVWESSSDHWV (SEQ ID NO: 258) |
| | 2-408 | lambda | λ3 | LV3-21*02 | LJ2*01 | QVWDSSSDHVV (SEQ ID NO: 262) |
| TTP3 | 3-302 | lambda | λ3 | LV3-1*01 | LJ2*01 | QVWESSSDHLV (SEQ ID NO: 263) |

TABLE 3-continued

Genetic features and clonality of anti-ADAMTS13 light chains

| Patient | Antibodies grouped by similar LC-LCDR3 | Isotype | $V_L$ family | $V_L$ gene | $J_L$ gene | LC-CDR3 |
|---|---|---|---|---|---|---|
| | 3-405 | lambda | λ3 | LV3-21*01 | LJ2*01 | QVWDSSSDQRV (SEQ ID NO: 264) |
| | 3-305 | lambda | λ3 | LV3-21*03 | LJ3*02 | QVWDSSSDHWV (SEQ ID NO: 257) |
| | 3-301 | lambda | λ3 | LV3-25*03 | LJ3*02 | QSADSNGTYKV (SEQ ID NO: 265) |
| TTP4 | 4-303 | lambda | λ3 | LV3-21*01 | LJ2*01 | EVWDSLTDRVV (SEQ ID NO: 266) |
| | 4-307 | lambda | λ3 | LV3-21*01 | LJ2*01 | QVWDSSSDQGV (SEQ ID NO: 267) |

Legend for Table 3:
Antibody nomenclature same as in Table 2.
LC-CDR3 indicates light chain complementarity determining region 3
Each line indicates one or more light chains with the identical LC-CDR3 and VL and JL consistent with those light chains being clonally related.
Antibodies listed on separate lines that have identical LC-CDR3 have patterns of somatic mutation in their VL and/or JL that suggests different clonal origins (See FIG. 9B).

Figure 3A:
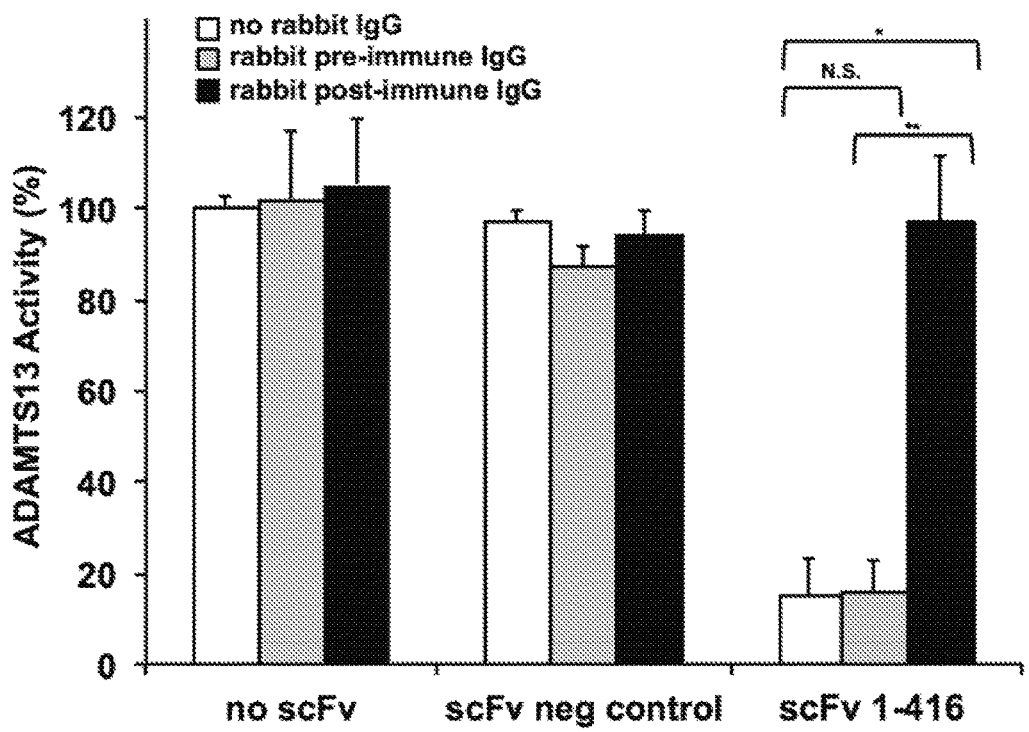
FIGS. 3A-3C are series of histograms demonstrating that ADAMTS13 inhibitory antibodies are blocked by rabbit anti-idiotypic IgG.

Binding of post-immune rabbit IgG to its scFv immunogen was ~100-fold greater than pre-immune IgG by ELISA. Post-immune, but not pre-immune, IgG blocked its respective scFv's ability to inhibit ADAMTS13 as illustrated for 1-416 (FIG. 3A). Similar patterns of reactions were found for rabbit IgG raised against 1-420, 1-428, and 1-431. The ability to block scFv-mediated inhibition of ADAMTS13 was not simply due to rabbit IgG molecules directed to human isotype (e.g., Fcγ) because scFv have no isotype (they comprise only $V_H$ and $V_L$ chains). The ability to block scFv-mediated inhibition could not be due to rabbit IgG being directed to conserved human $V_H/V_L$ framework regions or even to conserved $V_H$1-69-specific structural elements because the ability of rabbit IgG raised against 1-428 to block 1-428's inhibition of ADAMTS13 was unaffected by the presence of 8-fold excess human $V_H$3-33-encoded E1M2 (an anti-Rh(D) scFv) or human $V_H$1-69-encoded PX4-3 (an anti-keratinocyte scFv, FIG. 3B). In the present investigation, the amount of rabbit IgG was titered down to the point of just being able to block 1-428 in order to increase its sensitivity to any effects of E1M2 or PX4-3.

To explore whether the idiotypes among the four scFv's share common features, anti-idiotypic IgG raised against a given scFv was tested for its ability to block the inhibition of ADAMTS13 by the other 3 scFv's. To increase the sensitivity of these assays, the amounts of scFv used were 2.5-fold less than the amounts used in FIGS. 1A-1B. As shown in Table 4, there was evidence of broad cross reactivity among 3 of the 4 scFv. Marked inhibition of ADAMTS13 by 1-420 could not be blocked by anti-idiotypic IgG to any of the other 3 scFv's nor could anti-idiotypic IgG raised against 1-420 block the inhibition of ADAMTS13 by the other 3 scFv's. This finding served as a convenient internal control showing that the rabbit IgG were not acting by binding to common human or $V_H$1-69 structures. This finding also suggested that for inhibitory antibodies directed to cysteine-rich/spacer region-containing domains, $V_H$1-69 features alone did not define the antibody's idiotype.

These data suggest that with one exception, a small set of ADAMTS13 inhibitory monoclonal antibodies derived from a single TTP patient share idiotypic determinants that can be targeted to prevent inhibition of ADAMTS13. The larger question is how representative these idiotypes are of the repertoire of idiotypes of polyclonal inhibitory immunoglobulin in the plasma of patients other than TTP1 from which the scFv's were derived.

TABLE 4

Blocking of scFv-induced ADAMTS13 inhibition by rabbit anti-idiotypic IgG

| Rabbit IgG added | % ADAMTS13 activity in presence of scFv inhibitor | | | |
|---|---|---|---|---|
| | scFv 1-416 | scFv 1-420 | scFv 1-428 | scFv 1-431 |
| none | 20* | 0 | 7* | 19* |
| anti-scFv 1-416 | 93 | 0 | 84 | 13 |
| anti-scFv 1-420 | 0 | 99 | 0 | 0 |
| anti-scFv 1-428 | 75 | 8 | 100 | 72 |
| anti-scFv 1-431 | 70 | 3 | 94 | 92 |

*Residual ADAMTS13 activities with scFv's alone are higher than in FIGS. 1A-1B because a 2.5-fold lower amount of scFv was used in order to increase sensitivity of blocking scFv by rabbit IgG To address this question, inhibition of ADAMTS13 by plasma from TTP4 and three additional TTP patients (TTP5-TTP7) was measured in the presence of anti-idiotypic IgG. As shown in FIG. 3C, inhibition of ADAMTS13 by polyclonal patient plasma-derived immunoglobulin was blocked to varying extents by anti-idiotypic IgG generated to a single monoclonal scFv from a completely unrelated TTP patient. The ability to block ADAMTS13 inhibition was striking in some cases (e.g., TTP7) with each of the anti-idiotypic IgG. These results could not be attributed to rabbit antibodies to patient IgG Fc domains because the rabbits were immunized with scFv. That rabbit antisera might have pre-existing reactivity to human IgG was ruled out through the use of preimmune sera. Therefore, these data provide support for the clinical relevance of these cloned scFv's and suggest their use as targets for the design of small molecules that could block enough ADAMTS13 inhibitory IgG to raise ADAMTS13 activity above a clinical threshold.

IP Injections of Human Anti-ADAMTS13 scFv Cross React and Inhibit Murine ADAMTS13 In Vivo Data presented herein describes a set of human monoclonal anti-ADAMTS13 single chain antibody fragments (scFv's) cloned from four unrelated TTP patients that displayed characteristics in vitro one would expect from disease-related pathogenic antibodies, e.g., ability to inhibit ADAMTS13 enzymatic activity, epitope specificities shared with patient plasma IgG, etc. To test the clinical relevance of these recombinant antibodies and to provide an in vivo system for studying the pathophysiology of TTP, these in vitro findings were extended to the development of a murine model of acquired TTP.

First, human scFv antibody fragments were screened for their ability to inhibit the activity of murine plasma ADAMTS13 in vitro, and the majority of scFv's that inhibited human ADAMTS13 activity were found to also inhibit murine ADAMTS13. Of the human scFv's that cross reacted with murine ADAMTS13, antibody clones 1-416, 1-420, 1-428, and 1-431 were chosen to pursue because characterization of these antibodies in vitro showed potent inhibition of ADAMTS13 activity, binding to human ADAMTS13 epitopes most commonly targeted by patient plasma IgG, and idiotopes shared by patient plasma IgG.

Figure 4A:
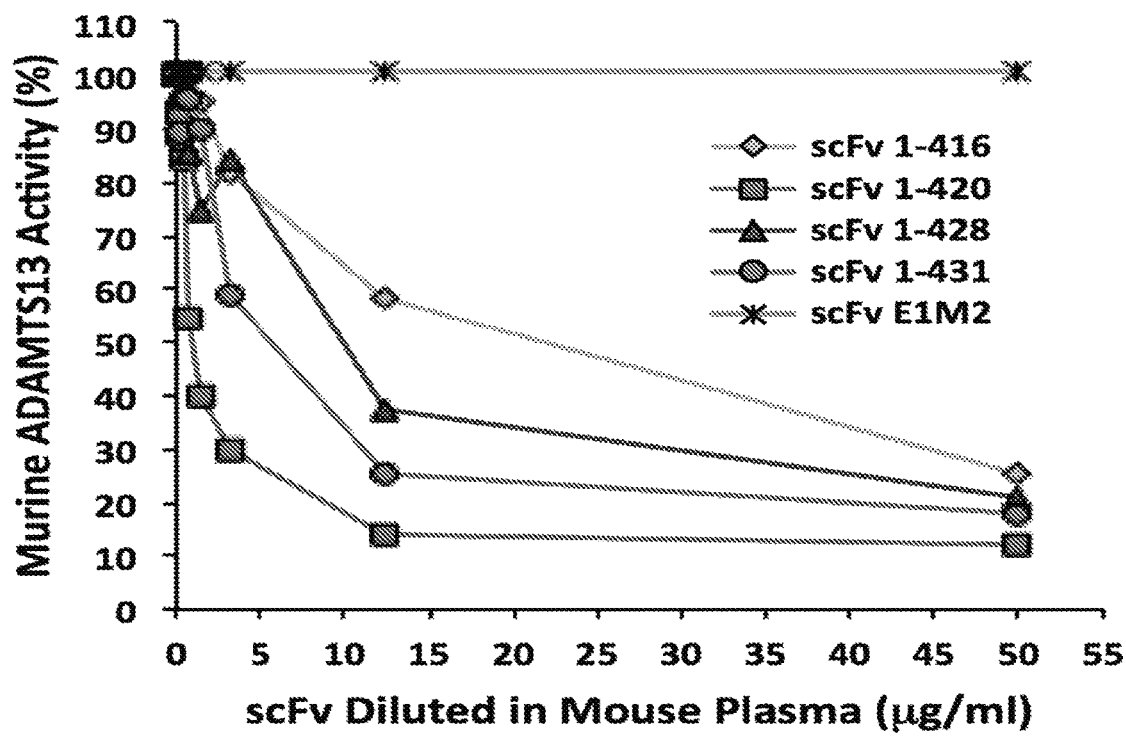
FIGS. 4A-4B are series of graphs illustrating the inhibition of murine ADAMTS13 by human anti-ADAMTS13.
Figure 4B:
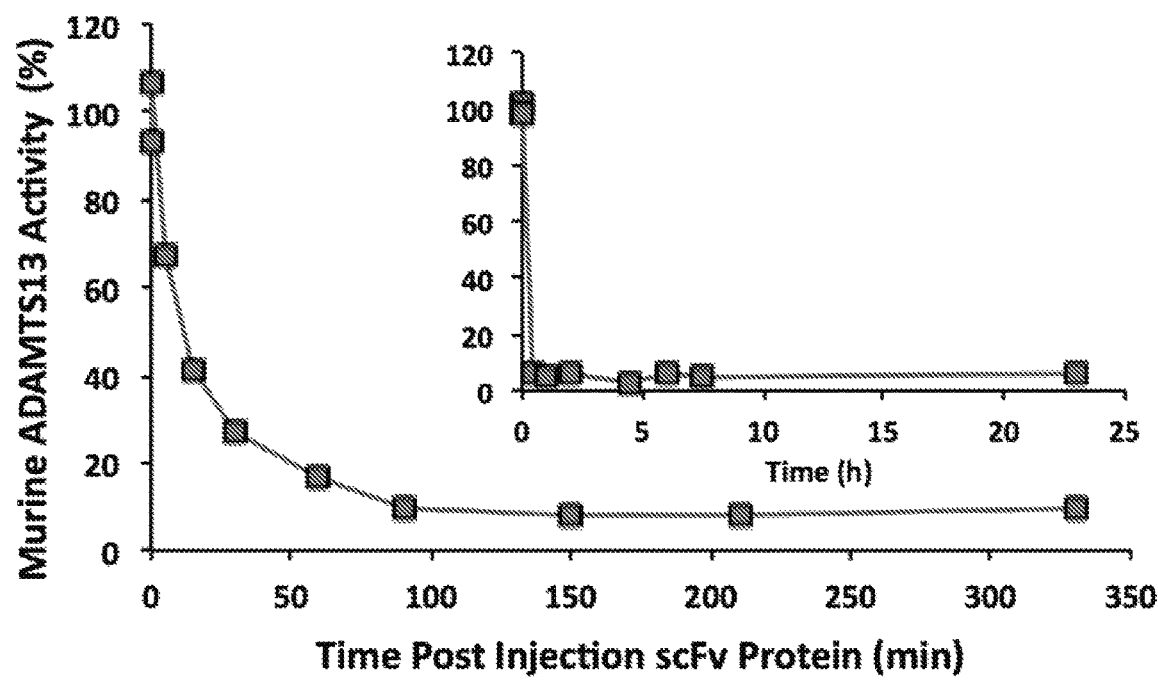

Dose response inhibition curves with mouse plasma revealed 1-420 to be most potent (FIG. 4A) so it was chosen for evaluation in vivo. Mice were given intraperitoneal injections of 30 μg 1-420 and mouse plasma showed rapid inhibition of ADAMTS13 resulting in <10% pre-injection activity within ~2 hours (FIG. 4B) which persisted for ~24 hours (FIG. 4B, inset).

Figure 5A:
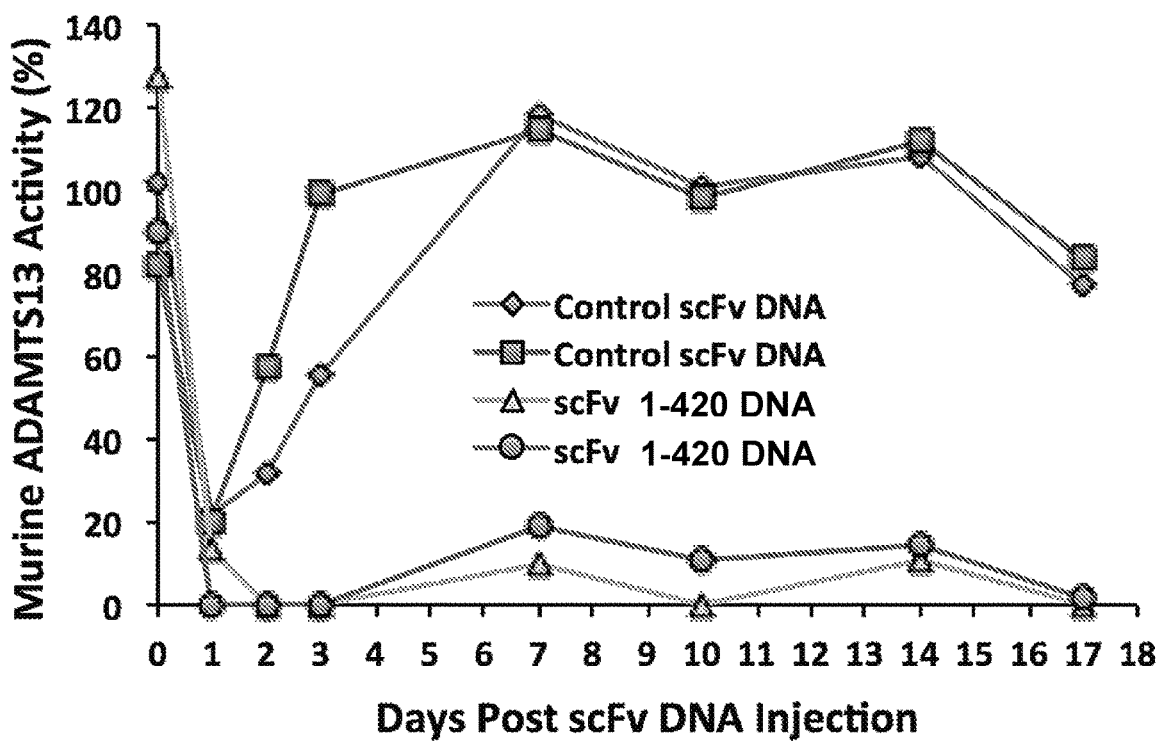
FIGS. 5A-5C are series of graphs and histograms illustrating the inhibition of murine ADAMTS13 by in vivo-expressed human anti-ADAMTS13 scFv.

Transfection of Mouse Liver with scFv cDNA Leads to Prolonged ADAMTS13 Deficiency Next, a sustained antibody-mediated ADAMTS13 deficiency was created in order to simulate TTP disease and observe the effect of such deficiency on thrombus formation in the settings of focal and systemic vascular injury. To accomplish this, the cDNA for scFv 1-420 was cloned into the pLIVE plasmid vector, a vector designed for the hydrodynamic gene transfer of naked DNA. The vector was modified to facilitate the insertion of phage display-derived scFv antibody fragment cDNA's upstream of a liver-specific promoter composed of the minimal mouse albumin promoter and the mouse a-fetoprotein enhancer (FIG. 11). Tail vein injection of a 2-mL solution of pLIVE plasmid over 4-7 seconds delivers the scFv cDNA to mouse liver by hydrostatic force. Both control scFv cDNA and 1-420-containing plasmids initially led to a drop in ADAMTS13 activity in vivo for several days that was then followed by recovery of ADAMTS13 in the control group after the expected physiological effects of rapid hydrodynamic injection of a one blood volume-equivalent through the portal circulation to the liver resolved. Inhibition of ADAMTS13 activity by in vivo-expressed 1-420 persisted for over 2 weeks (FIG. 5A) and for as long as 3 months.

Figure 5B:
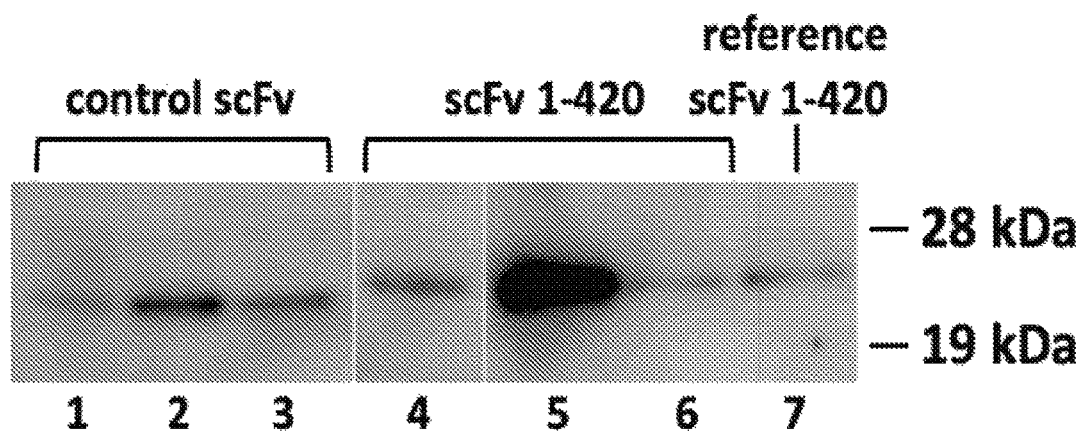
Figure 5C:
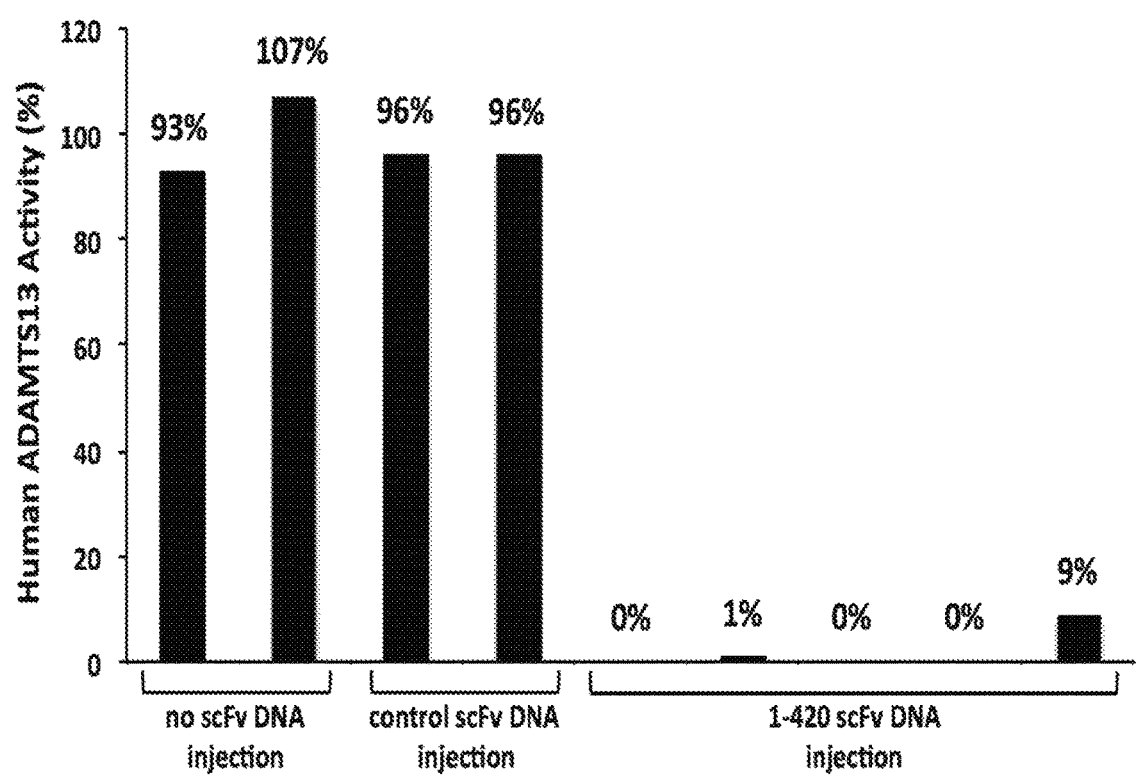

That the recombinant human antibodies were expressed in mouse plasma was confirmed by immunoprecipitation of scFv 7 days after scFv DNA vector injection (FIG. 5B). To estimate plasma levels of scFv in vivo, an aliquot of normal mouse plasma was spiked with 20 ng of recombinant 1-420, and immunoprecipitation was performed in parallel. Quantification using the spiked sample as a reference led to estimates of 0.4-0.8 μg/ml mouse plasma for scFv's from 3 control mice and 0.4-10 μg/ml mouse plasma for 1-420 from 3 experimental mice. If the concentration of mouse plasma ADAMTS13 was similar to that in humans (~1 μg/ml), the stoichiometric ratio of scFv to ADAMTS13 was ~3 to ~5 except for one of the 1-420 mice in which it was ~10-fold higher. Excess unbound plasma scFv was affirmed by mixing plasma derived from cDNA-transfected mice 1:1 with normal human plasma, analogous to the "inhibitor assay" used clinically to diagnose patients with antibody-mediated ADAMTS13 deficiency (FIG. 5C).

Figure 6A:
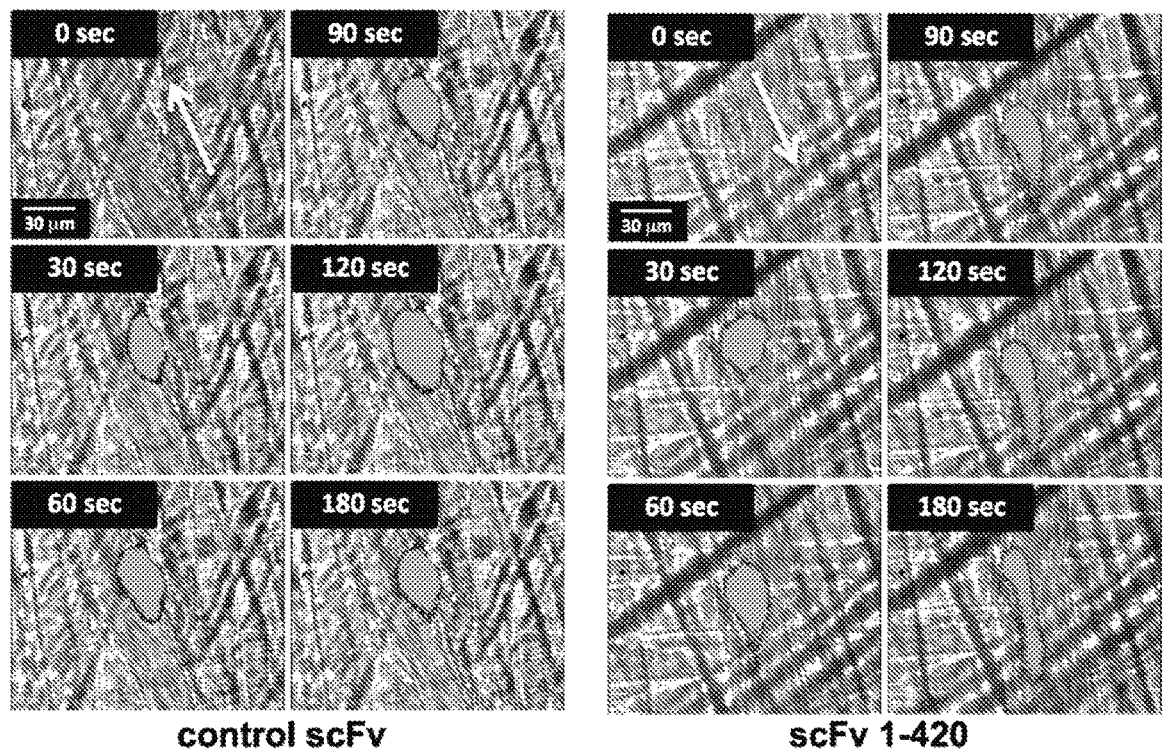
FIGS. 6A-6B are series of graphs exemplifying the platelet thrombus formation after cremaster arteriole injury in mice transfected with human anti-ADAMTS13 cDNA.
Figure 6B:
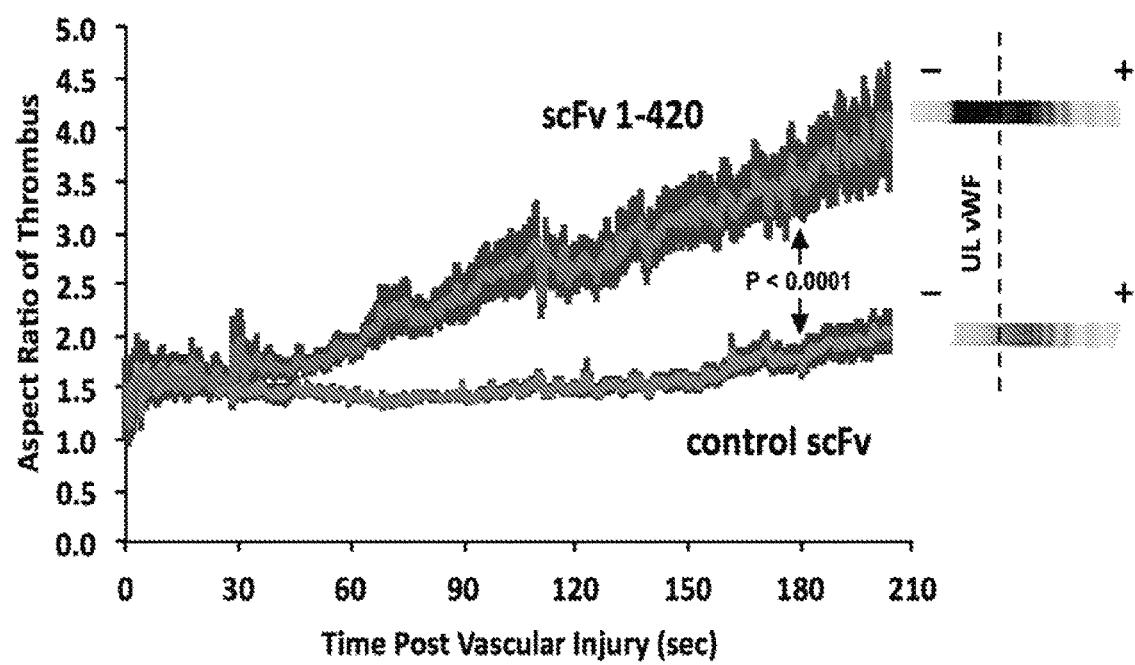

Laser-Induced Vascular Injury in scFv-Transfected Mice Leads to Thrombus Elongation The data described herein demonstrate that DNA transfection of human anti-ADAMTS13 antibodies using hydrodynamic delivery leads to rapid and stable ADAMTS13 inhibition in vivo. Next the effects of ADAMTS13 inhibition on the temporal and spatial aspects of platelet thrombus formation was examined in these mice using the cremaster arteriole laser injury model (FIG. 6A). Thrombi in control mice enlarged spherically around the ~1 μm injury site to a diameter of ~30 μm and then remained relatively constant in size during the 3-minute observation period due to frequent embolization. In clear contrast, thrombi in ADAMTS13-inhibited mice grew in an asymmetrically elongating fashion to a length >80 μm beyond the injury site (P<0.0001) consistent with the presence of strings of unprocessed UL-VWF multimers, although a contribution from adhesion of plasma VWF multimers to the damaged vasculature could not be excluded. Length/width aspect ratio measurements of thrombi quantified these differences (FIG. 6B). Agarose gel electrophoresis of plasma confirmed the presence of UL-VWF multimers in mice expressing 1-420 (FIG. 6B, inset) relating the findings to underlying mechanism.

Shigatoxin Challenge Induces the TTP Phenotype in scFv-Transfected Mice

Figure 7A:
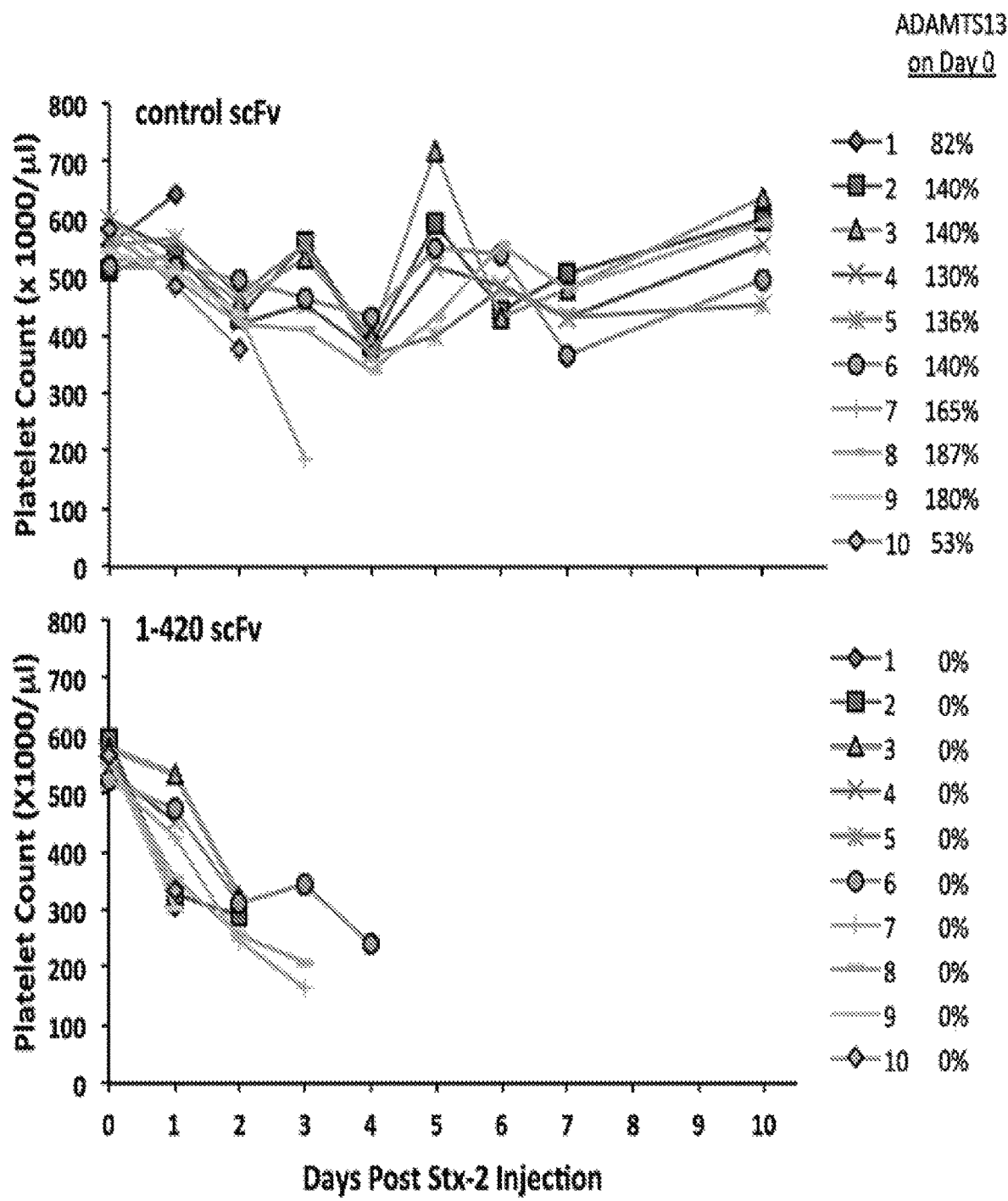
FIGS. 7A-7C are series of graphs illustrating thrombocytopenia, thrombus formation, and death after injection of Shigatoxin-2 in mice transfected with human anti-AD-AMTS13 cDNA.

Though pathogenesis of TTP has been linked to ADAMTS13 deficiency, the natural history of the disease has suggested that additional genetic or environmental factors were required for the onset of disease. In murine models of congenital TTP that a state of ADAMTS13 deficiency was induced genetically, the administration of the bacterial agent Shigatoxin-2 (Stx-2) was found to precipitate disease phenotype presumably due to endothelial injury. To further test the clinical relevance of the cloned human scFv, it was determined whether "TTP" could be induced in mice expressing human anti-ADAMTS13 inhibitory antibodies following challenge with Stx-2. CAST/Ei strain mice, which have 5 times more circulating VWF and are sensitive to the development of TTP in ADAMTS13 knock-out mice, were injected hydrodynamically with scFv 1-420 or scFv X24-3 control antibody plasmid, challenged with a sublethal dose of Stx-2 10 days later after full recovery from the side effects of hydrodynamic challenge, and followed for an additional 10 days. As shown in FIG. 7A, 6 of 10 control mice survived and maintained platelet counts in the normal range throughout the 10-day post-Stx-2 period. However, all mice (10/10) rendered ADAMTS13 deficient by scFv 1-420 died by day 4 post-Stx-2 (half within 24-48 hours of injection, FIG. 7B) and each suffered a fall in platelet count to less than one-third its starting value. Schistocytes were seen on peripheral blood smear and thrombi were readily detected in brain, heart and kidney (FIG. 7C, right panel), but not in control animals (FIG. 7C, left panel) that had died from Stx-2 challenge alone. These experiments demonstrated that the in vivo expression of the variable region of a single human anti-ADAMTS13 inhibitory antibody fragment in mice sufficed to mediate the most salient features of TTP in an animal model.

Acquired TTP is a potentially fatal disease with a mortality that has remained relatively constant over the past 25 years despite improvements in diagnosis, early initiation of therapy, and the use of adjunctive immunosuppressive agents when plasma exchange alone is not entirely effective. An understanding of the repertoire of ADAMTS13 autoantibodies on a molecular level is a prerequisite to the development of innovative, targeted therapies and to the design of animal models to evaluate such approaches.

By analogy to acquired TTP, pemphigus vulgaris is a potentially fatal blistering skin disease caused by autoantibodies to the keratinocyte adhesion protein desmoglein. Current therapies are non-specific and limited to systemic immunosuppression. Previous studies conducted in the laboratory using an antibody phage display cloning approach similar to that used in the study described herein were successful in defining the genetic origins of pathogenic and non-pathogenic desmoglein autoantibodies and their autoepitopes. This information has recently facilitated the engineering of T lymphocytes expressing novel chimeric autoantibody/T cell receptors that specifically kill anti-desmoglein antibody producing cells and lead to prolonged survival in a mouse model of pemphigus vulgaris. Critical to the success of these studies was the ability to clone repertoires of desmoglein autoantibodies that were representative of the diversity of epitope specificities contained within patient plasma, and the ability to assess the clinical relevance of the cloned antibodies in an animal model of the disease. To apply this approach for destruction of anti-ADAMTS13 producing B cells, or for the development of other targeted therapeutic approaches for acquired TTP, such as autoantibody blocking with idiotype-directed agents or the use of ADAMTS13 preparations engineered to lack such idiotypes, an animal model utilizing human autoantibodies recognizing human autoepitopes would be required. To date, animal models of the disease have been limited to the use of xenoantibodies to human ADAMTS13 made in rabbits or mice to simulate disease pathophysiology in mice or baboons, respectively.

Though the plasma of patients with acquired TTP contains IgG to multiple domains of ADAMTS13, it is only those directed at the spacer domain that human monoclonal antibodies have been described so far (Luken, et al., J. Thromb. Haemost., 2006, 4:2355-2364, Pos, et al., J. Thromb. Heamost., 2009, 7:421-428, and Schaller, et al., Blood 2014, 124:3469-3479). It is unknown whether anti-ADAMTS13 autoantibodies directed to epitopes other than those expressed within the spacer domain are inhibitory or may in some other way contribute to disease pathogenesis. Furthermore, no animal models for assessing the clinical relevance of cloned human ADAMTS13 autoantibodies have been described.

In the current study, 51 unique human ADAMTS13 autoantibodies from 4 unrelated TTP patients with respect to their genetic origins, clonality, and ADAMTS13 inhibitory activity were cloned and characterized. Although 75% of the antibodies used the $V_H1$-69 heavy chain and bound to epitopes in the Cys-rich/spacer domain, antibodies encoded by 6 other $V_H$ genes were also represented in the group and included specificities for each of the domains targeted by IgG in a large cohort of patient plasmas (Table 2, FIG. 3). With respect to antibody light chains, the cohort of antibodies described herein was encoded by a large diversity of light chain germline genes with the use of lambda light chain gene segments predominating (Table 2). The relatively high prevalence of lambda light chain usage was also seen in both antibody phage display technology and single B cell cloning in 2 TTP patients (Schaller, et al., Blood, 2014, 28:3469-3479). Kappa light chains dominated anti-ADAMTS13 antibodies in a set of 9 antibodies described previously using phage display (Luken, et al., J. Thromb. Haemost., 2006, 4:2355-2364; Pos, et al., J. Thromb. Heamost., 2009, 7:421-428), but the light chains in those antibodies were derived from a normal healthy donor so the relationship of the associated light chains to those present in the TTP patients in these studies was not clear.

Analysis of the heavy chain CDR3 regions within the cohort of antibodies described herein indicates that they were derived from the clonal expansion of 30 individual B cells across the 4 TTP patients (Table 2, FIGS. 9A and 9B). This relatively large number of clonally-unrelated anti-ADAMTS13 antibodies may explain the diversity in epitope specificities that was found (FIG. 3) when compared to antibodies characterized in previous studies derived from 6 (Pos, et al., J. Thromb. Heamost., 2009, 7:421-428) and 12 (Schaller, et al., Blood 2014, 124:3469-3479) B cell clonotypes where all but one antibody were identified as being specific to the spacer domain. Analysis of the pattern of somatic mutation in nearly half of the 30 B cell clonotypes showed replacement-to-silent mutation ratios greater than 4.7 in heavy chain CDR1 and CDR2 regions (FIG. 9A) that is characteristic of antigen-driven clonal expansion in the setting of autoimmune disease. These observations along with predominant use of a particular heavy chain germline gene ($V_H1$-69) were analogous to those found previously for human alloantibodies to the red cell Rh(D) antigen ($V_H3$-33 gene), for human autoantibodies against platelets in ITP ($V_H3$-30 gene), and to human autoantibodies against desmoglein that cause pemphigus vulgaris ($V_H1$-46 gene).

Initial observations identifying the use of the $V_H1$-69 heavy chain gene for spacer domain-specific inhibitory antibodies cloned from TTP patients led investigators to hypothesize a "shape complementarity" between $V_H1$-69-encoded variable domain residues and exposed exosites in the spacer domain. It was noted that the heavy chain CDR2 of the $V_H1$-69 germline gene contained a unique hydrophobic "Ile-Ile-Pro-Ile-Phe" motif that might facilitate interaction with hydrophobic residues present on the antigenic surface of the spacer domain, including Tyr661 and Tyr665 (Akiyama, et al., PNAS, 2009, 106:19274-19279). More recently, four additional $V_H1$-69-encoded spacer domain-directed patient antibodies were reported that also have an "Ile-Ile-Pro-Ile-Phe" in their CDR2 (Schaller et al., Blood 2014; 124:3469-79). Alignment of these seven previously-reported $V_H1$-69-encoded antibodies bearing this CDR2 motif with the 38 $V_H1$-69-encoded antibodies reported herein revealed some variability in amino acid residues occupying these CDR2 positions, though much of the variability was conservative (FIG. 8). The variability was, in part, because only certain alleles of the $V_H1$-69 gene (e.g., 1-69*01) encoded the "Ile-Ile-Pro-Ile-Phe" motif that was described initially. Of note, 37 of the 38 $V_H1$-69-encoded antibodies were derived from 1-69*09 or 1-69*10 alleles that have a leucine at position 62. Overall, all antibodies retained a proline at position 58, and two of the previously-reported antibodies, II-1 and 3b have substituted a tyrosine for the phenylalanine at position 62.

Figure 3B:
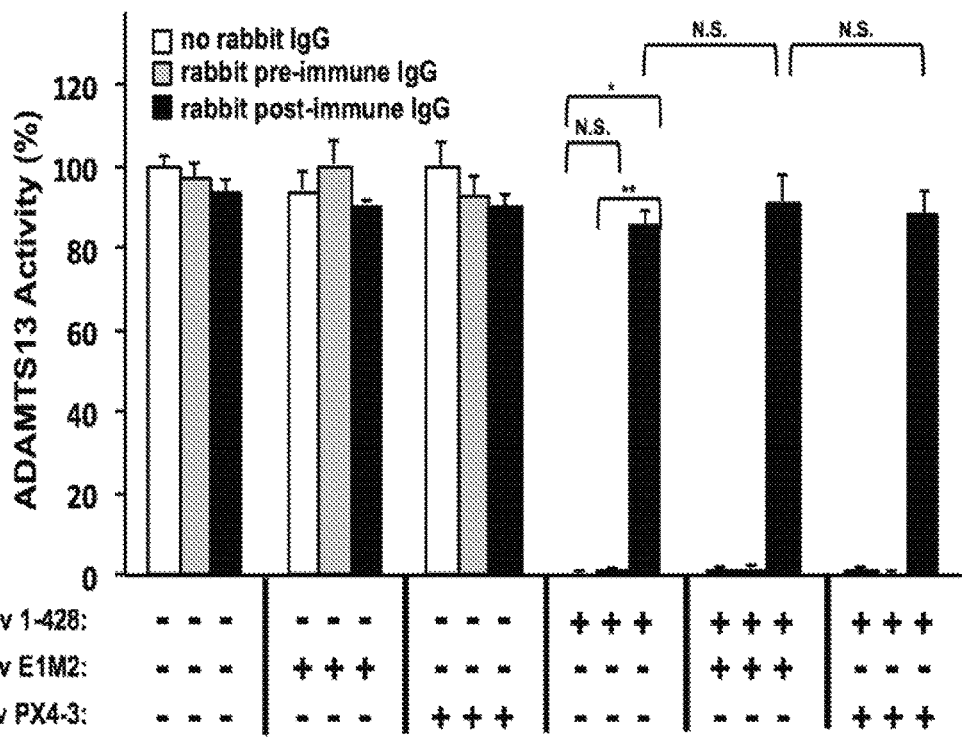
Figure 3C:
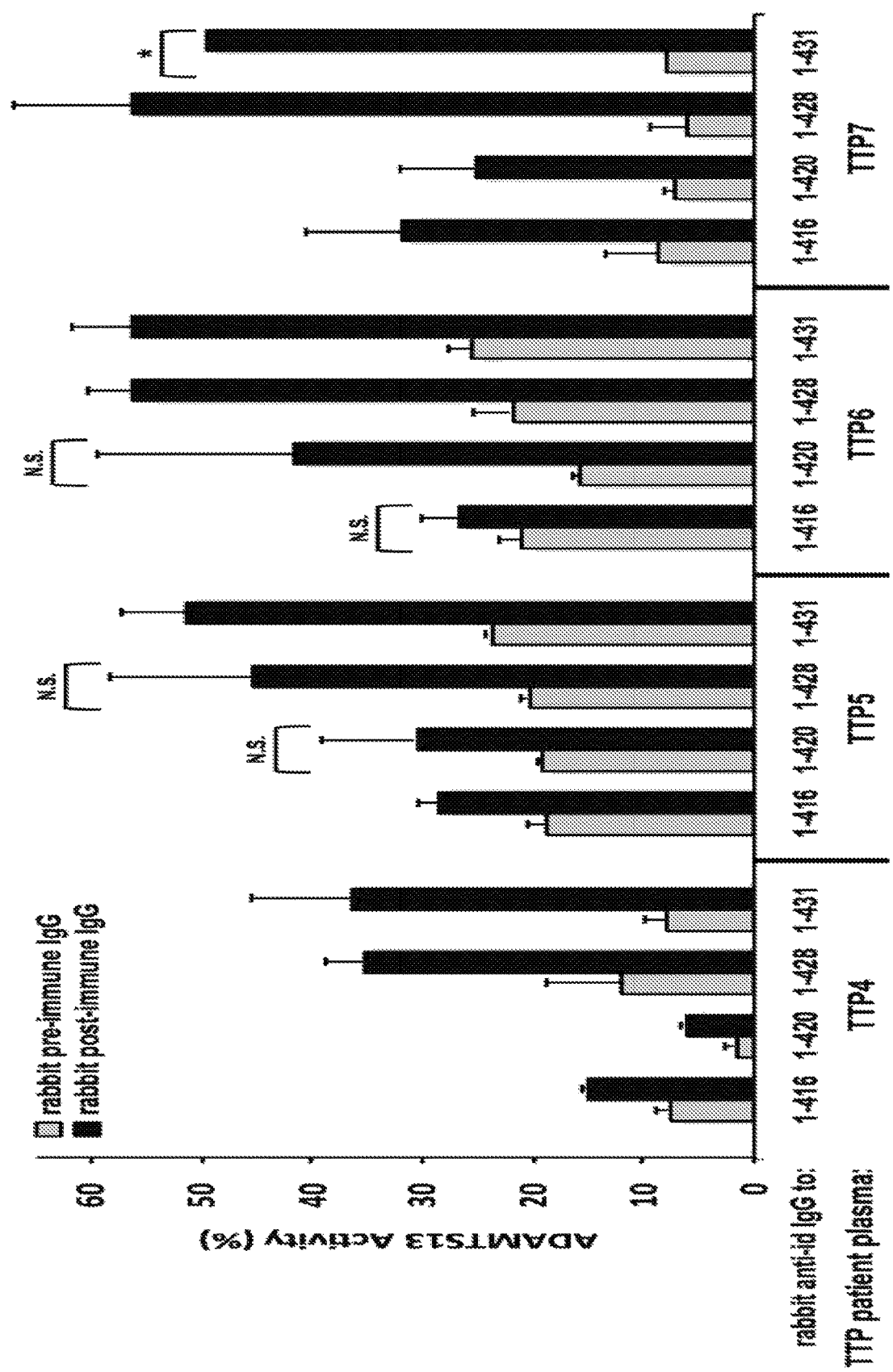

Also shown in FIG. 8, is the CDR2 region of PX4-3, a $V_H1$-69-encoded anti-keratinocyte autoantibody that did not bind to or inhibit ADAMTS13 (FIGS. 1A-1B) or prevent anti-idiotypic IgG from neutralizing ADAMTS13 inhibitory scFv (FIG. 3B). Unless amino acid residues isoleucine, valine, or methionine at position 59 could not be replaced by threonine as in PX4-3, the present results suggest that the hydrophobic CDR2 motifs of $V_H$1-69-encoded heavy chains could not be solely responsible for ADAMTS13 binding. The present findings that anti-idiotypic IgG cross react and block ADAMTS13 inhibition mediated by 1-416, 1-428, and 1-431, but not 1-420 (Table 4), when considered in the context of their CDR2 residues (FIG. 8), also suggest that the idiotopes of spacer domain-directed $V_H$1-69-encoded inhibitory antibodies comprise more than just their $V_H$ CDR2 regions.

The collection of anti-ADAMTS13 autoantibody clones described herein closely mimics the diversity of ADAMTS13 binding domains found in the plasma of patients with acquired TTP. The idiotypic relatedness of the present set of inhibitory antibodies to patient IgG supported their clinical relevance and might serve as useful targets for the design of therapeutic agents that block IgG binding.

Given the observation that viral infections often precede initial or recurrent episodes of TTP, it has also been suggested that preferential use of $V_H$1-69 to encode ADAMTS13 autoantibodies may have resulted from the presence of pre-existing, cross-reactive antibodies to the hemagglutinin (HA) ectodomain of influenza A virus, which also preferentially use the $V_H$1-69 germline gene. Twelve of the 38 $V_H$1-69-encoded antibodies (1-416, 1-420, 1-428, 1-431, 1-303, 1-438, 1-434, 2-102, 2-103, 3-301, 3-302 and 3-405) did not bind to the hemagglutinin ectodomain of four strains of influenza virus (H1/PR/8/34, H3/Perth/16/2009, H3/Perth/1609, and H5/Vietnam/1203/2004) by either immunoassay or flow cytometry. These results, however, do not rule out the possibility that infection with influenza activated a pool of naïve B-cells that underwent somatic mutation and divergence into distinct populations of HA-binding and ADAMTS13-binding clones. It may be possible to test this hypothesis by panning a TTP patient antibody libraries for HA binders and comparing HC-CDR3 domains with ADAMTS13 antibodies for identical $V_H$-D-$J_H$ rearrangements within the same patient.

Described in this invention are the first examples of human antibodies specific for ADAMST13 amino-terminal (MDT1) and carboxy-terminal (T5-8/CUB) domains, and their apparent diversity in $V_H$ gene usage (Table 2) contrasts significantly to the marked $V_H$1-69 restriction of antibodies targeting ADAMTS13 domains containing the cysteine-rich/spacer region. Antibodies directed toward these amino- and carboxy-terminal domains are known to be present in TTP patient plasma and correlate with platelet count at disease onset (Zheng et al., Haematologica 2010; 95:1555-62), but their ability to inhibit ADAMTS13 proteolytic activity has not been demonstrated. In the present invention, MDT1-binding 1-437 was found to be a potent inhibitor as any cysteine-rich/spacer region-directed antibody, perhaps by interfering with catalysis mediated by the metalloprotease domain. The present antibody cohort includes 6 CUB-specific antibodies and one TSP 2-8/CUB-specific antibody, none of which inhibit ADAMTS13 activity as assessed by cleavage of VWF peptide. However, 1-404 is an inhibitory antibody and independently binds to cysteine-rich/spacer-containing fragments and CUB regions, suggesting that its epitope comprises amino acid residues located in both regions. In light of recent reports proposing that ADAMTS13 normally circulates in a "closed" inactive form comprising an intramolecular CUB-to-spacer binding interaction subject to allosteric activation by VWF (Muia et al., Proc Natl Acad Sci USA 2014; 111:18584-9; South et al., Proc Natl Acad Sci USA 2014; 111:18578-83), the antibody 1-404 may be exemplary of a class of autoantibodies that exert their pathogenic effect by stabilizing the enzyme's closed conformation. Though CUB-binding antibodies could reduce ADAMTS13 activity by enhanced clearance or by inhibiting other functions of the protease, they might function synergistically to stabilize the enzyme in an open conformation allowing spacer domain-specific antibodies to bind and block VWF binding to ADAMTS13.

Figure 7B:
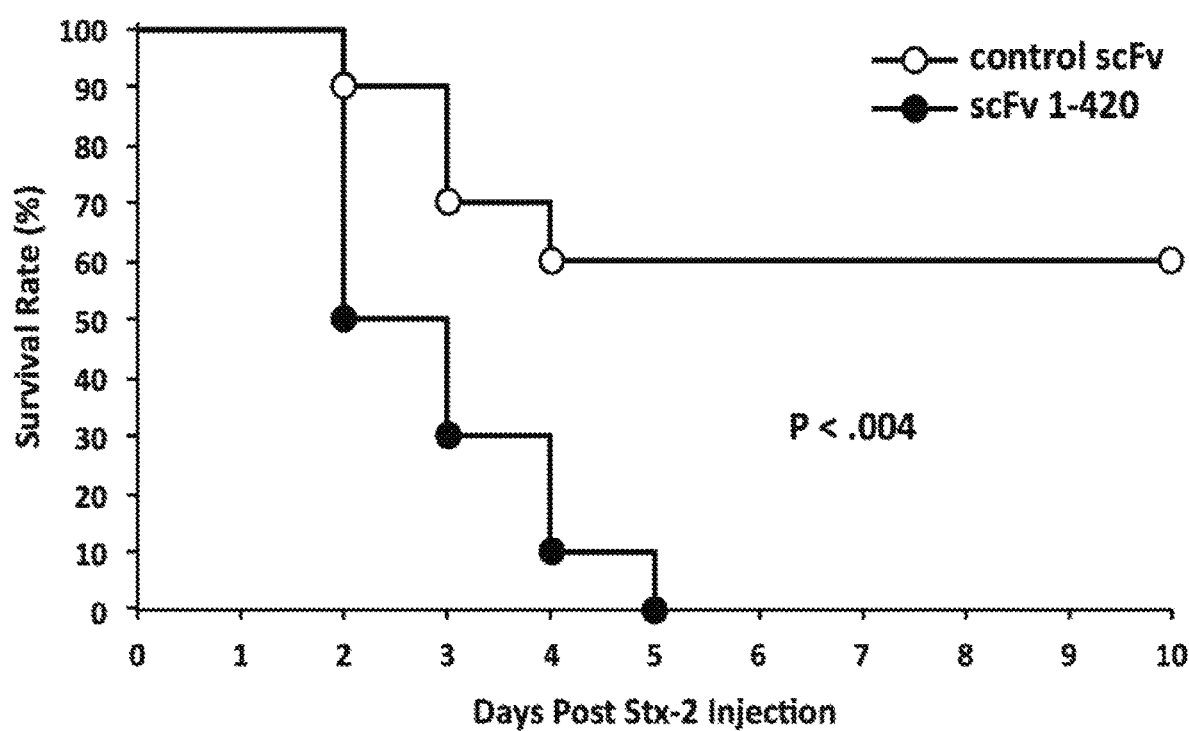
Figure 7C:
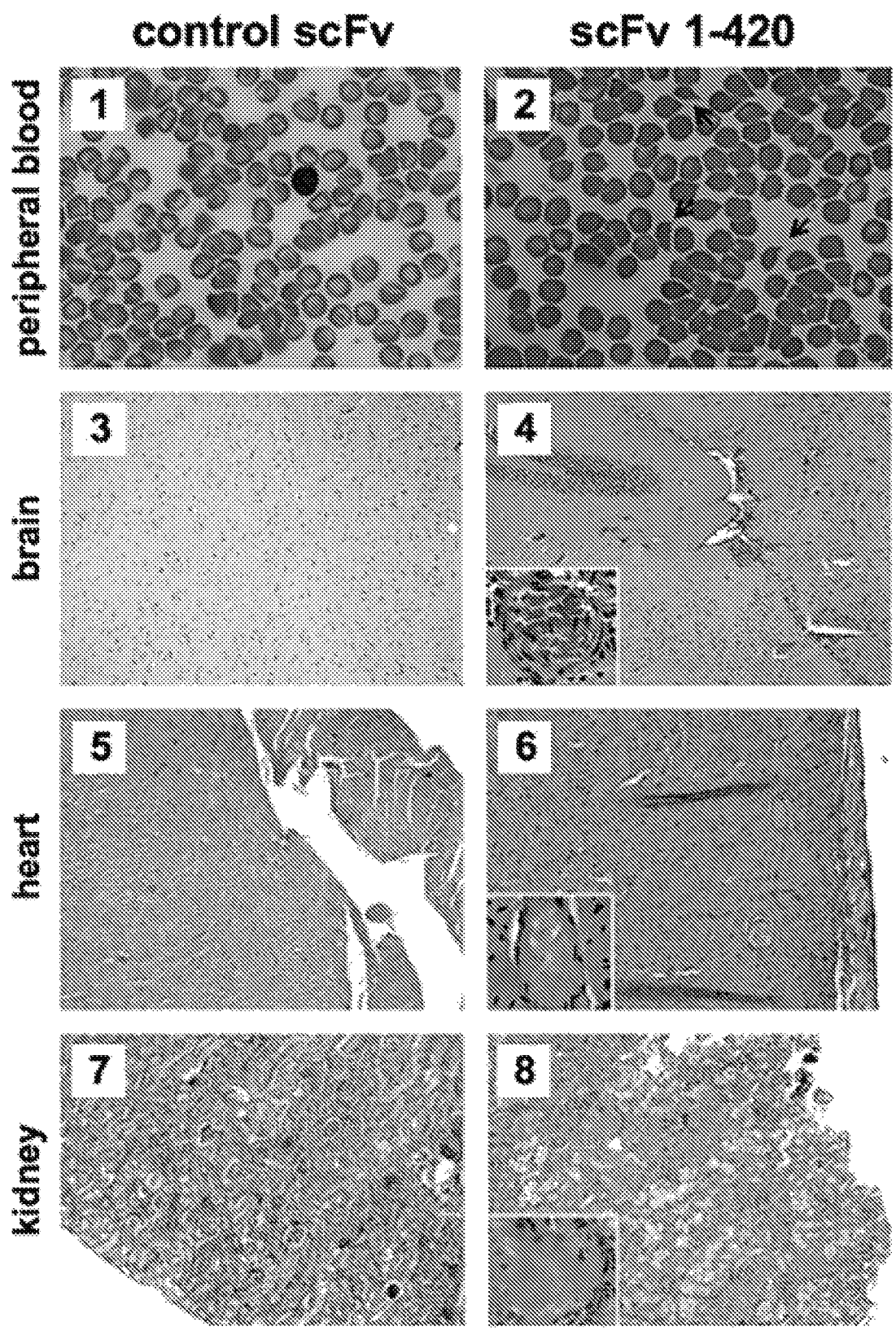

The present invention discloses human anti-ADAMTS13 autoantibodies that function in an animal model. Whether by injection of scFv protein (FIGS. 4B-4C) or by in vivo expression of antibody mediated by hydrodynamic gene transfer of scFv DNA-containing plasmids (FIGS. 5A-5C and FIGS. 6A-6B), murine ADAMTS13 proteolytic activity was inhibited, resulting in the accumulation of UL-VWF multimers. After triggering endothelial injury with Shiga-toxin-2, key pathologic features of TTP were observed including thrombocytopenia, microangiopathic hemolytic anemia, formation of platelet thrombi in vital organs, and death (FIGS. 7A-7C). As in patients with antibody-mediated ADAMTS13 deficiency, these mice exhibited sustained inhibition of ADAMTS13 (<5%) and "positive inhibitor assays", i.e. their plasmas inhibited ADAMTS13 activity when mixed with normal human plasma (FIG. 5C). The altered clot morphology revealed by focal arteriole injury via laser and intravital video-microscopy in the setting of prolonged autoantibody-mediated ADAMTS13 inhibition (FIGS. 6A-6B) may illustrate the process by which clots extend linearly and cause the blockage of microvessels in patients with acquired TTP. The present observation that inhibition of ADAMTS13 function and the subsequent pathology that develops can be mediated by a monomeric antibody fragment lacking a constant region domain suggests that antibody-mediated clearance of ADAMTS13 or other effector functions conferred by IgG Fc domains may not be necessary for the expression of disease in patients.

To date, animal models of acquired TTP have been limited to the use of rabbit or mouse antibodies to human ADAMTS13 that produce transient enzyme inhibition (Chauhan et al., J Exp Med 2006; 203:767-76; Chauhan et al., J Thromb Haemost 2007; 5:583-9; Feys et al., Blood 2010; 116:2005-10). Such xenoantibodies would not be expected to necessarily primarily target human autoepitopes and, if so, would therefore not be helpful for testing novel therapies such as altered forms of recombinant ADAMTS13 that are engineered to be unrecognizable by human pathogenic autoantibodies (Jian et al., Blood 2012; 119:3836-43; Zheng et al., Annu Rev Med 2015; 66:211-25). In point of fact, antibodies to human ADAMTS13 generated by mice are not expected to bind to the same epitopes as the present clones 1-416, 1-420, 1-428, and 1-431 because these four human antibodies also cross react with murine ADAMTS13 (FIGS. 4A-4C). Tolerance mechanisms in healthy murine immune systems would not permit such antibodies to be made because they would be autoreactive.

Of the 51 anti-ADAMTS13 scFv antibodies described herein, 1-416, 1-420, 1-428, and 1-431 were initially selected for further evaluation not only because of their ability to inhibit ADAMTS13 in vitro but because rabbit anti-idiotypic antisera raised to each of these scFv demonstrated the presence of cross reactive idiotypes in a number of unrelated patient plasma samples. Of the four antibodies, scFv 1-420 was then chosen to pursue in an animal model because it appeared the most potent (FIGS. 4A-4C).

The use of rapid, large volume intravenous injection of plasmid DNA for transfer of exogenous genes into mice is a much simpler approach than those employing viral vectors for transfection and avoids the laborious steps necessary for virus preparation and purification as well as safety concerns associated with systemic administration of recombinant virus to animals. There are numerous examples in the literature of hydrodynamic-based transfections of plasmid DNA in animals used to study the effects of in vivo-expressed transgenes such as those encoding recombinant enzymes, hormones, cytokines and other proteins but not antibody fragments. The approach described herein could be useful for exploring the pathophysiological effects of autoantibodies in other disorders where the antibodies, as in acquired TTP, may not require the expression of full-length IgG for bivalency or Fc domains for effector function. In addition to its utility for the study of acquired TTP, the sustained inhibition of ADAMTS13 mediated by anti-ADAMTS13 DNA transfection may prove useful in murine models of other disease states such as ischemic stroke, myocardial infarction, atherosclerosis, malignant (cerebral) malaria, and pre-eclampsia where perturbations in ADAMTS13 is believed to play a role in disease pathogenesis.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

```
Antibody Heavy Chains - nucleic acid sequences 1-303, SEQ ID NO: 1
CAGGTGCAGCTGGTGCAGTCTGGGGCTGAGGTGAAGAAGTTTGGGTCCTCAGTGAA
GGTCTCCTGCAAGGCTTCTGGAGGCACCTTCAGCAGTTATACTATGAGCTGGGTGCG
ACAGGCCCCTGGGCAAGGGCTTGAGTGGATGGGAAGTTTCATCCCTATTCTTGAGAG
AGCAAACTACGCACAGAAGTTCCAGGGCAGAGTCACTTTAACCGCGGACAAAAGTA
CGAGCACAGCCTACATGGAGCTGGGCAGCCTGAGATCTGAGGACACGGCCGTGTAT
TATTGTGCGAGAGACCTTGGGGACTTCGGTGACTCCTGGGGCCAGGGAACCCTGGTC
ACCGTCTCCTCAG 1-304, SEQ ID NO: 2
CAGGTGCAGCTGGTGCAGTCTGGGGCTGAGGTGAAGAAGCCTGGGTCCTCGGTGAG
GGTCTCCTGCAAGGCTTCTGGAAGCAATTTCAGCAGCCACACCATCAATTGGGTACG
ACAGGCCCCTGGACACGGGCTTGAGTGGATGGGCAAGATCATCCCTGTCCTTGATAT
ATCTAAACACGCACAGACATTCCTGGGCAGAGTCATAATTACCGCGGACAAATCCA
CGAGCACAGCCTACATGGAGCTGAGCAGCCTGAGATCTGAGGACACGGCCATTTAT
TACTGTGCGATGGATAGTGTCTACGGCAACTTTGACTTTTGGGGCCAGGGAACCCCG
GTCACCGTCTCCTCAG 1-401 (same heavy chain as antibody 1-458), SEQ ID NO: 3
CAGGTGCAGCTGGTGCAGTCTGGGGCTGAGTTGAAGAAGCCTGGGTCCTCGGTGAA
GGTCTCCTGCAAGGCTTCTGGAGGCGCCTTCACCATGTACACTATCAACTGGGTGCG
ACAGGCCCCTGGACGAGGGCTTGAGTGGATGGGAAGGATCATACCTATTCTAGGTA
TAACAGACTACGCACAGAAATTCCAGGGCAGAGGCACGATTACCGCGGACAAATCC
ACAAGCACAGCCTACCTGGAGCTGAGCGGCCTGACTTCTGAGGACACGGCCGTGTA
TTACTGTGCGAGAGAGTTTAGTGGGGGCAACTATTTCGACTTCTGGGGCCAGGGAAC
CCTGGTCACCGTCTCCTCAG 1-403 (same heavy chain as antibody 1-415), SEQ ID NO: 4
CAGGTGCAGCTGCAGGAGTCGGGGGGAGGCGTGGTCCAGCCTGGGAGGTCCCTGAG
ACTCTCCTGTGCAGCCTCTGGATTCACCTTCAGGAACTATGCTATGCACTGGGTCCG
CCAGGCTCCAGGCAAGGGGCTGGAGTGGGTGGCAGTTATATCATATGATGGAGGTA
AGGAATACTACGCAGACTCCGTGAAGGGCCGATTCACCATCTCCAGAGACAATTCC
AAGAACACGCTGTATTTGCAAATGAACAGCCTGAGAGCTGAGGACACGGCTGTGTA
TTACTGTGCGAGAGATACTTTTTCGTATTACGATTTTTGGAGGGCTTTTGACTACTGG
GGCCAGGGAACCCTGGTCACCGTCTCCTCAG 1-404, SEQ ID NO: 5
CAGGTGCAGCTGCAGGAGTCGGGGGGAGGCGTGGTCCAGCCTGGGAGGTCCCTGAG
ACTCTCCTGTACAGACTCTGGATTCACCTTCAGTCGCTATGTTATGCACTGGGTCCGC
CAGGCTCCAGGCAAGGGGCTGGAGTGGGTGGCAGGTATATCATATGATGGAAGTTA
TGAATACTACGCAGACTCCGTGAAGGGCCGATTCACCATCTCCAGAGACAATTCCA
AGAACACGCTATATGTGCAAATGAACAGCCTGAGAGGTGAGGACACGGCTGTGTAT
TACTGTGCGAGAGATTTACGTGGTGGGGAAGACTACTGGGGCCAGGGAACCCTGGT
CACCGTCTCCTCAG 1-405, SEQ ID NO: 6
GAGGTGCAGCTGGTGGAGTCTGGGGCTGAGGTGAAGAAGCCTGGGTCCTCGGTGAA
GGTCTCCTGCAAGGCTTCTGGAGGCATCTTCGGCACCTATACTATCAGCTGGGTGCG
ACAGGCCCCTGGACAAGGGCTTGAGTGGATGGGAGGGATCATCCCTGTCCTTGATGT
CACTCACTACGCGCAGGATTTCCAGGACAGAGTCACCATTACCGCGGACAAGTCCA
CGAGCACTGCCTCCATGGAGCTGAGCAGCCTGAAATCTGACGACACGGCCATATAT
TACTGTGCGAGAAGTTCCTATTATAGCACCTTTGACTACTGGGGCCAGGGAACCCTT
GTCACCGTCTCCTCAG
```

| Antibody Heavy Chains - nucleic acid sequences |
| --- |

1-406, SEQ ID NO: 7
CAGGTGCAGCTGGTGCAGTCTGGGGCTGAGGTGAAGAAGTTTGGGTCCTCAGTGAA
GGTCTCCTGCAAGGCTTCTGGAGGCATGTTCAGCAGTTATACTATCAGCTGGGTGCG
ACAGGGCCCTGGACAAGGGCTTGAGTGGATGGGAAGTTTCATCCCTATTCTTGAGAG
AGCAAACTACGCACAGAAGTTCCAGGGCAGAGTCTCTTTTACCGCGGACAAAAGCA
CGAGCACAGCCTACATGGAGCTGGCAGCCTGACATCTGAGGACACGGCCGTGTAT
TTTTGTGCGAGAGACGTTGGGGACTTCGGTGACTCCTGGGGCCAGGGAACCCTGGTC
ACCGTCTCCTCAG 1-407, SEQ ID NO: 8
GAGGTGCAGCTGGTGGAGTCTGGGGGAGTCGTGGTACAGCCTGGGGGGTCCCTGAG
ACTCTCCTGTGCAGCCTCTGGATTCACCTTTGATGATTATACCATGCACTGGGTCCGT
CAAGCTCCGGGGAAGGGTCTGGAGTGGGTCTCTCTTATTAGTTGGGATGGTGGTAGC
ACATACTATGCAGACTCTGTGAAGGGCCGATTCACCATCTCCAGAGACAACAGCAA
AAACTCCCTGTATCTGCAAATGAACAGTCTGAGAACTGAGGACACCGCCTTGTATTA
CTGTGCAAAAGATAACGGTTACGATATTTTGACTGATTATCTTGACTACTGGGGCCA
GGGAACCCTGGTCACCGTCTCCTCAG 1-408, SEQ ID NO: 9
CAGGTGCAGCTGGTGCAGTCTGGGGCTGAGGTGAAGAAGCCTGGGTCCTCGGTGAA
GGTCTCCTGCAAGGCTTCTGGAGGCTCCTTCAGCAATTATACTATCACCTGGGTGCG
CCAGGCCCCTGGACAAGGACTTGAGTGGATGGGAAGGATCATCCCTGTCCTTGGTCT
GACAGACTCCGCACAGAAGTTCAAGGGCAGAGTCACGATTACCGCGGACAAGTCCA
CGAGCACAGCCTACATGGAGCTGAGCAGCCTGACATCTGAAGACACGGCCGTGTAT
TACTGTGCGAGAGATTCGGTAATTGGAACGTCCGACTGGGGCCAGGGAACCCTGGT
CACCGTCTCCTCAG 1-410, SEQ ID NO: 10
CAGGTGCAGCTGCAGGAGTCGGGGGGGGCGTGGTACAGCCTGGGGGGTCCCTGAG
ACTCTCCTGTGCAGCCTCTGGATTCACCTTTGATGATTATACCATGCACTGGGTCCGT
CAAGCTCCGGGGAAGGGTCTGGAGTGGGTCTCTCTTATTAGTTGGGATGGTGGTAGC
ACATACTATGCAGACTCTGTGAAGGGCCGATTCACCATCTCCAGAGACAACAGCAA
AAACTCCCTGTATCTGCAAATGAACAGTCTGAGAACTGAGGACACCGCCTTGTATTA
CTGTGCAAAAGATAACGGTTACGATATTTTGACTGATTATCTTGACTCCTGGGGCCA
GGGAACCCTGGTCACCGTCTCCTCAG 1-413, SEQ ID NO: 11
CAGGTGCAGCTGGTGCAGTCTGGGTCTGAGGTGAAGAAGCCTGGGTCCTCGGTGAA
AGTCTCCTGCAAGGCTTCTGGAGGCACCTTCAGCAGTCATACTCTCAGCTGGGTACG
ACAGGCCCCTGGACAAGGGCTTGAGTGGATGGGAGAGATCATCCCTATCCTTGATA
GAGTGAAGTATTCACGAACTTCCAGGGCAGAGTCACGATTACCGCGGACAAATCC
ACAAACACAACCTACATGGAGCTGAGCAGCGTGAGATCTGAGGACACGGCCGTATA
CTATTGTGTTAGCAATGGCTGGTCCAACTTTGACTTCTGGGGCCAGGGAACCCTGGT
CACCGTCTCCCCAG 1-416, SEQ ID NO: 12
CAGGTGCAGCTGGTGCAGTCTGGGGCTGAGGTGAAGAAGCCTGGGTCCTCGGTGAG
GGTCTCCTGCACGGCTTCTGGAAGCAATTTCAGCAGCCACACCATCAACTGGGTACG
ACAGGCCCCTGGACAAGGACTTGAGTGGATGGGCAAGGTCATCCCTGTCCTTGATAT
ATCAAAACACGCACAGACATTCCTGGGCAGAGTCATTATTACCGCGGACAAATCCA
CGAGCACAGCCTACTTGGAGCTGAGCAGCCTGAGATCTGAGGACACGGCCATTTATT
ACTGTGCGATGGATAGTGTCTACGGCAACTTTGACTTTTGGGGTCAGGGAACCCTGG
TCACCGTCTCCTCAG 1-417, SEQ ID NO: 13
CAGGTGCAGCTGGTGCAGTCTGGGACTGAGGTGAAGAAGTTTGGGTCCTCGGTGAA
GGTCTCCTGCAAGGCTTCTGGAGGCAGCTTCAGTAGTTATACTATCAGCTGGGTGCG
ACAGGCCCCTGGACAAGGGCTTGAGTGGATGGGAAGTTTCATCCCTATCCTTGAGAG
AGCAAACTACGCACAGAAGTTCCAGGGCAGAGTCACTTTTACCGCGGACAAAACCA
CGAGCACAGCCTACATGGAGCTGGCGGCCTGAGATCTCAGGACACGGCCGTCTAT
TATTGTGCGAGAGACCTTGGGGACTTCGGTGACTCCTGGGGCCAGGGAACCCTGGTC
ACCGTCTCCTCAG 1-418, SEQ ID NO: 14
CAGGTGCAGCTGGTGCAGTCTGGGTCTGAGGTGAAGAAGCCTGGGTCCTCGGTGAA
GGTCTCCTGCAAGGCTTCTGGAGGCACCTTCAGCAGTCACACTGTCAGCTGGGTACG
ACAGGCCCCTGGACAAGGGCTTGAATGGATGGGAGAGATCATCCCTATCCTTGATA
GAGTGAACTATGCAGAGAACTTCCAGGGCAGAGTCACGATTACCGCGGACAAGTCC
ACGAATACAACCTATATGGACCTGAGCAGCCTGAGATCTGAGGACACGGCCGTATA
TTATTGTACTAGCAATGGCTGGTCCAACTTTGACTTCTGGGGCCAGGGAACCCTGGT
CACCGTCTCCTCAG 1-420, SEQ ID NO: 15
CAGGTGCAGCTGGTGCAGTCTGGGGCTGAGGTGAAGAAGCCTGGGTCCTCGGTGAA
GGTCTCCTGCAAGGCTTCTGGAGGCGCCTTCACCATGTACACTATCAACTGGGTGCG
ACAGGCCCCTGGACGAGGGCTTGAGTGGATGGGAAGGATCATACCTATTCTAGGTA

| Antibody Heavy Chains - nucleic acid sequences |
| --- |
| TAACAGACTACGCACAGAAATTCCAGGGCAGAGGCACGATTACCGCGGACAAATCC<br>ACAAGCACAGCCTACCTGGAGCTGAGCGGCCTGACTTCTGAGGACACGGCCGTGTA<br>TTACTGTGCGAGAGAGTTTAGTGGGGGCAACTATTTCGACTTCTGGGGCCAGGGAAC<br>CCTGGTCACCGTCTCCTCAG<br><br>1-423, SEQ ID NO: 16<br>CAGGTGCAGCTGGTGCAGTCTGGGGCTGAGGTGAAGAGGCCTGGGTCCTCGGTGAA<br>GGTCTCCTGCAAGGCCTCTGGAGGCACCTTCAGCAGCTACACTATCAGCTGGGTGCG<br>ACAGGCCCCAGGACAAGGGCTTGAATGGATGGGAAGTATCATCCCTGTCCTTGATGT<br>CACATCCTACGCACAGCAATTCCAGGGCAGAGTCACTATTACCGCGGACAAATCCA<br>CGAAGACAGCCTACATGGACCTGAGCAGCCTAACATTTGAGGACACGGCCCTGTAT<br>TTCTGTTCGATTGGTAGATATACTTATGGACACTTTGACACCTGGGGCCAGGGAACC<br>CAGGTCACCGTCTCCTCAG<br><br>1-428, SEQ ID NO: 17<br>GAGGTGCAGCTGGTGCAGTCTGGGGCTGAGGTGAAGAAGCCTGGGTCCTCGGTGAA<br>GGTCTCCTGCAAGGCCTCTGGAAGCAATTTCAGCAGCCACACCATCAATTGGGTCCG<br>ACAGGCCCCTGGACACGGGCTTGAGTGGATGGGAAAGATCATCCCTGTCCTTGATAT<br>ATCAAAAGACGCAGAGACATTCCTGGGCAGAGTCGTAATTACCGCGGACAAGTCCA<br>CGAGCACAGCCTACATGGAGCTGAGCAGCCTGAGATCTGAGGACACGGCCATTTAT<br>TACTGTGCGATGGATAGTGTCTACGGCAACTTTGACTTTTGGGGCCAGGGAACCCTG<br>GTCACCGTCTCCTCAG<br><br>1-431, SEQ ID NO: 18<br>CAGGTGCAGCTGGTGCAGTCTGGGGCTGAGGTGAAGAAGTTTGGGTCCTCAGTGAA<br>GGTCTCCTGCAAGGCTTCTGGAGGCACCTTCAGCAGTTATACTATGAGCTGGGTGCG<br>ACAGGCCCCTGGACAAGGGCTTGAGTGGATGGGAAGTTTCGTCCCTATTCTTGAGAG<br>AGCAAACTACGCACAGGGATTCCAGGGCAGAGTCACTTTTACCGCGGACAAAAGCA<br>CGAGCACAGCCTACATGGAGCTGGGCAGCCTGAGATCTGAGGACACGGCCGTGTAT<br>TATTGTGCGAGAGACCTTGGGGACTTCGGTGACTCCTGGGGCCAGGGAACCCTGGTC<br>ACCGTCTCCTCAG<br><br>1-432, SEQ ID NO: 19<br>CAGGTGCAGCTGGTGCAGTCTGGGGCTGAGGTGAAGAAGCCTCTGTCCTCAGTGAA<br>GGTCTCCTGCAAGGCCTCTGGAGGCACCTTCAACATGTATGATATCAACTGGGTGCG<br>ACAGGCCCCTGGACAAGGGCTTGAGTGGATGGGAGGGATCGTCCCTATTCTTGGTGT<br>GACAAACTACGCACAGAACTTCCAGGGCAGACTAACAATTACCGCGGACAAATCAA<br>CGAGCACAGCCTACATGGAGCTGAGCAGCCTGAGATCTGAGGACACGGCCGTGTAT<br>TACTGTGCGAGAGGCGTGGCAGCAGGATGGAATGCTTTTGATGTCTGGGGCCAAGG<br>GACAATGGTCACCGTCTCTGCAG<br><br>1-434, SEQ ID NO: 20<br>CAGGTGCAGCTGGTGCAGTCTGGGGCTGAGGTGAAGAAGCCTGGGTCCTCGGTGAA<br>GGTCTCCTGCAAGGCTTCTGGAGGCAGCTTCAGTGATTATACTATCATTTGGTTGCG<br>ACAGGCCCGTGGACACGGGCTTGAGTGGATGGGAAAAATCGTCCCTATACTTGGTG<br>TCACAACCTACGCACAGGAGTTCCAGGGCAGAATCACGATCACCGCGGACAGGTCC<br>ACGAGCACAGCCTACATGGAGCTGAGCAGCCTGAGATCTGAGGACACGGCCGTCTA<br>TTACTGTGCGAGGTTCTTGTGGGGTTTGGACGTCTGGGGCCAAGGGACCACGGTCAC<br>CGTCTCCTCA<br><br>1-437, SEQ ID NO: 21<br>CAGGTGCAGCTGGTGCAGTCTGGGGGAGGCCTGGTCAAGCCTGGGGGGTCCCTGAG<br>ACTCTCCTGTGCAGCCTCTGGATTCATCTTCAGTAACTATATCATGAACTGGGTCCGC<br>CAGGCTCCAGGGAAGGGGCTGGAGTGGGTCTCGTCCATTAGTAGTAGTGGTAGTTA<br>CATATACTACGCAGACTCAGTGAAGGGCCGATTCACCATCTCCAGAGACAACGCCA<br>AGAACTCAATGTATCTGCAAATGAACAGTCTGAGAGGCGAGGACACGGCTGTGTAT<br>TACTGTGCGGCCGCTTACGATTTTTGGAGTGGTTATTATTTCTGGGGCCAAGGGACC<br>ACGGTCACCGTCTCCTCA<br><br>1-438, SEQ ID NO: 22<br>CAGGTGCAGCTGGTGCAGTCTGGGGCTGAGGTGAAGAAGCCTGGGTCCTCGGTGAA<br>GGTCTCCTGCAAGGCTTCTGGAGGCACCTTCAGCAACTATGATATCACCTGGGTGCG<br>ACAGGCCCCAGGACAAGGGCTTGAGTGGTGGGAAAAGTCATCCCTATCCTTGATG<br>TAACAAACTACGCACAGAAGTTCCAGGGCAGAGTCACTATTACCGCGGACAAATCC<br>ACGAGCACAGCCTACATGGAGCTGAGCAACCTGACATCTGAGGACACGGCCGTTTA<br>TTTCTGTGCGAGGTTCTTATGGGTTTGGACGTCTGGGGCCAAGGGACCATGGTCAC<br>CGTCTCCTCA<br><br>1-440, SEQ ID NO: 23<br>GAGGTGCAGCTGTTGGAGTCTGGGGGAGGCTTGGTACAGCCTGGCAGGTCCCTGAG<br>ACTCTCCTGTGCAGCCTCTGGATTCATCTTTGATGATTATGCCATGCACTGGGTCCGG<br>CAAGCTCCAGGGAAGGGCCTGGAGTGGGTCTCAGGTATTAGTTGGAATAGTGGTAG<br>CATAGGCTATGCGGACTCTGTGAAGGGCCGATTCACCATCTCCAGAGACAACGCCA<br>AGAACTCCCTGTATCTGCAAATGAACAGTCTGAGAGCTGAGGACACGGCCTTGTATT<br>ACTGTGCAAAAGACCCTAATTCGCTGTATAGAAGTGGTTCCTTTGACTACTGGGGCC<br>AGGGAACGCTGGTCACCGTCTCCTCAG |

| Antibody Heavy Chains - nucleic acid sequences |
| --- |

1-441, SEQ ID NO: 24
CAGGTGCAGCTGCAGGAGTCGGGGGGAGGCGTGGTCCAGCCTGGGAGGTCCCTGAG
ACTCTCCTGTACAGACTCTGGATTCACCTTCAGTCGCTATGCTATGCACTGGGTCCGC
CAGGCTCCAGGCAAGGGGCTGGAGTGGGTGGCAGGTATATCATATGATGGAAGTTA
TGAATACTACGCAGACTCCGTGAAGGGCCGATTCACCATCTCCAGAGACAATTCCA
AGAACACGCTATATGTGCAAATGAACAGCCTGAGAGGTGAGGACACGGCTGTGTAT
TACTGTGCGAGAGATCTACGTGGTGGGGAAGACTACTGGGGCCAGGGAACCCTGGT
CACCGTCTCCTCAG 1-450, SEQ ID NO: 25
CAGGTGCAGCTGGTGCAGTCTGGGGCTGAGGTGAAGAAGCCTGGGTCCTCGATGAA
TGTCTCCTGCAAGGCCTCTGGAGGCACCTTCAGCAGGCATACCATCAACTGGGTGCG
ACAGGCCCCTGGACAAGGGCTTGAGTGGATGGGAAGCATCATCCCTATTCTTGGTAT
AACAAACTACGCACAGAACTTCCAGGGCAGACTCACGTTTAGCGCGGACAAATCCA
CGAACACAGCCTATGTGGAGTTGAGTGGCCTGAGATCTGAGGACACGGCCGTCTATT
ACTGTGCGAGTGGGGACTACTACTATGACATGGCCGTTTGGGGCCAAGGGACCACG
GTCGCCGTCACCTCA 1-451, SEQ ID NO: 26
CAGGTGCAGCTGGTGCAGTCTGGGGGAGGCTTGGTACAGCCTGGCAGGTCCCTGAG
ACTCTCCTGTGCAGCCTCTGGATTCATCTTTGATGATTATGCCATGCACTGGGTCCGG
CAAGCTCCAGGGAAGGGCCTGGAGTGGGTCTCAGGTATTAGTTGGAATAGTGGTAG
CATAGGCTATGCGGACTCTGTGAAGGGCCGATTCACCATCTCCAGAGACAACGCCA
AGAACTCCCTGTATCTGCAAATGAACAGTCTGAGAGCTGAGGACACGGCCTTGTATT
ACTGTGCAAAAGACCCTAATTCGCTGTATAGAAGTGGTTCCTTTGACTACTGGGGCC
AGGGAACGCTGGTCACCGTCTCCTCAG 2-102, SEQ ID NO: 27
CAGGTGCAGCTGGTGCAGTCTGGGGCTGAGGTGAAGAAGCCTGGGTCCTCGGTGAA
GGTCTCCTGCAGGGCTTCTGGAGGCACCTTCAGCAGCTATACTATCAACTGGGTGCG
ACAGGCCCCTGGACAAGGGCTTGAGTGGATGGGAAGGGTCGTCCCTATCCTTGGTGT
AACAAACTACGCACAGAAGTTCCAGGGCAGAGTCACCATTACCGCGGACAAATCCA
CGAGCACAGCCTACATGGAGCTGAGCAGCCTGAGATCTGAGGACACGGCCGTGTAT
TACTGTGCGAGAGATAAGGGCTATGATAATAATTACGGGGCCTACTGGGGCCAGGG
AACCCTGGTCACCGTCTCCTCAG 2-103, SEQ ID NO: 28
CAGGTGCAGCTGGTGCAGTCTGGGGCTGAGGTGAAGAAGCCTGGGTCCTCGGTGAA
GGTCTCCTGCAAGGCTTCTGGAGGCACCTTCAGCAGCTATGATATCAACTGGGTGCG
ACAGGCCCCTGGACAAGGGCTTGAGTGGATGGGAAGCATCATCCCTATCCTTGGTAT
ATCAAACTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGAGATCAGGGCTATGCCAATAATTACGGGGCCTACTGGGGCCAGGG
AACCCTGGTCACCGTCTCCTCAG 2-106, SEQ ID NO: 29
CAGGTGCAGCTGGTGCAGTCTGGGGCTGAGGTGAAGAAGCCTGGGTCCTCGGTGAA
GGTCTCCTGCAAGGCTTCTGGAGGCACCTTCAGCAGCTATGATATCAATTGGGTGCG
ACAGGCCCCTGGACAAGGGCTTGAGTGGATGGGAAGCATCATCCCTATCCTTGGTAT
ACGAAATTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGAGATCAGGGCTATGCTAATAATTACGGGGCCTACTGGGGCCAGGG
AACCCTGGTCACCGTCTCCTCAG 2-108, SEQ ID NO: 30
GAGGTGCAGCTGGTGCAGTCTGGGGGAGGCTTGGTCCAGCCTGGGGGGTCCCTGAG
ACTCTCCTGTGCAGCCTCTGGATTCACGTTTAGTAGCTATTGGATGAGCTGGGTCCG
CCAGGCTCCAGGGAAGGGGCTGGAGTGGGTGGCCAACATAAAGCAAGATGGAAGT
GAGAAACACTATGTGGACTCTATGAAGGGCCGATTCACCATCTCCAGAGACAACGG
CAAGAACTCACTGTATCTGCAAATGAACAGCCTGAGAGCCGAGGACACGGCTGTGT
ATTACTGTGCGAGGTCCCCGGGATACTACTTTGACTACTGGGGCCAGGGAACCCTGG
TCACCGTCTCCTCAG 2-203, SEQ ID NO: 31
CAGGTGCAGCTGGTGCAGTCTGGGGCTGAGGTGAAGAAGCCTGGGTCCTCGGTGAA
GGTCTCCTGCAAGGCTTCTGGAGGCACCTTCAGCAGCTATCGCATGGGTGCG
ACAGGCCCCTGGACAAGGGCTTGAGTGGATGGGAAGGATCGTCCCTATCCTTGGTAT
AGCAAACTACGCACAGAAGTTCCAGGGCAGAGTCACGATTACCGCGGACAAATCCA
CGAGCACGGCCTACATGGAACTGAGCAGCCTGAGATCTGACGACACGGCCGTATAT
TACTGTGCGAGAGATCGGGGCTATGCTAATACTTACGGGGCCTACTGGGGCCAGGG
AACCCTGGTCACCGTCTCCTCAG 2-204, SEQ ID NO: 32
CAGGTGCAGCTGGTGCAGTCTGGGGCTGAGGTGAAGAAGCCTGGGTCCTCGGTGAA
GGTCTCCTGCAAGGCTTCTGGAGGCACCTTCAGCAGTTATGCTATTAGCTGGGTGCG
ACAGGCCCCTGGACAGGGGCTTGAGTGGATGGGAAGCATCGTCCCTATCCTTGGTGT
AGTAAACTACGCACAGAACTTCCAGGGCAGAGTCACGATTACCGCGGACAAATCCA

| Antibody Heavy Chains - nucleic acid sequences |
|---|
| CGAGCACAGCCTACATGGAGCTGAGCAGCCTGAGATCTGAGGACACGGCCGTGTAT<br>TACTGTGCGAGAGATAAGGGGTATGCTAATAATTACGGGGCCTACTGGGGCCAGGG<br>AACCCTGGTCACCGTCTCCTCAG<br><br>2-206, SEQ ID NO: 33<br>CAGGTGCAGCTGGTGCAGTCTGGGGCTGACGTGAAGAAGCCTGGGTCCTCGGTGAA<br>GGTCTCCTGCAAGGCTTCTGGAGGCACCTTCAGCAGCTATACTATCAACTGGGTGCG<br>ACAGGCCCCTGGACAAGGGCTTGAGTGGATGGGAAGGATCGTCCCTATCCTTGATAT<br>TGCAAACTACGCACAGAAGTTCCAGGGCAGAGTCACGATTACCGCGGACAAATCCA<br>CGAGCACAGCCTACATGGAGCTGAGCAGCCTGACATCTGAGGACACGGCCGTGTAT<br>TATTGTGCGAGAGATCGGGGCTATGATAATAAATACGGGGCCTACTGGGGCCAGGG<br>AACCCTGGTCACCGTCTCCTCAG<br><br>2-207 (same heavy chain as antibody 2-301), SEQ ID NO: 34<br>CAGGTGCAGCTGGTGCAGTCTGGGGCTGAGGTGAAGAAGCCTGGGTCCTCGGTGAA<br>GGTCTCCTGCAAGGCTTCTGGAGGCACCTTCAGCAGCTATGCTATCAGCTGGGTGCG<br>ACAGGCCCCTGGACAAGGGCTTGAGTGGATGGGAGGGATCACCCCTATCCTTGGTG<br>TAACAAACTACTCACAGAAGTTCCAGGGCAGAGTCACCGTTACCGCGGACATATCC<br>ACGACCACAGCCTACATGGAGCTGAGCAGCCTGACATCTGAGGACACGGCCGTGTA<br>TTACTGTGCGAGAGATCAGGGCTATGCTAATGATTACGGGGCCTACTGGGGCCAGG<br>GAACCCTGGTCACCGTCTCCTCAG<br><br>2-302, SEQ ID NO: 35<br>GAGGTGCAGCTGGTGCAGTCTGGGGCTGAGGTGAAGAAGCCTGGGTCCTCGGTGAA<br>GGTCTCCTGCAAGGCTTCTGGAGGCACCTTCAGCAGCTATACTATCAACTGGGTGCG<br>ACAGGCCCCTGGACAAGGACTTGAGTGGATGGGAAGGATCATCCCTATCCTTGGTAT<br>AGAAAACTACGCACAGAAGTTCCAGGGCAGAGTCACGATTTCCGCGGACAAATCCA<br>CGAGCACAGCCTACATGGAGCTGAGCAGCCTGAGATCTGACGACACGGCCGTGTAT<br>TACTGTGCGAGAGATCAGGTCTTCGGGGCCTACTGGGGCCCGGGAACCCTGGTCAC<br>CGTCTCCTCAG<br><br>2-304, SEQ ID NO: 36<br>CAGGTGCATCTGGTGCAGTCTGGGGCTGAGGTGAAGAAGCCTGGGTCCTCGGTGAA<br>GGTCTCCTGCAAGGCTTCTGGAGGCACCTTCAGCAGCTATGCTATCAGCTGGGTGCG<br>ACAGGCCCCTGGACAAGGGCTTGAGTGGATGGGAGGGATCACCCCTATCCTTGGTG<br>TAACAAACTACTCACAGAAGTTCCAGGGCAGAGTCACCGTTACCGCGGACATATCC<br>ACGACCACAGCCTACATGGAGCTGAGCAGCCTGACATCTGAGGACACGGCCGTGTA<br>TTACTGTGCGAGAGATCAGGGCTATGCTAATGATTACGGGGCCTACTGGGGCCAGG<br>GAACCCTGGTCACCGTCTCCTCAG<br><br>2-305 (same heavy chain as antibody 2-406), SEQ ID NO: 37<br>CAGGTGCAGCTGGTGCAGTCTGGGGCTGAGGTGAAGAAGCCTGGGTCCTCGGTGAA<br>GGTCTCCTGCAAGGCTTCTGGAGGCACCTTCAGCAGCTATGAAATCAGTTGGGTGCG<br>ACAGGCCCCTGGACAAGGGCTTGAGTGGATGGGGAGGATCGTCCCTATCCTGGGTTT<br>GGCAAACTACGCACAGAACTTCCAGGGCAGAGTCACCATTACCGCGGACAAATCCA<br>CGAGCACAGCCTACATGGAGCTGAGCAGCCTGAGATTCGAGGATACGGCCGTGTAT<br>TACTGTGCGAGAGATCAGGGCTATGCTAATAATTACGGGGCCTACTGGGGCCAGGG<br>AACCCTGGTCAGCGTCTCCTCAG<br><br>2-408, SEQ ID NO: 38<br>CAGGTGCAGCTGGTGCAGTCTGGGGCTGAGGTGAAGAAGCCTGGGTCCTCGGTGAA<br>GGTCTCCTGCGAGGCTTCTGGAGGCACCTTCAGCAGCTATGCTATCACCTGGGTGCG<br>ACAGGCCCCTGGACAAGGGCTTGAGTGGATGGGAAGCATCCTCCCTATCCTTGATAT<br>AACAAACTACGCACAGAAGTTCCAGGGCAGAGTCACGCTTACCGCGGACAAATCCA<br>CGAGCACAGCCTACATGGAGCTGAGCAGCCTGAGATCTGAGGACACGGCCGTGTAT<br>TTCTGTGCGAGAGATCGGGCTATAGTAATAATTATGGGGCCTACTGGGGCCAGGG<br>AACCCTGGTCACCGTCTCCTCAG<br><br>3-301, SEQ ID NO: 39<br>GAGGTGCAGCTGGTGCAGTCTGGGGCTGAGGTGAAGAAGCCTGGGTCCTCAGTGAA<br>GGTCTCCTGCAAGGCTTCTGGAGGCACCTTCAGCAGCTATGCTATCAGCTGGGTGCG<br>ACAGGCCCCTGGACAAGGGCTTGAGTGGATGGGAGGGATCATCCCTATCCTTGGTAT<br>AACAAACTACGCACAGAAGTTCCAGGGCAGAGTCACGATTACCGCGGACGAATCCA<br>CGGGCGCAGCCTACATGGAGCTGAGCAGCCTGGCATCTGAGGACACGGCCGTATAT<br>TACTGTGCGAGAGATGATACTGGCCGGGACGACTACTTTGAGTACTGGGGTCAGGG<br>AACCCTGGTCACCGTCTCCTCAG<br><br>3-302 (same heavy chain as antibodies 3-305 and 3-405), SEQ ID NO: 40<br>CAGGTGCAGCTGGTGCAGTCTGGGGCTGAGGTGAAGAGGCCTGGGTCCTCAGTGAA<br>GGTCTCCTGCAAGGCTTCTGGAAACACCTTCAGTAACTATCATATCAACTGGGTGCG<br>ACAGGCCCCTGGACAAGGGCTTCAGTGGATGGGAGGAATCATCCCTATTCTTGGGA<br>GAACAAACTACGCACAGAACTTCCAGGGCAGAGTCACGATTACCACGGACGAATCA<br>ACGAACACAGCCTACATGGAGCTGACTAGCCTGAGATCCGAGGACACGGCCGTTTA<br>TTATTGTGCGAGGGAGGCCCGGGATAGTTTTGATTTCTGGGGCCAAGGGACAATGGT<br>CACCGTCTCTTCAG |

| Antibody Heavy Chains - nucleic acid sequences |
| --- |

4-303, SEQ ID NO: 41
CAGGTGCAGCTGGTGCAGTCTGGGGCTGAGGTGAAGAAGCCTGGGTCCTCAGTGAA
GGTCTCCTGCAAGGCTTCTGGAGGCACCTTCAGCAACTATGGTATCAGCTGGGTGCG
ACAGGCCCCTGGACAAGGGCTTGAGTGGATGGGAAAGATCATCCCTATCCTTGGTAT
AACAAACTACGCACAGAAGTTCCAGGGCAGGGTCACGATTACCGCGGACAAATCCA
CGAGCACAGCCTACATGGAGCTGAGCAGCCTGAGATCTGAGGACACGGCCGTGTAT
TACTGTGCGAGAGGGGGTGGGAGCTACGACTTCTTTGACTACTGGGGCCAGGGAAC
GCTGGTCACCGTCTCCTCAG 4-307, SEQ ID NO: 42
CAGGTGCAGCTGGTGCAGTCTGGGGCTGAGGTGAAGAAGCCTGGGTCCTCGGTGAA
GGTCTCCTGCAAGGCTTCTGGTGGCACCTTCAGCACCTATACTATCAACTGGATGCG
ACAGGCCCCTGGACAAGGGCTTGAGTGGATGGGAAGGATCATCCCTATGTTCGGTA
CAGCAAACTACGCACAGAAGTTCCGGGGCAGAGTCACGATTACCGCGGACGAATCC
ACGAGCACAGCCTACATGGAGCTGAGCAGCCTGATATCTGAGGACACGGCCATCTA
TTACTGTGCGAGAAGTGGCTACAGTGATGCTTTTGATATCTGGGGCCAAGGGACAAT
GGTCACCGTCTCTTCAG z1-201, SEQ ID NO: 43
CAGGTGCAGCTGGTGCAGTTTGGGGGAGGCTTGGTACAGCCTGGCAGGTCCCTGAG
ACTCTCCTGTGCAGCCTCTGGATTCATCTTTGATGATTATGCCATGCACTGGGTCCGG
CAAGCTCCAGGGAAGGGCCTGGAGTGGGTCTCAGGTATTAGTTGGAATAGTGGTAG
CATAGGCTATGCGGACTCTGTGAAGGGCCGATTCACCATCTCCAGAGACAACGCCA
AGAACTCCCTGTATCTGCAAATGAACAGTCTGAGAGCTGAGGACACGGCCTTGTATT
ACTGTGCAAAAGACCCTAATTCGCTATATAGAAGTGGTTCCTTTGACTACTGGGGCC
AGGGAACGCTGGTCACCGTCTCCTCAG z1-303, SEQ ID NO: 44
CAGGTGCAGCTGCAGGAGTCGGGTCCAGGACTGGTGAGGCCCTCGCAGACCCTCTC
ACTCACCTGTGCCATCTCCGGGGACAGTGTCTCAAACAACAATGCTGCTTGGAACTG
GATTAGGCAGTCCCCATCGAGAGGCCTTGAGTGGCTGGGAAGGACATTCTACAGGT
CCAGGTGGTATAATGATTATGCAGTTTCTGTGAAAAGTCGAATAATCATCAACCCAG
ACACATCCAAGAACCAATTCTCCCTGGACCTGACCTCTGTGACTCCCGAAGACACGG
CTGTGTATTTCTGTGCAAGAGAAGGACAGTGGCTGCCCAACTACTTCGACCCCTGGG
GCCAGGGGACCCTGGTCACCGTCTCCTCAG z1-402, SEQ ID NO: 45
CAGGTGCAGCTGGTGCAGTCTGGGGGAGGCGTCGTCCAGCCTGGGACGTCCCTAAG
ACTCTCCTGTGCAGCCTCTGGATTCACCTTCCGCAACCATGCTATGCACTGGGTCCG
CCAGGCTCCAGGGAGGGGGCTGGAGTGGGTGGCAGATATACTGTACGATTCAAGTA
ACAAATACTACGCAGACTCTGTGAAGGGCCGATTCACCATCTCCAGAGACAATTCC
AAGAACACGCTGTATCTGCAAATGAGCAGCCTGAGAGCTGAGGACACGGCCGTCTA
TTTCTGTGCGGCCAGTTCATATTTTCCATTTGACTTCTGGGGCCAGGGAACCCTGGTC
ACCGTCTCCTCAG

Antibody Heavy Chains - amino acid sequences
1-303, SEQ ID NO: 46
QVQLVQSGAEVKKFGSSVKVSCKASGGTFSSYTMSWVRQAPGQGLEWMGSFIPILERA
NYAQKFQGRVTLTADKSTSTAYMELGSLRSEDTAVYYCARDLGDFGDSWGQGTLVTV
SS 1-304, SEQ ID NO: 47
QVQLVQSGAEVKKPGSSVRVSCKASGSNFSSHTINWVRQAPGHGLEWMGKIIPVLDISK
HAQTFLGRVIITADKSTSTAYMELSSLRSEDTAIYYCAMDSVYGNFDFWGQGTPVTVSS 1-401 (same heavy chain as antibody 1-458), SEQ ID NO: 48
QVQLVQSGAELKKPGSSVKVSCKASGGAFTMYTINWVRQAPGRGLEWMGRIIPILGITD
YAQKFQGRGTITADKSTSTAYLELSGLTSEDTAVYYCAREFSGGNYFDFWGQGTLVTVS
S 1-403 (same heavy chain as antibody 1-415), SEQ ID NO: 49
QVQLQESGGGVVQPGRSLRLSCAASGFTFRNYAMHWVRQAPGKGLEWVAVISYDGGK
EYYADSVKGRFTISRDNSKNTLYLQMNSLRAEDTAVYYCARDTFSYYDFWRAFDYWG
QGTLVTVSS 1-404, SEQ ID NO: 50
QVQLQESGGGVVQPGRSLRLSCTDSGFTFSRYVMHWVRQAPGKGLEWVAGISYDGSY
EYYADSVKGRFTISRDNSKNTLYVQMNSLRGEDTAVYYCARDLRGGEDYWGQGTLVT
VSS 1-405, SEQ ID NO: 51
EVQLVESGAEVKKPGSSVKVSCKASGGIFGTYTISWVRQAPGQGLEWMGGIIPVLDVTH
YAQDFQDRVTITADKSTSTASMELSSLKSDDTAIYYCARSSYYSTFDYWGQGTLVTVSS

| Antibody Heavy Chains - nucleic acid sequences |
| --- |

1-406, SEQ ID NO: 52
QVQLVQSGAEVKKFGSSVKVSCKASGGMFSSYTISWVROGPGQGLEWMGSFIPILERAN
YAQKFQGRVSFTADKSTSTAYMELGSLTSEDTAVYFCARDVGDFGDSWGQGTLVTVSS 1-407, SEQ ID NO: 53
EVQLVESGGVVVQPGGSLRLSCAASGFTFDDYTMHWVRQAPGKGLEWVSLISWDGGS
TYYADSVKGRFTISRDNSKNSLYLQMNSLRTEDTALYYCAKDNGYDILTDYLDYWGQG
TLVTVSS 1-408, SEQ ID NO: 54
QVQLVQSGAEVKKPGSSVKVSCKASGGSFSNYTITWVRQAPGQGLEWMGRIIPVLGLT
DSAQKFKGRVTITADKSTSTAYMELSSLTSEDTAVYYCARDSVIGTSDWGQGTLVTVSS 1-410, SEQ ID NO: 55
QVQLQESGGGVVQPGGSLRLSCAASGFTFDDYTMHWVRQAPGKGLEWVSLISWDGGS
TYYADSVKGRFTISRDNSKNSLYLQMNSLRTEDTALYYCAKDNGYDILTDYLDSWGQG
TLVTVSS 1-413, SEQ ID NO: 56
QVQLVQSGSEVKKPGSSVKVSCKASGGTFSSHTLSWVRQAPGQGLEWMGEITPILDRVK
YSQNFQGRVTITADKSTNTTYMELSSVRSEDTAVYYCVSNGWSNFDFWGQGTLVTVSP 1-416, SEQ ID NO: 57
QVQLVQSGAEVKKPGSSVRVSCTASGSNFSSHTINWVRQAPGQGLEWMGKVIPVLDISK
HAQTFLGRVIITADKSTSTAYLELSSLRSEDTAIYYCAMDSVYGNFDFWGQGTLVTVSS 1-417, SEQ ID NO: 58
QVQLVQSGTEVKKFGSSVKVSCKASGGSFSSYTISWVRQAPGQGLEWMGSFIPILERAN
YAQKFQGRVTFTADKTTSTAYMELGGLRSQDTAVYYCARDLGDFGDSWGQGTLVTVS
S 1-418, SEQ ID NO: 59
QVQLVQSGSEVKKPGSSVKVSCKASGGTFSSHTVSWVRQAPGQGLEWMGEIIPILDRVN
YAENFQGRVTITADKSTNTTYMDLSSLRSEDTAVYYCTSNGWSNFDFWGQGTLVTVSS 1-420, SEQ ID NO: 60
QVQLVQSGAEVKKPGSSVKVSCKASGGAFTMYTINWVRQAPGRGLEWMGRIIPILGITD
YAQKFQGRGTITADKSTSTAYLELSGLTSEDTAVYYCAREFSGGNYFDFWGQGTLVTVS
S 1-423, SEQ ID NO: 61
QVQLVQSGAEVKRPGSSVKVSCKASGGTFSSYTISWVRQAPGQGLEWMGSIIPVLDVTS
YAQQFQGRVTITADKSTKTAYMDLSSLTFEDTALYFCSIGRYTYGHFDTWGQGTQVTVS
S 1-428, SEQ ID NO: 62
EVQLVQSGAEVKKPGSSVKVSCKASGSNFSSHTINWVRQAPGHGLEWMGKIIPVLDISK
DAETFLGRVVITADKSTSTAYMELSSLRSEDTAIYYCAMDSVYGNFDFWGQGTLVTVSS 1-431, SEQ ID NO: 63
QVQLVQSGAEVKKFGSSVKVSCKASGGTFSSYTMSWVRQAPGQGLEWMGSFVPILERA
NYAQGFQGRVTFTADKSTSTAYMELGSLRSEDTAVYYCARDLGDFGDSWGQGTLVTV
SS 1-432, SEQ ID NO: 64
QVQLVQSGAEVKKPLSSVKVSCKASGGTFNMYDINWVRQAPGQGLEWMGGIVPILGV
TNYAQNFQGRLTITADKSTSTAYMELSSLRSEDTAVYYCARGVAAGWNAFDVWGQGT
MVTVSA 1-434, SEQ ID NO: 65
QVQLVQSGAEVKKPGSSVKVSCKASGGSFSDYTIIWLRQARGHGLEWMGKIVPILGVTT
YAQEFQGRITITADRSTSTAYMELSSLRSEDTAVYYCARFLWGLDVWGQGTTVTVSS 1-437, SEQ ID NO: 66
QVQLVQSGGGLVKPGGSLRLSCAASGFIFSNYIMNWVRQAPGKGLEWVSSISSSGSYIY
YADSVKGRFTISRDNAKNSMYLQMNSLRGEDTAVYYCAAAYDFWSGYYFWGQGTTV
TVSS 1-438, SEQ ID NO: 67
QVQLVQSGAEVKKPGSSVKVSCKASGGTFSNYDITWVRQAPGQGLEWVGKVIPILDVT
NYAQKFQGRVTITADKSTSTAYMELSNLTSEDTAVYFCARFLWGLDVWGQGTMVTVS
S

| Antibody Heavy Chains - nucleic acid sequences |
| --- |

1-440, SEQ ID NO: 68
EVQLLESGGGLVQPGRSLRLSCAASGFIFDDYAMHWVRQAPGKGLEWVSGISWNSGSI
GYADSVKGRFTISRDNAKNSLYLQMNSLRAEDTALYYCAKDPNSLYRSGSFDYWGQGT
LVTVSS 1-441, SEQ ID NO: 69
QVQLQESGGGVVQPGRSLRLSCTDSGFTFSRYAMHWVRQAPGKGLEWVAGISYDGSY
EYYADSVKGRFTISRDNSKNTLYVQMNSLRGEDTAVYYCARDLRGGEDYWGQGTLVT
VSS 1-450, SEQ ID NO: 70
QVQLVQSGAEVKKPGSSMNVSCKASGGTFSRHTINWVRQAPGQGLEWMGSIIPILGITN
YAQNFQGPvLTFSADKSTNTAYVELSGLRSEDTAVYYCASGDYYYDMAVWGQGTTVAV
TS 1-451, SEQ ID NO: 71
QVQLVQSGGGLVQPGRSLRLSCAASGFIFDDYAMHWVRQAPGKGLEWVSGISWNSGSI
GYADSVKGRFTISRDNAKNSLYLQMNSLRAEDTALYYCAKDPNSLYRSGSFDYWGQGT
LVTVSS 2-102, SEQ ID NO: 72
QVOLVOSGAEVKKPGSSVKVSCRASGGTFSSYTINWVRQAPGQGLEWMGRVVPILGVT
NYAQKFQGRVTITADKSTSTAYMELSSLRSEDTAVYYCARDKGYDNNYGAYWGQGTL
VTVSS 2-103, SEQ ID NO: 73
QVQLVQSGAEVKKPGSSVKVSCKASGGTFSSYDINWVRQAPGQGLEWMGSIIPILGISN
YAQKFQGRVTITADKSTSTAYMELSSLRSEDTAVYYCARDQGYANNYGAYWGQGTLV
TVSS 2-106, SEQ ID NO: 74
QVQLVQSGAEVKKPGSSVKVSCKASGGTFSSYDINWVRQAPGQGLEWMGSIIPILGIRN
YAQKFQGRVTITADKSTSTAYMELSSLRSEDTAVYYCARDQGYANNYGAYWGQGTLV
TVSS 2-108, SEQ ID NO: 75
EVQLVQSGGGLVQPGGSLRLSCAASGFTFSSYWMSWVRQAPGKGLEWVANIKQDGSE
KHYVDSMKGRFTISRDNGKNSLYLQMNSLRAEDTAVYYCARSPGYYFDYWGQGTLVT
VSS 2-203, SEQ ID NO: 76
QVQLVQSGAEVKKPGSSVKVSCKASGGTFSSYAIDWVRQAPGQGLEWMGRIVPILGIA
NYAQKFQGRVTITADKSTSTAYMELSSLRSDDTAVYYCARDRGYANTYGAYWGQGTL
VTVSS 2-204, SEQ ID NO: 77
QVQLVQSGAEVKKPGSSVKVSCKASGGTFSSYAISWVRQAPGQGLEWMGSIVPILGVV
NYAQNFQGRVTITADKSTSTAYMELSSLRSEDTAVYYCARDKGYANNYGAYWGQGTL
VTVSS 2-206, SEQ ID NO: 78
OVOLVQSGADVKKPGSSVKVSCKASGGTFSSYTINWVRQAPGQGLEWMGRIVPILDIA
NYAQKFOGRVTITADKSTSTAYMELSSLTSEDTAVYYCARDRGYDNKYGAYWGQGTL
VTVSS 2-207 (same heavy chain as antibody 2-301), SEQ ID NO: 79
QVQLVQSGAEVKKPGSSVKVSCKASGGTFSSYAISWVRQAPGQGLEWMGGITPILGVT
NYSQKFQGRVTVTADISTTTAYMELSSLTSEDTAVYYCARDQGYANDYGAYWGQGTL
VTVSS 2-302, SEQ ID NO: 80
EVQLVQSGAEVKKPGSSVKVSCKASGGTFSSYTINWVRQAPGQGLEWMGRIIPILGIEN
YAQKFQGRVTISADKSTSTAYMELSSLRSDDTAVYYCARDQVFGAYWGPGTLVTVSS 2-304, SEQ ID NO: 81
QVHLVQSGAEVKKPGSSVKVSCKASGGTFSSYAISWVRQAPGQGLEWMGGITPILGVT
NYSQKFQGRVTVTADISTTTAYMELSSLTSEDTAVYYCARDQGYANDYGAYWGQGTL
VTVSS 2-305 (same heavy chain as antibody 2-406), SEQ ID NO: 82
QVQLVQSGAEVKKPGSSVKVSCKASGGTFSSYEISWVRQAPGQGLEWMGRIVPILGLA
NYAQNFQGRVTITADKSTSTAYMELSSLRFEDTAVYYCARDQGYANNYGAYWGQGTL
VSVSS

| Antibody Heavy Chains - nucleic acid sequences |
| --- |

2-408, SEQ ID NO: 83
QVQLVQSGAEVKKPGSSVKVSCEASGGTFSSYAITWVRQAPGQGLEWMGSILPILDITN
YAQKFQGRVTLTADKSTSTAYMELSSLRSEDTAVYFCARDRGYSNNYGAYWGQGTLV
TVSS 3-301, SEQ ID NO: 84
EVQLVQSGAEVKKPGSSVKVSCKASGGTFSSYAISWVRQAPGQGLEWMGGIIPILGITN
YAQKFQGRVTITADESTGAAYMELSSLASEDTAVYYCARDDTGRDDYFEYWGQGTLV
TVSS 3-302 (same heavy chain as antibodies 3-305 and 3-405), SEQ ID NO: 85
QVQLVQSGAEVKRPGSSVKVSCKASGNTFSNYHINWVRQAPGQGLQWMGGIIPILGRT
NYAQNFQGRVTITTDESTNTAYMELTSLRSEDTAVYYCAREARDSFDFWGQGTMVTVS
S 4-303, SEQ ID NO: 86
QVQLVQSGAEVKKPGSSVKVSCKASGGTFSNYGISWVRQAPGQGLEWMGKIIPILGITN
YAQKFQGRVTITADKSTSTAYMELSSLRSEDTAVYYCARGGGSYDFFDYWGQGTLVTV
SS 4-307, SEQ ID NO: 87
QVQLVQSGAEVKKPGSSVKVSCKASGGTFSTYTINWMRQAPGQGLEWMGRIIPMFGTA
NYAQKFRGRVTITADESTSTAYMELSSLISEDTAIYYCARSGYSDAFDIWGQGTMVTVSS z1-201, SEQ ID NO: 88
QVQLVQFGGGLVQPGRSLRLSCAASGFIFDDYAMHWVRQAPGKGLEWVSGISWNSGSI
GYADSVKGRFTISRDNAKNSLYLQMNSLRAEDTALYYCAKDPNSLYRSGSFDYWGQGT
LVTVSS z1-303, SEQ ID NO: 89
QVQLQESGPGLVRPSQTLSLTCAISGDSVSNNNAAWNWIRQSPSRGLEWLGRTFYRSRW
YNDYAVSVKSRIIINPDTSKNQFSLDLTSVTPEDTAVYFCAREGQWLPNYFDPWGQGTL
VTVSS z1-402, SEQ ID NO: 90
QVQLVQSGGGVVQPGTSLRLSCAASGFTFRNHAMHWVRQAPGRGLEWVADILYDSSN
KYYADSVKGRFTISRDNSKNTLYLQMSSLRAEDTAVYFCAASSYFPFDFWGQGTLVTVS
S Antibody Light Chains - nucleic acid sequences
1-303, SEQ ID NO: 91
GAGCTCGAGCTGACTCAGCCACCCTCAGTGTCAGTGGCCCCAGGAAAGACGGCCAG
GATTACCTGTGGGGGAAACAACATTGGAAGTAAAAGTGTGCACTGGTACCAGCAGA
AGCCAGGCCAGGCCCCTGTGCTGGTCGTCTATGATGATAGCGACCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATCATTATGTCTTCGGAACTGGGACCAAGGTGACCGTCCTAG 1-304, SEQ ID NO: 92
GAGCTCGTGCTGACTCAGCCACCCTCGGTGTCAGTGTCCCCAGGACAGACGGCCAG
GATCACCTGCTCTGGAGATGCATTGCCAAAGCATTATGCTTATTGGTACCAGCAGAA
GCCAGGCCAGGCCCCTGTGGTGGTTATATATAAAGACACTGAGAGGCCCTCAGGGA
TCCCTGAGCGATTCTCTGGCGCCACCTCAGGGACAACAACCACGTTGACCATCAGTG
GAGTCCAGGCAGAAGACGAGGCTGACTATTTTTGTCAATCATCAGACATCAATGGTA
CATCTTGGATATTCGGCGGCGGCACCAAGCTGACCGTCCTAG 1-401, SEQ ID NO: 93
GAGCTCGTGCTGACTCAGCCACCCTCAGTGTCAGTGGCCCCAGGAAAGACGGCCAG
GATGACCTGTGGGGGAAACAACATTGGAGGTTATAGTGTGCACTGGTACCAGCAGA
AGCCAGGCCAGGCCCCTGTGCTGGTCGTCTATCATGATAGCGACCGGCCCTCAGGG
ATCCCTGAGCGATTCACTGGCTCCAATTCTGGGAACATGGCCACCCTGACCATCAGC
AGGGTCGAGGCCGGGGATGAGGCCGACTATTACTGTCAGGTGTGGGATAGTAGTAA
TGATCATTCGGTATTCGGCGGAGGCACCGAGCTGACCGTCCTCG 1-403, SEQ ID NO: 94
GAGCTCGTGATGACCCAGTCTCCATCGTCTCTGTCTGCATCTGTAGGAGACACCGTC
ACCATCACTTGCCGGGCAAGTCAGAGCCTTAGGGGATATTTAAATTGGTATCAACAG
AAGCCAGGGGAAGCCCCTAAACTCCTCATCTACGCTGCGTCCACTTTGCGGGCTGGG
GTCCCACCAAGGTTCAGTGGCGCCGGGTATGAGACAGATTTCAGTCTCACCATCAGC
AATCTGCAACTTGAAGATTTTGCAACTTACTATTGTCAACAGTCTCACAATGTCCCCC
TCACCTTCGGCGGAGGGACCAAGGTGGAAATCAAAG 1-404, SEQ ID NO: 95
GAGCTCGTGGTGACGCAGCCGCCCTCAGTGTCTGCGGCCCCAGGACAGAAGGTCAC
CATCTCCAGCTCTGGAAGCACCTCCAACATTGGGAACAATTATGTATCCTGGTACCA
GCAGTTCCCACGAACAGCCCCCAAACTCCTCATTTATGACAATAATAAGCGACCCTC

| Antibody Heavy Chains - nucleic acid sequences |
|---|
| AGGGATTCCTGACCGATTCTCTGGCTCCAAGTCTGGCACGTCAGCCACCCTGGGCAT<br>CACCGGGCTCCAGACTGGGGACGAGGCCGATTATTACTGCGAACATGGGATAGCA<br>GCCTGAGTGCTGTGGTATTCGGCGGAGGCACCAAGGTGACCGTCCTAG<br><br>1-405, SEQ ID NO: 96<br>GAGCTCGAGCTGATTCAGCCACCCTCAGTGTCAGTGTCCCCAGGACAGACGGCCAG<br>GATCACCTGCTCTGGAGATGCATTGCCAAAGCAATACGCTTATTGGTACCAGCAGA<br>AGCCAGGCCAGGCCCCTGCGATGGTGATATATAAAGACACTGAGAGGCCCCCAGGGA<br>TCTCTGAGCGAATCTCTGGCTTCATCTCAGGGACAACAGCCACGTTGACCATCAGTG<br>GAGTCCAGGCAGAGGACGAGGCTGACTATTACTGTCAATCAGAAGACAGCAGTGGT<br>ATCCTTTTTGGCGGAGGGACCAAGCTGACCGTCCTAG<br><br>1-406, SEQ ID NO: 97<br>GAGCTCGAGCTGACTCAGCCACCCTCAGTGTCAGTTTTCCCAGGACAGACGGCCAG<br>GATCACCTGTTCTGGAGATACATTGCCAAAGCAATACGGTAATTGGTACCAGCAGA<br>AGCCAGGCCAGGCCCCTGTGGTCGTGATATATAAAGACACTGAGAGGCCCCTCAGGG<br>ATCCCTGAGCGATTCTCTGGCTCCAGTTCAGGGACAACAGCCACGTTGACCATCAGT<br>GGGGTCCAGGCAGAAGACGAGGCTGATTATTACTGTCAATCAGCAGACAGCAATGA<br>TTGGGTGCTATTCGGCGGAGGGACCAAGCTGACCGTCCTAG<br><br>1-407, SEQ ID NO: 98<br>GAGCTCCAGATGACCCAGTCTCCATCCTCCCTGTCTGCATCTGTAGGAGACAGAGTC<br>ACCATCACTTGCCAGGCGAGTCAGGACATTAGCAACTATTTAAATTGGTATCAGCAG<br>AAACCAGGGAAAGCCCCTAAGCTCCTGATCTACGATGCATCCAATTTGGAAACAGG<br>GGTCCCATCAAGGTTCAGTGGAGGTGGGTCTGGGACAGACTTTTACCTTCACCATCAG<br>CAGCCTGCAGGCTGAAGATTTTGCAACATATTATTGTCAACAGTATGCTAATCTCCC<br>GCTCACTTTCGGCGGAGGGACCAAGCTGGAGATCAAAG<br><br>1-408, SEQ ID NO: 99<br>GAGCTCGTGCTGACTCAGCCACCCTCGGTGTCAGTGTCCCCAGGACAGACGGCCAG<br>GATCACCTGCTCTGGAGATGCATTGCCAAAGCAATATGCTTATTGGTACCAGCAGAA<br>GCCAGGCCAGGCCCCTGTGCTGGTGATATATAAAGACAGTGAGAGGCCCTCAGGGA<br>TCCCTGAGCGATTCTCTGGCTCCAGCTCAGGGACAACAGTCACGTTGACCATCAGTG<br>GAGTCCAGGCAGAAGACGAGGCTGACTATTACTGTCAATCAGCAGACAGCAGTGGT<br>ACTTCCTGGGTGTTCGGCGGAGGCACCAAGCTGACCGTCCTAG<br><br>1-410, SEQ ID NO: 100<br>GAGCTCCAGATGACCCAGTCTCCATCCTCCCTGTCTGCATCTGTAGGAGACAGAGTC<br>ACCATCACTTGCCAGGCGAGTCAGGACATTAGCAACTATTTAAATTGGTATCAGCAG<br>AAACCAGGGAAAGCCCCTAAGCTCCTGATCTACGATGCATCCAATTTGGAAACAGG<br>GGTCCCATCAAGGTTCAGTGGAAGTGGATCTGGGACAGATTTTACTTTCACCATCAG<br>CAGCCTGCAGCTGAAGATATTGCAACATATTACTGTCAACAGTATGATAATCTCCC<br>CCTCACCTTCGGCCAAGGGACACGACTGGAGATTAAAG<br><br>1-413, SEQ ID NO: 101<br>GAGCTCGAGCTGACTCAGCCACCCTCAGTGTCAGTGTCCCCAGGACAGACGGCCAG<br>GATCACCTGCTCTGGAGGTGCATTGCCAAAGCATTATGTTTATTGGTACCAGCAGAA<br>GCCAGGCCAGGCCCCTGCGGTGGTAATATATAAAGACACTGAGAGGCCCTCAGGGA<br>TCCCTGAGCGATTCTCTGGCTCCACCTCAGGGGCAACAGTCACGTTGACCATCAGTG<br>GAGTCCAGGCAGATGACGACGCTGTCTATTTCTGTCAATCAGTAGACAGCAATGATA<br>CTTCTTGGATATTCGGCGGAGGCACCAAGCTGACCGTCCTAG<br><br>1-415, SEQ ID NO: 102<br>GAGCTCGAGCTGACTCAGCCACCCTCAGTGTCTGGGTCTCCTGGACAGTCGATCACC<br>ATCTCCTGCACTGGAACCAGCAGTGACGTTGGTGGTTATAACTATGTCTCCTGGTAC<br>CAACAGCACCCAGGCAAAGCCCCCAAACTCATGATTTATGAGGTCAGTAATCGGCC<br>CTCAGGGGTTTCTAATCGCTTCTCTGGCTCCAAGTCTGGCAACACGGCCTCCCTGAC<br>CATCTCTGGGCTCCAGGCTGAGGACGAGGCTGATTATTACTGCAGCTCATATACAAG<br>CAGCAGCACTGTGGTATTCGGCGGAGGCACCAAGCTGACCGTCCTAG<br><br>1-416, SEQ ID NO: 103<br>GAGCTCGTGCTGACTCAGCCACCCTCGGTGTCAGTGTCCCCAGGACAGACGGCCAG<br>GATCACCTGCTCTGGAGATGCATTTCCTAAGCACTATGCTTATTGGTACCAGCAGAA<br>GCCAGGCCAGGCCCCTGTATTGGTGATCTATAAAGACACTGAGAGGCCCTCAGGGA<br>TACCTGAGCGATTCTCTGGCTCCAGCTCAGGGACAACAGCCACGTTGACCATCAGTG<br>GAGTCCAGGCAGAAGATGAAGCTGACTATTACTGTCAATCAACAGACTCCAGTGAT<br>ACCTGGGTCTTCGGAGCTGGCACCAAGGTGACCGTCCTAG<br><br>1-417, SEQ ID NO: 104<br>GAGCTCGTGCTGACTCAGCCACCCTCAGTGTCAGTGGCCCCAGGAAAGACGGCCAG<br>AATTACCTGTGGGGGAAACAACATCGGAAGTAAAACTGTGCACTGGTACCAGCAGA<br>AGCCAGGCCAGGCCCCTGTGGTGGTCGTCTCTGATGATAGCGAACGGCCCTCAGGG<br>ATCCCTGAGCGATTCTCTGGCTCCAACTCTGGGAACACGGCCACCCTTACCATCAGC<br>AGGGTCGAAGGCGGGGATGAGGCCGACTATTACTGTCAGGTGTGGGATAGCAGTAA<br>TGATCAGGTAGTGTTCGGCGGAGGCACCGAGCTGACCGTCCTCG |

| Antibody Heavy Chains - nucleic acid sequences |
| --- |

1-418, SEQ ID NO: 105
GAGCTCGTGCTGACTCAGCCACCCTCGGTGTCAGTGTCCCCAGGACAGACGGCCAG
GATCACCTGCTCTGGAGGTGCATTGCCAAAGCATTATGCCTATTGGTACCAGCAGAA
GCCAGGCCAGGCCCCTGCGGTGGTAATATATAAAGACACTGAGAGGCCCTCCGGGA
TCCCTGAGCGATTCTCTGGCTCCACCTCAGGGACAACAGTCACGTTGACCATCAGTG
GAGTCCAGGCAGATGACGACGCTGTCTATTTCTGTCAATCAGTAGACAGCAATGATA
CTTCTTGGATATTCGGCGGAGGCACTAAGCTGACCGTCCTAG 1-420, SEQ ID NO: 106
GAGCTCGAGCTGACTCAGCCACCCTCAGTGTCAATTTCCCCGGGAAAGACGGCCAA
GATTTTCTGTGGGGGAAACAGCATTGGACGTAAAAGTGTGCACTGGTACCAGCAGA
AGCCAGGCCAGGCCCCTGTGCTGGTCGTCTATGATGATAGCGACCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATTACGTGGTATTCGGCGGAGGCACCAAGCTGACCGTCCTAG 1-423, SEQ ID NO: 107
GAGCTCGTGCTGACTCAGCCACCCTCAGTGTCAGTGGCCCCAGGAAAGACGGCCAG
GGTTACCTGTGGGGGAGGCAACATTGGAGATAAAGCTGTACACTGGTACCAGCAGA
GGCCAGGCCAGGCCCCTGTGCTGGTCGTCTTTGGTGATAGCGCCCGGCCCTCAGGGA
TCCCTGAGCGATTCTCTGGCTCCAACTCTGGGAACACGGCCACCCTGACCATCAGCA
GGGTCGAAGTCGGGGATGAGGCCGACTATTACTGTCAGGTGTGGGATAGTAATAGT
GATCATCAGGTGTTCGGCGGAGGCACCAAGCTGACCGTCCTAG 1-428, SEQ ID NO: 108
GAGCTCGAGCTGACTCAGCCGCCCTCGGTGTCAGTGTCCCCAGGACAGACGGCCAG
GATCACCTGCTCTGGAGATGCATTGCCAAAGCAATATGCTTATTGGTACCAGCAGAA
GCCAGGCCAGGCCCCTGTGCTGGTGATATATAAAGACAGTGAGAGGCCCTCAGGGA
TCCCTGAGCGATTCTCTGGCTCCAGCTCAGGGACAACAGTCACGTTGACCATCAGTG
GAGTCCAGGCAGAAGACGAGGCTGACTATTACTGTCAATCAGCAGACAGCAGTGGT
ACTTATGAGGTGTTCGGCGGAGGGACCAAGCTGACCGTCCTAG 1-431, SEQ ID NO: 109
GAGCTCGAGCTGACTCAGCCACCCTCAGTGTCAGTGTCCCCAGGACAGACGGCCAG
GATCACCTGCTCTGGAGATGCATTGCCAAAGCAATATGCTTATTGGTACCAGCAGAA
GCCAGGCCAGGCCCCTGTGCTGGTGATATATAAAGACAGTGAGAGGCCCTCAGGGA
TCCCTGAGCGATTCTCTGGCTCCAGCTCAGGGACAACAGTCACGTTGACCATCAGTG
GAGTCCAGGCAGAAGACGAGGCTGACTATTACTGTCAATCAGCAGACAGCAGTGGT
ACTTACGTGTTCGGCGGAGGCACCAAGCTGACCGTCCTAG 1-432, SEQ ID NO: 110
GAGCTCGTGCTGACTCAGCCACCTTCGATGTCAGTGGTCCCAGGACAGACGGCCAG
GATTACCTGTGGGGGAGACAACATTGGAAGTAAAAGTGTTCATTGGTACCAGCAAA
AGCCAGGCCAGGCCCCTGTTCTGGTCGTCAATGATGATACCGAGCGGCCCTCAGGA
ATCCCCGACCGATTCTCTGGCTCCAACTCTGGGAACACGGCCACCCTGGTCATCAGC
AGGGTCGGGGCCGGGGATGAGGCCGACTATTTCTGTCAGGTGTGGGATAGCAGGAG
TGATCATCAGGTGTTCGGCGGAGGCACCAAGCTGACCGTCCTAG 1-434, SEQ ID NO: 111
GAGCTCGTGTTGACGCAGCCGCCCTCGGTGTCAGTGGCCCCAGGACAGACGGCCAG
GATTACCTGTGGGGGAAACAACATTGGAAGTAAAAGTGTGCACTGGTACCAGCAGA
AGCCAGGCCAGGCCCCTGTGCTGGTCGTCTATGATGATAGCGACCGGCCCTCAGGG
ATCCCTGAGCGATTCTCTGGCTCCAATTCTGGGAACACGGCCACCCTGACCATCAGC
AGGGTCGAAGCCGGGGATGAGGCCGACTATTACTGTCAGGTGTGGGATAGTAGTAG
TGATCATGTGGTATTCGGCGGAGGGACCGAGCTGACCGTCCTCG 1-437, SEQ ID NO: 112
GAGCTCGCCCTGACTCAGCCTCCCTCCGTGTCTGGGTCTCCTGGACAGTCGATCACC
ATCTCCTGCACTGGAACCAGCAGTGACGTTGGTGGTTATAACTATGTCTCCTGGTAC
CAACAGCACCCAGGCAAAGCCCCCAAACTCATGATTTATGAGGTCAGTAATCGGCC
CTCAGGGGTTTCTAATCGCTTCTCTGGCTCCAAGTCTGGCAACACGGCCTCCCTGAC
CATCTCTGGGCTCCAGGCTGAGGACGAGGCTGATTATTACTGCAGCTCATATACAAG
CAGCACCCCTTATGTCTTCGGAACTGGGACCAAGGTGACCGTCCTAG 1-438, SEQ ID NO: 113
GAGCTCGTGCTGACTCAGCCACCTTCGGTGTCAGTGGCCCCAGGACAGACGGCCAG
GATTACCTGTGGGGGAAACAACATTGGAAGTAAAAGTGTGCACTGGTACCAGCAGA
AGCCAGGCCAGGCCCCTGTGCTGGTCGTCTATGATGATAGCGACCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATCATAAGGTATTCGGCGGAGGGACCGAGCTGACCGTCCTCG 1-440, SEQ ID NO: 114
GAGCTCCAGATGACCCAGTCTCCATCCTCCCTGTCTGCATCTGTAGGAGACAGAGTC
ACCATCACTTGCCGGGCAAGTCAGAGCATTAGCAGCTATTTAAATTGGTATCAGCAG
AAACCAGGGAAAGCCCCTAAGCTCCTGATCTATGCTGCATCCAGTTTGGAAAGTGG

| Antibody Heavy Chains - nucleic acid sequences |
|---|
| GGTCCCATCAAGGTTCAGTGGCAGTGGATCTGGGACAGATTTCACTCTCACCATCAG<br>CAGTCTGCAACCTGAAGATTTTGCAAGTTACTACTGTCAACAGAGTTACAGTACCCC<br>ATTCACTTTCGGCCCTGGGACCAAAGTGGATATCAAAG<br><br>1-441, SEQ ID NO: 115<br>GAGCTCGTGGTGACGCAGCCGCCCTCAGTGTCTGCGGCCCCAGGACAGAAGGTCAC<br>CATCTCCTGCTCTGGAAGCACCTCCAACATTGGGAACAATTATGTATCCTGGTACCA<br>GCAGTTCCCAGGAACAGCCCCCAAACTCCTCATTTATGACAATAATAAGCGACCCTC<br>AGGGATTCCTGACCGATTCTCTGGCTCCAAGTCTGGCACGTCAGCCACCCTGGGCAT<br>CACCGGGCTCCAGACTGGGGACGAGGCCGATTATTACTGCGGAACATGGGATAGCA<br>GCCTGAGTGCTGTGGTATTCGGCGGAGGCACCAAGGTGACCGTCCTAG<br><br>1-450, SEQ ID NO: 116<br>GAGCTCGTGCTGACTCAGCCACCCTCGGTGTCAGTGTCCCCAGGACAGACGGCCAG<br>GATCACCTGCTCTGGAGATGCATTGCCAAAGCAATATGCTTATTGGTACCAGCAGAA<br>GCCAGGCCAGGCCCCTGTGCTGGTGATATATAAAGACAGTGAGAGGCCCTCAGGGA<br>TCCCTGAGCGATTCTCTGGCTCCAGCTCAGGGACAACAGCCACGTTGACCATTAGTG<br>GAGTCCAGGCAGAAGACGAGGCTGACTATTACTGTCAATCAGCATACAGCAGTGGT<br>ACTGTGGTATTCGGCGGAGGGACCGAGCTGACCGTCCTCG<br><br>1-451, SEQ ID NO: 117<br>GAGCTCCAGATGACCCAGTCTCCATCCTCCCTGTCTGCATCTGTAGGAGACAGAGTC<br>ACCATCACTTGCCGGGCAAGTCAGAGCATTAGCAGCTATTTAAATTGGTATCAGCAG<br>AAACCAGGGAAAGCCCCTAAGCTCCTGATCTATGCTGCATCCAGTTTGCAAAGTGGG<br>GTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCG<br>TACACTTTTGGCCAGGGGACCAAGCTGGAGATCAAAG<br><br>1-458, SEQ ID NO: 118<br>GAGCTCGTGCTGACTCAGCCACCCTCAGTGTCAGTGGCCCCAGGAAAGACGGCCAG<br>GATTCCCTGTGGGGGAAACAACATTGGAGGTAAAAGTGTGCACTGGTACCAGCAGA<br>GGCCAGGCCAGGCCCCTGTGCTGGTCGTCTATTCTGATAGCGTCCGGCCCTCGGGGA<br>TCCCTGAGCGATTCTCTGGCTCCAACTCTGGGAACACGGCCACCCTGACCATCAGCA<br>GGGTCGAAGCCGGGGATGAGGCCGACTATTACTGTCAGGTGTGGGATAGAAGTAGT<br>GATCATGTGGTATTCGGCGGAGGCACCCAGCTGACCGTCCTCG<br><br>2-102, SEQ ID NO: 119<br>GAGCTCGTGGTGACGCAGCCGCCCTCGGTGTCAGTGGCCCCAGGACAGACGGCCAG<br>GATTACCTGTGGGGGAAACAACATTGGAAGTATAAATGTGCACTGGTACCAGCAGA<br>AGCCAGGCCAGGCCCCTGTACTGGTCGTCTATGATGATAGCGCCCGGCCCTCAGGG<br>ATCCCTGAGCGATTTTCTGGCTCCAACTCTGGGAACACGGCCACCCTGACCATCAGC<br>AGGGTCGAAGCCGGGGATGAGGCCGACTATTACTGTCAGGTGTGGGATAGTAGAAG<br>TGATTATTGGGTGTTCGGCGGAGGCACCAAGGTGACCGTCCTAG<br><br>2-103, SEQ ID NO: 120<br>GAGCTCGTGCTGACTCAGCCACCCTCGGTGTCAGTGGCCCCAGGACAGACGGCCAG<br>GATTACCTGTGGGGGAAACAACATTGGAAGTAAAAGTGTGCACTGGTACCAGCAGA<br>AGCCAGGCCAGGCCCCTGTAGTGGTCGTCTATGATGATAGCGACCGGCCCTCAGGG<br>ATCCCTGAGCGATTCTCTGGCTCCAACTCTGGGAACACGGCCACCCTGACCATCAGC<br>AGGGTCGAAGCCGGGGATGAGGCCGACTATTACTGTCAGGTGTGGGATAGTAGTAG<br>TGATCATTGGGTGTTCGGCGGAGGCACCGAGCTGACCGTCCTCG<br><br>2-106, SEQ ID NO: 121<br>GAGCTCGTGCTGACTCAGCCACCCTCGGTGTCAGTGGCCCCAGGACAGACGGCCAG<br>GATTACCTGTGGGGGAAACAACATTGGAAGTAAAAGTGTGCACTGGTACCAGCAGA<br>AGCCAGGCCAGGCCCCTGTGCTGGGCGTCTATGATGATAGCAACCGGCCCTCAGGG<br>ATCCCTGAGCGATTCTCTGGCTCCAACTCTGGGAACACGGCCACCCTGACCATCAGC<br>AGGGTCGAAGCCGGGGATGAGGCCGACTATTACTGTCAGGTGTGGGATAGTAGTAG<br>TGATCATTGGGTGTTCGGCGGAGGCACCCAGCTGACCGTCCTCG<br><br>2-108, SEQ ID NO: 122<br>GAGCTCGTGGTGACGCAGCCGCCCTCAGCGTCTGGGACCCCCGGGCAGAGGGTCAC<br>CATCTCTTGTTCTGGAAGCAGCTCCAACATCGGAAGTAATTATGTATACTGGTACGA<br>GCAGCTCCCAGGAACGGCCCCCAAACTCCTCATCTATAGGAATAATCAGCGGCCCTC<br>AGGGGTCCCTGACCGATTCTCTGGCTCCAAGTCTGGCACCTCAGCCTCCCTGGCCAT<br>CAGTGGGCTCCGGTCCGAGGATGAGGCTGATTATTACTGTGCAGCATGGGATGACA<br>GCCTGCGTGTTTATGTCTTCGGAACTGGCACCAAGCTGACCGTCCTAG<br><br>2-203, SEQ ID NO: 123<br>GAGCTCGTGCTGACTCAGCCACCTTCGGTGTCAGTGGCCCCAGGACAGACGGCCAG<br>GATTACCTGTGGGGGAAACAACATTGGAAGTAAAGGTGTGCACTGGTACCAGCAGA<br>AGCCAGGCCAGGCCCCTGTACTGGTCGTCTATGATGATAGCGACCGGCCCTCAGGG<br>ATCCCTGAGCGATTATCTGGCTCCAACTCTGGGAACACGGCCACCCTGACCATCAGC<br>AGGGTCGAAGCCGGGGATGAGGCCGACTATTACTGTCAGGTGTGGGATAGTAGTAG<br>TGATCATTGGGTGTTCGGCGGAGGCACCGAGCTGACCGTCCTCG |

| Antibody Heavy Chains - nucleic acid sequences |
| --- |

2-204, SEQ ID NO: 124
GAGCTCGTGCTGACTCAGCCACCCTCGGTGTCAGTGGCCCCAGGACAGACGGCCAC
GCTTACGTGTGGGGGGAACAACATTGGAAGTAGAAGTGTGCACTGGTACCAGCAGA
AGCCAGGCCAGGGCCCTGTGCTGGTCGTCTATGATGATAGCGACCGGCCCTCAGGG
ATCCCTGAGCGATTCTCTGGCTCCAACTCTGGGAACACGGCCACCCTGACTATCAGC
AGGGTCGAAGCCGGGGATGACGCCGACTATTACTGTCAGGTGTGGGAGAGTACTAC
TGATCATTATGTCTTCGGAACTGGGACCAAGCTGACCGTCCTAG 2-206, SEQ ID NO: 125
GAGCTCGTGTTGACGCAGCCGCCCTCGGTGTCAGTGGCCCCAGGACAGACGGCCAG
GATTACCTGTGGGGGAAACAACATTGGAAGTAAAAATGTGCACTGGTACCAGCAGA
AGCCAGGCCAGGCCCCTGTGCTGGTCGTCTATGATGATAGCGACCGACCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATCATTGGGTGTTCGGCGGAGGCACCAAGGTGACCGTCCTAG 2-207, SEQ ID NO: 126
GAGCTCGTGCTGACTCAGCCACCTTCGGTGTCAGTGGCCCCAGGACAGACGGCCAG
GATTACCTGTGGGGGAAACAACATTGGAAGTAAAAGTGTGCACTGGTACCAGCAGA
AGCCAGGCCAGGCCCCTGTGCTGGTCGTCCATGATGATAGCGACCGGCCCTCAGGG
ATCCCTGAGCGATTCTCTGGCTCCAACTCTGGGAACACGGCCACCCTGACCATCGGC
AGGGTCGGAGCCGGGGATGAGGCCGACTATTACTGTCAGGTGTGGGATAGTAGTAG
TGATCATTGGGTGTTCGGCGGAGGCACCCAGCTGACCGTCCTCG 2-301, SEQ ID NO: 127
GAGCTCGTGCTGACTCAGCCACCCTCGGTGTCAGTGGCCCCAGGACAGACGGCCAG
GATTATCTGTGGGGGAAACAACATTGGAAGTAAAACTGTGCACTGGTACCAGCAGA
AGCCAGGCCAGGCCCCTGTGTTGGTCGTCTATGATGATAGCGACCGGCCCTCAGGG
ATCCCTGAGCGATTCTCTGGCTCCAACTCTGGGAACACGGCCGCCCTGACCATCAGC
AGGGTCGAAGCCGGGGATGAGGCCGACTATTATTGTCAGGTGTGGCATAGTAGTAG
TGATCATTGGGTGTTCGGCGGAGGCACCAAGGTGACCGTCCTAG 2-302, SEQ ID NO: 128
GAGCTCGTGCTGACTCAGCCACCTTCGGTGTCAGTGGCCCCAGGACAGACGGCCAT
AATTACCTGTGGGGGAAGCAACATTGGAACTAAAAGTGTGCACTGGTATCAGCAGA
AGTCAGGCCAGGCCCCTGTGCTGGTCGTCCATGATGATGCCCACCGGCCCTCAGGGA
TCCCTGAGCGATTCTCTGGCTCCAACTCTGGGAACACGGCCACCCTGACCATCAGCA
GGGTCGAAGCCGGGGATGAGGCCGACTATTACTGTCAGGTGTGGGAAAGTAGTAGT
GATCATTGGGTGTTCGGCGAGGCACCAAGGTGACCGTCCTAG 2-304, SEQ ID NO: 129
GAGCTCGTGCTGACTCAGCCACCCTCGGTGTCAGTGGCACCAGGACAGACGGCCAG
GATTACCTGTGGGGGAAACAACATTGAAAGTAAAAATGTGCACTGGTACCAGCAGA
AGCCAGGCCAGGCCCCTGTGCTGGTCGTCTATGATGATAGCGGCCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATCATTGGGTGTTCGGCGGAGGCACCAAGCTGACCGTCCTAG 2-305, SEQ ID NO: 130
GAGCTCGTGCTGACTCAGCCACCCTCGGTGTCAGTGGCACCAGGACAGACGGCCAG
GATTACCTGTGGGGGAAACAACATTGGAAGTAAAAGTGTGCACTGGTACCAGCAGA
AGCCAGGCCAGGCCCCTGTGCTGGTCGTCTATGATGATAGCGACCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAATAG
TGATCATTGGGTGTTCGGCGGAGGCACCGAGCTGACCGTCTTCG 2-406, SEQ ID NO: 131
GAGCTCGTGCTGACTCAGCCACCCTCGGTGTCAGTGGCCCCAGGACAGACGGCCAG
GATTACCTGTGGGGGAAACAACATTGGAAGTAAAAGTGTGCACTGGTACCAGCAGA
AGCCAGGCCGGGCCCCTGTGCTGGTCGTCTATGATGATAGCGAGCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGAGAGTAGTAG
TGATCATTGGGTGTTCGGCGGAGGGACCAAGGTGACCGTCCTAG 2-408, SEQ ID NO: 132
GAGCTCGTGCTGACTCAGCCACCCTCGGTGTCAGTGGCCCCAGGACAGACGGCCAG
GATTACCTGTGGGGGAAACAACATTGGAAGTAAAAATGTGCACTGGTACCAGCAGA
AGCCAGGCCAGGCCCCTCTACTGGTCGTCTATGATGATAGCGACCGGCCCTCAGGG
ATCCCTGAGCGATTCTCTGGCTCCAACTCTGGGAACATGGCCACCCTGACCATCAGC
AGGGTCGAAGCCGGGGATGAGGCCAACTATTACTGTCAGGTGTGGGATAGTAGTAG
TGATCATGTGGTATTCGGCGGAGGGACCAAGCTGACCGTCCTAG 3-301, SEQ ID NO: 133
GAGCTCGTGCTGACTCAGCCACCCTCGGTGTCAGTGTCCCCAGGACAGACGGCCAG
GATCACCTGCTCTGGAGATGCATTGCCAAAGCAATATGCTTATTGGTACCAGCAGAA
GCCAGGCCAGGCCCCTGTGTTGGTGATATATAAAGACAGTGAGAGGCCCTCAGGGA

| Antibody Heavy Chains - nucleic acid sequences |
| --- |

```
TCCCTGAGCGATTCTCTGGCTCCAGCTCAGGGACAACAGTCACGTTGACCATCAGTG
GAGTCCAGGCAGAAGACGAGGCTGACTATTACTGTCAATCAGCAGACAGCAATGGT
ACTTATAAGGTGTTCGGCGGAGGCACCGAGCTGACCGTCCTCG 3-302, SEQ ID NO: 134
GAGCTCGTGCTGACTCAGCCACCCTCAGTGTCCGTGTCCCCGGGACAGACAGCCAGC
ATCACCTGCTCTGGAGATAAATTGGGACATACATACACTTCCTGGTATCAACAGAAG
CCAGGCCAGTCCCCTGTCCTAGTCATCTATCAAGATAACAGGCGGCCCTCAGGGCTC
CCTGAGCGATTCTCTGGCTCCAACTCTGGGAACACGGCCACCCTGACCATCAGCAGG
GTCGAAGCCGGGGATGAGGCCGACTATTACTGTCAGGTGTGGGAAAGTAGTAGTGA
TCATCTTGTATTCGGCGGAGGCACCGAGCTGACCGTCCTCG 3-305, SEQ ID NO: 135
GAGCTCGTGCTGACTCAGCCACCCTCAGTGTCAGTGGCCCCAGGAAAGACGGCCAG
GATTACCTGTGGGGAAAACAACATTGGAAGTAAAAGTGTGCACTGGTACCAGCAGA
AGCCAGGCCAGGCCCCTGTGCTGGTCGTCTATGATGATAGCCAGGCGACCGGCCCTCAGGG
ATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAG
TGATCATTGGGTGTTCGGCGGAGGGACCCAGCTGACCGTCCTCG 3-405, SEQ ID NO: 136
GAGCTCGTGCTGACTCAGCCACCCTCAGTGTCAGTGGCCCCAGGAAAGACGGCCAG
GATTACCTGTGGGGAAAACAACATTGGAAGTAAAAGTGTGCACTGGTACCAGCAGA
AGCCAGGCCAGGCCCCTGTCCTGGTCATCTATTATGATACCGACCGGCCCTCAGGGA
TCCCTGCGCGCTTCTCTGGCTCCAACTCTGGGAACACGGCCACCCTGACCATCAGCA
GGGTCGAAGCCGGGGATGAGGCCGACTATTACTGTCAGGTGTGGGATAGTAGTAGT
GACCAGAGGGTATTCGGCGGAGGCACCGAGCTGACCGTCCTCG 4-303, SEQ ID NO: 137
GAGCTCGAGCTGACTCAGCCACCCTCAGTGTCAGTGGCCCCAGGAAAGGCGGCCAG
ACTTTCCTGCGGGGGAGAGGACATTGGAATTAAAAGTGTCCACTGGTACCAACAGA
AGACAGGCCGGGCCCCTGTGTTGGTCATCTATAATGATGACGACCGGCCCTCAGGG
ATCCCTGAGCGGTTCGCTGGCTCCAATTCTGGGAACACGGCCACCCTGACCATCAGC
AGGGTCGAGGCCGGGGATGAGGCCGACTACTATTGTGAGGTGTGGGACAGTCTTAC
TGATCGTGTCGTGTTCGGCGGAGGCACCAAGCTGACCGTCCTAG 4-307, SEQ ID NO: 138
GAGCTCGTGCTGACTCAGCCACCCTCAGTGTCAGTGGCCCCAGGAACGACGGCCAG
GATTACCTGTGGGGGAAACAACATTGGAAGTAAAAGTGTGCACTGGTACCAGCAGA
AGCCAGGCCAGGCCCCTGTGCTGGTCATTTATTATGATAGCGACCGGCCCTCAGGGA
TCCCTGAGCGATTCTCTGGCTCCAACTCTGGGAACACGGCCACCCTGACCATCAGCA
GGGTCGAAGCCGGGGATGAGGCCGACTATTACTGTCAGGTGTGGGATAGTAGTAGT
GATCAGGGGTATTCGGCGGAGGGACCCAGCTGACCGTCCTCG z1-201, SEQ ID NO: 139
GAGCTCGTGATGACCCAGTCTCCATCCTCCCTGTCTGCATCTGTAGGAGACAGAGTC
ACCATCACTTGCCGGGCAAGTCAGAGCATTAGCAGCTATTTAAATTGGTATCAGCAG
AAACCAGGGAAAGCCCCTAAGCTCCTGATCTATGCTGCATCCAGTTTGCAAAGTGGG
GTCCCATCAAGGTTCAGTGGCAGTGGATCTGGGACAGATTTCACTCTCACCATCAGC
AGTCTGCAACCTGAAGATTTTGCAACTTACTACTGTCAACAGAGTTACAGTACCCCG
TACACTTTTGGCCAGGGGACCAAGCTGGAGATCAAAG z1-303, SEQ ID NO: 140
GAGCTCGTGCTGACTCAGCCACCCTCGGTGTCAGTGGCCCCAGGACAGACGGCCAG
GATTACCTGTGGGGAAACAACATTGGAAGTAAAAGTGTGCACTGGTACCAGCAGA
AGCCAGGCCAGGCCCCTGTGTTGGTCGTCTATGATGATAGCGACCGGCCCTCAGGG
ATCCCTGAGCGATTCTCTGGCTCCAACTCTGGGAACACGGCCACCCTGACCATCAGC
GGGGTCGAAGTCGGGGATGAGGCCGACTATTACTGTCAGGTGTGGGATAGTAGTCG
TGATCATGTGGTATTCGGCGGAGGGACCGAGCTGACCGTCCTCG z1-402, SEQ ID NO: 141
GAGCTCGTGATGACCCAGTCTCCACTCTCCCTGCCCGTCACCCCTGGAGAGCCGGCC
TCCATCTCCTGCAGGTCTAGTCAGAGCCTCCTGCATAGTAATGGATACAACTATTTG
GATTGGTACCTGCAGAAGCCAGGGCAGTCTCCACAGCTCCTGATCTATTTGGGTTCT
AATCGGGCCTCCGGGGTCCCTGACAGGTTCAGTGGCAGTGGATCAGGCACAGATTTT
ACACTGAAAATCAGCAGAGTGGAGGCTGAGGATGTTGGGGTTTATTACTGTATGCA
AGCTCTACAAACTCCTCAGACTTTTGGCCAGGGGACCAAGCTGGAGATCAAAG

Antibody Light Chains - amino acid sequences
1-303, SEQ ID NO: 142
ELELTQPPSVSVAPGKTARITCGGNNIGSKSVHWYQQKPGQAPVLVVYDDSDRPSGIPE
RFSGSNSGNTATLTISRVEAGDEADYYCQVWDSSSDHYVFGTGTKVTVL 1-304, SEQ ID NO: 143
ELVLTQPPSVSVSPGQTARITCSGDALPKHYAYWYQQKPGQAPVVVIYKDTERPSGIPER
FSGATSGTTTTLTISGVQAEDEADYFCQSSDINGTSWIFGGGTKLTVL
```

| Antibody Heavy Chains - nucleic acid sequences |
| --- |

1-401, SEQ ID NO: 144
ELVLTQPPSVSVAPGKTARMTCGGNNIGGYSVHWYQQKPGQAPVLVVYHDSDRPSGIP
ERFTGSNSGNMATLTISRVEAGDEADYYCQVWDSSNDHSVFGGGTELTVL 1-403, SEQ ID NO: 145
ELVMTQSPSSLSASVGDTVTITCRASQSLRGYLNWYQQKPGEAPKLLIYAASTLRAGVP
PRFSGAGYETDFSLTISNLQLEDFATYYCQQSHNVPLTFGGGTKVEIK 1-404, SEQ ID NO: 146
ELWTQPPSVSAAPGQKVTISSSGSTSNIGNNYVSWYQQFPRTAPKLLIYDNNKRPSGIPD
RFSGSKSGTSATLGITGLQTGDEADYYCGTWDSSLSAVVFGGGTKVTVL 1-405, SEQ ID NO: 147
ELELIQPPSVSVSPGQTARITCSGDALPKQYAYWYQQKPGQAPAMVIYKDTFRPPGISER
ISGFISGTTATLTISGVQAEDEADYYCQSEDSSGILFGGGTKLTVL 1-406, SEQ ID NO: 148
ELELTQPPSVSVFPGQTARITCSGDTLPKQYGNWYQQKPGQAPVVVIYKDTERPSGIPER
FSGSSSGTTATLTISGVQAEDEADYYCQSADSNDWVLFGGGTKLTVL 1-407, SEQ ID NO: 149
ELQMTQSPSSLSASVGDRVTITCQASQDISNYLNWYQQKPGKAPKLLIYDASNLETGVPS
RFSGGGSGTDFTFTISSLQAEDFATYYCQQYANLPLTFGGGTKLEIK 1-408, SEQ ID NO: 150
ELVLTQPPSVSVSPGQTARITCSGDALPKQYAYWYQQKPGQAPVLVIYKDSERPSGIPER
FSGSSSGTTVTLTISGVQAEDEADYYCQSADSSGTSWVFGGGTKLTVL 1-410, SEQ ID NO: 151
ELQMTQSPSSLSASVGDRVTITCQASQDISNYLNWYQQKPGKAPKLLIYDASNLETGVPS
RFSGSGSGTDFTFTISSLQPEDIATYYCQQYDNLPLTFGQGTRLEIK 1-413, SEQ ID NO: 152
ELELTQPPSVSVSPGQTARITCSGGALPKHYVYWYQQKPGQAPVVVIYKDTERPSGIPER
FSGSTSGATVTLTISGVQADDDAVYFCQSVDSNDTSWIFGGGTKLTVL 1-415, SEQ ID NO: 153
ELELTQPPSVSGSPGQSITISCTGTSSDVGGYNYVSWYQQHPGKAPKLMIYEVSNRPSGV
SNRFSGSKSGNTASLTISGLQAEDEADYYCSSYTSSSTVVFGGGTKLTVL 1-416, SEQ ID NO: 154
ELVLTQPPSVSVSPGQTARITCSGDAFPKHYAYWYQQKPGQAPVLVIYKDTERPSGIPER
FSGSSSGTTATLTISGVQAEDEADYYCQSTDSSDTWVFGAGTKVTVL 1-417, SEQ ID NO: 155
ELVLTQPPSVSVAPGKTARITCGGNNIGSKTVHWYQQKPGQAPVVVVSDDSERPSGIPE
RFSGSNSGNTATLTISRVEGGDEADYYCQVWDSSNDQVVFGGGTELTVL 1-418, SEQ ID NO: 156
ELVLTQPPSVSVSPGQTARITCSGGALPKHYAYWYQQKPGQAPVVVIYKDTERPSGIPER
FSGSTSGTTVTLTISGVQADDDAVYFCQSVDSNDTSWIFGGGTKLTVL 1-420, SEQ ID NO: 157
ELELTQPPSVSISPGKTAKIFCGGNSIGRKSVHWYQQKPGQAPVLVVYDDSDRPSGIPERF
SGSNSGNTATLTISRVEAGDEADYYCQVWDSSSDYVVFGGGTKLTVL 1-423, SEQ ID NO: 158
ELVLTQPPSVSVAPGKTARVTCGGGNIGDKAVHWYQQRPGQAPVLVVFGDSARPSGIPE
RFSGSNSGNTATLTISRVEVGDEADYYCQVWDSNSDHQVFGGGTKLTVL 1-428, SEQ ID NO: 159
ELELTQPPSVSVSPGQTARITCSGDALPKQYAYWYQQKPGQAPVLVIYKDSERPSGIPER
FSGSSSGTTVTLTISGVQAEDEADYYCQSADSSGTYEVFGGGTKLTVL 1-431, SEQ ID NO: 160
ELELTQPPSVSVSPGQTARITCSGDALPKQYAYWYQQKPGQAPVLVIYKDSERPSGIPER
FSGSSSGTTVTLTISGVQAEDEADYYCQSADSSGTYVFGGGTKLTVL 1-432, SEQ ID NO: 161
ELVLTQPPSMSVVPGQTARITCGGDNIGSKSVHWYQQKPGQAPVLVVNDDTERPSGIPD
RFSGSNSGNTATLVISRVGAGDEADYFCQVWDSRSDHQVFGGGTKLTVL 1-434, SEQ ID NO: 162
ELVLTQPPSVSVAPGQTARITCGGNNIGSKSVHWYQQKPGQAPVLVVYDDSDRPSGIPE
RFSGSNSGNTATLTISRVEAGDEADYYCQVWDSSSDHVVFGGGTELTVL

| Antibody Heavy Chains - nucleic acid sequences |
| --- |

1-437, SEQ ID NO: 163
ELALTQPPSVSGSPGQSITISCTGTSSDVGGYNYVSWYQQHPGKAPKLMIYEVSNRPSGV
SNRFSGSKSGNTASLTISGLQAEDEADYYCSSYTSSTPYVFGTGTKVTVL 1-438, SEQ ID NO: 164
ELVLTQPPSVSVAPGQTARITCGGNNIGSKSVHWYQQKPGQAPVLVVYDDSDRPSGIPE
RFSGSNSGNTATLTISRVEAGDEADYYCQVWDSSSDHKVFGGGTELTVL 1-440, SEQ ID NO: 165
ELQMTQSPSSLSASVGDRVTITCRASQSISSYLNWYQQKPGKAPKLLIYAASSLESGVPS
RFSGSGSGTDFTLTISSLQPEDFASYYCQQSYSTPFTFGPGTKVDIK 1-441, SEQ ID NO: 166
ELVVTQPPSVSAAPGQKVTISCSGSTSNIGNNYVSWYQQFPGTAPKLLIYDNNKRPSGIP
DRFSGSKSGTSATLGITGLQTGDEADYYCGTWDSSLSAVVFGGGTKVTVL 1-450, SEQ ID NO: 167
ELVLTQPPSVSVSPGQTARITCSGDALPKQYAYWYQQKPGQAPVLVIYKDSERPSGIPER
FSGSSSGTTATLTISGVQAEDEADYYCQSAYSSGTVVFGGGTELTVL 1-451, SEQ ID NO: 168
ELQMTQSPSSLSASVGDRVTITCRASQSISSYLNWYQQKPGKAPKLLIYAASSLQSGVPS
RFSGSGSGTDFTLTISSLQPEDFATYYCQQSYSTPYTFGQGTKLEIK 1-458, SEQ ID NO: 169
ELVLTQPPSVSVAPGKTARIPCGGNNIGGKSVHWYQQRPGQAPVLVVYSDSVRPSGIPE
RFSGSNSGNTATLTISRVEAGDEADYYCQVWDRSSDHVVFGGGTQLTVL 2-102, SEQ ID NO: 170
ELVVTQPPSVSVAPGQTARITCGGNNIGSINVHWYQQKPGQAPVLVVYDDSARPSGIPE
RFSGSNSGNTATLTISRVEAGDEADYYCQVWDSRSDYWVFGGGTKVTVL 2-103, SEQ ID NO: 171
ELVLTQPPSVSVAPGQTARITCGGNNIGSKSVHWYQQKPGQAPVVVVYDDSDRPSGIPE
RFSGSNSGNTATLTISRVEAGDEADYYCQVWDSSSDHWVFGGGTELTVL 2-106, SEQ ID NO: 172
ELVLTQPPSVSVAPGQTARITCGGNNIGSKSVHWYQQKPGQAPVLGVYDDSNRPSGIPE
RFSGSNSGNTATLTISRVEAGDEADYYCQVWDSSSDHWVFGGGTQLTVL 2-108, SEQ ID NO: 173
ELVVTQPPSASGTPGQRVTISCSGSSSNIGSNYVYWYEQLPGTAPKLLIYRNNQRPSGVP
DRFSGSKSGTSASLAISGLRSEDEADYYCAAWDDSLRVYVFGTGTKLTVL 2-203, SEQ ID NO: 174
ELVLTQPPSVSVAPGQTARITCGGNNIGSKGVHWYQQKPGQAPVLVVYDDSDRPSGIPE
RLSGSNSGNTATLTISRVEAGDEADYYCQVWDSSSDHWVFGGGTELTVL 2-204, SEQ ID NO: 175
ELVLTQPPSVSVAPGQTATLTCGGNNIGSRSVHWYQQKPGQGPVLVVYDDSDRPSGIPE
RFSGSNSGNTATLTISRVEAGDDADYYCQVWESTTDHYVFGTGTKLTVL 2-206, SEQ ID NO: 176
ELVLTQPPSVSVAPGQTARITCGGNNIGSKNVHWYQQKPGQAPVLVVYDDSDRPSGIPE
RFSGSNSGNTATLTISRVEAGDEADYYCQVWDSSSDIWVFGGGTKVTVL 2-207, SEQ ID NO: 177
ELVLTQPPSVSVAPGQTARITCGGNNIGSKSVHWYQQKPGQAPVLVVHDDSDRPSGIPE
RFSGSNSGNTATLTIGRVGAGDEADYYCQVWDSSSDHWVFGGGTQLTVL 2-301, SEQ ID NO: 178
ELVLTQPPSVSVAPGQTARIICGGNNIGSKTVHWYQQKPGQAPVLVVYDDSDRPSGIPER
FSGSNSGNTAALTISRVEAGDEADYYCQVWHSSSDHWVFGGGTKVTVL 2-302, SEQ ID NO: 179
ELVLTQPPSVSVAPGQTAIITCGGSNIGTKSVHWYQQKSGQAPVLVVHDDAHRPSGIPER
FSGSNSGNTATLTISRVEAGDEADYYCQVWESSSDHWVFGGGTKVTVL 2-304, SEQ ID NO: 180
ELVLTQPPSVSVAPGQTARITCGGNNIESKNVHWYQQKPGQAPVLVVYDDSGRPSGIPE
RFSGSNSGNTATLTISRVEAGDEADYYCQVWDSSSDHWVFGGGTKLTVL 2-305, SEQ ID NO: 181
ELVLTQPPSVSVAPGQIARITCGGNNIGSKSVHWYQQKPGQAPVLVVYDDSDRPSGIPE
RFSGSNSGNTATLTISRVEAGDEADYYCQVWDSNSDHWVFGGGTELTVF

-continued

---
Antibody Heavy Chains - nucleic acid sequences
---

2-406, SEQ ID NO: 182
ELVLTQPPSVSVAPGQTARITCGGNNIGSKSVHWYQQKPGRAPVLVVYDDSERPSGIPER
FSGSNSGNTATLTISRVEAGDEADYYCQVWESSSDHWVFGGGTKVTVL 2-408, SEQ ID NO: 183
ELVLTQPPSVSVAPGQTARITCGGNNIGSKNVHWYQQKPGQAPLLWYDDSDRPSGIPE
RFSGSNSGNMATLTISRVEAGDEANYYCQVWDSSSDHVVFGGGTKLTVL 3-301, SEQ ID NO: 184
ELVLTQPPSVSVSPGQTARITCSGDALPKQYAYWYQQKPGQAPVLVIYKDSERPSGIPER
FSGSSSGTTVTLTISGVQAEDEADYYCQSADSNGTYKVFGGGTELTVL 3-302, SEQ ID NO: 185
ELVLTQPPSVSVSPGQTASITCSGDKLGHTYTSWYQQKPGQSPVLVIYQDNRRPSGLPER
FSGSNSGNTATLTISRVEAGDEADYYCQVWESSSDHLVFGGGTELTVL 3-305, SEQ ID NO: 186
ELVLTQPPSVSVAPGKTARITCGGNNIGSKSVHWYQOKPGQAPVLVVYDDSRPSGIPE
RFSGSNSGNTATLTISRVEAGDEADYYCQVWDSSSDHWVFGGGTQLTVL 3-405, SEQ ID NO: 187
ELVLTQPPSVSVAPGKTARITCGENNIGSKSVHWYQQKPGQAPVLVIYYDTDRPSGIPAR
FSGSNSGNTATLTISRVEAGDEADYYCQVWDSSSDQRVFGGGTELTVL 4-303, SEQ ID NO: 188
ELELTQPPSVSVAPGKAARLSCGGEDIGIKSVHWYQOKTGRAPVLVIYNDDDRPSGIPER
FAGSNSGNTATLTISRVEAGDEADYYCEVWDSLTDRVVFGGGTKLTVL 4-307, SEQ ID NO: 189
ELVLTQPPSVSVAPGTTARITCGGNNIGSKSVHWYQQKPGQAPVLVIYYDSDRPSGIPER
FSGSNSGNTATLTISRVEAGDEADYYCQVWDSSSDQGVFGGGTQLTVL z1-201, SEQ ID NO: 190
ELVMTQSPSSLSASVGDRVTITCRASQSISSYLNWYQOKPGKAPKLLIYAASSLQSGVPS
RFSGSGSGTDFTLTISSLQPEDFATYYCQQSYSTPYTFGQGTKLEIK z1-303, SEQ ID NO: 191
ELVLTQPPSVSVAPGQTARITCGGNNIGSKSVHWYQQKPGQAPVLVVYDDSDRPSGIPE
RFSGSNSGNTATLTISGVEVGDEADYYCQVWDSSRDHVVFGGGTELTVL z1-402, SEQ ID NO: 192
ELVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQALQTPQTFGQGTKLEIK

TABLE 6

Sequence listings of heavy and light chains.

| SEQ ID NO | Nucleic acid Ab | Chain | SEQ ID NO | Amino Acid Ab | Chain | SEQ ID NO | Nucleic acid Ab | Chain | SEQ ID NO | Amino Acid Ab | Chain |
|---|---|---|---|---|---|---|---|---|---|---|---|
| 1 | 1-303 | Heavy chain | 46 | 1-303 | Heavy chain | 25 | 1-450 | Heavy chain | 70 | 1-450 | Heavy chain |
| 2 | 1-304 | Heavy chain | 47 | 1-304 | Heavy chain | 26 | 1-451 | Heavy chain | 71 | 1-451 | Heavy chain |
| 3 | 1-401 | Heavy chain | 48 | 1-401 | Heavy chain | 27 | 2-102 | Heavy chain | 72 | 2-102 | Heavy chain |
| 4 | 1-403 | Heavy chain | 49 | 1-403 | Heavy chain | 28 | 2-103 | Heavy chain | 73 | 2-103 | Heavy chain |
| 5 | 1-404 | Heavy chain | 50 | 1-404 | Heavy chain | 29 | 2-106 | Heavy chain | 74 | 2-106 | Heavy chain |
| 6 | 1-405 | Heavy chain | 51 | 1-405 | Heavy chain | 30 | 2-108 | Heavy chain | 75 | 2-108 | Heavy chain |
| 7 | 1-406 | Heavy chain | 52 | 1-406 | Heavy chain | 31 | 2-203 | Heavy chain | 76 | 2-203 | Heavy chain |
| 8 | 1-407 | Heavy chain | 53 | 1-407 | Heavy chain | 32 | 2-204 | Heavy chain | 77 | 2-204 | Heavy chain |
| 9 | 1-408 | Heavy chain | 54 | 1-408 | Heavy chain | 33 | 2-206 | Heavy chain | 78 | 2-206 | Heavy chain |
| 10 | 1-410 | Heavy chain | 55 | 1-410 | Heavy chain | 34 | 2-207 | Heavy chain | 79 | 2-207 | Heavy chain |
| 11 | 1-413 | Heavy chain | 56 | 1-413 | Heavy chain | 35 | 2-302 | Heavy chain | 80 | 2-302 | Heavy chain |
| 12 | 1-416 | Heavy chain | 57 | 1-416 | Heavy chain | 36 | 2-304 | Heavy chain | 81 | 2-304 | Heavy chain |
| 13 | 1-417 | Heavy chain | 58 | 1-417 | Heavy chain | 37 | 2-305 | Heavy chain | 82 | 2-305 | Heavy chain |
| 14 | 1-418 | Heavy chain | 59 | 1-418 | Heavy chain | 38 | 2-408 | Heavy chain | 83 | 2-408 | Heavy chain |
| 15 | 1-420 | Heavy chain | 60 | 1-420 | Heavy chain | 39 | 3-301 | Heavy chain | 84 | 3-301 | Heavy chain |
| 16 | 1-423 | Heavy chain | 61 | 1-423 | Heavy chain | 40 | 3-302 | Heavy chain | 85 | 3-302 | Heavy chain |
| 17 | 1-428 | Heavy chain | 62 | 1-428 | Heavy chain | 41 | 4-303 | Heavy chain | 86 | 4-303 | Heavy chain |
| 18 | 1-431 | Heavy chain | 63 | 1-431 | Heavy chain | 42 | 4-307 | Heavy chain | 87 | 4-307 | Heavy chain |
| 19 | 1-432 | Heavy chain | 64 | 1-432 | Heavy chain | 43 | z1-201 | Heavy chain | 88 | z1-201 | Heavy chain |
| 20 | 1-434 | Heavy chain | 65 | 1-434 | Heavy chain | 44 | z1-303 | Heavy chain | 89 | z1-303 | Heavy chain |
| 21 | 1-437 | Heavy chain | 66 | 1-437 | Heavy chain | 45 | z1-402 | Heavy chain | 90 | z1-402 | Heavy chain |
| 22 | 1-438 | Heavy chain | 67 | 1-438 | Heavy chain | 91 | 1-303 | Light chain | 142 | 1-303 | Light chain |
| 23 | 1-440 | Heavy chain | 68 | 1-440 | Heavy chain | 92 | 1-304 | Light chain | 143 | 1-304 | Light chain |
| 24 | 1-441 | Heavy chain | 69 | 1-441 | Heavy chain | 93 | 1-401 | Light chain | 144 | 1-401 | Light chain |

TABLE 6-continued

Sequence listings of heavy and light chains.

| SEQ ID NO | Nucleic acid Ab | Chain | SEQ ID NO | Amino Acid Ab | Chain |
|---|---|---|---|---|---|
| 94 | 1-403 | Light chain | 145 | 1-403 | Light chain |
| 95 | 1-404 | Light chain | 146 | 1-404 | Light chain |
| 96 | 1-405 | Light chain | 147 | 1-405 | Light chain |
| 97 | 1-406 | Light chain | 148 | 1-406 | Light chain |
| 98 | 1-407 | Light chain | 149 | 1-407 | Light chain |
| 99 | 1-408 | Light chain | 150 | 1-408 | Light chain |
| 100 | 1-410 | Light chain | 151 | 1-410 | Light chain |
| 101 | 1-413 | Light chain | 152 | 1-413 | Light chain |
| 102 | 1-415 | Light chain | 153 | 1-415 | Light chain |
| 103 | 1-416 | Light chain | 154 | 1-416 | Light chain |
| 104 | 1-417 | Light chain | 155 | 1-417 | Light chain |
| 105 | 1-418 | Light chain | 156 | 1-418 | Light chain |
| 106 | 1-420 | Light chain | 157 | 1-420 | Light chain |
| 107 | 1-423 | Light chain | 158 | 1-423 | Light chain |
| 108 | 1-428 | Light chain | 159 | 1-428 | Light chain |
| 109 | 1-431 | Light chain | 160 | 1-431 | Light chain |
| 110 | 1-432 | Light chain | 161 | 1-432 | Light chain |
| 111 | 1-434 | Light chain | 162 | 1-434 | Light chain |
| 112 | 1-437 | Light chain | 163 | 1-437 | Light chain |
| 113 | 1-438 | Light chain | 164 | 1-438 | Light chain |
| 114 | 1-440 | Light chain | 165 | 1-440 | Light chain |
| 115 | 1-441 | Light chain | 166 | 1-441 | Light chain |
| 116 | 1-450 | Light chain | 167 | 1-450 | Light chain |
| 117 | 1-451 | Light chain | 168 | 1-451 | Light chain |
| 118 | 1-458 | Light chain | 169 | 1-458 | Light chain |
| 119 | 2-102 | Light chain | 170 | 2-102 | Light chain |
| 120 | 2-103 | Light chain | 171 | 2-103 | Light chain |
| 121 | 2-106 | Light chain | 172 | 2-106 | Light chain |
| 122 | 2-108 | Light chain | 173 | 2-108 | Light chain |
| 123 | 2-203 | Light chain | 174 | 2-203 | Light chain |
| 124 | 2-204 | Light chain | 175 | 2-204 | Light chain |
| 125 | 2-206 | Light chain | 176 | 2-206 | Light chain |
| 126 | 2-207 | Light chain | 177 | 2-207 | Light chain |
| 127 | 2-301 | Light chain | 178 | 2-301 | Light chain |
| 128 | 2-302 | Light chain | 179 | 2-302 | Light chain |
| 129 | 2-304 | Light chain | 180 | 2-304 | Light chain |
| 130 | 2-305 | Light chain | 181 | 2-305 | Light chain |
| 131 | 2-306 | Light chain | 182 | 2-306 | Light chain |
| 132 | 2-408 | Light chain | 183 | 2-408 | Light chain |
| 133 | 3-301 | Light chain | 184 | 3-301 | Light chain |
| 134 | 3-302 | Light chain | 185 | 3-302 | Light chain |
| 135 | 3-305 | Light chain | 186 | 3-305 | Light chain |
| 136 | 3-405 | Light chain | 187 | 3-405 | Light chain |
| 137 | 4-303 | Light chain | 188 | 4-303 | Light chain |
| 138 | 4-307 | Light chain | 189 | 4-307 | Light chain |
| 139 | z1-201 | Light chain | 190 | z1-201 | Light chain |
| 140 | z1-303 | Light chain | 191 | z1-303 | Light chain |
| 141 | z1-402 | Light chain | 192 | z1-402 | Light chain |

What is claimed is:

1. A composition comprising an anti-ADAMTS13 autoantibody comprising a single chain variable fragment (scFv) and pharmaceutically acceptable carrier,
wherein the autoantibody comprises (i) a heavy chain variable region comprising three complementarity determining regions of a heavy chain and (ii) a light chain variable region comprising three complementarity determining regions of a light chain,
wherein the heavy and light chains respectively comprise the amino acid sequences shown in SEQ ID NOs: 46 and 142; 47 and 143; 48 and 144; 49 and 145; 50 and 146; 51 and 147; 52 and 148; 53 and 149; 54 and 150; 55 and 151; 56 and 152; 57 and 154; 58 and 155; 59 and 156; 60 and 157; 61 and 158; 62 and 159; 63 and 160; 64 and 161; 65 and 162; 66 and 163; 67 and 164; 68 and 165; 69 and 166; 70 and 167; 71 and 168; 72 and 170; 73 and 171; 74 and 172; 75 and 173; 76 and 174; 77 and 175; 78 and 176; 79 and 177; 80 and 179; 81 and 180; 82 and 181; 83 and 183; 84 and 184; 85 and 185; 86 and 188; 87 and 189; 88 and 190; 89 and 191; and 90 and 192.

2. The composition of claim 1, wherein the anti-ADAMTS13 autoantibody is capable of decreasing ADAMTS13 activity.

3. The composition of claim 2, wherein the ADAMTS13 activity is selected from the group consisting of proteolytic activity, disulfide reducing activity, interacting or attaching to an endothelial cell surface, and any combination thereof.

4. The composition of claim 1, wherein the anti-ADAMTS13 autoantibody binds at least one of the ADAMTS13 region selected from the group consisting of amino-terminal (MDT1) domain, carboxy-terminal (T5-8/CUB) domain and cysteine-rich/spacer region.

5. A method for generating an in vivo model of thrombotic thrombocytopenic purpura (TTP), the method comprising introducing at least one anti-ADAMTS13 autoantibody of claim 1 into a model organism.

6. The method of claim 5, wherein the model organism is selected from the group consisting of a non-mammalian organism and a non-human mammalian organism.

7. The method of claim 6, wherein the mammalian organism is selected from the group consisting of a non-human primate, an ovine, a bovine, a porcine, a canine, a feline and a murine organism.

8. The method of claim 5, wherein introducing the anti-ADAMTS13 autoantibody comprises formulating the anti-ADAMTS13 autoantibody in a composition for administration to the model organism.

9. The method of claim 8, wherein introducing the anti-ADAMTS13 autoantibody further comprises injecting the anti-ADAMTS13 autoantibody into the model organism.

10. The method of claim 5, wherein introducing the anti-ADAMTS13 autoantibody comprises inducing in vivo expression in the model organism.

11. The method of claim 10, wherein inducing in vivo expression comprises delivering nucleic acids to the model organism.

12. The method of claim 11, wherein delivering the nucleic acids through a method selected from the group consisting of injection through hydrodynamic delivery, electroporation, transfection, transduction and other methods of viral delivery, and any combination thereof.

13. The method of claim 5, wherein the anti-ADAMTS13 autoantibody or fragment thereof binds at least one of the ADAMTS13 region selected from the group consisting of amino-terminal (MDT1) domain, carboxy-terminal (T5-8/CUB) domain and cysteine-rich/spacer region.

14. A method for identifying an anti-autoimmune reagent for treating thrombotic thrombocytopenic purpura (TTP), the method comprising contacting a panel of agents with at least one anti-ADAMTS13 autoantibody of claim 1; and identifying the agents that bind to the anti-ADAMTS13 autoantibody.

15. The method of claim 14, wherein identifying the agents comprises identifying agents that block binding of the anti-ADAMTS13 autoantibody or fragment thereof to ADAMTS13.

16. The method of claim 15, wherein the binding of the anti-ADAMTS13 autoantibody or fragment thereof to ADAMTS13 is blocked to at least one of the ADAMTS13 regions selected from the group consisting of amino-terminal (MDT1) domain, carboxy-terminal (T5-8/CUB) domain and cysteine-rich/spacer region.

17. The composition of claim 1, wherein the autoantibody comprises the heavy and light chains respectively comprise the amino acid sequences shown in SEQ ID NOs: 46 and 142; 47 and 143; 48 and 144; 49 and 145; 50 and 146; 51 and 147; 52 and 148; 53 and 149; 54 and 150; 55 and 151; 56 and 152; 57 and 154; 58 and 155; 59 and 156; 60 and 157; 61 and 158; 62 and 159; 63 and 160; 64 and 161; 65 and 162; 66 and 163; 67 and 164; 68 and 165; 69 and 166; 70 and 167; 71 and 168; 72 and 170; 73 and 171; 74 and 172; 75 and 173; 76 and 174; 77 and 175; 78 and 176; 79 and 177; 80 and 179; 81 and 180; 82 and 181; 83 and 183; 84 and 184; 85 and 185; 86 and 188; 87 and 189; 88 and 190; 89 and 191; and 90 and 192.

* * * * *

SEQUENCE LISTING

```
<160> NUMBER OF SEQ ID NOS: 267

<210> SEQ ID NO 1
<211> LENGTH: 352
<212> TYPE: DNA
<213> ORGANISM: Homo Sapiens

<400> SEQUENCE: 1
caggtgcagc tggtgcagtc tggggctgag gtgaagaagt ttgggtcctc agtgaaggtc     60
tcctgcaagg cttctggagg caccttcagc agttatacta tgagctgggt gcgacaggcc    120
cctgggcaag ggcttgagtg gatgggaagt ttcatcccta ttcttgagag agcaaactac    180
gcacagaagt tccagggcag agtcacttta accgcggaca aaagtacgag cacagcctac    240
atggagctgg gcagcctgag atctgaggac acggccgtgt attattgtgc gagagacctt    300
ggggacttcg gtgactcctg gggccaggga accctggtca ccgtctcctc ag            352

<210> SEQ ID NO 2
<211> LENGTH: 355
<212> TYPE: DNA
<213> ORGANISM: Homo Sapiens

<400> SEQUENCE: 2
caggtgcagc tggtgcagtc tggggctgag gtgaagaagc ctgggtcctc ggtgagggtc     60
tcctgcaagg cttctggaag caatttcagc agccacacca tcaattgggt acgacaggcc    120
cctggacacg ggcttgagtg gatgggcaag atcatccctg tccttgatat atctaaacac    180
gcacagacat tcctgggcag agtcataatt accgcggaca aatccacgag cacagcctac    240
atggagctga gcagcctgag atctgaggac acggccattt attactgtgc gatggatagt    300
gtctacggca actttgactt ttggggccag ggaacccccgg tcaccgtctc ctcag         355

<210> SEQ ID NO 3
```

```
<211> LENGTH: 358
<212> TYPE: DNA
<213> ORGANISM: Homo Sapiens

<400> SEQUENCE: 3
caggtgcagc tggtgcagtc tggggctgag ttgaagaagc ctgggtcctc ggtgaaggtc      60
tcctgcaagg cttctggagg cgccttcacc atgtacacta tcaactgggt gcgacaggcc     120
cctggacgag ggcttgagtg gatgggaagg atcatacctt tctaggtat aacagactac      180 gcacagaaat tccagggcag aggcacgatt accgcggaca atccacaag cacagcctac      240 ctggagctga gcggcctgac ttctgaggac acggccgtgt attactgtgc gagagagttt     300
agtgggggca actatttcga cttctggggc cagggaaccc tggtcaccgt ctcctcag      358

<210> SEQ ID NO 4
<211> LENGTH: 370
<212> TYPE: DNA
<213> ORGANISM: Homo Sapiens

<400> SEQUENCE: 4
caggtgcagc tgcaggagtc ggggggaggc gtggtccagc ctgggaggtc cctgagactc      60
tcctgtgcag cctctggatt caccttcagg aactatgcta tgcactgggt ccgccaggct     120
ccaggcaagg ggctggagtg ggtggcagtt atatcatatg atggaggtaa ggaatactac     180
gcagactccg tgaagggccg attcaccatc tccagagaca attccaagaa cacgctgtat     240
ttgcaaatga acagcctgag agctgaggac acggctgtgt attactgtgc gagagatact     300 tttttcgtatt acgattttg gagggctttt gactactggg gccagggaac cctggtcacc     360
gtctcctcag                                                            370

<210> SEQ ID NO 5
<211> LENGTH: 352
<212> TYPE: DNA
<213> ORGANISM: Homo Sapiens

<400> SEQUENCE: 5
caggtgcagc tgcaggagtc ggggggaggc gtggtccagc ctgggaggtc cctgagactc      60
tcctgtacag actctggatt caccttcagt cgctatgtta tgcactgggt ccgccaggct     120
ccaggcaagg ggctggagtg gtggcaggt atatcatatg atggaagtta tgaatactac      180
gcagactccg tgaagggccg attcaccatc tccagagaca attccaagaa cacgctatat     240
gtgcaaatga acagcctgag aggtgaggac acggctgtgt attactgtgc gagagattta     300
cgtggtgggg aagactactg ggccaggga accctggtca ccgtctcctc ag              352

<210> SEQ ID NO 6
<211> LENGTH: 355
<212> TYPE: DNA
<213> ORGANISM: Homo Sapiens

<400> SEQUENCE: 6
gaggtgcagc tggtggagtc tggggctgag gtgaagaagc ctgggtcctc ggtgaaggtc      60
tcctgcaagg cttctggagg catcttcggc acctatacta tcagctgggt gcgacaggcc     120
cctggacaag ggcttgagtg gatgggaggg atcatccctg tccttgatgt cactcactac     180
gcgcaggatt tccaggacag agtcaccatt accgcggaca gtccacgag cactgcctcc      240 atggagctga gcagctgaa atctgacgac acggccatat attactgtgc gagagttcc       300 tattatagca cctttgacta ctggggccag ggaacccttg tcaccgtctc ctcag          355
```

<210> SEQ ID NO 7
<211> LENGTH: 352
<212> TYPE: DNA
<213> ORGANISM: Homo Sapiens

<400> SEQUENCE: 7

| caggtgcagc tggtgcagtc tggggctgag gtgaagaagt ttgggtcctc agtgaaggtc | 60 |
| tcctgcaagg cttctggagg catgttcagc agttatacta tcagctgggt gcgacagggc | 120 |
| cctggacaag ggcttgagtg gatgggaagt tcatcccta ttcttgagag agcaaactac | 180 |
| gcacagaagt tccagggcag agtctctttt accgcggaca aaagcacgag cacagcctac | 240 |
| atggagctgg gcagcctgac atctgaggac acggccgtgt attttgtgc gagagacgtt | 300 |
| ggggacttcg gtgactcctg gggccaggga accctggtca ccgtctcctc ag | 352 |

<210> SEQ ID NO 8
<211> LENGTH: 367
<212> TYPE: DNA
<213> ORGANISM: Homo Sapiens

<400> SEQUENCE: 8

| gaggtgcagc tggtggagtc tgggggagtc gtggtacagc ctggggggtc cctgagactc | 60 |
| tcctgtgcag cctctggatt caccttgat gattatacca tgcactgggt ccgtcaagct | 120 |
| ccggggaagg gtctggagtg gtctctctt attagttggg atggtggtag cacatactat | 180 |
| gcagactctg tgaagggccg attcaccatc tccagagaca acagcaaaaa ctccctgtat | 240 |
| ctgcaaatga acagtctgag aactgaggac accgccttgt attactgtgc aaaagataac | 300 |
| ggttacgata ttttgactga ttatcttgac tactggggcc agggaaccct ggtcaccgtc | 360 |
| tcctcag | 367 |

<210> SEQ ID NO 9
<211> LENGTH: 352
<212> TYPE: DNA
<213> ORGANISM: Homo Sapiens

<400> SEQUENCE: 9

| caggtgcagc tggtgcagtc tggggctgag gtgaagaagc ctgggtcctc ggtgaaggtc | 60 |
| tcctgcaagg cttctggagg ctccttcagc aattatacta tcacctgggt gcgccaggcc | 120 |
| cctggacaag gacttgagtg gatgggaagg atcatccctg tccttggtct gacagactcc | 180 |
| gcacagaagt tcaagggcag agtcacgatt accgcggaca gtccacgag cacagcctac | 240 |
| atggagctga gcagcctgac atctgaagac acggccgtgt attactgtgc gagagattcg | 300 |
| gtaattggaa cgtccgactg gggccaggga accctggtca ccgtctcctc ag | 352 |

<210> SEQ ID NO 10
<211> LENGTH: 367
<212> TYPE: DNA
<213> ORGANISM: Homo Sapiens

<400> SEQUENCE: 10

| caggtgcagc tgcaggagtc gggggggggc gtggtacagc ctggggggtc cctgagactc | 60 |
| tcctgtgcag cctctggatt caccttgat gattatacca tgcactgggt ccgtcaagct | 120 |
| ccggggaagg gtctggagtg gtctctctt attagttggg atggtggtag cacatactat | 180 |
| gcagactctg tgaagggccg attcaccatc tccagagaca acagcaaaaa ctccctgtat | 240 | ctgcaaatga acagtctgag aactgaggac accgccttgt attactgtgc aaaagataac    300 ggttacgata ttttgactga ttatcttgac tcctggggcc agggaaccct ggtcaccgtc    360 tcctcag                                                              367

<210> SEQ ID NO 11
<211> LENGTH: 352
<212> TYPE: DNA
<213> ORGANISM: Homo Sapiens

<400> SEQUENCE: 11
caggtgcagc tggtgcagtc tgggtctgag gtgaagaagc ctgggtcctc ggtgaaagtc     60
tcctgcaagg cttctggagg caccttcagc agtcatactc tcagctgggt acgacaggcc    120
cctggacaag ggcttgagtg gatgggagag atcatcccta tccttgatag agtgaagtat    180
tcacagaact tccagggcag agtcacgatt accgcggaca aatccacaaa cacaacctac    240
atggagctga gcagcgtgag atctgaggac acggccgtat actattgtgt tagcaatggc    300
tggtccaact ttgacttctg ggccaggga accctggtca ccgtctcccc ag             352

<210> SEQ ID NO 12
<211> LENGTH: 355
<212> TYPE: DNA
<213> ORGANISM: Homo Sapiens

<400> SEQUENCE: 12
caggtgcagc tggtgcagtc tggggctgag gtgaagaagc ctgggtcctc ggtgagggtc     60
tcctgcacgg cttctggaag caatttcagc agccacacca tcaactgggt acgacaggcc    120
cctggacaag gacttgagtg gatgggcaag gtcatccctg tccttgatat atcaaaacac    180
gcacagacat tcctgggcag agtcattatt accgcggaca aatccacgag cacagcctac    240
ttggagctga gcagcctgag atctgaggac acggcattt attactgtgc gatggatagt    300
gtctacggca actttgactt ttggggtcag ggaaccctgg tcaccgtctc ctcag         355

<210> SEQ ID NO 13
<211> LENGTH: 352
<212> TYPE: DNA
<213> ORGANISM: Homo Sapiens

<400> SEQUENCE: 13
caggtgcagc tggtgcagtc tgggactgag gtgaagaagt ttgggtcctc ggtgaaggtc     60
tcctgcaagg cttctggagg cagcttcagt agttatacta tcagctgggt gcgacaggcc    120
cctggacaag ggcttgagtg gatgggaagt ttcatcccta tccttgagag agcaaactac    180
gcacagaagt tccagggcag agtcactttt accgcggaca aaaccacgag cacagcctac    240
atggagctgg gcggcctgag atctcaggac acggccgtct attattgtgc gagagacctt    300
ggggacttcg gtgactcctg ggccaggga accctggtca ccgtctcctc ag             352

<210> SEQ ID NO 14
<211> LENGTH: 352
<212> TYPE: DNA
<213> ORGANISM: Homo Sapiens

<400> SEQUENCE: 14
caggtgcagc tggtgcagtc tgggtctgag gtgaagaagc ctgggtcctc ggtgaaggtc     60
tcctgcaagg cttctggagg caccttcagc agtcacactg tcagctgggt acgacaggcc    120
cctggacaag ggcttgaatg gatgggagag atcatcccta tccttgatag agtgaactat    180

```
gcagagaact tccagggcag agtcacgatt accgcggaca agtccacgaa tacaacctat    240
atggacctga gcagcctgag atctgaggac acggccgtat attattgtac tagcaatggc    300
tggtccaact ttgacttctg gggccaggga accctggtca ccgtctcctc ag            352
```

<210> SEQ ID NO 15
<211> LENGTH: 358
<212> TYPE: DNA
<213> ORGANISM: Homo Sapiens

<400> SEQUENCE: 15

```
caggtgcagc tggtgcagtc tggggctgag gtgaagaagc ctgggtcctc ggtgaaggtc    60
tcctgcaagg cttctggagg cgccttcacc atgtacacta tcaactgggt gcgacaggcc    120
cctggacgag ggcttgagtg gatgggaagg atcatacctg ttctaggtat aacagactac    180
gcacagaaat tccagggcag aggcacgatt accgcggaca aatccacaag cacagcctac    240
ctggagctga gcggcctgac ttctgaggac acggccgtgt attactgtgc gagagagttt    300 agtggggggca actatttcga cttctggggc cagggaaccc tggtcaccgt ctcctcag     358
```

<210> SEQ ID NO 16
<211> LENGTH: 358
<212> TYPE: DNA
<213> ORGANISM: Homo Sapiens

<400> SEQUENCE: 16

```
caggtgcagc tggtgcagtc tggggctgag gtgaagaggc ctgggtcctc ggtgaaggtc    60
tcctgcaagg cctctggagg caccttcagc agctacacta tcagctgggt gcgacaggcc    120
ccaggacaag ggcttgaatg gatgggaagt atcatccctg tccttgatgt cacatcctac    180
gcacagcaat tccagggcag agtcactatt accgcggaca aatccacgaa gacagcctac    240
atggacctga gcagcctaac atttgaggac acggccctgt atttctgttc gattggtaga    300
tatacttatg gacactttga cacctggggc cagggaaccc aggtcaccgt ctcctcag     358
```

<210> SEQ ID NO 17
<211> LENGTH: 355
<212> TYPE: DNA
<213> ORGANISM: Homo Sapiens

<400> SEQUENCE: 17

```
gaggtgcagc tggtgcagtc tggggctgag gtgaagaagc ctgggtcctc ggtgaaggtc    60
tcctgcaagg cctctggaag caatttcagc agccacacca tcaattgggt ccgacaggcc    120
cctggacacg ggcttgagtg gatgggaaag atcatccctg tccttgatat atcaaaagac    180
gcagagacat tcctgggcag agtcgtaatt accgcggaca agtccacgag cacagcctac    240
atggagctga gcagcctgag atctgaggac acggccattt attactgtgc gatggatagt    300
gtctacggca actttgactt ttgggggccag ggaaccctgg tcaccgtctc ctcag        355
```

<210> SEQ ID NO 18
<211> LENGTH: 352
<212> TYPE: DNA
<213> ORGANISM: Homo Sapiens

<400> SEQUENCE: 18

```
caggtgcagc tggtgcagtc tggggctgag gtgaagaagt ttgggtcctc agtgaaggtc    60
tcctgcaagg cttctggagg caccttcagc agttatacta tgagctgggt gcgacaggcc    120
```

```
cctggacaag ggcttgagtg gatgggaagt ttcgtcccta ttcttgagag agcaaactac    180
gcacagggat ccagggcag  agtcactttt accgcggaca aaagcacgag cacagcctac    240
atggagctgg gcagcctgag atctgaggac acggccgtgt attattgtgc gagagacctt    300
ggggacttcg gtgactcctg gggccaggga accctggtca ccgtctcctc ag            352

<210> SEQ ID NO 19
<211> LENGTH: 361
<212> TYPE: DNA
<213> ORGANISM: Homo Sapiens

<400> SEQUENCE: 19
caggtgcagc tggtgcagtc tggggctgag gtgaagaagc ctctgtcctc agtgaaggtc     60
tcctgcaagg cctctggagg caccttcaac atgtatgata tcaactgggt gcgacaggcc    120
cctggacaag ggcttgagtg gatgggaggg atcgtcccta ttcttggtgt gacaaactac    180
gcacagaact tccagggcag actaacaatt accgcggaca aatcaacgag cacagcctac    240
atggagctga gcagcctgag atctgaggac acggccgtgt attactgtgc gagaggcgtg    300
gcagcaggat ggaatgcttt tgatgtctgg ggccaaggga caatggtcac cgtctctgca    360
g                                                                    361

<210> SEQ ID NO 20
<211> LENGTH: 348
<212> TYPE: DNA
<213> ORGANISM: Homo Sapiens

<400> SEQUENCE: 20
caggtgcagc tggtgcagtc tggggctgag gtgaagaagc ctgggtcctc ggtgaaggtc     60
tcctgcaagg cttctggagg cagcttcagt gattatacta tcatttggtt gcgacaggcc    120
cgtggacacg ggcttgagtg gatgggaaaa atcgtcccta tacttggtgt cacaacctac    180
gcacaggagt tccagggcag aatcacgatc accgcggaca ggtccacgag cacagcctac    240
atggagctga gcagcctgag atctgaggac acggccgtct attactgtgc gaggttcttg    300
tggggtttgg acgtctgggg ccaagggacc acggtcaccg tctcctca                 348

<210> SEQ ID NO 21
<211> LENGTH: 357
<212> TYPE: DNA
<213> ORGANISM: Homo Sapiens

<400> SEQUENCE: 21
caggtgcagc tggtgcagtc tgggggaggc ctggtcaagc ctgggggtc  cctgagactc     60 tcctgtgcag cctctggatt catcttcagt aactatatca tgaactgggt ccgccaggct    120
ccagggaagg ggctggagtg gtctcgtcc  attagtagta gtggtagtta catatactac    180
gcagactcag tgaagggccg attcaccatc tccagagaca acgccaagaa ctcaatgtat    240
ctgcaaatga acagtctgag aggcgaggac acggctgtgt attactgtgc ggccgcttac    300
gattttggga gtggttatta tttctggggc caagggacca cggtcaccgt ctcctca       357

<210> SEQ ID NO 22
<211> LENGTH: 348
<212> TYPE: DNA
<213> ORGANISM: Homo Sapiens

<400> SEQUENCE: 22
caggtgcagc tggtgcagtc tggggctgag gtgaagaagc ctgggtcctc ggtgaaggtc     60
```

-continued

```
tcctgcaagg cttctggagg caccttcagc aactatgata tcacctgggt gcgacaggcc      120
ccaggacaag ggcttgagtg ggtgggaaaa gtcatcccta tccttgatgt aacaaactac      180
gcacagaagt tccagggcag agtcactatt accgcggaca atccacgag cacagcctac       240 atggagctga gcaacctgac atctgaggac acggccgttt atttctgtgc gaggttctta      300
tggggtttgg acgtctgggg ccaagggacc atggtcaccg tctcctca                   348
```

<210> SEQ ID NO 23
<211> LENGTH: 367
<212> TYPE: DNA
<213> ORGANISM: Homo Sapiens

<400> SEQUENCE: 23

```
gaggtgcagc tgttggagtc tgggggaggc ttggtacagc ctggcaggtc cctgagactc      60
tcctgtgcag cctctggatt catctttgat gattatgcca tgcactgggt ccggcaagct      120
ccagggaagg gcctggagtg gtctcaggt attagttgga atagtggtag cataggctat       180
gcggactctg tgaagggccg attcaccatc tccagagaca cgccaagaa ctccctgtat       240 ctgcaaatga acagtctgag agctgaggac acggccttgt attactgtgc aaaagaccct     300
aattcgctgt atagaagtgg ttcctttgac tactggggcc agggaacgct ggtcaccgtc     360
tcctcag                                                                367
```

<210> SEQ ID NO 24
<211> LENGTH: 352
<212> TYPE: DNA
<213> ORGANISM: Homo Sapiens

<400> SEQUENCE: 24

```
caggtgcagc tgcaggagtc ggggggaggc gtggtccagc ctggaggtc cctgagactc       60 tcctgtacag actctggatt caccttcagt cgctatgcta tgcactgggt ccgccaggct      120
ccaggcaagg ggctggagtg gtggcaggt atatcatatg atggaagtta tgaatactac       180
gcagactccg tgaagggccg attcaccatc tccagagaca attccaagaa cacgctatat      240
gtgcaaatga acagcctgag aggtgaggac acggctgtgt attactgtgc gagagatcta     300
cgtggtgggg aagactactg ggccaggga accctggtca ccgtctcctc ag              352
```

<210> SEQ ID NO 25
<211> LENGTH: 354
<212> TYPE: DNA
<213> ORGANISM: Homo Sapiens

<400> SEQUENCE: 25

```
caggtgcagc tgtgcagtc tggggctgag gtgaagaagc ctgggtcctc gatgaatgtc       60
tcctgcaagg cctctggagg caccttcagc aggcatacca tcaactgggt gcgacaggcc      120
cctggacaag ggcttgagtg gatgggaagc atcatcccta ttcttggtat aacaaactac      180
gcacagaact tccagggcag actcacgttt agcgcggaca atccacgaa cacagcctat      240 gtggagttga gtggcctgag atctgaggac acggccgtct attactgtgc gagtggggac     300
tactactatg acatggccgt ttggggccaa gggaccacgg tcgccgtcac ctca           354
```

<210> SEQ ID NO 26
<211> LENGTH: 367
<212> TYPE: DNA
<213> ORGANISM: Homo Sapiens

```
<400> SEQUENCE: 26
caggtgcagc tggtgcagtc tggggggaggc ttggtacagc ctggcaggtc cctgagactc        60
tcctgtgcag cctctggatt catctttgat gattatgcca tgcactgggt ccggcaagct       120
ccagggaagg gcctggagtg gtctcaggt attagttgga atagtggtag cataggctat       180
gcggactctg tgaagggccg attcaccatc tccagagaca acgccaagaa ctccctgtat       240
ctgcaaatga acagtctgag agctgaggac acggccttgt attactgtgc aaaagaccct       300
aattcgctgt atagaagtgg ttcctttgac tactggggcc agggaacgct ggtcaccgtc       360
tcctcag                                                                  367

<210> SEQ ID NO 27
<211> LENGTH: 361
<212> TYPE: DNA
<213> ORGANISM: Homo Sapiens

<400> SEQUENCE: 27
caggtgcagc tggtgcagtc tggggctgag gtgaagaagc ctgggtcctc ggtgaaggtc        60
tcctgcaggg cttctggagg caccttcagc agctatacta tcaactgggt gcgacaggcc       120
cctggacaag gcttgagtg gatgggaagg gtcgtcccta ccttggtgt aacaaactac       180 gcacagaagt tccagggcag agtcaccatt accgcggaca atccacgag cacagcctac       240 atggagctga gcagcctgag atctgaggac acggccgtgt attactgtgc gagagataag       300
ggctatgata taattacgg ggcctactgg ggccagggaa ccctggtcac cgtctcctca       360
g                                                                        361

<210> SEQ ID NO 28
<211> LENGTH: 361
<212> TYPE: DNA
<213> ORGANISM: Homo Sapiens

<400> SEQUENCE: 28
caggtgcagc tggtgcagtc tggggctgag gtgaagaagc ctgggtcctc ggtgaaggtc        60
tcctgcaagg cttctggagg caccttcagc agctatgata tcaactgggt gcgacaggcc       120
cctggacaag gcttgagtg gatgggaagc atcatcccta ccttggtat atcaaactac       180 gcacagaagt tccagggcag agtcacgatt accgcggaca atccacgag cacagcctac       240 atggagctga gcagcctgag atctgaggac acggccgtgt attactgtgc gagagatcag       300
ggctatgcca ataattacgg ggcctactgg ggccagggaa ccctggtcac cgtctcctca       360
g                                                                        361

<210> SEQ ID NO 29
<211> LENGTH: 361
<212> TYPE: DNA
<213> ORGANISM: Homo Sapiens

<400> SEQUENCE: 29
caggtgcagc tggtgcagtc tggggctgag gtgaagaagc ctgggtcctc ggtgaaggtc        60
tcctgcaagg cttctggagg caccttcagc agctatgata tcaattgggt gcgacaggcc       120
cctggacaag gcttgagtg gatgggaagc atcatcccta ccttggtat acgaaattac       180 gcacagaagt tccagggcag agtcacgatt accgcggaca atccacgag cacagcctac       240 atggagctga gcagcctgag atctgaggac acggccgtgt attactgtgc gagagatcag       300
ggctatgcta ataattacgg ggcctactgg ggccagggaa ccctggtcac cgtctcctca       360
``` g                                                                        361

<210> SEQ ID NO 30
<211> LENGTH: 352
<212> TYPE: DNA
<213> ORGANISM: Homo Sapiens

<400> SEQUENCE: 30
gaggtgcagc tggtgcagtc tgggggaggc ttggtccagc ctgggggtc cctgagactc         60 tcctgtgcag cctctggatt cacgtttagt agctattgga tgagctgggt ccgccaggct       120
ccagggaagg ggctggagtg ggtggccaac ataaagcaag atggaagtga gaaacactat       180
gtggactcta tgaagggccg attcaccatc tccagagaca acggcaagaa ctcactgtat       240
ctgcaaatga acagcctgag agccgaggac acggctgtgt attactgtgc gaggtccccg       300
ggatactact ttgactactg gggccaggga accctggtca ccgtctcctc ag              352

<210> SEQ ID NO 31
<211> LENGTH: 361
<212> TYPE: DNA
<213> ORGANISM: Homo Sapiens

<400> SEQUENCE: 31
caggtgcagc tggtgcagtc tggggctgag gtgaagaagc ctgggtcctc ggtgaaggtc        60
tcctgcaagg cttctggagg caccttcagc agctatgcta tcgactgggt gcgacaggcc      120
cctggacaag ggcttgagtg gatgggaagg atcgtcccta tccttggtat agcaaactac      180
gcacagaagt tccagggcag agtcacgatt accgcggaca aatccacgag cacggcctac      240
atggaactga gcagcctgag atctgacgac acggccgtat attactgtgc gagagatcgg      300
ggctatgcta atacttacgg ggcctactgg ggccagggaa ccctggtcac cgtctcctca      360
g                                                                       361

<210> SEQ ID NO 32
<211> LENGTH: 361
<212> TYPE: DNA
<213> ORGANISM: Homo Sapiens

<400> SEQUENCE: 32
caggtgcagc tggtgcagtc tggggctgag gtgaagaagc ctgggtcctc ggtgaaggtc        60
tcctgcaagg cttctggagg caccttcagc agttatgcta ttagctgggt gcgacaggcc      120
cctggacagg ggcttgagtg gatgggaagc atcgtcccta tccttggtgt agtaaactac      180
gcacagaact tccagggcag agtcacgatt accgcggaca aatccacgag cacagcctac      240
atggagctga gcagcctgag atctgaggac acggccgtgt attactgtgc gagagataag      300
gggtatgcta ataattacgg ggcctactgg ggccagggaa ccctggtcac cgtctcctca      360
g                                                                       361

<210> SEQ ID NO 33
<211> LENGTH: 361
<212> TYPE: DNA
<213> ORGANISM: Homo Sapiens

<400> SEQUENCE: 33
caggtgcagc tggtgcagtc tggggctgac gtgaagaagc ctgggtcctc ggtgaaggtc        60
tcctgcaagg cttctggagg caccttcagc agctatacta tcaactgggt gcgacaggcc      120

```
cctggacaag ggcttgagtg gatgggaagg atcgtcccta tccttgatat tgcaaactac    180
gcacagaagt tccagggcag agtcacgatt accgcggaca aatccacgag cacagcctac    240
atggagctga gcagcctgac atctgaggac acggccgtgt attattgtgc gagagatcgg    300
ggctatgata taaatacggg gcctactggg ggccagggaa ccctggtcac cgtctcctca    360
g                                                                   361
```

<210> SEQ ID NO 34
<211> LENGTH: 361
<212> TYPE: DNA
<213> ORGANISM: Homo Sapiens

<400> SEQUENCE: 34

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag ggcttgagtg gatgggaggg atcaccccta ccttggtgt aacaaactac    180 tcacagaagt tccagggcag agtcaccgtt accgcggaca tatccacgac cacagcctac    240
atggagctga gcagcctgac atctgaggac acggccgtgt attactgtgc gagagatcag    300
ggctatgcta atgattacgg ggcctactgg ggccagggaa ccctggtcac cgtctcctca    360
g                                                                   361
```

<210> SEQ ID NO 35
<211> LENGTH: 349
<212> TYPE: DNA
<213> ORGANISM: Homo Sapiens

<400> SEQUENCE: 35

```
gaggtgcagc tggtgcagtc tggggctgag gtgaagaagc ctgggtcctc ggtgaaggtc    60
tcctgcaagg cttctggagg caccttcagc agctatacta tcaactgggt gcgacaggcc    120
cctggacaag gacttgagtg gatgggaagg atcatcccta ccttggtat agaaaactac    180 gcacagaagt tccagggcag agtcacgatt tccgcggaca aatccacgag cacagcctac    240
atggagctga gcagcctgag atctgacgac acggccgtgt attactgtgc gagagatcag    300
gtcttcgggg cctactgggg cccgggaacc ctggtcaccg tctcctcag              349
```

<210> SEQ ID NO 36
<211> LENGTH: 361
<212> TYPE: DNA
<213> ORGANISM: Homo Sapiens

<400> SEQUENCE: 36

```
caggtgcatc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag ggcttgagtg gatgggaggg atcaccccta ccttggtgt aacaaactac    180 tcacagaagt tccagggcag agtcaccgtt accgcggaca tatccacgac cacagcctac    240
atggagctga gcagcctgac atctgaggac acggccgtgt attactgtgc gagagatcag    300
ggctatgcta atgattacgg ggcctactgg ggccagggaa ccctggtcac cgtctcctca    360
g                                                                   361
```

<210> SEQ ID NO 37
<211> LENGTH: 361
<212> TYPE: DNA
<213> ORGANISM: Homo Sapiens

<400> SEQUENCE: 37

| | |
|---|---|
| caggtgcagc tggtgcagtc tggggctgag gtgaagaagc ctgggtcctc ggtgaaggtc | 60 |
| tcctgcaagg cttctggagg caccttcagc agctatgaaa tcagttgggt gcgacaggcc | 120 |
| cctggacaag gcttgagtg gatgggaggg atcgtccta tcctgggttt ggcaaactac | 180 |
| gcacagaact tccagggcag agtcaccatt accgcggaca atccacgag cacagcctac | 240 |
| atggagctga gcagcctgag attcgaggat acggccgtgt attactgtgc gagagatcag | 300 |
| ggctatgcta ataattacgg ggcctactgg ggccagggaa ccctggtcag cgtctcctca | 360 |
| g | 361 |

<210> SEQ ID NO 38
<211> LENGTH: 361
<212> TYPE: DNA
<213> ORGANISM: Homo Sapiens

<400> SEQUENCE: 38

| | |
|---|---|
| caggtgcagc tggtgcagtc tggggctgag gtgaagaagc ctgggtcctc ggtgaaggtc | 60 |
| tcctgcgagg cttctggagg caccttcagc agctatgcta tcacctgggt gcgacaggcc | 120 |
| cctggacaag gcttgagtg gatgggaagc atcctcccta tccttgatat aacaaactac | 180 |
| gcacagaagt tccagggcag agtcacgctt accgcggaca atccacgag cacagcctac | 240 |
| atggagctga gcagcctgag atctgaggac acggccgtgt atttctgtgc gagagatcgg | 300 |
| ggctatagta ataattatgg ggcctactgg ggccagggaa ccctggtcac cgtctcctca | 360 |
| g | 361 |

<210> SEQ ID NO 39
<211> LENGTH: 361
<212> TYPE: DNA
<213> ORGANISM: Homo Sapiens

<400> SEQUENCE: 39

| | |
|---|---|
| gaggtgcagc tggtgcagtc tggggctgag gtgaagaagc ctgggtcctc agtgaaggtc | 60 |
| tcctgcaagg cttctggagg caccttcagc agctatgcta tcagctgggt gcgacaggcc | 120 |
| cctggacaag gcttgagtg gatgggaggg atcatcccta tccttggtat aacaaactac | 180 |
| gcacagaagt tccagggcag agtcacgatt accgcggacg aatccacggg cgcagcctac | 240 |
| atggagctga gcagcctggc atctgaggac acggccgtat attactgtgc gagagatgat | 300 |
| actggccggg acgactactt tgagtactgg ggtcagggaa ccctggtcac cgtctcctca | 360 |
| g | 361 |

<210> SEQ ID NO 40
<211> LENGTH: 352
<212> TYPE: DNA
<213> ORGANISM: Homo Sapiens

<400> SEQUENCE: 40

| | |
|---|---|
| caggtgcagc tggtgcagtc tggggctgag gtgaagaggc ctgggtcctc agtgaaggtc | 60 |
| tcctgcaagg cttctggaaa caccttcagt aactatcata tcaactgggt gcgacaggcc | 120 |
| cctggacaag gcttcagtg gatgggagga atcatcccta ttcttgggag aacaaactac | 180 |
| gcacagaact tccagggcag agtcacgatt accacggacg aatcaacgaa cacagcctac | 240 |
| atggagctga ctagcctgag atccgaggac acggccgttt attattgtgc gagggaggcc | 300 |

```
cgggatagtt ttgatttctg gggccaaggg acaatggtca ccgtctcttc ag          352
```

<210> SEQ ID NO 41
<211> LENGTH: 358
<212> TYPE: DNA
<213> ORGANISM: Homo Sapiens

<400> SEQUENCE: 41

```
caggtgcagc tggtgcagtc tggggctgag gtgaagaagc ctgggtcctc agtgaaggtc   60
tcctgcaagg cttctggagg caccttcagc aactatggta tcagctgggt gcgacaggcc  120
cctggacaag ggcttgagtg gatgggaaag atcatcccta tccttggtat aacaaactac  180
gcacagaagt tccagggcag ggtcacgatt accgcggaca atccacgag cacagcctac  240
atggagctga gcagcctgag atctgaggac acggccgtgt attactgtgc gagaggggt  300
gggagctacg acttctttga ctactggggc cagggaacgc tggtcaccgt ctcctcag   358
```

<210> SEQ ID NO 42
<211> LENGTH: 355
<212> TYPE: DNA
<213> ORGANISM: Homo Sapiens

<400> SEQUENCE: 42

```
caggtgcagc tggtgcagtc tggggctgag gtgaagaagc ctgggtcctc ggtgaaggtc   60
tcctgcaagg cttctggtgg caccttcagc acctatacta tcaactggat gcgacaggcc  120
cctggacaag ggcttgagtg gatgggaagg atcatcccta tgttcggtac agcaaactac  180
gcacagaagt tccggggcag agtcacgatt accgcggacg aatccacgag cacagcctac  240
atggagctga gcagcctgat atctgaggac acggccatct attactgtgc gagaagtggc  300
tacagtgatg cttttgatat ctggggccaa gggacaatgg tcaccgtctc ttcag       355
```

<210> SEQ ID NO 43
<211> LENGTH: 367
<212> TYPE: DNA
<213> ORGANISM: Homo Sapiens

<400> SEQUENCE: 43

```
caggtgcagc tggtgcagtt tggggaggc ttggtacagc ctggcaggtc cctgagactc   60
tcctgtgcag cctctggatt catctttgat gattatgcca tgcactgggt ccggcaagct  120
ccagggaagg gcctggagtg gtctcaggt attagttgga atagtggtag cataggctat  180
gcggactctg tgaagggccg attcaccatc tccagagaca cgccaagaa ctccctgtat  240
ctgcaaatga acagtctgag agctgaggac acggccttgt attactgtgc aaaagaccct  300
aattcgctat atagaagtgg ttcctttgac tactggggcc agggaacgct ggtcaccgtc  360
tcctcag                                                           367
```

<210> SEQ ID NO 44
<211> LENGTH: 370
<212> TYPE: DNA
<213> ORGANISM: Homo Sapiens

<400> SEQUENCE: 44

```
caggtgcagc tgcaggagtc gggtccagga ctggtgaggc cctcgcagac cctctcactc   60
acctgtgcca tctccgggga cagtgtctca aacaacaatg ctgcttggaa ctggattagg  120
cagtccccat cgagaggcct tgagtggctg gaaggacat tctacaggtc caggtggtat  180
aatgattatg cagtttctgt gaaaagtcga ataatcatca cccagacac atccaagaac  240
```

-continued

```
caattctccc tggacctgac ctctgtgact cccgaagaca cggctgtgta tttctgtgca      300
agagaaggac agtggctgcc caactacttc gaccccaggg gccaggggac cctggtcacc      360
gtctcctcag                                                            370
```

<210> SEQ ID NO 45
<211> LENGTH: 352
<212> TYPE: DNA
<213> ORGANISM: Homo Sapiens

<400> SEQUENCE: 45

```
caggtgcagc tggtgcagtc tggggggaggc gtcgtccagc ctgggacgtc cctaagactc       60
tcctgtgcag cctctggatt caccttccgc aaccatgcta tgcactgggt ccgccaggct      120
ccagggaggg ggctggagtg ggtggcagat atactgtacg attcaagtaa caaatactac      180
gcagactctg tgaagggccg attcaccatc tccagagaca attccaagaa cacgctgtat      240
ctgcaaatga gcagcctgag agctgaggac acggccgtct atttctgtgc ggccagttca      300 tatttccat ttgacttctg gggccaggga accctggtca ccgtctcctc ag              352
```

<210> SEQ ID NO 46
<211> LENGTH: 117
<212> TYPE: PRT
<213> ORGANISM: Homo Sapiens

<400> SEQUENCE: 46

```
Gln Val Gln Leu Val Gln Ser Gly Ala Glu Val Lys Lys Phe Gly Ser
1               5                   10                  15

Ser Val Lys Val Ser Cys Lys Ala Ser Gly Gly Thr Phe Ser Ser Tyr
            20                  25                  30

Thr Met Ser Trp Val Arg Gln Ala Pro Gly Gln Gly Leu Glu Trp Met
        35                  40                  45

Gly Ser Phe Ile Pro Ile Leu Glu Arg Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Gly Ser Leu Arg Ser Glu Asp Thr Ala Val Tyr Tyr Cys
                85                  90                  95

Ala Arg Asp Leu Gly Asp Phe Gly Asp Ser Trp Gly Gln Gly Thr Leu
            100                 105                 110

Val Thr Val Ser Ser
        115
```

<210> SEQ ID NO 47
<211> LENGTH: 118
<212> TYPE: PRT
<213> ORGANISM: Homo Sapiens

<400> SEQUENCE: 47

```
Gln Val Gln Leu Val Gln Ser Gly Ala Glu Val Lys Lys Pro Gly Ser
1               5                   10                  15

Ser Val Arg Val Ser Cys Lys Ala Ser Gly Ser Asn Phe Ser Ser His
            20                  25                  30

Thr Ile Asn Trp Val Arg Gln Ala Pro Gly His Gly Leu Glu Trp Met
        35                  40                  45

Gly Lys Ile Ile Pro Val Leu Asp Ile Ser Lys His Ala Gln Thr Phe
    50                  55                  60
```

Leu Gly Arg Val Ile Ile Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Met Asp Ser Val Tyr Gly Asn Phe Asp Phe Trp Gly Gln Gly Thr
            100                 105                 110

Pro Val Thr Val Ser Ser
        115

<210> SEQ ID NO 48
<211> LENGTH: 119
<212> TYPE: PRT
<213> ORGANISM: Homo Sapiens

<400> SEQUENCE: 48

Gln Val Gln Leu Val Gln Ser Gly Ala Glu Leu Lys Lys Pro Gly Ser
1               5                   10                  15

Ser Val Lys Val Ser Cys Lys Ala Ser Gly Ala Phe Thr Met Tyr
            20                  25                  30

Thr Ile Asn Trp Val Arg Gln Ala Pro Gly Arg Gly Leu Glu Trp Met
            35                  40                  45

Gly Arg Ile Ile Pro Ile Leu Gly Ile Thr Asp Tyr Ala Gln Lys Phe
50                  55                  60

Gln Gly Arg Gly Thr Ile Thr Ala Asp Lys Ser Thr Ser Thr Ala Tyr
65                  70                  75                  80

Leu Glu Leu Ser Gly Leu Thr Ser Glu Asp Thr Ala Val Tyr Tyr Cys
                85                  90                  95

Ala Arg Glu Phe Ser Gly Gly Asn Tyr Phe Asp Phe Trp Gly Gln Gly
            100                 105                 110

Thr Leu Val Thr Val Ser Ser
        115

<210> SEQ ID NO 49
<211> LENGTH: 123
<212> TYPE: PRT
<213> ORGANISM: Homo Sapiens

<400> SEQUENCE: 49

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Arg Asn Tyr
            20                  25                  30

Ala Met His Trp Val Arg Gln Ala Pro Gly Lys Gly Leu Glu Trp Val
            35                  40                  45

Ala Val Ile Ser Tyr Asp Gly Lys Glu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Phe Ser Tyr Tyr Asp Phe Trp Arg Ala Phe Asp Tyr
            100                 105                 110

Trp Gly Gln Gly Thr Leu Val Thr Val Ser Ser
        115                 120

<210> SEQ ID NO 50
<211> LENGTH: 117

```
<212> TYPE: PRT
<213> ORGANISM: Homo Sapiens

<400> SEQUENCE: 50

Gln Val Gln Leu Gln Glu Ser Gly Gly Gly Val Val Gln Pro Gly Arg
1               5                   10                  15

Ser Leu Arg Leu Ser Cys Thr Asp Ser Gly Phe Thr Phe Ser Arg Tyr
            20                  25                  30

Val Met His Trp Val Arg Gln Ala Pro Gly Lys Gly Leu Glu Trp Val
        35                  40                  45

Ala Gly Ile Ser Tyr Asp Gly Ser Tyr Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Gly Glu Asp Thr Ala Val Tyr Tyr Cys
                85                  90                  95

Ala Arg Asp Leu Arg Gly Gly Glu Asp Tyr Trp Gly Gln Gly Thr Leu
            100                 105                 110

Val Thr Val Ser Ser
        115

<210> SEQ ID NO 51
<211> LENGTH: 118
<212> TYPE: PRT
<213> ORGANISM: Homo Sapiens

<400> SEQUENCE: 51

Glu Val Gln Leu Val Glu Ser Gly Ala Glu Val Lys Lys Pro Gly Ser
1               5                   10                  15

Ser Val Lys Val Ser Cys Lys Ala Ser Gly Gly Ile Phe Gly Thr Tyr
            20                  25                  30

Thr Ile Ser Trp Val Arg Gln Ala Pro Gly Gln Gly Leu Glu Trp Met
        35                  40                  45

Gly Gly Ile Ile Pro Val Leu Asp Val Thr His Tyr Ala Gln Asp Phe
    50                  55                  60

Gln Asp Arg Val Thr Ile Thr Ala Asp Lys Ser Thr Ser Thr Ala Ser
65                  70                  75                  80

Met Glu Leu Ser Ser Leu Lys Ser Asp Asp Thr Ala Ile Tyr Tyr Cys
                85                  90                  95

Ala Arg Ser Ser Tyr Tyr Ser Thr Phe Asp Tyr Trp Gly Gln Gly Thr
            100                 105                 110

Leu Val Thr Val Ser Ser
        115

<210> SEQ ID NO 52
<211> LENGTH: 117
<212> TYPE: PRT
<213> ORGANISM: Homo Sapiens

<400> SEQUENCE: 52

Gln Val Gln Leu Val Gln Ser Gly Ala Glu Val Lys Lys Phe Gly Ser
1               5                   10                  15

Ser Val Lys Val Ser Cys Lys Ala Ser Gly Gly Met Phe Ser Ser Tyr
            20                  25                  30

Thr Ile Ser Trp Val Arg Gln Gly Pro Gly Gln Gly Leu Glu Trp Met
        35                  40                  45

Gly Ser Phe Ile Pro Ile Leu Glu Arg Ala Asn Tyr Ala Gln Lys Phe
```

-continued

```
                50                  55                  60
Gln Gly Arg Val Ser Phe Thr Ala Asp Lys Ser Thr Ser Thr Ala Tyr
 65                  70                  75                  80

Met Glu Leu Gly Ser Leu Thr Ser Glu Asp Thr Ala Val Tyr Phe Cys
                    85                  90                  95

Ala Arg Asp Val Gly Asp Phe Gly Asp Ser Trp Gly Gln Gly Thr Leu
               100                 105                 110

Val Thr Val Ser Ser
            115

<210> SEQ ID NO 53
<211> LENGTH: 122
<212> TYPE: PRT
<213> ORGANISM: Homo Sapiens

<400> SEQUENCE: 53

Glu Val Gln Leu Val Glu Ser Gly Gly Val Val Gln Pro Gly Gly
  1               5                  10                  15

Ser Leu Arg Leu Ser Cys Ala Ala Ser Gly Phe Thr Phe Asp Asp Tyr
                 20                  25                  30

Thr Met His Trp Val Arg Gln Ala Pro Gly Lys Gly Leu Glu Trp Val
             35                  40                  45

Ser Leu Ile Ser Trp Asp Gly Gly Ser Thr Tyr Tyr Ala Asp Ser Val
         50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                    85                  90                  95

Ala Lys Asp Asn Gly Tyr Asp Ile Leu Thr Asp Tyr Leu Asp Tyr Trp
               100                 105                 110

Gly Gln Gly Thr Leu Val Thr Val Ser Ser
               115                 120

<210> SEQ ID NO 54
<211> LENGTH: 117
<212> TYPE: PRT
<213> ORGANISM: Homo Sapiens

<400> SEQUENCE: 54

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Ser Phe Ser Asn Tyr
                 20                  25                  30

Thr Ile Thr Trp Val Arg Gln Ala Pro Gly Gln Gly Leu Glu Trp Met
             35                  40                  45

Gly Arg Ile Ile Pro Val Leu Gly Leu Thr Asp Ser Ala Gln Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                    85                  90                  95

Ala Arg Asp Ser Val Ile Gly Thr Ser Asp Trp Gly Gln Gly Thr Leu
               100                 105                 110

Val Thr Val Ser Ser
            115
```

-continued

```
<210> SEQ ID NO 55
<211> LENGTH: 122
<212> TYPE: PRT
<213> ORGANISM: Homo Sapiens

<400> SEQUENCE: 55

Gln Val Gln Leu Gln Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Asn Gly Tyr Asp Ile Leu Thr Asp Tyr Leu Asp Ser Trp
            100                 105                 110

Gly Gln Gly Thr Leu Val Thr Val Ser Ser
        115                 120

<210> SEQ ID NO 56
<211> LENGTH: 117
<212> TYPE: PRT
<213> ORGANISM: Homo Sapiens

<400> SEQUENCE: 56

Gln Val Gln Leu Val Gln Ser Gly Ser Glu Val Lys Lys Pro Gly Ser
1               5                   10                  15

Ser Val Lys Val Ser Cys Lys Ala Ser Gly Gly Thr Phe Ser Ser His
            20                  25                  30

Thr Leu Ser Trp Val Arg Gln Ala Pro Gly Gln Gly Leu Glu Trp Met
        35                  40                  45

Gly Glu Ile Ile Pro Ile Leu Asp Arg Val Lys Tyr Ser Gln Asn Phe
    50                  55                  60

Gln Gly Arg Val Thr Ile Thr Ala Asp Lys Ser Thr Asn Thr Thr Tyr
65                  70                  75                  80

Met Glu Leu Ser Ser Val Arg Ser Glu Asp Thr Ala Val Tyr Tyr Cys
                85                  90                  95

Val Ser Asn Gly Trp Ser Asn Phe Asp Phe Trp Gly Gln Gly Thr Leu
            100                 105                 110

Val Thr Val Ser Pro
        115

<210> SEQ ID NO 57
<211> LENGTH: 118
<212> TYPE: PRT
<213> ORGANISM: Homo Sapiens

<400> SEQUENCE: 57

Gln Val Gln Leu Val Gln Ser Gly Ala Glu Val Lys Lys Pro Gly Ser
1               5                   10                  15

Ser Val Arg Val Ser Cys Thr Ala Ser Gly Ser Asn Phe Ser Ser His
            20                  25                  30

Thr Ile Asn Trp Val Arg Gln Ala Pro Gly Gln Gly Leu Glu Trp Met
        35                  40                  45
```

```
Gly Lys Val Ile Pro Val Leu Asp Ile Ser Lys His Ala Gln Thr Phe
         50                  55                  60

Leu Gly Arg Val Ile Ile Thr Ala Asp Lys Ser Thr Ser Thr Ala Tyr
 65                  70                  75                  80

Leu Glu Leu Ser Ser Leu Arg Ser Glu Asp Thr Ala Ile Tyr Tyr Cys
                 85                  90                  95

Ala Met Asp Ser Val Tyr Gly Asn Phe Asp Phe Trp Gly Gln Gly Thr
            100                 105                 110

Leu Val Thr Val Ser Ser
            115

<210> SEQ ID NO 58
<211> LENGTH: 117
<212> TYPE: PRT
<213> ORGANISM: Homo Sapiens

<400> SEQUENCE: 58

Gln Val Gln Leu Val Gln Ser Gly Thr Glu Val Lys Lys Phe Gly Ser
 1               5                  10                  15

Ser Val Lys Val Ser Cys Lys Ala Ser Gly Gly Ser Phe Ser Ser Tyr
             20                  25                  30

Thr Ile Ser Trp Val Arg Gln Ala Pro Gly Gln Gly Leu Glu Trp Met
         35                  40                  45

Gly Ser Phe Ile Pro Ile Leu Glu Arg Ala Asn Tyr Ala Gln Lys Phe
     50                  55                  60

Gln Gly Arg Val Thr Phe Thr Ala Asp Lys Thr Thr Ser Thr Ala Tyr
 65                  70                  75                  80

Met Glu Leu Gly Gly Leu Arg Ser Gln Asp Thr Ala Val Tyr Tyr Cys
                 85                  90                  95

Ala Arg Asp Leu Gly Asp Phe Gly Asp Ser Trp Gly Gln Gly Thr Leu
            100                 105                 110

Val Thr Val Ser Ser
            115

<210> SEQ ID NO 59
<211> LENGTH: 117
<212> TYPE: PRT
<213> ORGANISM: Homo Sapiens

<400> SEQUENCE: 59

Gln Val Gln Leu Val Gln Ser Gly Ser Glu Val Lys Lys Pro Gly Ser
 1               5                  10                  15

Ser Val Lys Val Ser Cys Lys Ala Ser Gly Gly Thr Phe Ser Ser His
             20                  25                  30

Thr Val Ser Trp Val Arg Gln Ala Pro Gly Gln Gly Leu Glu Trp Met
         35                  40                  45

Gly Glu Ile Ile Pro Ile Leu Asp Arg Val Asn Tyr Ala Glu Asn Phe
     50                  55                  60

Gln Gly Arg Val Thr Ile Thr Ala Asp Lys Ser Thr Asn Thr Thr Tyr
 65                  70                  75                  80

Met Asp Leu Ser Ser Leu Arg Ser Glu Asp Thr Ala Val Tyr Tyr Cys
                 85                  90                  95

Thr Ser Asn Gly Trp Ser Asn Phe Asp Phe Trp Gly Gln Gly Thr Leu
            100                 105                 110

Val Thr Val Ser Ser
            115
```

<210> SEQ ID NO 60
<211> LENGTH: 119
<212> TYPE: PRT
<213> ORGANISM: Homo Sapiens

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Thr Met Tyr
            20                  25                  30

Thr Ile Asn Trp Val Arg Gln Ala Pro Gly Arg Gly Leu Glu Trp Met
        35                  40                  45

Gly Arg Ile Ile Pro Ile Leu Gly Ile Thr Asp Tyr Ala Gln Lys Phe
    50                  55                  60

Gln Gly Arg Gly Thr Ile Thr Ala Asp Lys Ser Thr Ser Thr Ala Tyr
65                  70                  75                  80

Leu Glu Leu Ser Gly Leu Thr Ser Glu Asp Thr Ala Val Tyr Tyr Cys
                85                  90                  95

Ala Arg Glu Phe Ser Gly Gly Asn Tyr Phe Asp Phe Trp Gly Gln Gly
            100                 105                 110

Thr Leu Val Thr Val Ser Ser
        115

<210> SEQ ID NO 61
<211> LENGTH: 119
<212> TYPE: PRT
<213> ORGANISM: Homo Sapiens

<400> SEQUENCE: 61

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Ser Ile Ile Pro Val Leu Asp Val Thr Ser Tyr Ala Gln Gln Phe
    50                  55                  60

Gln Gly Arg Val Thr Ile Thr Ala Asp Lys Ser Thr Lys Thr Ala Tyr
65                  70                  75                  80

Met Asp Leu Ser Ser Leu Thr Phe Glu Asp Thr Ala Leu Tyr Phe Cys
                85                  90                  95

Ser Ile Gly Arg Tyr Thr Tyr Gly His Phe Asp Thr Trp Gly Gln Gly
            100                 105                 110

Thr Gln Val Thr Val Ser Ser
        115

<210> SEQ ID NO 62
<211> LENGTH: 118
<212> TYPE: PRT
<213> ORGANISM: Homo Sapiens

<400> SEQUENCE: 62

Glu Val Gln Leu Val Gln Ser Gly Ala Glu Val Lys Lys Pro Gly Ser
1               5                   10                  15

Ser Val Lys Val Ser Cys Lys Ala Ser Gly Ser Asn Phe Ser Ser His
            20                  25                  30

```
Thr Ile Asn Trp Val Arg Gln Ala Pro Gly His Gly Leu Glu Trp Met
         35                  40                  45

Gly Lys Ile Ile Pro Val Leu Asp Ile Ser Lys Asp Ala Glu Thr Phe
 50                  55                  60

Leu Gly Arg Val Val Ile Thr Ala Asp Lys Ser Thr Ser Thr Ala Tyr
 65                  70                  75                  80

Met Glu Leu Ser Ser Leu Arg Ser Glu Asp Thr Ala Ile Tyr Tyr Cys
                 85                  90                  95

Ala Met Asp Ser Val Tyr Gly Asn Phe Asp Phe Trp Gly Gln Gly Thr
            100                 105                 110

Leu Val Thr Val Ser Ser
        115
```

<210> SEQ ID NO 63
<211> LENGTH: 117
<212> TYPE: PRT
<213> ORGANISM: Homo Sapiens

<400> SEQUENCE: 63

```
Gln Val Gln Leu Val Gln Ser Gly Ala Glu Val Lys Lys Phe Gly Ser
 1               5                  10                  15

Ser Val Lys Val Ser Cys Lys Ala Ser Gly Gly Thr Phe Ser Ser Tyr
                20                  25                  30

Thr Met Ser Trp Val Arg Gln Ala Pro Gly Gln Gly Leu Glu Trp Met
         35                  40                  45

Gly Ser Phe Val Pro Ile Leu Glu Arg Ala Asn Tyr Ala Gln Gly Phe
 50                  55                  60

Gln Gly Arg Val Thr Phe Thr Ala Asp Lys Ser Thr Ser Thr Ala Tyr
 65                  70                  75                  80

Met Glu Leu Gly Ser Leu Arg Ser Glu Asp Thr Ala Val Tyr Tyr Cys
                 85                  90                  95

Ala Arg Asp Leu Gly Asp Phe Gly Asp Ser Trp Gly Gly Thr Leu
            100                 105                 110

Val Thr Val Ser Ser
        115
```

<210> SEQ ID NO 64
<211> LENGTH: 120
<212> TYPE: PRT
<213> ORGANISM: Homo Sapiens

<400> SEQUENCE: 64

```
Gln Val Gln Leu Val Gln Ser Gly Ala Glu Val Lys Lys Pro Leu Ser
 1               5                  10                  15

Ser Val Lys Val Ser Cys Lys Ala Ser Gly Gly Thr Phe Asn Met Tyr
                20                  25                  30

Asp Ile Asn Trp Val Arg Gln Ala Pro Gly Gln Gly Leu Glu Trp Met
         35                  40                  45

Gly Gly Ile Val Pro Ile Leu Gly Val Thr Asn Tyr Ala Gln Asn Phe
 50                  55                  60

Gln Gly Arg Leu Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Ala Ala Gly Trp Asn Ala Phe Asp Val Trp Gly Gln
            100                 105                 110
```

```
Gly Thr Met Val Thr Val Ser Ala
        115             120

<210> SEQ ID NO 65
<211> LENGTH: 116
<212> TYPE: PRT
<213> ORGANISM: Homo Sapiens

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asp Tyr
            20                  25                  30

Thr Ile Ile Trp Leu Arg Gln Ala Arg Gly His Gly Leu Glu Trp Met
        35                  40                  45

Gly Lys Ile Val Pro Ile Leu Gly Val Thr Thr Tyr Ala Gln Glu Phe
    50                  55                  60

Gln Gly Arg Ile Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Leu Trp Gly Leu Asp Val Trp Gly Gln Gly Thr Thr Val
            100                 105                 110

Thr Val Ser Ser
        115

<210> SEQ ID NO 66
<211> LENGTH: 119
<212> TYPE: PRT
<213> ORGANISM: Homo Sapiens

<400> SEQUENCE: 66

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Ile Met Asn Trp Val Arg Gln Ala Pro Gly Lys Gly Leu Glu Trp Val
        35                  40                  45

Ser Ser Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Arg Gly Glu Asp Thr Ala Val Tyr Tyr Cys
                85                  90                  95

Ala Ala Ala Tyr Asp Phe Trp Ser Gly Tyr Tyr Phe Trp Gly Gln Gly
            100                 105                 110

Thr Thr Val Thr Val Ser Ser
        115

<210> SEQ ID NO 67
<211> LENGTH: 116
<212> TYPE: PRT
<213> ORGANISM: Homo Sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
```

```
                20                  25                  30
Asp Ile Thr Trp Val Arg Gln Ala Pro Gly Gln Gly Leu Glu Trp Val
            35                  40                  45

Gly Lys Val Ile Pro Ile Leu Asp Val Thr Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Asn Leu Thr Ser Glu Asp Thr Ala Val Tyr Phe Cys
            85                  90                  95

Ala Arg Phe Leu Trp Gly Leu Asp Val Trp Gly Gln Gly Thr Met Val
            100                 105                 110

Thr Val Ser Ser
        115

<210> SEQ ID NO 68
<211> LENGTH: 122
<212> TYPE: PRT
<213> ORGANISM: Homo Sapiens

<400> SEQUENCE: 68

Glu Val Gln Leu Leu Glu Ser Gly Gly Gly Leu Val Gln Pro Gly Arg
 1               5                  10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
            85                  90                  95

Ala Lys Asp Pro Asn Ser Leu Tyr Arg Ser Gly Ser Phe Asp Tyr Trp
            100                 105                 110

Gly Gln Gly Thr Leu Val Thr Val Ser Ser
            115                 120

<210> SEQ ID NO 69
<211> LENGTH: 117
<212> TYPE: PRT
<213> ORGANISM: Homo Sapiens

<400> SEQUENCE: 69

Gln Val Gln Leu Gln Glu Ser Gly Gly Gly Val Val Gln Pro Gly Arg
 1               5                  10                  15

Ser Leu Arg Leu Ser Cys Thr Asp Ser Gly Phe Thr Phe Ser Arg Tyr
            20                  25                  30

Ala Met His Trp Val Arg Gln Ala Pro Gly Lys Gly Leu Glu Trp Val
            35                  40                  45

Ala Gly Ile Ser Tyr Asp Gly Ser Tyr Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Val Gln Met Asn Ser Leu Arg Gly Glu Asp Thr Ala Val Tyr Tyr Cys
            85                  90                  95

Ala Arg Asp Leu Arg Gly Gly Glu Asp Tyr Trp Gly Gln Gly Thr Leu
```

```
                100                 105                 110
Val Thr Val Ser Ser
        115

<210> SEQ ID NO 70
<211> LENGTH: 118
<212> TYPE: PRT
<213> ORGANISM: Homo Sapiens

<400> SEQUENCE: 70

Gln Val Gln Leu Val Gln Ser Gly Ala Glu Val Lys Lys Pro Gly Ser
1               5                   10                  15

Ser Met Asn Val Ser Cys Lys Ala Ser Gly Gly Thr Phe Ser Arg His
            20                  25                  30

Thr Ile Asn Trp Val Arg Gln Ala Pro Gly Gln Gly Leu Glu Trp Met
        35                  40                  45

Gly Ser Ile Ile Pro Ile Leu Gly Ile Thr Asn Tyr Ala Gln Asn Phe
    50                  55                  60

Gln Gly Arg Leu Thr Phe Ser Ala Asp Lys Ser Thr Asn Thr Ala Tyr
65                  70                  75                  80

Val Glu Leu Ser Gly Leu Arg Ser Glu Asp Thr Ala Val Tyr Tyr Cys
                85                  90                  95

Ala Ser Gly Asp Tyr Tyr Tyr Asp Met Ala Val Trp Gly Gln Gly Thr
            100                 105                 110

Thr Val Ala Val Thr Ser
        115

<210> SEQ ID NO 71
<211> LENGTH: 122
<212> TYPE: PRT
<213> ORGANISM: Homo Sapiens

<400> SEQUENCE: 71

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Pro Asn Ser Leu Tyr Arg Ser Gly Ser Phe Asp Tyr Trp
            100                 105                 110

Gly Gln Gly Thr Leu Val Thr Val Ser Ser
        115                 120

<210> SEQ ID NO 72
<211> LENGTH: 120
<212> TYPE: PRT
<213> ORGANISM: Homo Sapiens

<400> SEQUENCE: 72

Gln Val Gln Leu Val Gln Ser Gly Ala Glu Val Lys Lys Pro Gly Ser
1               5                   10                  15
```

Ser Val Lys Val Ser Cys Arg Ala Ser Gly Gly Thr Phe Ser Ser Tyr
            20                  25                  30

Thr Ile Asn Trp Val Arg Gln Ala Pro Gly Gln Gly Leu Glu Trp Met
            35                  40                  45

Gly Arg Val Val Pro Ile Leu Gly Val Thr Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Lys Gly Tyr Asp Asn Asn Tyr Gly Ala Tyr Trp Gly Gln
            100                 105                 110

Gly Thr Leu Val Thr Val Ser Ser
            115                 120

<210> SEQ ID NO 73
<211> LENGTH: 120
<212> TYPE: PRT
<213> ORGANISM: Homo Sapiens

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Asn Trp Val Arg Gln Ala Pro Gly Gln Gly Leu Glu Trp Met
            35                  40                  45

Gly Ser Ile Ile Pro Ile Leu Gly Ile Ser Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Gln Gly Tyr Ala Asn Asn Tyr Gly Ala Tyr Trp Gly Gln
            100                 105                 110

Gly Thr Leu Val Thr Val Ser Ser
            115                 120

<210> SEQ ID NO 74
<211> LENGTH: 120
<212> TYPE: PRT
<213> ORGANISM: Homo Sapiens

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Asn Trp Val Arg Gln Ala Pro Gly Gln Gly Leu Glu Trp Met
            35                  40                  45

Gly Ser Ile Ile Pro Ile Leu Gly Ile Arg Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Gln Gly Tyr Ala Asn Asn Tyr Gly Ala Tyr Trp Gly Gln
            100                 105                 110

Gly Thr Leu Val Thr Val Ser Ser
        115                 120

<210> SEQ ID NO 75
<211> LENGTH: 117
<212> TYPE: PRT
<213> ORGANISM: Homo Sapiens

<400> SEQUENCE: 75

Glu Val Gln Leu Val Gln Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys His Tyr Val Asp Ser Met
    50                  55                  60

Lys Gly Arg Phe Thr Ile Ser Arg Asp Asn Gly Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Tyr Tyr Phe Asp Tyr Trp Gly Gln Gly Thr Leu
            100                 105                 110

Val Thr Val Ser Ser
        115

<210> SEQ ID NO 76
<211> LENGTH: 120
<212> TYPE: PRT
<213> ORGANISM: Homo Sapiens

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asp Trp Val Arg Gln Ala Pro Gly Gln Gly Leu Glu Trp Met
        35                  40                  45

Gly Arg Ile Val Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Arg Gly Tyr Ala Asn Thr Tyr Gly Ala Tyr Trp Gly Gln
            100                 105                 110

Gly Thr Leu Val Thr Val Ser Ser
        115                 120

<210> SEQ ID NO 77
<211> LENGTH: 120
<212> TYPE: PRT
<213> ORGANISM: Homo Sapiens

<400> SEQUENCE: 77

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Val Pro Ile Leu Gly Val Val Asn Tyr Ala Gln Asn Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Lys Gly Tyr Ala Asn Asn Tyr Gly Ala Tyr Trp Gly Gln
            100                 105                 110

Gly Thr Leu Val Thr Val Ser Ser
            115                 120

<210> SEQ ID NO 78
<211> LENGTH: 120
<212> TYPE: PRT
<213> ORGANISM: Homo Sapiens

<400> SEQUENCE: 78

Gln Val Gln Leu Val Gln Ser Gly Ala Asp Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Arg Ile Val Pro Ile Leu Asp Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Asp Arg Gly Tyr Asp Asn Lys Tyr Gly Ala Tyr Trp Gly Gln
            100                 105                 110

Gly Thr Leu Val Thr Val Ser Ser
            115                 120

<210> SEQ ID NO 79
<211> LENGTH: 120
<212> TYPE: PRT
<213> ORGANISM: Homo Sapiens

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Ile Leu Gly Val Thr Asn Tyr Ser Gln Lys Phe
    50                  55                  60

Gln Gly Arg Val Thr Val Thr Ala Asp Ile Ser Thr Thr Thr Ala Tyr
65                  70                  75                  80
```

```
Met Glu Leu Ser Ser Leu Thr Ser Glu Asp Thr Ala Val Tyr Tyr Cys
                85                  90                  95

Ala Arg Asp Gln Gly Tyr Ala Asn Asp Tyr Gly Ala Tyr Trp Gly Gln
            100                 105                 110

Gly Thr Leu Val Thr Val Ser Ser
        115                 120

<210> SEQ ID NO 80
<211> LENGTH: 116
<212> TYPE: PRT
<213> ORGANISM: Homo Sapiens

<400> SEQUENCE: 80

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Arg Ile Ile Pro Ile Leu Gly Ile Glu Asn Tyr Ala Gln Lys Phe
    50                  55                  60

Gln Gly Arg Val Thr Ile Ser Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gln Val Phe Gly Ala Tyr Trp Gly Pro Gly Thr Leu Val
            100                 105                 110

Thr Val Ser Ser
        115

<210> SEQ ID NO 81
<211> LENGTH: 120
<212> TYPE: PRT
<213> ORGANISM: Homo Sapiens

<400> SEQUENCE: 81

Gln Val His Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Ile Leu Gly Val Thr Asn Tyr Ser Gln Lys Phe
    50                  55                  60

Gln Gly Arg Val Thr Val Thr Ala Asp Ile Ser Thr Thr Thr Ala Tyr
65                  70                  75                  80

Met Glu Leu Ser Ser Leu Thr Ser Glu Asp Thr Ala Val Tyr Tyr Cys
                85                  90                  95

Ala Arg Asp Gln Gly Tyr Ala Asn Asp Tyr Gly Ala Tyr Trp Gly Gln
            100                 105                 110

Gly Thr Leu Val Thr Val Ser Ser
        115                 120

<210> SEQ ID NO 82
<211> LENGTH: 120
<212> TYPE: PRT
<213> ORGANISM: Homo Sapiens
```

-continued

<400> SEQUENCE: 82

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Glu Ile Ser Trp Val Arg Gln Ala Pro Gly Gln Gly Leu Glu Trp Met
        35                  40                  45
Gly Arg Ile Val Pro Ile Leu Gly Leu Ala Asn Tyr Ala Gln Asn Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Phe Glu Asp Thr Ala Val Tyr Tyr Cys
                85                  90                  95
Ala Arg Asp Gln Gly Tyr Ala Asn Asn Tyr Gly Ala Tyr Trp Gly Gln
            100                 105                 110
Gly Thr Leu Val Ser Val Ser Ser
        115                 120

<210> SEQ ID NO 83
<211> LENGTH: 120
<212> TYPE: PRT
<213> ORGANISM: Homo Sapiens

<400> SEQUENCE: 83

Gln Val Gln Leu Val Gln Ser Gly Ala Glu Val Lys Lys Pro Gly Ser
1               5                   10                  15
Ser Val Lys Val Ser Cys Glu Ala Ser Gly Gly Thr Phe Ser Ser Tyr
            20                  25                  30
Ala Ile Thr Trp Val Arg Gln Ala Pro Gly Gln Gly Leu Glu Trp Met
        35                  40                  45
Gly Ser Ile Leu Pro Ile Leu Asp Ile Thr Asn Tyr Ala Gln Lys Phe
    50                  55                  60
Gln Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Phe Cys
                85                  90                  95
Ala Arg Asp Arg Gly Tyr Ser Asn Asn Tyr Gly Ala Tyr Trp Gly Gln
            100                 105                 110
Gly Thr Leu Val Thr Val Ser Ser
        115                 120

<210> SEQ ID NO 84
<211> LENGTH: 120
<212> TYPE: PRT
<213> ORGANISM: Homo Sapiens

<400> SEQUENCE: 84

Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Leu Gly Ile Thr Asn Tyr Ala Gln Lys Phe
    50                  55                  60
Gln Gly Arg Val Thr Ile Thr Ala Asp Glu Ser Thr Gly Ala Ala Tyr

```
              65                  70                  75                  80
Met Glu Leu Ser Ser Leu Ala Ser Glu Asp Thr Ala Val Tyr Tyr Cys
                    85                  90                  95

Ala Arg Asp Asp Thr Gly Arg Asp Asp Tyr Phe Glu Tyr Trp Gly Gln
                100                 105                 110

Gly Thr Leu Val Thr Val Ser Ser
                115                 120

<210> SEQ ID NO 85
<211> LENGTH: 117
<212> TYPE: PRT
<213> ORGANISM: Homo Sapiens

<400> SEQUENCE: 85

Gln Val Gln Leu Val Gln Ser Gly Ala Glu Val Lys Arg Pro Gly Ser
1               5                   10                  15

Ser Val Lys Val Ser Cys Lys Ala Ser Gly Asn Thr Phe Ser Asn Tyr
                20                  25                  30

His Ile Asn Trp Val Arg Gln Ala Pro Gly Gln Gly Leu Gln Trp Met
                35                  40                  45

Gly Gly Ile Ile Pro Ile Leu Gly Arg Thr Asn Tyr Ala Gln Asn Phe
            50                  55                  60

Gln Gly Arg Val Thr Ile Thr Thr Asp Glu Ser Thr Asn Thr Ala Tyr
65                  70                  75                  80

Met Glu Leu Thr Ser Leu Arg Ser Glu Asp Thr Ala Val Tyr Tyr Cys
                    85                  90                  95

Ala Arg Glu Ala Arg Asp Ser Phe Asp Phe Trp Gly Gln Gly Thr Met
                100                 105                 110

Val Thr Val Ser Ser
            115

<210> SEQ ID NO 86
<211> LENGTH: 119
<212> TYPE: PRT
<213> ORGANISM: Homo Sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Gly Ile Ser Trp Val Arg Gln Ala Pro Gly Gln Gly Leu Glu Trp Met
                35                  40                  45

Gly Lys Ile Ile Pro Ile Leu Gly Ile Thr Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Gly Gly Ser Tyr Asp Phe Phe Asp Tyr Trp Gly Gln Gly
                100                 105                 110

Thr Leu Val Thr Val Ser Ser
            115

<210> SEQ ID NO 87
<211> LENGTH: 118
<212> TYPE: PRT
```

<213> ORGANISM: Homo Sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Thr Ile Asn Trp Met Arg Gln Ala Pro Gly Gln Gly Leu Glu Trp Met
        35                  40                  45

Gly Arg Ile Ile Pro Met Phe Gly Thr Ala Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Ile Ser Glu Asp Thr Ala Ile Tyr Tyr Cys
                85                  90                  95

Ala Arg Ser Gly Tyr Ser Asp Ala Phe Asp Ile Trp Gly Gln Gly Thr
            100                 105                 110

Met Val Thr Val Ser Ser
            115

<210> SEQ ID NO 88
<211> LENGTH: 122
<212> TYPE: PRT
<213> ORGANISM: Homo Sapiens

<400> SEQUENCE: 88

Gln Val Gln Leu Val Gln Phe Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Pro Asn Ser Leu Tyr Arg Ser Gly Ser Phe Asp Tyr Trp
            100                 105                 110

Gly Gln Gly Thr Leu Val Thr Val Ser Ser
            115                 120

<210> SEQ ID NO 89
<211> LENGTH: 123
<212> TYPE: PRT
<213> ORGANISM: Homo Sapiens

<400> SEQUENCE: 89

Gln Val Gln Leu Gln Glu Ser Gly Pro Gly Leu Val Arg Pro Ser Gln
1               5                   10                  15

Thr Leu Ser Leu Thr Cys Ala Ile Ser Gly Asp Ser Val Ser Asn Asn
            20                  25                  30

Asn Ala Ala Trp Asn Trp Ile Arg Gln Ser Pro Ser Arg Gly Leu Glu
        35                  40                  45

Trp Leu Gly Arg Thr Phe Tyr Arg Ser Arg Trp Tyr Asn Asp Tyr Ala
    50                  55                  60

```
Val Ser Val Lys Ser Arg Ile Ile Asn Pro Asp Thr Ser Lys Asn
 65                  70                  75                  80

Gln Phe Ser Leu Asp Leu Thr Ser Val Thr Pro Glu Asp Thr Ala Val
                 85                  90                  95

Tyr Phe Cys Ala Arg Glu Gly Gln Trp Leu Pro Asn Tyr Phe Asp Pro
            100                 105                 110

Trp Gly Gln Gly Thr Leu Val Thr Val Ser Ser
        115                 120

<210> SEQ ID NO 90
<211> LENGTH: 117
<212> TYPE: PRT
<213> ORGANISM: Homo Sapiens

<400> SEQUENCE: 90

Gln Val Gln Leu Val Gln Ser Gly Gly Gly Val Val Gln Pro Gly Thr
 1               5                  10                  15

Ser Leu Arg Leu Ser Cys Ala Ala Ser Gly Phe Thr Phe Arg Asn His
                 20                  25                  30

Ala Met His Trp Val Arg Gln Ala Pro Gly Arg Gly Leu Glu Trp Val
             35                  40                  45

Ala Asp Ile Leu Tyr Asp Ser Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Phe Cys
                 85                  90                  95

Ala Ala Ser Ser Tyr Phe Pro Phe Asp Phe Trp Gly Gln Gly Thr Leu
            100                 105                 110

Val Thr Val Ser Ser
        115

<210> SEQ ID NO 91
<211> LENGTH: 325
<212> TYPE: DNA
<213> ORGANISM: Homo Sapiens

<400> SEQUENCE: 91
gagctcgagc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatta tgtcttcgga   300
actgggacca aggtgaccgt cctag                                         325

<210> SEQ ID NO 92
<211> LENGTH: 325
<212> TYPE: DNA
<213> ORGANISM: Homo Sapiens

<400> SEQUENCE: 92
gagctcgtgc tgactcagcc accctcggtg tcagtgtccc caggacagac ggccaggatc    60
acctgctctg gagatgcatt gccaaagcat tatgcttatt ggtaccagca gaagccaggc   120
caggcccctg tggtggttat atataaagac actgagaggc cctcagggat ccctgagcga   180
```

```
ttctctggcg ccacctcagg acaacaacc acgttgacca tcagtggagt ccaggcagaa    240
gacgaggctg actattttg tcaatcatca gacatcaatg gtacatcttg gatattcggc    300
ggcggcacca agctgaccgt cctag                                          325
```

<210> SEQ ID NO 93
<211> LENGTH: 325
<212> TYPE: DNA
<213> ORGANISM: Homo Sapiens

<400> SEQUENCE: 93

```
gagctcgtgc tgactcagcc accctcagtg tcagtggccc caggaaagac ggccaggatg    60
acctgtgggg gaaacaacat tggaggttat agtgtgcact ggtaccagca gaagccaggc   120
caggcccctg tgctggtcgt ctatcatgat agcgaccggc cctcagggat ccctgagcga   180
ttcactggct ccaattctgg gaacatggcc accctgacca tcagcagggt cgaggccggg   240
gatgaggccg actattactg tcaggtgtgg gatagtagta atgatcattc ggtattcggc   300
ggaggcaccg agctgaccgt cctcg                                          325
```

<210> SEQ ID NO 94
<211> LENGTH: 322
<212> TYPE: DNA
<213> ORGANISM: Homo Sapiens

<400> SEQUENCE: 94

```
gagctcgtga tgacccagtc tccatcgtct ctgtctgcat ctgtaggaga caccgtcacc    60
atcacttgcc gggcaagtca gagccttagg ggatatttaa attggtatca acagaagcca   120
ggggaagccc ctaaactcct catctacgct gcgtccactt tgcgggctgg ggtcccacca   180
aggttcagtg gcgccgggta tgagacagat ttcagtctca ccatcagcaa tctgcaactt   240
gaagattttg caacttacta ttgtcaacag tctcacaatg tccccctcac cttcggcgga   300
gggaccaagg tggaaatcaa ag                                             322
```

<210> SEQ ID NO 95
<211> LENGTH: 331
<212> TYPE: DNA
<213> ORGANISM: Homo Sapiens

<400> SEQUENCE: 95

```
gagctcgtgg tgacgcagcc gccctcagtg tctgcggccc caggacagaa ggtcaccatc    60
tccagctctg gaagcacctc caacattggg aacaattatg tatcctggta ccagcagttc   120
ccacgaacag cccccaaact cctcatttat gacaataata agcgaccctc agggattcct   180
gaccgattct ctggctccaa gtctggcacg tcagccaccc tgggcatcac cgggctccag   240
actggggacg aggccgatta ttactgcgga acatgggata gcagcctgag tgctgtggta   300
ttcggcggag gcaccaaggt gaccgtccta g                                   331
```

<210> SEQ ID NO 96
<211> LENGTH: 319
<212> TYPE: DNA
<213> ORGANISM: Homo Sapiens

<400> SEQUENCE: 96

```
gagctcgagc tgattcagcc accctcagtg tcagtgtccc caggacagac ggccaggatc    60
acctgctctg gagatgcatt gccaaagcaa tacgcttatt ggtaccagca gaagccaggc   120
caggcccctg cgatggtgat atataaagac actgagaggc ccccagggat ctctgagcga   180
```

```
atctctggct tcatctcagg gacaacagcc acgttgacca tcagtggagt ccaggcagag    240
gacgaggctg actattactg tcaatcagaa gacagcagtg gtatcctttt tggcggaggg    300
accaagctga ccgtcctag                                                 319
```

<210> SEQ ID NO 97
<211> LENGTH: 322
<212> TYPE: DNA
<213> ORGANISM: Homo Sapiens

<400> SEQUENCE: 97

```
gagctcgagc tgactcagcc accctcagtg tcagtttcc caggacagac ggccaggatc     60
acctgttctg gagatacatt gccaaagcaa tacggtaatt ggtaccagca gaagccaggc   120
caggcccctg tggtcgtgat atataaagac actgagaggc cctcaggat ccctgagcga    180 ttctctggct ccagttcagg gacaacagcc acgttgacca tcagtggggt ccaggcagaa   240
gacgaggctg attattactg tcaatcagca gacagcaatg attgggtgct attcggcgga   300
gggaccaagc tgaccgtcct ag                                            322
```

<210> SEQ ID NO 98
<211> LENGTH: 322
<212> TYPE: DNA
<213> ORGANISM: Homo Sapiens

<400> SEQUENCE: 98

```
gagctccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtgggtc tgggacagac tttaccttca ccatcagcag cctgcaggct   240
gaagattttg caacatatta ttgtcaacag tatgctaatc tcccgctcac tttcggcgga   300
gggaccaagc tggagatcaa ag                                            322
```

<210> SEQ ID NO 99
<211> LENGTH: 325
<212> TYPE: DNA
<213> ORGANISM: Homo Sapiens

<400> SEQUENCE: 99

```
gagctcgtgc tgactcagcc accctcggtg tcagtgtccc caggacagac ggccaggatc    60
acctgctctg gagatgcatt gccaaagcaa tatgcttatt ggtaccagca gaagccaggc   120
caggcccctg tgctggtgat atataaagac agtgagaggc cctcagggat ccctgagcga   180
ttctctggct ccagctcagg gacaacagtc acgttgacca tcagtggagt ccaggcagaa   240
gacgaggctg actattactg tcaatcagca gacagcagtg gtacttcctg ggtgttcggc   300
ggaggcacca agctgaccgt cctag                                         325
```

<210> SEQ ID NO 100
<211> LENGTH: 322
<212> TYPE: DNA
<213> ORGANISM: Homo Sapiens

<400> SEQUENCE: 100

```
gagctccaga tgacccagtc tccatcctcc ctgtctgcat ctgtaggaga cagagtcacc    60
atcacttgcc aggcgagtca ggacattagc aactatttaa attggtatca gcagaaacca   120
```

```
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tccccctcac cttcggccaa      300
gggacacgac tggagattaa ag                                               322

<210> SEQ ID NO 101
<211> LENGTH: 325
<212> TYPE: DNA
<213> ORGANISM: Homo Sapiens

<400> SEQUENCE: 101
gagctcgagc tgactcagcc accctcagtg tcagtgtccc caggacagac ggccaggatc       60
acctgctctg gaggtgcatt gccaaagcat tatgtttatt ggtaccagca gaagccaggc      120
caggcccctg cggtggtaat atataaagac actgagaggc cctcagggat ccctgagcga      180
ttctctggct ccacctcagg ggcaacagtc acgttgacca tcagtggagt ccaggcagat      240
gacgacgctg tctatttctg tcaatcagta gacagcaatg atacttcttg gatattcggc      300
ggaggcacca agctgaccgt cctag                                            325

<210> SEQ ID NO 102
<211> LENGTH: 331
<212> TYPE: DNA
<213> ORGANISM: Homo Sapiens

<400> SEQUENCE: 102
gagctcgagc tgactcagcc accctcagtg tctgggtctc ctggacagtc gatcaccatc       60
tcctgcactg gaaccagcag tgacgttggt ggttataact atgtctcctg gtaccaacag      120
cacccaggca aagccccaa actcatgatt tatgaggtca gtaatcggcc ctcagggttt       180
tctaatcgct tctctggctc caagtctggc aacacggcct ccctgaccat ctctgggctc      240
caggctgagg acgaggctga ttattactgc agctcatata caagcagcag cactgtggta      300
ttcggcggag gcaccaagct gaccgtccta g                                     331

<210> SEQ ID NO 103
<211> LENGTH: 322
<212> TYPE: DNA
<213> ORGANISM: Homo Sapiens

<400> SEQUENCE: 103
gagctcgtgc tgactcagcc accctcggtg tcagtgtccc caggacagac ggccaggatc       60
acctgctctg gagatgcatt tcctaagcac tatgcttatt ggtaccagca gaagccaggc      120
caggcccctg tattggtgat ctataaagac actgagaggc cctcagggat acctgagcga      180
ttctctggct ccagctcagg gacaacagcc acgttgacca tcagtggagt ccaggcagaa      240
gatgaagctg actattactg tcaatcaaca gactccagtg atacctgggt cttcggagct      300
ggcaccaagg tgaccgtcct ag                                               322

<210> SEQ ID NO 104
<211> LENGTH: 325
<212> TYPE: DNA
<213> ORGANISM: Homo Sapiens

<400> SEQUENCE: 104
gagctcgtgc tgactcagcc accctcagtg tcagtggccc caggaaagac ggccagaatt       60
acctgtgggg gaaacaacat cggaagtaaa actgtgcact ggtaccagca gaagccaggc      120
```

```
caggcccctg tggtggtcgt ctctgatgat agcgaacggc cctcagggat ccctgagcga    180
ttctctggct ccaactctgg gaacacggcc acccttacca tcagcagggt cgaaggcggg    240
gatgaggccg actattactg tcaggtgtgg gatagcagta atgatcaggt agtgttcggc    300
ggaggcaccg agctgaccgt cctcg                                          325
```

<210> SEQ ID NO 105
<211> LENGTH: 325
<212> TYPE: DNA
<213> ORGANISM: Homo Sapiens

<400> SEQUENCE: 105

```
gagctcgtgc tgactcagcc accctcggtg tcagtgtccc caggacagac ggccaggatc     60
acctgctctg gaggtgcatt gccaaagcat tatgcctatt ggtaccagca gaagccaggc    120
caggcccctg cggtggtaat atataaagac actgagaggc cctccgggat ccctgagcga    180
ttctctggct ccacctcagg acaacagtc acgttgacca tcagtggagt ccaggcagat    240
gacgacgctg tctatttctg tcaatcagta gacagcaatg atacttcttg gatattcggc    300
ggaggcacta agctgaccgt cctag                                          325
```

<210> SEQ ID NO 106
<211> LENGTH: 325
<212> TYPE: DNA
<213> ORGANISM: Homo Sapiens

<400> SEQUENCE: 106

```
gagctcgagc tgactcagcc accctcagtg tcaatttccc cgggaaagac ggccaagatt     60
ttctgtgggg gaaacagcat tggacgtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgattacgt ggtattcggc    300
ggaggcacca agctgaccgt cctag                                          325
```

<210> SEQ ID NO 107
<211> LENGTH: 325
<212> TYPE: DNA
<213> ORGANISM: Homo Sapiens

<400> SEQUENCE: 107

```
gagctcgtgc tgactcagcc accctcagtg tcagtggccc caggaaagac ggccagggtt     60
acctgtgggg gaggcaacat tggagataaa gctgtacact ggtaccagca gaggccaggc    120
caggcccctg tgctggtcgt ctttggtgat agcgcccggc cctcagggat ccctgagcga    180
ttctctggct ccaactctgg gaacacggcc accctgacca tcagcagggt cgaagtcggg    240
gatgaggccg actattactg tcaggtgtgg gatagtaata gtgatcatca ggtgttcggc    300
ggaggcacca agctgaccgt cctag                                          325
```

<210> SEQ ID NO 108
<211> LENGTH: 325
<212> TYPE: DNA
<213> ORGANISM: Homo Sapiens

<400> SEQUENCE: 108

```
gagctcgagc tgactcagcc gccctcggtg tcagtgtccc caggacagac ggccaggatc     60
```

```
acctgctctg gagatgcatt gccaaagcaa tatgcttatt ggtaccagca gaagccaggc      120
caggcccctg tgctggtgat atataaagac agtgagaggc cctcagggat ccctgagcga      180
ttctctggct ccagctcagg gacaacagtc acgttgacca tcagtggagt ccaggcagaa      240
gacgaggctg actattactg tcaatcagca gacagcagtg gtacttatga ggtgttcggc      300
ggagggacca agctgaccgt cctag                                            325

<210> SEQ ID NO 109
<211> LENGTH: 322
<212> TYPE: DNA
<213> ORGANISM: Homo Sapiens

<400> SEQUENCE: 109
gagctcgagc tgactcagcc accctcagtg tcagtgtccc caggacagac ggccaggatc       60
acctgctctg gagatgcatt gccaaagcaa tatgcttatt ggtaccagca gaagccaggc      120
caggcccctg tgctggtgat atataaagac agtgagaggc cctcagggat ccctgagcga      180
ttctctggct ccagctcagg gacaacagtc acgttgacca tcagtggagt ccaggcagaa      240
gacgaggctg actattactg tcaatcagca gacagcagtg gtacttacgt gttcggcgga      300
ggcaccaagc tgaccgtcct ag                                               322

<210> SEQ ID NO 110
<211> LENGTH: 325
<212> TYPE: DNA
<213> ORGANISM: Homo Sapiens

<400> SEQUENCE: 110
gagctcgtgc tgactcagcc accttcgatg tcagtggtcc caggacagac ggccaggatt       60
acctgtgggg gagacaacat tggaagtaaa agtgttcatt ggtaccagca aaagccaggc      120
caggcccctg ttctggtcgt caatgatgat accgagcggc cctcaggaat ccccgaccga      180
ttctctggct ccaactctgg gaacacggcc accctggtca tcagcagggt cggggccggg      240
gatgaggccg actatttctg tcaggtgtgg gatagcagga gtgatcatca ggtgttcggc      300
ggaggcacca agctgaccgt cctag                                            325

<210> SEQ ID NO 111
<211> LENGTH: 325
<212> TYPE: DNA
<213> ORGANISM: Homo Sapiens

<400> SEQUENCE: 111
gagctcgtgt tgacgcagcc gccctcggtg tcagtggccc caggacagac ggccaggatt       60
acctgtgggg gaaacaacat tggaagtaaa agtgtgcact ggtaccagca gaagccaggc      120
caggcccctg tgctggtcgt ctatgatgat agcgaccggc cctcagggat ccctgagcga      180
ttctctggct ccaattctgg gaacacggcc accctgacca tcagcagggt cgaagcgggg      240
gatgaggccg actattactg tcaggtgtgg gatagtagta gtgatcatgt ggtattcggc      300
ggagggaccg agctgaccgt cctcg                                            325

<210> SEQ ID NO 112
<211> LENGTH: 331
<212> TYPE: DNA
<213> ORGANISM: Homo Sapiens

<400> SEQUENCE: 112
gagctcgccc tgactcagcc tccctccgtg tctgggtctc ctggacagtc gatcaccatc       60
```

```
tcctgcactg gaaccagcag tgacgttggt ggttataact atgtctcctg gtaccaacag    120
cacccaggca aagcccccaa actcatgatt tatgaggtca gtaatcggcc ctcagggtt     180 tctaatcgct tctctggctc caagtctggc aacacggcct ccctgaccat ctctgggctc    240
caggctgagg acgaggctga ttattactgc agctcatata caagcagcac cccttatgtc    300
ttcggaactg ggaccaaggt gaccgtccta g                                   331
```

<210> SEQ ID NO 113
<211> LENGTH: 325
<212> TYPE: DNA
<213> ORGANISM: Homo Sapiens

<400> SEQUENCE: 113

```
gagctcgtgc tgactcagcc accttcggtg tcagtggccc caggacagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcataa ggtattcggc   300
ggagggaccg agctgaccgt cctcg                                          325
```

<210> SEQ ID NO 114
<211> LENGTH: 322
<212> TYPE: DNA
<213> ORGANISM: Homo Sapiens

<400> SEQUENCE: 114

```
gagctccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tggaaagtgg ggtcccatca   180
aggttcagtg gcagtggatc tgggacagat ttcactctca ccatcagcag tctgcaacct   240
gaagattttg caagttacta ctgtcaacag agttacagta ccccattcac tttcggccct   300
gggaccaaag tggatatcaa ag                                             322
```

<210> SEQ ID NO 115
<211> LENGTH: 331
<212> TYPE: DNA
<213> ORGANISM: Homo Sapiens

<400> SEQUENCE: 115

```
gagctcgtgg tgacgcagcc gccctcagtg tctgcggccc caggacagaa ggtcaccatc    60
tcctgctctg gaagcaccte caacattggg aacaattatg tatcctggta ccagcagttc   120
ccaggaacag cccccaaact cctcatttat gacaataata agcgaccctc agggattcct   180
gaccgattct ctggctccaa gtctggcacg tcagccaccc tgggcatcac cgggctccag   240
actggggacg aggccgatta ttactgcgga acatgggata gcagcctgag tgctgtggta   300
ttcggcggag gcaccaaggt gaccgtccta g                                   331
```

<210> SEQ ID NO 116
<211> LENGTH: 322
<212> TYPE: DNA
<213> ORGANISM: Homo Sapiens

<400> SEQUENCE: 116

```
gagctcgtgc tgactcagcc accctcgtgt cagtgtccc caggacagac ggccaggatc      60
acctgctctg gagatgcatt gccaaagcaa tatgcttatt ggtaccagca gaagccaggc    120
caggcccctg tgctggtgat atataaagac agtgagaggc cctcagggat ccctgagcga    180
ttctctggct ccagctcagg gacaacagcc acgttgacca ttagtggagt ccaggcagaa    240
gacgaggctg actattactg tcaatcagca tacagcagtg gtactgtggt attcggcgga    300
gggaccgagc tgaccgtcct cg                                             322
```

<210> SEQ ID NO 117
<211> LENGTH: 322
<212> TYPE: DNA
<213> ORGANISM: Homo Sapiens

<400> SEQUENCE: 117

```
gagctccaga tgacccagtc tccatcctcc ctgtctgcat ctgtaggaga cagagtcacc     60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgtacac ttttggccag   300
gggaccaagc tggagatcaa ag                                             322
```

<210> SEQ ID NO 118
<211> LENGTH: 325
<212> TYPE: DNA
<213> ORGANISM: Homo Sapiens

<400> SEQUENCE: 118

```
gagctcgtgc tgactcagcc accctcagtg tcagtggccc caggaaagac ggccaggatt     60
ccctgtgggg gaaacaacat tggaggtaaa agtgtgcact ggtaccagca gaggccaggc   120
caggcccctg tgctggtcgt ctattctgat agcgtccggc cctcgggat ccctgagcga    180 ttctctggct ccaactctgg gaacacggcc accctgacca tcagcagggt cgaagccggg   240
gatgaggccg actattactg tcaggtgtgg gatagaagta gtgatcatgt ggtattcggc   300
ggaggcaccc agctgaccgt cctcg                                          325
```

<210> SEQ ID NO 119
<211> LENGTH: 325
<212> TYPE: DNA
<213> ORGANISM: Homo Sapiens

<400> SEQUENCE: 119

```
gagctcgtgg tgacgcagcc gccctcggtg tcagtggccc caggacagac ggccaggatt     60
acctgtgggg gaaacaacat tggaagtata aatgtgcact ggtaccagca gaagccaggc   120
caggcccctg tactggtcgt ctatgatgat agcgcccggc cctcagggat ccctgagcga    180
ttttctggct ccaactctgg gaacacggcc accctgacca tcagcagggt cgaagccggg   240
gatgaggccg actattactg tcaggtgtgg gatagtagaa gtgattattg ggtgttcggc    300
ggaggcacca aggtgaccgt cctag                                          325
```

<210> SEQ ID NO 120
<211> LENGTH: 325
<212> TYPE: DNA
<213> ORGANISM: Homo Sapiens

<400> SEQUENCE: 120

```
gagctcgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tagtggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcattg ggtgttcggc   300
ggaggcaccg agctgaccgt cctcg                                         325

<210> SEQ ID NO 121
<211> LENGTH: 325
<212> TYPE: DNA
<213> ORGANISM: Homo Sapiens

<400> SEQUENCE: 121
gagctcgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgctgggcgt ctatgatgat agcaaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcattg ggtgttcggc   300
ggaggcaccc agctgaccgt cctcg                                         325

<210> SEQ ID NO 122
<211> LENGTH: 331
<212> TYPE: DNA
<213> ORGANISM: Homo Sapiens

<400> SEQUENCE: 122
gagctcgtgg tgacgcagcc gccctcagcg tctgggaccc ccgggcagag ggtcaccatc    60
tcttgttctg gaagcagctc caacatcgga agtaattatg tatactggta cgagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgcg tgtttatgtc   300
ttcggaactg gcaccaagct gaccgtccta g                                  331

<210> SEQ ID NO 123
<211> LENGTH: 325
<212> TYPE: DNA
<213> ORGANISM: Homo Sapiens

<400> SEQUENCE: 123
gagctcgtgc tgactcagcc accttcggtg tcagtggccc caggacagac ggccaggatt    60
acctgtgggg gaaacaacat tggaagtaaa ggtgtgcact ggtaccagca gaagccaggc   120
caggcccctg tactggtcgt ctatgatgat agcgaccggc cctcagggat ccctgagcga   180
ttatctggct ccaactctgg gaacacggcc accctgacca tcagcagggt cgaagccggg   240
gatgaggccg actattactg tcaggtgtgg gatagtagta gtgatcattg ggtgttcggc   300
ggaggcaccg agctgaccgt cctcg                                         325

<210> SEQ ID NO 124
<211> LENGTH: 325
<212> TYPE: DNA
<213> ORGANISM: Homo Sapiens
```

```
<400> SEQUENCE: 124
gagctcgtgc tgactcagcc accctcggtg tcagtggccc caggacagac ggccacgctt    60
acgtgtgggg ggaacaacat tggaagtaga agtgtgcact ggtaccagca gaagccaggc   120
cagggccctg tgctggtcgt ctatgatgat agcgaccggc cctcaggat ccctgagcga    180 ttctctggct ccaactctgg gaacacggcc accctgacta tcagcagggt cgaagccggg   240
gatgacgccg actattactg tcaggtgtgg gagagtacta ctgatcatta tgtcttcgga   300
actgggacca agctgaccgt cctag                                          325

<210> SEQ ID NO 125
<211> LENGTH: 325
<212> TYPE: DNA
<213> ORGANISM: Homo Sapiens

<400> SEQUENCE: 125
gagctcgtgt tgacgcagcc gccctcggtg tcagtggccc caggacagac ggccaggatt    60
acctgtgggg gaaacaacat tggaagtaaa aatgtgcact ggtaccagca gaagccaggc   120
caggcccctg tgctggtcgt ctatgatgat agcgaccgac cctcaggat ccctgagcga    180 ttctctggct ccaactctgg gaacacggcc accctgacca tcagcagggt cgaagccggg   240
gatgaggccg actattactg tcaggtgtgg gatagtagta gtgatcattg ggtgttcggc   300
ggaggcacca aggtgaccgt cctag                                          325

<210> SEQ ID NO 126
<211> LENGTH: 325
<212> TYPE: DNA
<213> ORGANISM: Homo Sapiens

<400> SEQUENCE: 126
gagctcgtgc tgactcagcc accttcggtg tcagtggccc caggacagac ggccaggatt    60
acctgtgggg gaaacaacat tggaagtaaa agtgtgcact ggtaccagca gaagccaggc   120
caggcccctg tgctggtcgt ccatgatgat agcgaccggc cctcaggat ccctgagcga    180 ttctctggct ccaactctgg gaacacggcc accctgacca tcggcagggt cggagccggg   240
gatgaggccg actattactg tcaggtgtgg gatagtagta gtgatcattg ggtgttcggc   300
ggaggcaccc agctgaccgt cctcg                                          325

<210> SEQ ID NO 127
<211> LENGTH: 325
<212> TYPE: DNA
<213> ORGANISM: Homo Sapiens

<400> SEQUENCE: 127
gagctcgtgc tgactcagcc accctcggtg tcagtggccc caggacagac ggccaggatt    60
atctgtgggg gaaacaacat tggaagtaaa actgtgcact ggtaccagca gaagccaggc   120
caggcccctg tgttggtcgt ctatgatgat agcgaccggc cctcaggat ccctgagcga    180 ttctctggct ccaactctgg gaacacggcc gccctgacca tcagcagggt cgaagccggg   240
gatgaggccg actattattg tcaggtgtgg catagtagta gtgatcattg ggtgttcggc   300
ggaggcacca aggtgaccgt cctag                                          325

<210> SEQ ID NO 128
<211> LENGTH: 325
<212> TYPE: DNA
<213> ORGANISM: Homo Sapiens
```

<400> SEQUENCE: 128

```
gagctcgtgc tgactcagcc accttcggtg tcagtggccc caggacagac ggccataatt    60
acctgtgggg aagcaacat tggaactaaa agtgtgcact ggtatcagca gaagtcaggc    120
caggcccctg tgctggtcgt ccatgatgat gcccaccggc cctcagggat ccctgagcga   180
ttctctggct ccaactctgg gaacacggcc accctgacca tcagcagggt cgaagccggg   240
gatgaggccg actattactg tcaggtgtgg gaaagtagta gtgatcattg ggtgttcggc   300
ggaggcacca aggtgaccgt cctag                                         325
```

<210> SEQ ID NO 129
<211> LENGTH: 325
<212> TYPE: DNA
<213> ORGANISM: Homo Sapiens

<400> SEQUENCE: 129

```
gagctcgtgc tgactcagcc accctcggtg tcagtggcac caggacagac ggccaggatt    60
acctgtgggg aaacaacat tgaaagtaaa aatgtgcact ggtaccagca gaagccaggc    120
caggcccctg tgctggtcgt ctatgatgat agcggccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcattg ggtgttcggc   300
ggaggcacca agctgaccgt cctag                                         325
```

<210> SEQ ID NO 130
<211> LENGTH: 325
<212> TYPE: DNA
<213> ORGANISM: Homo Sapiens

<400> SEQUENCE: 130

```
gagctcgtgc tgactcagcc accctcggtg tcagtggcac caggacagac ggccaggatt    60
acctgtgggg aaacaacat tggaagtaaa agtgtgcact ggtaccagca gaagccaggc    120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtaata gtgatcattg ggtgttcggc   300
ggaggcaccg agctgaccgt cttcg                                         325
```

<210> SEQ ID NO 131
<211> LENGTH: 325
<212> TYPE: DNA
<213> ORGANISM: Homo Sapiens

<400> SEQUENCE: 131

```
gagctcgtgc tgactcagcc accctcggtg tcagtggccc caggacagac ggccaggatt    60
acctgtgggg aaacaacat tggaagtaaa agtgtgcact ggtaccagca gaagccaggc    120
cgggcccctg tgctggtcgt ctatgatgat agcgagcggc cctcagggat ccctgagcga   180
ttctctggct ccaactctgg gaacacggcc accctgacca tcagcagggt cgaagccggg   240
gatgaggccg actattactg tcaggtgtgg gagagtagta gtgatcattg ggtgttcggc   300
ggagggacca aggtgaccgt cctag                                         325
```

<210> SEQ ID NO 132
<211> LENGTH: 325
<212> TYPE: DNA

<213> ORGANISM: Homo Sapiens

<400> SEQUENCE: 132

```
gagctcgtgc tgactcagcc accctcggtg tcagtggccc caggacagac ggccaggatt    60
acctgtgggg gaaacaacat tggaagtaaa aatgtgcact ggtaccagca gaagccaggc   120
caggcccctc tactggtcgt ctatgatgat agcgaccggc cctcagggat ccctgagcga   180
ttctctggct ccaactctgg gaacatggcc accctgacca tcagcagggt cgaagccggg   240
gatgaggcca actattactg tcaggtgtgg gatagtagta gtgatcatgt ggtattcggc   300
ggagggacca agctgaccgt cctag                                         325
```

<210> SEQ ID NO 133
<211> LENGTH: 325
<212> TYPE: DNA
<213> ORGANISM: Homo Sapiens

<400> SEQUENCE: 133

```
gagctcgtgc tgactcagcc accctcggtg tcagtgtccc caggacagac ggccaggatc    60
acctgctctg gagatgcatt gccaaagcaa tatgcttatt ggtaccagca gaagccaggc   120
caggcccctg ttggtgat atataaagac agtgagaggc cctcagggat ccctgagcga    180
ttctctggct ccagctcagg gacaacagtc acgttgacca tcagtggagt ccaggcagaa   240
gacgaggctg actattactg tcaatcagca gacagcaatg gtacttataa ggtgttcggc   300
ggaggcaccg agctgaccgt cctcg                                         325
```

<210> SEQ ID NO 134
<211> LENGTH: 325
<212> TYPE: DNA
<213> ORGANISM: Homo Sapiens

<400> SEQUENCE: 134

```
gagctcgtgc tgactcagcc accctcagtg tccgtgtccc cgggacagac agccagcatc    60
acctgctctg gagataaatt gggacataca tacacttcct ggtatcaaca gaagccaggc   120
cagtcccctg tcctagtcat ctatcaagat aacaggcggc cctcagggct ccctgagcga   180
ttctctggct ccaactctgg gaacacggcc accctgacca tcagcagggt cgaagccggg   240
gatgaggccg actattactg tcaggtgtgg gaaagtagta gtgatcatct tgtattcggc   300
ggaggcaccg agctgaccgt cctcg                                         325
```

<210> SEQ ID NO 135
<211> LENGTH: 325
<212> TYPE: DNA
<213> ORGANISM: Homo Sapiens

<400> SEQUENCE: 135

```
gagctcgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcattg ggtgttcggc   300
ggagggaccc agctgaccgt cctcg                                         325
```

<210> SEQ ID NO 136
<211> LENGTH: 325

<212> TYPE: DNA
<213> ORGANISM: Homo Sapiens

<400> SEQUENCE: 136

| | | | | | |
|---|---|---|---|---|---|
| gagctcgtgc | tgactcagcc | accctcagtg | tcagtggccc | caggaaagac | ggccaggatt | 60 |
| acctgtgggg | aaaacaacat | tggaagtaaa | agtgtgcact | ggtaccagca | gaagccaggc | 120 |
| caggcccctg | tcctggtcat | ctattatgat | accgaccggc | cctcagggat | ccctgcgcgc | 180 |
| ttctctggct | ccaactctgg | gaacacggcc | accctgacca | tcagcagggt | cgaagccggg | 240 |
| gatgaggccg | actattactg | tcaggtgtgg | gatagtagta | gtgaccagag | ggtattcggc | 300 |
| ggaggcaccg | agctgaccgt | cctcg | | | | 325 |

<210> SEQ ID NO 137
<211> LENGTH: 325
<212> TYPE: DNA
<213> ORGANISM: Homo Sapiens

<400> SEQUENCE: 137

| | | | | | |
|---|---|---|---|---|---|
| gagctcgagc | tgactcagcc | accctcagtg | tcagtggccc | caggaaaggc | ggccagactt | 60 |
| tcctgcgggg | gagaggacat | tggaattaaa | agtgtccact | ggtaccaaca | gaagacaggc | 120 |
| cgggcccctg | tgttggtcat | ctataatgat | gacgaccggc | cctcagggat | ccctgagcgg | 180 |
| ttcgctggct | ccaattctgg | gaacacggcc | accctgacca | tcagcagggt | cgaggccggg | 240 |
| gatgaggccg | actactattg | tgaggtgtgg | gacagtctta | ctgatcgtgt | cgtgttcggc | 300 |
| ggaggcacca | agctgaccgt | cctag | | | | 325 |

<210> SEQ ID NO 138
<211> LENGTH: 325
<212> TYPE: DNA
<213> ORGANISM: Homo Sapiens

<400> SEQUENCE: 138

| | | | | | |
|---|---|---|---|---|---|
| gagctcgtgc | tgactcagcc | accctcagtg | tcagtggccc | caggaacgac | ggccaggatt | 60 |
| acctgtgggg | gaaacaacat | tggaagtaaa | agtgtgcact | ggtaccagca | gaagccaggc | 120 |
| caggcccctg | tgctggtcat | ttattatgat | agcgaccggc | cctcagggat | ccctgagcga | 180 |
| ttctctggct | ccaactctgg | gaacacggcc | accctgacca | tcagcagggt | cgaagccggg | 240 |
| gatgaggccg | actattactg | tcaggtgtgg | gatagtagta | gtgatcaggg | ggtattcggc | 300 |
| ggagggaccc | agctgaccgt | cctcg | | | | 325 |

<210> SEQ ID NO 139
<211> LENGTH: 322
<212> TYPE: DNA
<213> ORGANISM: Homo Sapiens

<400> SEQUENCE: 139

| | | | | | |
|---|---|---|---|---|---|
| gagctcgtga | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacagta | ccccgtacac | ttttggccag | 300 |
| gggaccaagc | tggagatcaa | ag | | | | 322 |

<210> SEQ ID NO 140

<211> LENGTH: 325
<212> TYPE: DNA
<213> ORGANISM: Homo Sapiens

<400> SEQUENCE: 140

```
gagctcgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgttggtcgt ctatgatgat agcgaccggc cctcaggat ccctgagcga   180
ttctctggct ccaactctgg gaacacggcc accctgacca tcagcggggt cgaagtcggg   240
gatgaggccg actattactg tcaggtgtgg gatagtagtc gtgatcatgt ggtattcggc   300
ggagggaccg agctgaccgt cctcg                                         325
```

<210> SEQ ID NO 141
<211> LENGTH: 337
<212> TYPE: DNA
<213> ORGANISM: Homo Sapiens

<400> SEQUENCE: 141

```
gagctcgtga tgacccagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgta tgcaagctct acaaactcct   300
cagacttttg gccaggggac caagctggag atcaaag                            337
```

<210> SEQ ID NO 142
<211> LENGTH: 108
<212> TYPE: PRT
<213> ORGANISM: Homo Sapiens

<400> SEQUENCE: 142

```
Glu Leu Glu Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Tyr Val Phe Gly Thr Gly Thr Lys Val Thr Val Leu
                100                 105
```

<210> SEQ ID NO 143
<211> LENGTH: 108
<212> TYPE: PRT
<213> ORGANISM: Homo Sapiens

<400> SEQUENCE: 143

```
Glu Leu Val Leu Thr Gln Pro Pro Ser Val Ser Val Ser Pro Gly Gln
 1               5                  10                  15

Thr Ala Arg Ile Thr Cys Ser Gly Asp Ala Leu Pro Lys His Tyr Ala
```

```
                    20                  25                  30

Tyr Trp Tyr Gln Gln Lys Pro Gly Gln Ala Pro Val Val Ile Tyr
            35                  40                  45

Lys Asp Thr Glu Arg Pro Ser Gly Ile Pro Glu Arg Phe Ser Gly Ala
 50                  55                  60

Thr Ser Gly Thr Thr Thr Thr Leu Thr Ile Ser Gly Val Gln Ala Glu
 65                  70                  75                  80

Asp Glu Ala Asp Tyr Phe Cys Gln Ser Ser Asp Ile Asn Gly Thr Ser
                85                  90                  95

Trp Ile Phe Gly Gly Gly Thr Lys Leu Thr Val Leu
                100                 105

<210> SEQ ID NO 144
<211> LENGTH: 108
<212> TYPE: PRT
<213> ORGANISM: Homo Sapiens

<400> SEQUENCE: 144

Glu Leu Val Leu Thr Gln Pro Pro Ser Val Ser Val Ala Pro Gly Lys
 1               5                   10                  15

Thr Ala Arg Met Thr Cys Gly Gly Asn Asn Ile Gly Gly Tyr Ser Val
                20                  25                  30

His Trp Tyr Gln Gln Lys Pro Gly Gln Ala Pro Val Leu Val Val Tyr
            35                  40                  45

His Asp Ser Asp Arg Pro Ser Gly Ile Pro Glu Arg Phe Thr Gly Ser
 50                  55                  60

Asn Ser Gly Asn Met Ala Thr Leu Thr Ile Ser Arg Val Glu Ala Gly
 65                  70                  75                  80

Asp Glu Ala Asp Tyr Tyr Cys Gln Val Trp Asp Ser Ser Asn Asp His
                85                  90                  95

Ser Val Phe Gly Gly Gly Thr Glu Leu Thr Val Leu
                100                 105

<210> SEQ ID NO 145
<211> LENGTH: 107
<212> TYPE: PRT
<213> ORGANISM: Homo Sapiens

<400> SEQUENCE: 145

Glu Leu Val Met Thr Gln Ser Pro Ser Ser Leu Ser Ala Ser Val Gly
 1               5                   10                  15

Asp Thr Val Thr Ile Thr Cys Arg Ala Ser Gln Ser Leu Arg Gly Tyr
                20                  25                  30

Leu Asn Trp Tyr Gln Gln Lys Pro Gly Glu Ala Pro Lys Leu Leu Ile
            35                  40                  45

Tyr Ala Ala Ser Thr Leu Arg Ala Gly Val Pro Pro Arg Phe Ser Gly
 50                  55                  60

Ala Gly Tyr Glu Thr Asp Phe Ser Leu Thr Ile Ser Asn Leu Gln Leu
 65                  70                  75                  80

Glu Asp Phe Ala Thr Tyr Tyr Cys Gln Gln Ser His Asn Val Pro Leu
                85                  90                  95

Thr Phe Gly Gly Gly Thr Lys Val Glu Ile Lys
                100                 105

<210> SEQ ID NO 146
<211> LENGTH: 110
<212> TYPE: PRT
```

<213> ORGANISM: Homo Sapiens

<400> SEQUENCE: 146

Glu Leu Val Val Thr Gln Pro Pro Ser Val Ser Ala Ala Pro Gly Gln
1               5                   10                  15

Lys Val Thr Ile Ser Ser Ser Gly Ser Thr Ser Asn Ile Gly Asn Asn
            20                  25                  30

Tyr Val Ser Trp Tyr Gln Gln Phe Pro Arg Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
            100                 105                 110

<210> SEQ ID NO 147
<211> LENGTH: 106
<212> TYPE: PRT
<213> ORGANISM: Homo Sapiens

<400> SEQUENCE: 147

Glu Leu Glu Leu Ile Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Ala Met Val Ile Tyr
        35                  40                  45

Lys Asp Thr Glu Arg Pro Pro Gly Ile Ser Glu Arg Ile Ser Gly Phe
    50                  55                  60

Ile Ser Gly Thr Thr Ala Thr Leu Thr Ile Ser Gly Val Gln Ala Glu
65                  70                  75                  80

Asp Glu Ala Asp Tyr Tyr Cys Gln Ser Glu Asp Ser Ser Gly Ile Leu
                85                  90                  95

Phe Gly Gly Gly Thr Lys Leu Thr Val Leu
            100                 105

<210> SEQ ID NO 148
<211> LENGTH: 107
<212> TYPE: PRT
<213> ORGANISM: Homo Sapiens

<400> SEQUENCE: 148

Glu Leu Glu Leu Thr Gln Pro Pro Ser Val Ser Val Phe Pro Gly Gln
1               5                   10                  15

Thr Ala Arg Ile Thr Cys Ser Gly Asp Thr Leu Pro Lys Gln Tyr Gly
            20                  25                  30

Asn Trp Tyr Gln Gln Lys Pro Gly Gln Ala Pro Val Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Asn Asp Trp Val
                85                  90                  95

Leu Phe Gly Gly Gly Thr Lys Leu Thr Val Leu
            100                 105

<210> SEQ ID NO 149
<211> LENGTH: 107
<212> TYPE: PRT
<213> ORGANISM: Homo Sapiens

<400> SEQUENCE: 149

Glu Leu Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Gly Gly Ser Gly Thr Asp Phe Thr Phe Thr Ile Ser Ser Leu Gln Ala
65                  70                  75                  80

Glu Asp Phe Ala Thr Tyr Tyr Cys Gln Gln Tyr Ala Asn Leu Pro Leu
                85                  90                  95

Thr Phe Gly Gly Gly Thr Lys Leu Glu Ile Lys
            100                 105

<210> SEQ ID NO 150
<211> LENGTH: 108
<212> TYPE: PRT
<213> ORGANISM: Homo Sapiens

<400> SEQUENCE: 150

Glu Leu Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Ser
                85                  90                  95

Trp Val Phe Gly Gly Gly Thr Lys Leu Thr Val Leu
            100                 105

<210> SEQ ID NO 151
<211> LENGTH: 107
<212> TYPE: PRT
<213> ORGANISM: Homo Sapiens

<400> SEQUENCE: 151

Glu Leu Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

```
Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Leu
                 85                  90                  95

Thr Phe Gly Gln Gly Thr Arg Leu Glu Ile Lys
            100                 105

<210> SEQ ID NO 152
<211> LENGTH: 108
<212> TYPE: PRT
<213> ORGANISM: Homo Sapiens

<400> SEQUENCE: 152

Glu Leu Glu Leu Thr Gln Pro Pro Ser Val Ser Val Ser Pro Gly Gln
 1               5                  10                  15

Thr Ala Arg Ile Thr Cys Ser Gly Gly Ala Leu Pro Lys His Tyr Val
                 20                  25                  30

Tyr Trp Tyr Gln Gln Lys Pro Gly Gln Ala Pro Ala Val Val Ile Tyr
             35                  40                  45

Lys Asp Thr Glu Arg Pro Ser Gly Ile Pro Glu Arg Phe Ser Gly Ser
 50                  55                  60

Thr Ser Gly Ala Thr Val Thr Leu Thr Ile Ser Gly Val Gln Ala Asp
 65                  70                  75                  80

Asp Asp Ala Val Tyr Phe Cys Gln Ser Val Asp Ser Asn Asp Thr Ser
                 85                  90                  95

Trp Ile Phe Gly Gly Gly Thr Lys Leu Thr Val Leu
            100                 105

<210> SEQ ID NO 153
<211> LENGTH: 110
<212> TYPE: PRT
<213> ORGANISM: Homo Sapiens

<400> SEQUENCE: 153

Glu Leu Glu Leu Thr Gln Pro Pro Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Val Val Phe Gly Gly Gly Thr Lys Leu Thr Val Leu
            100                 105                 110

<210> SEQ ID NO 154
<211> LENGTH: 107
<212> TYPE: PRT
<213> ORGANISM: Homo Sapiens

<400> SEQUENCE: 154

Glu Leu Val Leu Thr Gln Pro Pro Ser Val Ser Val Ser Pro Gly Gln
 1               5                  10                  15
```

```
1               5                   10                  15
Thr Ala Arg Ile Thr Cys Ser Gly Asp Ala Phe Pro Lys His Tyr Ala
            20                  25                  30
Tyr Trp Tyr Gln Gln Lys Pro Gly Gln Ala Pro Val Leu Val Ile Tyr
            35                  40                  45
Lys Asp Thr Glu Arg Pro Ser Gly Ile Pro Glu Arg Phe Ser Gly Ser
            50                  55                  60
Ser Ser Gly Thr Thr Ala Thr Leu Thr Ile Ser Gly Val Gln Ala Glu
65                  70                  75                  80
Asp Glu Ala Asp Tyr Tyr Cys Gln Ser Thr Asp Ser Ser Asp Thr Trp
                    85                  90                  95
Val Phe Gly Ala Gly Thr Lys Val Thr Val Leu
                    100                 105
```

<210> SEQ ID NO 155
<211> LENGTH: 108
<212> TYPE: PRT
<213> ORGANISM: Homo Sapiens

<400> SEQUENCE: 155

```
Glu Leu Val Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Thr Val
            20                  25                  30
His Trp Tyr Gln Gln Lys Pro Gly Gln Ala Pro Val Val Val Val Ser
            35                  40                  45
Asp Asp Ser Glu Arg Pro Ser Gly Ile Pro Glu Arg Phe Ser Gly Ser
            50                  55                  60
Asn Ser Gly Asn Thr Ala Thr Leu Thr Ile Ser Arg Val Glu Gly Gly
65                  70                  75                  80
Asp Glu Ala Asp Tyr Tyr Cys Gln Val Trp Asp Ser Ser Asn Asp Gln
                    85                  90                  95
Val Val Phe Gly Gly Gly Thr Glu Leu Thr Val Leu
                    100                 105
```

<210> SEQ ID NO 156
<211> LENGTH: 108
<212> TYPE: PRT
<213> ORGANISM: Homo Sapiens

<400> SEQUENCE: 156

```
Glu Leu Val Leu Thr Gln Pro Pro Ser Val Ser Val Ser Pro Gly Gln
1               5                   10                  15
Thr Ala Arg Ile Thr Cys Ser Gly Gly Ala Leu Pro Lys His Tyr Ala
            20                  25                  30
Tyr Trp Tyr Gln Gln Lys Pro Gly Gln Ala Pro Ala Val Ile Tyr
            35                  40                  45
Lys Asp Thr Glu Arg Pro Ser Gly Ile Pro Glu Arg Phe Ser Gly Ser
            50                  55                  60
Thr Ser Gly Thr Thr Val Thr Leu Thr Ile Ser Gly Val Gln Ala Asp
65                  70                  75                  80
Asp Asp Ala Val Tyr Phe Cys Gln Ser Val Asp Ser Asn Asp Thr Ser
                    85                  90                  95
Trp Ile Phe Gly Gly Gly Thr Lys Leu Thr Val Leu
                    100                 105
```

```
<210> SEQ ID NO 157
<211> LENGTH: 108
<212> TYPE: PRT
<213> ORGANISM: Homo Sapiens

<400> SEQUENCE: 157

Glu Leu Glu Leu Thr Gln Pro Pro Ser Val Ser Ile Ser Pro Gly Lys
1               5                   10                  15

Thr Ala Lys Ile Phe Cys Gly Gly Asn Ser Ile Gly Arg Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu
            100                 105

<210> SEQ ID NO 158
<211> LENGTH: 108
<212> TYPE: PRT
<213> ORGANISM: Homo Sapiens

<400> SEQUENCE: 158

Glu Leu Val Leu Thr Gln Pro Pro Ser Val Ser Val Ala Pro Gly Lys
1               5                   10                  15

Thr Ala Arg Val Thr Cys Gly Gly Gly Asn Ile Gly Asp Lys Ala Val
            20                  25                  30

His Trp Tyr Gln Gln Arg Pro Gly Gln Ala Pro Val Leu Val Val Phe
        35                  40                  45

Gly Asp Ser Ala Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Tyr Cys Gln Val Trp Asp Ser Asn Ser Asp His
                85                  90                  95

Gln Val Phe Gly Gly Gly Thr Lys Leu Thr Val Leu
            100                 105

<210> SEQ ID NO 159
<211> LENGTH: 108
<212> TYPE: PRT
<213> ORGANISM: Homo Sapiens

<400> SEQUENCE: 159

Glu Leu Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80
```

```
Asp Glu Ala Asp Tyr Tyr Cys Gln Ser Ala Asp Ser Ser Gly Thr Tyr
                85                  90                  95

Glu Val Phe Gly Gly Gly Thr Lys Leu Thr Val Leu
            100                 105
```

<210> SEQ ID NO 160
<211> LENGTH: 107
<212> TYPE: PRT
<213> ORGANISM: Homo Sapiens

<400> SEQUENCE: 160

```
Glu Leu Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Phe Gly Gly Gly Thr Lys Leu Thr Val Leu
            100                 105
```

<210> SEQ ID NO 161
<211> LENGTH: 108
<212> TYPE: PRT
<213> ORGANISM: Homo Sapiens

<400> SEQUENCE: 161

```
Glu Leu Val Leu Thr Gln Pro Pro Ser Met Ser Val Val Pro Gly Gln
1               5                   10                  15

Thr Ala Arg Ile Thr Cys Gly Gly Asp Asn Ile Gly Ser Lys Ser Val
            20                  25                  30

His Trp Tyr Gln Gln Lys Pro Gly Gln Ala Pro Val Leu Val Val Asn
        35                  40                  45

Asp Asp Thr Glu Arg Pro Ser Gly Ile Pro Asp Arg Phe Ser Gly Ser
50                  55                  60

Asn Ser Gly Asn Thr Ala Thr Leu Val Ile Ser Arg Val Gly Ala Gly
65                  70                  75                  80

Asp Glu Ala Asp Tyr Phe Cys Gln Val Trp Asp Ser Arg Ser Asp His
                85                  90                  95

Gln Val Phe Gly Gly Gly Thr Lys Leu Thr Val Leu
            100                 105
```

<210> SEQ ID NO 162
<211> LENGTH: 108
<212> TYPE: PRT
<213> ORGANISM: Homo Sapiens

<400> SEQUENCE: 162

```
Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Glu Leu Thr Val Leu
            100                 105

<210> SEQ ID NO 163
<211> LENGTH: 110
<212> TYPE: PRT
<213> ORGANISM: Homo Sapiens

<400> SEQUENCE: 163

Glu Leu Ala Leu Thr Gln Pro Pro Ser Val Ser Gly Ser Pro Gly Gln
 1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Thr Pro Tyr Val Phe Gly Thr Gly Thr Lys Val Thr Val Leu
            100                 105                 110

<210> SEQ ID NO 164
<211> LENGTH: 108
<212> TYPE: PRT
<213> ORGANISM: Homo Sapiens

<400> SEQUENCE: 164

Glu Leu Val Leu Thr Gln Pro Pro Ser Val Ser Val Ala Pro Gly Gln
 1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Lys Val Phe Gly Gly Gly Thr Glu Leu Thr Val Leu
            100                 105

<210> SEQ ID NO 165
<211> LENGTH: 107
<212> TYPE: PRT
<213> ORGANISM: Homo Sapiens

<400> SEQUENCE: 165

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 166
<211> LENGTH: 110
<212> TYPE: PRT
<213> ORGANISM: Homo Sapiens

<400> SEQUENCE: 166

Glu Leu Val Val Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
            100                 105                 110

<210> SEQ ID NO 167
<211> LENGTH: 107
<212> TYPE: PRT
<213> ORGANISM: Homo Sapiens

<400> SEQUENCE: 167

Glu Leu Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Tyr Ser Ser Gly Thr Val
                85                  90                  95

Val Phe Gly Gly Gly Thr Glu Leu Thr Val Leu
            100                 105

```
                100                 105

<210> SEQ ID NO 168
<211> LENGTH: 107
<212> TYPE: PRT
<213> ORGANISM: Homo Sapiens

<400> SEQUENCE: 168

Glu Leu Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 169
<211> LENGTH: 108
<212> TYPE: PRT
<213> ORGANISM: Homo Sapiens

<400> SEQUENCE: 169

Glu Leu Val Leu Thr Gln Pro Pro Ser Val Ser Val Ala Pro Gly Lys
1               5                   10                  15

Thr Ala Arg Ile Pro Cys Gly Gly Asn Asn Ile Gly Gly Lys Ser Val
                20                  25                  30

His Trp Tyr Gln Gln Arg Pro Gly Gln Ala Pro Val Leu Val Val Tyr
            35                  40                  45

Ser Asp Ser Val Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp His
                85                  90                  95

Val Val Phe Gly Gly Gly Thr Gln Leu Thr Val Leu
            100                 105

<210> SEQ ID NO 170
<211> LENGTH: 108
<212> TYPE: PRT
<213> ORGANISM: Homo Sapiens

<400> SEQUENCE: 170

Glu Leu Val Val Thr Gln Pro Pro Ser Val Ser Val Ala Pro Gly Gln
1               5                   10                  15

Thr Ala Arg Ile Thr Cys Gly Gly Asn Asn Ile Gly Ser Ile Asn Val
                20                  25                  30

His Trp Tyr Gln Gln Lys Pro Gly Gln Ala Pro Val Leu Val Val Tyr
            35                  40                  45

Asp Asp Ser Ala Arg Pro Ser Gly Ile Pro Glu Arg Phe Ser Gly Ser
    50                  55                  60
```

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp Tyr
                85                  90                  95

Trp Val Phe Gly Gly Gly Thr Lys Val Thr Val Leu
            100                 105

<210> SEQ ID NO 171
<211> LENGTH: 108
<212> TYPE: PRT
<213> ORGANISM: Homo Sapiens

<400> SEQUENCE: 171

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Glu Leu Thr Val Leu
            100                 105

<210> SEQ ID NO 172
<211> LENGTH: 108
<212> TYPE: PRT
<213> ORGANISM: Homo Sapiens

<400> SEQUENCE: 172

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Gly Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Gln Leu Thr Val Leu
            100                 105

<210> SEQ ID NO 173
<211> LENGTH: 110
<212> TYPE: PRT
<213> ORGANISM: Homo Sapiens

<400> SEQUENCE: 173

Glu Leu Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Glu Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Arg Val Tyr Val Phe Gly Thr Gly Thr Lys Leu Thr Val Leu
            100                 105                 110

<210> SEQ ID NO 174
<211> LENGTH: 108
<212> TYPE: PRT
<213> ORGANISM: Homo Sapiens

<400> SEQUENCE: 174

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Leu Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Glu Leu Thr Val Leu
            100                 105

<210> SEQ ID NO 175
<211> LENGTH: 108
<212> TYPE: PRT
<213> ORGANISM: Homo Sapiens

<400> SEQUENCE: 175

Glu Leu Val Leu Thr Gln Pro Pro Ser Val Ser Val Ala Pro Gly Gln
1               5                   10                  15

Thr Ala Thr Leu Thr Cys Gly Gly Asn Asn Ile Gly Ser Arg Ser Val
                20                  25                  30

His Trp Tyr Gln Gln Lys Pro Gly Gln Gly Pro Val Leu Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Asp Ala Asp Tyr Tyr Cys Gln Val Trp Glu Ser Thr Thr Asp His
                85                  90                  95

Tyr Val Phe Gly Thr Gly Thr Lys Leu Thr Val Leu
            100                 105

<210> SEQ ID NO 176
<211> LENGTH: 108

```
<212> TYPE: PRT
<213> ORGANISM: Homo Sapiens

<400> SEQUENCE: 176

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Val Thr Val Leu
            100                 105

<210> SEQ ID NO 177
<211> LENGTH: 108
<212> TYPE: PRT
<213> ORGANISM: Homo Sapiens

<400> SEQUENCE: 177

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Gly Arg Val Gly Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Gln Leu Thr Val Leu
            100                 105

<210> SEQ ID NO 178
<211> LENGTH: 108
<212> TYPE: PRT
<213> ORGANISM: Homo Sapiens

<400> SEQUENCE: 178

Glu Leu Val Leu Thr Gln Pro Pro Ser Val Ser Val Ala Pro Gly Gln
1               5                   10                  15

Thr Ala Arg Ile Ile Cys Gly Gly Asn Asn Ile Gly Ser Lys Thr Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Ala Leu Thr Ile Ser Arg Val Glu Ala Gly
65                  70                  75                  80

Asp Glu Ala Asp Tyr Tyr Cys Gln Val Trp His Ser Ser Asp His
                85                  90                  95
```

```
                    85                  90                  95

Trp Val Phe Gly Gly Gly Thr Lys Val Thr Val Leu
                100                 105

<210> SEQ ID NO 179
<211> LENGTH: 108
<212> TYPE: PRT
<213> ORGANISM: Homo Sapiens

<400> SEQUENCE: 179

Glu Leu Val Leu Thr Gln Pro Pro Ser Val Ser Val Ala Pro Gly Gln
1               5                   10                  15

Thr Ala Ile Ile Thr Cys Gly Gly Ser Asn Ile Gly Thr Lys Ser Val
            20                  25                  30

His Trp Tyr Gln Gln Lys Ser Gly Gln Ala Pro Val Leu Val Val His
        35                  40                  45

Asp Asp Ala His Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Ser Ser Asp His
                85                  90                  95

Trp Val Phe Gly Gly Gly Thr Lys Val Thr Val Leu
                100                 105

<210> SEQ ID NO 180
<211> LENGTH: 108
<212> TYPE: PRT
<213> ORGANISM: Homo Sapiens

<400> SEQUENCE: 180

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Glu Ser Lys Asn Val
            20                  25                  30

His Trp Tyr Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu
                100                 105

<210> SEQ ID NO 181
<211> LENGTH: 108
<212> TYPE: PRT
<213> ORGANISM: Homo Sapiens

<400> SEQUENCE: 181

Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45
```

```
Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Asn Ser Asp His
                 85                  90                  95

Trp Val Phe Gly Gly Gly Thr Glu Leu Thr Val Phe
            100                 105
```

<210> SEQ ID NO 182
<211> LENGTH: 108
<212> TYPE: PRT
<213> ORGANISM: Homo Sapiens

<400> SEQUENCE: 182

```
Glu Leu Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Arg Ala Pro Val Leu Val Val Tyr
             35                  40                  45

Asp Asp Ser Glu Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Glu Ser Ser Asp His
                 85                  90                  95

Trp Val Phe Gly Gly Gly Thr Lys Val Thr Val Leu
            100                 105
```

<210> SEQ ID NO 183
<211> LENGTH: 108
<212> TYPE: PRT
<213> ORGANISM: Homo Sapiens

<400> SEQUENCE: 183

```
Glu Leu Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Asn Val
                 20                  25                  30

His Trp Tyr Gln Gln Lys Pro Gly Gln Ala Pro Leu Leu Val Val Tyr
             35                  40                  45

Asp Asp Ser Asp Arg Pro Ser Gly Ile Pro Glu Arg Phe Ser Gly Ser
        50                  55                  60

Asn Ser Gly Asn Met Ala Thr Leu Thr Ile Ser Arg Val Glu Ala Gly
 65                  70                  75                  80

Asp Glu Ala Asn Tyr Tyr Cys Gln Val Trp Asp Ser Ser Ser Asp His
                 85                  90                  95

Val Val Phe Gly Gly Gly Thr Lys Leu Thr Val Leu
            100                 105
```

<210> SEQ ID NO 184
<211> LENGTH: 108
<212> TYPE: PRT
<213> ORGANISM: Homo Sapiens

<400> SEQUENCE: 184

Glu Leu Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Asn Gly Thr Tyr
                85                  90                  95

Lys Val Phe Gly Gly Gly Thr Glu Leu Thr Val Leu
            100                 105

<210> SEQ ID NO 185
<211> LENGTH: 108
<212> TYPE: PRT
<213> ORGANISM: Homo Sapiens

<400> SEQUENCE: 185

Glu Leu Val Leu Thr Gln Pro Pro Ser Val Ser Val Ser Pro Gly Gln
1               5                   10                  15

Thr Ala Ser Ile Thr Cys Ser Gly Asp Lys Leu Gly His Thr Tyr Thr
            20                  25                  30

Ser Trp Tyr Gln Gln Lys Pro Gly Gln Ser Pro Val Leu Val Ile Tyr
        35                  40                  45

Gln Asp Asn Arg Arg Pro Ser Gly Leu Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Ser Ser Ser Asp His
                85                  90                  95

Leu Val Phe Gly Gly Gly Thr Glu Leu Thr Val Leu
            100                 105

<210> SEQ ID NO 186
<211> LENGTH: 108
<212> TYPE: PRT
<213> ORGANISM: Homo Sapiens

<400> SEQUENCE: 186

Glu Leu Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Gln Leu Thr Val Leu
            100                 105

<210> SEQ ID NO 187
<211> LENGTH: 108
<212> TYPE: PRT
<213> ORGANISM: Homo Sapiens

<400> SEQUENCE: 187

Glu Leu Val Leu Thr Gln Pro Pro Ser Val Ser Val Ala Pro Gly Lys
1               5                   10                  15

Thr Ala Arg Ile Thr Cys Gly Glu Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Thr Asp Arg Pro Ser Gly Ile Pro Ala Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Arg Val Phe Gly Gly Gly Thr Glu Leu Thr Val Leu
            100                 105

<210> SEQ ID NO 188
<211> LENGTH: 108
<212> TYPE: PRT
<213> ORGANISM: Homo Sapiens

<400> SEQUENCE: 188

Glu Leu Glu Leu Thr Gln Pro Pro Ser Val Ser Val Ala Pro Gly Lys
1               5                   10                  15

Ala Ala Arg Leu Ser Cys Gly Gly Glu Asp Ile Gly Ile Lys Ser Val
            20                  25                  30

His Trp Tyr Gln Gln Lys Thr Gly Arg Ala Pro Val Leu Val Ile Tyr
        35                  40                  45

Asn Asp Asp Asp Arg Pro Ser Gly Ile Pro Glu Arg Phe Ala Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Glu Val Trp Asp Ser Leu Thr Asp Arg
                85                  90                  95

Val Val Phe Gly Gly Gly Thr Lys Leu Thr Val Leu
            100                 105

<210> SEQ ID NO 189
<211> LENGTH: 108
<212> TYPE: PRT
<213> ORGANISM: Homo Sapiens

<400> SEQUENCE: 189

Glu Leu Val Leu Thr Gln Pro Pro Ser Val Ser Val Ala Pro Gly Thr
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly

```
                65                  70                  75                  80
Asp Glu Ala Asp Tyr Tyr Cys Gln Val Trp Asp Ser Ser Ser Asp Gln
                85                  90                  95

Gly Val Phe Gly Gly Gly Thr Gln Leu Thr Val Leu
            100                 105
```

<210> SEQ ID NO 190
<211> LENGTH: 107
<212> TYPE: PRT
<213> ORGANISM: Homo Sapiens

<400> SEQUENCE: 190

```
Glu Leu Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 191
<211> LENGTH: 108
<212> TYPE: PRT
<213> ORGANISM: Homo Sapiens

<400> SEQUENCE: 191

```
Glu Leu Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Val Gly
65                  70                  75                  80

Asp Glu Ala Asp Tyr Tyr Cys Gln Val Trp Asp Ser Ser Arg Asp His
                85                  90                  95

Val Val Phe Gly Gly Gly Thr Glu Leu Thr Val Leu
            100                 105
```

<210> SEQ ID NO 192
<211> LENGTH: 112
<212> TYPE: PRT
<213> ORGANISM: Homo Sapiens

<400> SEQUENCE: 192

```
Glu Leu Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Gln Thr Phe Gly Gln Gly Thr Lys Leu Glu Ile Lys
            100                 105                 110

<210> SEQ ID NO 193
<211> LENGTH: 88
<212> TYPE: DNA
<213> ORGANISM: Artificial Sequence
<220> FEATURE:
<223> OTHER INFORMATION: Artificially Synthesized

<400> SEQUENCE: 193
ttgcctttgt tggcctctcg ctcgggagat ctgcggccca ggcggcccca tggcccgggg    60
tacctactag tggccaggcc ggccagtt                                       88

<210> SEQ ID NO 194
<211> LENGTH: 93
<212> TYPE: DNA
<213> ORGANISM: Artificial Sequence
<220> FEATURE:
<223> OTHER INFORMATION: Artificially Synthesized

<400> SEQUENCE: 194
cgaactggcc ggcctggcca ctagtaggta ccccgggcca tggggccgcc tgggccgcag    60
atctcccgag cgagaggcca acaaaggcaa cga                                 93

<210> SEQ ID NO 195
<211> LENGTH: 13
<212> TYPE: DNA
<213> ORGANISM: Artificial Sequence
<220> FEATURE:
<223> OTHER INFORMATION: Artificially Synthesized
<220> FEATURE:
<221> NAME/KEY: misc_feature
<222> LOCATION: (5)..(9)
<223> OTHER INFORMATION: n is a, c, g, or t

<400> SEQUENCE: 195
ggccnnnnng gcc                                                       13

<210> SEQ ID NO 196
<211> LENGTH: 87
<212> TYPE: DNA
<213> ORGANISM: Artificial Sequence
<220> FEATURE:
<223> OTHER INFORMATION: Artificially Synthesized

<400> SEQUENCE: 196
ctagcactag tggccaggcc ggccagttcg aaggtaagcc tatccctaac cctctcctcg    60
gtctcgattc tacgcgtacc ggttagc                                        87

<210> SEQ ID NO 197
<211> LENGTH: 87
<212> TYPE: DNA
<213> ORGANISM: Artificial Sequence
```

```
<220> FEATURE:
<223> OTHER INFORMATION: Artificially Synthesized

<400> SEQUENCE: 197
tcgagctaac cggtacgcgt agaatcgaga ccgaggagag ggttagggat aggcttacct    60
tcgaactggc cggcctggcc actagtg                                       87

<210> SEQ ID NO 198
<211> LENGTH: 121
<212> TYPE: DNA
<213> ORGANISM: Artificial Sequence
<220> FEATURE:
<223> OTHER INFORMATION: Artificially Synthesized

<400> SEQUENCE: 198
ctagcatgga gacagacaca ctcctgctat gggtactgct gctctgggtt ccaggttcca    60
ctggtgacgg agctgcggcc caggcggccc catggcccgg ggtacctact agtggccagg   120
c                                                                  121

<210> SEQ ID NO 199
<211> LENGTH: 114
<212> TYPE: DNA
<213> ORGANISM: Artificial Sequence
<220> FEATURE:
<223> OTHER INFORMATION: Artificially Synthesized

<400> SEQUENCE: 199
tggccactag taggtacccc gggccatggg gccgcctggg ccgcagctcc gtcaccagtg    60
gaacctggaa cccagagcag cagtacccat agcaggagtg tgtctgtctc catg         114

<210> SEQ ID NO 200
<211> LENGTH: 11
<212> TYPE: PRT
<213> ORGANISM: Homo Sapiens

<400> SEQUENCE: 200

Ala Met Asp Ser Val Tyr Gly Asn Phe Asp Phe
1               5                   10

<210> SEQ ID NO 201
<211> LENGTH: 10
<212> TYPE: PRT
<213> ORGANISM: Homo Sapiens

<400> SEQUENCE: 201

Ala Arg Asp Leu Gly Asp Phe Gly Asp Ser
1               5                   10

<210> SEQ ID NO 202
<211> LENGTH: 10
<212> TYPE: PRT
<213> ORGANISM: Homo Sapiens

<400> SEQUENCE: 202

Ala Arg Asp Ser Val Ile Gly Thr Ser Asp
1               5                   10

<210> SEQ ID NO 203
<211> LENGTH: 10
<212> TYPE: PRT
<213> ORGANISM: Homo Sapiens

<400> SEQUENCE: 203
```

Ala Arg Asp Val Gly Asp Phe Gly Asp Ser
1               5                   10

<210> SEQ ID NO 204
<211> LENGTH: 12
<212> TYPE: PRT
<213> ORGANISM: Homo Sapiens

<400> SEQUENCE: 204

Ala Arg Glu Phe Ser Gly Gly Asn Tyr Phe Asp Phe
1               5                   10

<210> SEQ ID NO 205
<211> LENGTH: 9
<212> TYPE: PRT
<213> ORGANISM: Homo Sapiens

<400> SEQUENCE: 205

Ala Arg Phe Leu Trp Gly Leu Asp Val
1               5

<210> SEQ ID NO 206
<211> LENGTH: 13
<212> TYPE: PRT
<213> ORGANISM: Homo Sapiens

<400> SEQUENCE: 206

Ala Arg Gly Val Ala Ala Gly Trp Asn Ala Phe Asp Val
1               5                   10

<210> SEQ ID NO 207
<211> LENGTH: 11
<212> TYPE: PRT
<213> ORGANISM: Homo Sapiens

<400> SEQUENCE: 207

Ala Arg Ser Ser Tyr Tyr Ser Thr Phe Asp Tyr
1               5                   10

<210> SEQ ID NO 208
<211> LENGTH: 11
<212> TYPE: PRT
<213> ORGANISM: Homo Sapiens

<400> SEQUENCE: 208

Ala Ser Gly Asp Tyr Tyr Tyr Asp Met Ala Val
1               5                   10

<210> SEQ ID NO 209
<211> LENGTH: 12
<212> TYPE: PRT
<213> ORGANISM: Homo Sapiens

<400> SEQUENCE: 209

Ser Ile Gly Arg Tyr Thr Tyr Gly His Phe Asp Thr
1               5                   10

<210> SEQ ID NO 210
<211> LENGTH: 10
<212> TYPE: PRT
<213> ORGANISM: Homo Sapiens
<220> FEATURE:
<221> NAME/KEY: Xaa
<222> LOCATION: (1)..(1)
<223> OTHER INFORMATION: Xaa denotes either Thr or Val

<400> SEQUENCE: 210

Xaa Ser Asn Gly Trp Ser Asn Phe Asp Phe
1               5                   10

<210> SEQ ID NO 211
<211> LENGTH: 12
<212> TYPE: PRT
<213> ORGANISM: Homo Sapiens

<400> SEQUENCE: 211

Ala Ala Ala Tyr Asp Phe Trp Ser Gly Tyr Tyr Phe
1               5                   10

<210> SEQ ID NO 212
<211> LENGTH: 10
<212> TYPE: PRT
<213> ORGANISM: Homo Sapiens

<400> SEQUENCE: 212

Ala Arg Asp Leu Arg Gly Gly Glu Asp Tyr
1               5                   10

<210> SEQ ID NO 213
<211> LENGTH: 16
<212> TYPE: PRT
<213> ORGANISM: Homo Sapiens

<400> SEQUENCE: 213

Ala Arg Asp Thr Phe Ser Tyr Tyr Asp Phe Trp Arg Ala Phe Asp Tyr
1               5                   10                  15

<210> SEQ ID NO 214
<211> LENGTH: 10
<212> TYPE: PRT
<213> ORGANISM: Homo Sapiens

<400> SEQUENCE: 214

Ala Ala Ser Ser Tyr Phe Pro Phe Asp Phe
1               5                   10

<210> SEQ ID NO 215
<211> LENGTH: 15
<212> TYPE: PRT
<213> ORGANISM: Homo Sapiens
<220> FEATURE:
<221> NAME/KEY: Xaa
<222> LOCATION: (15)..(15)
<223> OTHER INFORMATION: Xaa denotes either Ser or Tyr

<400> SEQUENCE: 215

Ala Lys Asp Asn Gly Tyr Asp Ile Leu Thr Asp Tyr Leu Asp Xaa
1               5                   10                  15

<210> SEQ ID NO 216
<211> LENGTH: 15
<212> TYPE: PRT
<213> ORGANISM: Homo Sapiens

<400> SEQUENCE: 216

Ala Lys Asp Pro Asn Ser Leu Tyr Arg Ser Gly Ser Phe Asp Tyr
1               5                   10                  15

<210> SEQ ID NO 217
<211> LENGTH: 13

```
<212> TYPE: PRT
<213> ORGANISM: Homo Sapiens

<400> SEQUENCE: 217

Ala Arg Glu Gly Gln Trp Leu Pro Asn Tyr Phe Asp Pro
1               5                   10

<210> SEQ ID NO 218
<211> LENGTH: 13
<212> TYPE: PRT
<213> ORGANISM: Homo Sapiens

<400> SEQUENCE: 218

Ala Arg Asp Lys Gly Tyr Ala Asn Asn Tyr Gly Ala Tyr
1               5                   10

<210> SEQ ID NO 219
<211> LENGTH: 13
<212> TYPE: PRT
<213> ORGANISM: Homo Sapiens

<400> SEQUENCE: 219

Ala Arg Asp Gln Gly Tyr Ala Asn Asp Tyr Gly Ala Tyr
1               5                   10

<210> SEQ ID NO 220
<211> LENGTH: 13
<212> TYPE: PRT
<213> ORGANISM: Homo Sapiens

<400> SEQUENCE: 220

Ala Arg Asp Gln Gly Tyr Ala Asn Asn Tyr Gly Ala Tyr
1               5                   10

<210> SEQ ID NO 221
<211> LENGTH: 9
<212> TYPE: PRT
<213> ORGANISM: Homo Sapiens

<400> SEQUENCE: 221

Ala Arg Asp Gln Val Phe Gly Ala Tyr
1               5

<210> SEQ ID NO 222
<211> LENGTH: 13
<212> TYPE: PRT
<213> ORGANISM: Homo Sapiens

<400> SEQUENCE: 222

Ala Arg Asp Arg Gly Tyr Ala Asn Thr Tyr Gly Ala Tyr
1               5                   10

<210> SEQ ID NO 223
<211> LENGTH: 13
<212> TYPE: PRT
<213> ORGANISM: Homo Sapiens

<400> SEQUENCE: 223

Ala Arg Asp Arg Gly Tyr Asp Asn Lys Tyr Gly Ala Tyr
1               5                   10

<210> SEQ ID NO 224
<211> LENGTH: 13
<212> TYPE: PRT
<213> ORGANISM: Homo Sapiens
```

<400> SEQUENCE: 224

Ala Arg Asp Arg Gly Tyr Ser Asn Asn Tyr Gly Ala Tyr
1               5                   10

<210> SEQ ID NO 225
<211> LENGTH: 10
<212> TYPE: PRT
<213> ORGANISM: Homo Sapiens

<400> SEQUENCE: 225

Ala Arg Ser Pro Gly Tyr Tyr Phe Asp Tyr
1               5                   10

<210> SEQ ID NO 226
<211> LENGTH: 10
<212> TYPE: PRT
<213> ORGANISM: Homo Sapiens

<400> SEQUENCE: 226

Ala Arg Glu Ala Arg Asp Ser Phe Asp Phe
1               5                   10

<210> SEQ ID NO 227
<211> LENGTH: 13
<212> TYPE: PRT
<213> ORGANISM: Homo Sapiens

<400> SEQUENCE: 227

Ala Arg Asp Asp Thr Gly Arg Asp Asp Tyr Phe Glu Tyr
1               5                   10

<210> SEQ ID NO 228
<211> LENGTH: 11
<212> TYPE: PRT
<213> ORGANISM: Homo Sapiens

<400> SEQUENCE: 228

Ala Arg Ser Gly Tyr Ser Asp Ala Phe Asp Ile
1               5                   10

<210> SEQ ID NO 229
<211> LENGTH: 12
<212> TYPE: PRT
<213> ORGANISM: Homo Sapiens

<400> SEQUENCE: 229

Ala Arg Gly Gly Gly Ser Tyr Asp Phe Phe Asp Tyr
1               5                   10

<210> SEQ ID NO 230
<211> LENGTH: 9
<212> TYPE: PRT
<213> ORGANISM: Homo Sapiens
<220> FEATURE:
<221> NAME/KEY: Xaa
<222> LOCATION: (4)..(4)
<223> OTHER INFORMATION: Xaa denotes either Ala or Asp

<400> SEQUENCE: 230

Gln Gln Tyr Xaa Asn Leu Pro Leu Thr
1               5

<210> SEQ ID NO 231
<211> LENGTH: 9

```
<212> TYPE: PRT
<213> ORGANISM: Homo Sapiens

<400> SEQUENCE: 231

Gln Gln Ser His Asn Val Pro Leu Thr
1               5

<210> SEQ ID NO 232
<211> LENGTH: 9
<212> TYPE: PRT
<213> ORGANISM: Homo Sapiens
<220> FEATURE:
<221> NAME/KEY: Xaa
<222> LOCATION: (8)..(8)
<223> OTHER INFORMATION: Xaa denotes either Phe or Tyr

<400> SEQUENCE: 232

Gln Gln Ser Tyr Ser Thr Pro Xaa Thr
1               5

<210> SEQ ID NO 233
<211> LENGTH: 9
<212> TYPE: PRT
<213> ORGANISM: Homo Sapiens

<400> SEQUENCE: 233

Met Gln Ala Leu Gln Thr Pro Gln Thr
1               5

<210> SEQ ID NO 234
<211> LENGTH: 11
<212> TYPE: PRT
<213> ORGANISM: Homo Sapiens

<400> SEQUENCE: 234

Gly Thr Trp Asp Ser Ser Leu Ser Ala Val Val
1               5                   10

<210> SEQ ID NO 235
<211> LENGTH: 10
<212> TYPE: PRT
<213> ORGANISM: Homo Sapiens

<400> SEQUENCE: 235

Ser Ser Tyr Thr Ser Ser Ser Thr Val Val
1               5                   10

<210> SEQ ID NO 236
<211> LENGTH: 10
<212> TYPE: PRT
<213> ORGANISM: Homo Sapiens

<400> SEQUENCE: 236

Ser Ser Tyr Thr Ser Ser Thr Pro Tyr Val
1               5                   10

<210> SEQ ID NO 237
<211> LENGTH: 11
<212> TYPE: PRT
<213> ORGANISM: Homo Sapiens

<400> SEQUENCE: 237

Gln Val Trp Asp Arg Ser Ser Asp His Val Val
1               5                   10
```

```
<210> SEQ ID NO 238
<211> LENGTH: 11
<212> TYPE: PRT
<213> ORGANISM: Homo Sapiens

<400> SEQUENCE: 238

Gln Val Trp Asp Ser Arg Ser Asp His Gln Val
1               5                   10

<210> SEQ ID NO 239
<211> LENGTH: 11
<212> TYPE: PRT
<213> ORGANISM: Homo Sapiens
<220> FEATURE:
<221> NAME/KEY: Xaa
<222> LOCATION: (10)..(10)
<223> OTHER INFORMATION: Xaa denotes either Ala or Asp

<400> SEQUENCE: 239

Gln Val Trp Asp Ser Ser Ser Asp His Xaa Val
1               5                   10

<210> SEQ ID NO 240
<211> LENGTH: 11
<212> TYPE: PRT
<213> ORGANISM: Homo Sapiens

<400> SEQUENCE: 240

Gln Val Trp Asp Ser Ser Arg Asp His Val Val
1               5                   10

<210> SEQ ID NO 241
<211> LENGTH: 11
<212> TYPE: PRT
<213> ORGANISM: Homo Sapiens

<400> SEQUENCE: 241

Gln Val Trp Asp Ser Asn Ser Asp His Gln Val
1               5                   10

<210> SEQ ID NO 242
<211> LENGTH: 11
<212> TYPE: PRT
<213> ORGANISM: Homo Sapiens

<400> SEQUENCE: 242

Gln Val Trp Asp Ser Ser Asn Asp His Ser Val
1               5                   10

<210> SEQ ID NO 243
<211> LENGTH: 11
<212> TYPE: PRT
<213> ORGANISM: Homo Sapiens

<400> SEQUENCE: 243

Gln Val Trp Asp Ser Ser Asn Asp Gln Val Val
1               5                   10

<210> SEQ ID NO 244
<211> LENGTH: 11
<212> TYPE: PRT
<213> ORGANISM: Homo Sapiens

<400> SEQUENCE: 244

Gln Val Trp Asp Ser Ser Ser Asp His Tyr Val
1               5                   10
```

```
<210> SEQ ID NO 245
<211> LENGTH: 11
<212> TYPE: PRT
<213> ORGANISM: Homo Sapiens

<400> SEQUENCE: 245

Gln Val Trp Asp Ser Ser Ser Asp Tyr Val Val
1               5                   10

<210> SEQ ID NO 246
<211> LENGTH: 10
<212> TYPE: PRT
<213> ORGANISM: Homo Sapiens

<400> SEQUENCE: 246

Gln Ser Ala Asp Ser Asn Asp Trp Val Leu
1               5                   10

<210> SEQ ID NO 247
<211> LENGTH: 9
<212> TYPE: PRT
<213> ORGANISM: Homo Sapiens

<400> SEQUENCE: 247

Gln Ser Glu Asp Ser Ser Gly Ile Leu
1               5

<210> SEQ ID NO 248
<211> LENGTH: 10
<212> TYPE: PRT
<213> ORGANISM: Homo Sapiens

<400> SEQUENCE: 248

Gln Ser Thr Asp Ser Ser Asp Thr Trp Val
1               5                   10

<210> SEQ ID NO 249
<211> LENGTH: 10
<212> TYPE: PRT
<213> ORGANISM: Homo Sapiens

<400> SEQUENCE: 249

Gln Ser Ala Asp Ser Ser Gly Thr Tyr Val
1               5                   10

<210> SEQ ID NO 250
<211> LENGTH: 10
<212> TYPE: PRT
<213> ORGANISM: Homo Sapiens

<400> SEQUENCE: 250

Gln Ser Ala Tyr Ser Ser Gly Thr Val Val
1               5                   10

<210> SEQ ID NO 251
<211> LENGTH: 11
<212> TYPE: PRT
<213> ORGANISM: Homo Sapiens

<400> SEQUENCE: 251

Gln Ser Ser Asp Ile Asn Gly Thr Ser Trp Ile
1               5                   10
```

```
<210> SEQ ID NO 252
<211> LENGTH: 11
<212> TYPE: PRT
<213> ORGANISM: Homo Sapiens

<400> SEQUENCE: 252

Gln Ser Val Asp Ser Asn Asp Thr Ser Trp Ile
1               5                   10

<210> SEQ ID NO 253
<211> LENGTH: 11
<212> TYPE: PRT
<213> ORGANISM: Homo Sapiens

<400> SEQUENCE: 253

Gln Ser Ala Asp Ser Ser Gly Thr Ser Trp Val
1               5                   10

<210> SEQ ID NO 254
<211> LENGTH: 11
<212> TYPE: PRT
<213> ORGANISM: Homo Sapiens

<400> SEQUENCE: 254

Gln Ser Ala Asp Ser Ser Gly Thr Tyr Glu Val
1               5                   10

<210> SEQ ID NO 255
<211> LENGTH: 11
<212> TYPE: PRT
<213> ORGANISM: Homo Sapiens

<400> SEQUENCE: 255

Ala Ala Trp Asp Asp Ser Leu Arg Val Tyr Val
1               5                   10

<210> SEQ ID NO 256
<211> LENGTH: 11
<212> TYPE: PRT
<213> ORGANISM: Homo Sapiens

<400> SEQUENCE: 256

Gln Val Trp Asp Ser Arg Ser Asp Tyr Trp Val
1               5                   10

<210> SEQ ID NO 257
<211> LENGTH: 11
<212> TYPE: PRT
<213> ORGANISM: Homo Sapiens

<400> SEQUENCE: 257

Gln Val Trp Asp Ser Ser Ser Asp His Trp Val
1               5                   10

<210> SEQ ID NO 258
<211> LENGTH: 11
<212> TYPE: PRT
<213> ORGANISM: Homo Sapiens

<400> SEQUENCE: 258

Gln Val Trp Glu Ser Ser Ser Asp His Trp Val
1               5                   10

<210> SEQ ID NO 259
<211> LENGTH: 11
```

```
<212> TYPE: PRT
<213> ORGANISM: Homo Sapiens

<400> SEQUENCE: 259

Gln Val Trp Glu Ser Thr Thr Asp His Tyr Val
1               5                   10

<210> SEQ ID NO 260
<211> LENGTH: 11
<212> TYPE: PRT
<213> ORGANISM: Homo Sapiens

<400> SEQUENCE: 260

Gln Val Trp Asp Ser Asn Ser Asp His Trp Val
1               5                   10

<210> SEQ ID NO 261
<211> LENGTH: 11
<212> TYPE: PRT
<213> ORGANISM: Homo Sapiens

<400> SEQUENCE: 261

Gln Val Trp His Ser Ser Ser Asp His Trp Val
1               5                   10

<210> SEQ ID NO 262
<211> LENGTH: 11
<212> TYPE: PRT
<213> ORGANISM: Homo Sapiens

<400> SEQUENCE: 262

Gln Val Trp Asp Ser Ser Ser Asp His Val Val
1               5                   10

<210> SEQ ID NO 263
<211> LENGTH: 11
<212> TYPE: PRT
<213> ORGANISM: Homo Sapiens

<400> SEQUENCE: 263

Gln Val Trp Glu Ser Ser Ser Asp His Leu Val
1               5                   10

<210> SEQ ID NO 264
<211> LENGTH: 11
<212> TYPE: PRT
<213> ORGANISM: Homo Sapiens

<400> SEQUENCE: 264

Gln Val Trp Asp Ser Ser Ser Asp Gln Arg Val
1               5                   10

<210> SEQ ID NO 265
<211> LENGTH: 11
<212> TYPE: PRT
<213> ORGANISM: Homo Sapiens

<400> SEQUENCE: 265

Gln Ser Ala Asp Ser Asn Gly Thr Tyr Lys Val
1               5                   10

<210> SEQ ID NO 266
<211> LENGTH: 11
<212> TYPE: PRT
<213> ORGANISM: Homo Sapiens
```

```
<400> SEQUENCE: 266

Glu Val Trp Asp Ser Leu Thr Asp Arg Val Val
1               5                   10

<210> SEQ ID NO 267
<211> LENGTH: 11
<212> TYPE: PRT
<213> ORGANISM: Homo Sapiens

<400> SEQUENCE: 267

Gln Val Trp Asp Ser Ser Ser Asp Gln Gly Val
1               5                   10
```